US006448476B1

(12) United States Patent
Barry

(10) Patent No.: US 6,448,476 B1
(45) Date of Patent: Sep. 10, 2002

(54) PLANTS AND PLANT CELLS TRANSFORMATION TO EXPRESS AN AMPA-N-ACETYLTRANSFERASE

(75) Inventor: Gerard F. Barry, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/441,340

(22) Filed: Nov. 16, 1999

Related U.S. Application Data
(60) Provisional application No. 60/108,763, filed on Nov. 17, 1998.

(51) Int. Cl.$^7$ .............................. A01N 5/00; A01N 5/10;
C12N 15/82; C12N 15/31; C12N 15/54;
C12N 15/52; C12N 15/75; C12N 15/62
(52) U.S. Cl. ...................... 800/300; 435/468; 435/471;
435/411; 435/413; 435/414; 435/415; 435/416;
435/419; 435/418; 435/422; 435/417; 435/427;
435/69.7; 435/69.8; 435/193; 800/278;
800/287; 800/298; 800/288
(58) Field of Search ............................. 800/300, 300.1,
800/305–315, 317.1–317.4, 319, 320.1–320.3,
322, 323.1, 298, 278, 286, 287, 288, 290,
21; 435/455, 69.7, 468, 69.8, 471, 193,
483, 484, 485, 486, 488, 418, 422, 419,
427, 410, 320.1, 417, 411, 413–416; 536/23.1,
23.2, 23.4, 23.7, 24.1

(56) References Cited

U.S. PATENT DOCUMENTS

| | | | |
|---|---|---|---|
| 4,735,649 A | 4/1988 | Dhingra et al. | 504/205 |
| 5,463,175 A | 10/1995 | Barry et al. | 800/300 |
| 5,633,435 A | 5/1997 | Barry et al. | 800/288 |

FOREIGN PATENT DOCUMENTS

| | | |
|---|---|---|
| WO | WO 94/26913 | 11/1994 |
| WO | WO 97/03205 | 1/1997 |

OTHER PUBLICATIONS

Yuan, L. et al., "Modification of plant components." 1997, Plant Biotechnology, vol. 8, pp. 227–233.*

Avila et al., BioOrganic & Medicinal Chemistry Letters, 1:51–54 (1991) Metabolites Associated with Organophosphonate C–P Bond Cleavage: Chemical Synthesis and Microbial Degradation of [32P]–Ethylphosphonic Acid.

Avila et al., J. Amer. Chem. Soc., 109:6758–6764 (1987), Chemical and Mutagenic Analysis of Aminomethylphosphonate Biodegradation.

Barry et al., Biosynthesis and Molecular Regulation of Amino Acids in Plants, BK Singh, HE Flores, JC Shannon, eds., (1992) American Society of Plant Physiologists, pp. 139–145, INhibitors of Amino Acid Biosynthesis: Strategies for Imparting Glyphosate Tolerance to Crop Plants.

Chen et al., J. Biol. Chem., 265:4461–4471 (1990), Molecular Biology of Carbon–Phosphorous Bond Cleavage.

Dumora et al., Biochim. et Biophys. Acta., 997:193–198 (1989), Phosphonoacetaldehyde Hydrolase from *Pseudomonas aeruginosa*: Purification Properties and Comparison with *Bacillus cereus* Enzyme.

Franz, Discovery, Development and Chemistry of Glyphosate, in The Herbicide Glyphosate, E. Grossbard and D. Atkinson eds., Butterworths. pp. 3–17 (1985).

Jacob et al., Appl. Environ. Microbiol., 54:2953–2958 (1988), Metabolism of Glyphosate in Pseudomonas sp. Strain LBr.

Jiang et al., J. Bacteriol. 177:6411–6421 (1995), Molecular Cloning, Mapping, and Regulation of Pho Regulation Genes for Phosphonate Breakdown by the Phosphonatase Pathway of *Salmonella typhimirium* LT2.

Kishore et al., J. Biol. Chem. 262:12164–12168 (1987), Degradation of Glyphosate by Pseudomonas sp. PG2982 via a Sarcosine Intermediate.

Lacoste et al., J. Gen. Microbiol., 138:1283–1287 (1992), Utilization of 2–aminoethylarsonic acid in *Pseudomonas aeruginosa*.

Burland et al., Analysis of *Escherichia coli* genome VI:DNA sequence of the region from 92.8 through 100 minutes, Nucleic Acids Reserach 23:2105–2119 (1995).

Saroha et al., Glyphosate–Tolerant Crops: Genes and Enzymes, J. Plant Biochemistry & Biotechnology 7:65–72 (1998).

Yakovleva et al., Phosphate–independent expression of the carbon–phosphorus lyase activity of *Escherichia coli*, Appl. Microbiol. Biotechnol 49:573–578 (1998).

Lee et al., Evidence for Two Phosphonate Degradative Pathways in Enterobacter Aerogenes, J. Bacteriol. 174:2501–2510 (1992).

Makino et al., Molecular Analysis of the Cryptic and Functional phn Operons for Phosphonate Use in *Escherichia coli* K–12, J. Bacteriol. 173:2665–2672 (1991).

McGrath et al., The Purification and Properties of Phosphonoacetate Hydrolase, a Novel Carbon–Phosphorous Bond–Cleavage Enzyme from Pseudomonas Fluorescens 23F, Eur. J. Biochem. 234:225–230 (1995).

(List continued on next page.)

Primary Examiner—David T. Fox
Assistant Examiner—David H Kruse
(74) Attorney, Agent, or Firm—Timothy K. Ball; Dennis R. Hoerner, Jr.

(57) ABSTRACT

The invention relates in general to plants, plant cells, methods of making, and methods of using plants and plant cells transformed to contain a DNA sequence encoding an AMPA-N-acetyltransferase, and to plants and plant cells exhibiting resistance to AMPA in an amount which inhibits the growth of a plant or plant cell lacking a sequence encoding an AMPA-N-acetyltransferase.

35 Claims, 8 Drawing Sheets

OTHER PUBLICATIONS

Metcalf et al., Involvement of the *Escherichia coli* phn (psiD) Gene Cluster in Assimilation of Phosphorous in the Form of Phosphonates, Phosphite, Pi Esters, and Pi, *J. Bacteriol.* 173:587–600 (1991).

Metcalf et al., Evidence for a Fourteen–gene, phnC to phnP Locus for Phosphonate Metabolism in *Escherichia coli*, *Gene* 129:27–32 (1993).

Ohtaki et al., Cloning and Sequencing of a phnO–like Gene from Streptomyces Griseus B2682, *Actinomycetol.* 8:66–68 (1994).

Pipke et al., Degradation of the Phosphonate Herbicide Glyphosate by Arthrobacter atrocyaneus ATCC 13752, *Appl. Environ. Microbiol.* 54:1293–1296 (1988).

Shinabarger et al., Glyphosate Catabolism by Pseudomonas sp. Strain PG2982, *J. Bacteriol.* 168:702–707 (1986).

Wackett et al., Bacterial Carbon–Phosphorous Lyase: Products, Rates, and Regulation of Phosphonic and Phosphinic Acid Metabolism, *J. Bacteriol.* 169:710–717 (1987).

Wackett et al., Involvement of the Phosphate Regulon and the spiD Locus in Carbon–Phosphorous Lyase Activity of *Escherichia coli* K–12, *J. Bacteriol.* 169:1753–1756 (1987).

Wanner et al., Molecular Genetic Studies of a 10.9–kb Operon in *Escherichia coli* for Phosphonate Uptake and Biodegradation, *FEMS Microbiol. Lett.* 100:133–140 (1992).

Wohllenben et al., On the Evolution of Tn21–like Multiresistance Transposons: Sequence Analysis of the Gene (aacC1) for Gentamicin Acetyltransferase–3–I(AAC(3)–I, Another Member of the Tn21–based Expression Cassette, *Mol. Gen. Genet.* 217:202–208 (1989).

* cited by examiner

SEQUENCE LISTING

<160> NUMBER OF SEQ ID NOS: 32

<210> SEQ ID NO 1
<211> LENGTH: 15611
<212> TYPE: DNA
<213> ORGANISM: Escherichia coli

<400> SEQUENCE: 1

```
ggatccagca tcgacgccag tttttccacc attgtcagtc gcaggctaag cggcgcattt      60
aacatgccgc cgttcgtcca tgtctgaagc tgcacacgcg aaagaagttc ctgcatcagt     120
cgttcacgaa actgctgctg atgggcttgt ggaaggcggg catcatcgcc ctgcgccaga     180
tccactaaaa agcggggata aaccgactcc agcacgcgac cggggccgtc cagtaacgtc     240
ttggtcaata tcgttctgcc gtgaaaagtg tttgaatatc atcgcgtaac agctgggcgt     300
cggtgtaaat ccagccgtga gtcatcacag tctgctgcaa ttgctgctgc atcagcctga     360
ccaccgattc attttgttga cgcagagcca ggctttcgcg taaacgcgtc tgtaattccg     420
tcaaacatga agcgaactca gcgaaaaaag tattcatgcc tgccgtaaca gattcatcga     480
cctgctctgc cagaacttta gccatttgtt ggcaataaag atcgacttct gcgcttaatg     540
ctcgttgcaa cacactgtaa tcaaccgttt ctgtcgggga tttctcattt ccccgtcccc     600
agtcgggctg attcaaccag cgcgaaaaag tctcacgcac aacgcctaaa cgcgtgctct     660
gctcgtccgt tgcatcctgg cgcgaaatga ctgcactgaa cagctggcga gtgttgaagt     720
```

-continued

```
ggggaactac gccgtgaaaa acaggaaaat gaaacccagg acgaaaccct gactcgctca      780
attccatttt gacttgttgc tcaatggggc gaataacatc ggttaacact cggcaaaggg      840
tggattccag ctcggcaaaa cgcagcgtaa agtcgcgact gatggtgttc tgcgccgtct      900
gtaacagtgt ctcacagcgg gtacgcatct cgcttaacgg ctccgaatca tcctgaaaca     960
aggcggctaa ctgcgcattc agcgcatctt gttgttgacg cagaaagtgg ttggcggagg    1020
tcagggccag ctcgatttca tgtttaatct cgccgctcac ctgcgcctga ttgagttgca    1080
atagctgcaa actttcttcg acctgatgga tattttgccg caattgttca caagcgacgt    1140
ttaacccgtg cgcacgaaaa tccaggtatt cccgcgcctg ctgcgcgtaa ttcaacagtt    1200
tatgcgcagc agatcgcaaa gcatacaacg aggcgttagc gtaagcggca tgaagcaacg    1260
cctgaattgg ctgggcgaac agcgaatctt cccacaactg atcggcagca tgacgaatat    1320
gttcgaggtc cgccagatcg gcatgacgcc agcgcctgcc gagcgcggca tgggcaaaat    1380
cttccaccca gcgttgttgc tctggcgctg gtaacttacc gttgttggct aactcatggc    1440
gcgcccgatt cgccaggtag ccccacatcg acgacaccgg aaatatctgc tgtggcgtaa    1500
tacagccttt catcagcgtc ccggaaatca gtgcccgcac ctggtcggcg tcgtcactgt    1560
tacgatcctg ttgatcgaac ttattgacca gcacatacag cggcaccgat tgccccaccg    1620
ccaaaatcgc ctcacggacc tcttcatcgg agatcgattt cagttgcgta taatccagca    1680
ccgccagtac cgccgaggcg cgtgccagct gctggttaag cattttttgc agatgcggtt    1740
gcccggcttc atttggcccg ggggtatcca gtaacgtcaa ctgaccggga taactctcca    1800
gccccgccag atggacaaac tccacttcaa tcacgggaat atgctcaatg gcggcgtaag    1860
cagaaaaagg aaaatcgacg tccagcgcct tcgccagtcg cactaaatca ttcaaacttt    1920
tcagacaatg aaaaataggc tgggcaccca gataatattt ttcgaaagcg acgccatttt    1980
cgatccgctg cataagcgca cgcatatctt tatctatttc cagcacatcg gtcagatgct    2040
taatatcgca atcacgcagg cgctgttgta attgttgaat taaacaatcg attggcgcga    2100
catgtgaaaa atgcagtacc ggttcctttt gcccgggcgt atggcgaata agcgtcggca    2160
gcgcagtcat tgggcgatta cgattaggca gaacctccgt accaacaatg gcattaatgg    2220
tggttgattt ccctgctttc atggtaccga caattgcaag caccatttcc agtcgggaaa    2280
ttttacgcaa ctcattattc agcatcgcgt gacgttcggc gatattaggc tgactccagg    2340
gtaaagccag ttgtggcgcg tcgtctccgg gtacagagag aggcatttt tccagtaact    2400 gcaactgttg gcgagaaagc tgtaacaggc gttcagcctc ctgacttaac tcatacaggg    2460
tctgtgtgta catagaaaat tcttccttaa agcaaatttt gttattttat ttagccagat    2520 tgttttttgag ttctgttttc ggcttttata attactgcaa gaaataattt tatatttagt    2580
gtgttgtttt ttatcagaat aaataacgtc ttctgatacg tttaaaacgt cagaaagata    2640
aaaatatcat gtgaattaaa aaagaacaa gtagagcatt aacattatct taaataataa    2700
atagaggcaa aaagattatt ttcttttttgc gtttcctttc aaatgaaaac gatcgtcgtc    2760
taaaatcagc agtaccccg acaaactcag ggattttgtg tataattgcg gcctttttcg    2820
gcaatctgcc gttttttggc gcttttgccc tgctgacttt tgaggaaatc cacatgtcat    2880
taccacactg cccaaaatgc aactccgaat acacttacga agataacggc atgtacatct    2940
gcccggaatg tgcctacgaa tggaacgacg cagaacctgc acaggaaagc gacgagctga    3000
tcgttaaaga tgctaacggc aatctgctgg ctgacggcga cagcgttacc atcattaaag    3060
atctgaaggt gaaaggtagc tcttcgatgc tgaaaattgg caccaaagtg aaaaacatcc    3120
```

| | |
|---|---|
| gcctggttga aggcgaccat aacatcgatt gcaaaatcga cggttttggt ccgatgaaac | 3180 |
| tgaaatctga gtttgtgaaa agaactgat tgtattgtga tcggtaagcc ggataaggcg | 3240 |
| ctcgcgccgc atccggcaac ggtgccagat gcctgatgcg acgcttgcgc gtcttatcag | 3300 |
| gcctacaaat tcccgcaccc tccgtaggcc ggataaggcg tttacgccgc atccggcaac | 3360 |
| ggtgccgact gcctgatgcg acgcttgcgc gtcttatcag gcctacaaat tcccgcaccc | 3420 |
| tccgtaggcc ggataaggcg tttacgccgc atccggcaac agtgccaact gcctgatgcg | 3480 |
| acgcttgcgc gtcttatcag gcctacaaat tcccgcaccc tccgtaggcc ggataaggcg | 3540 |
| tttacgccgc atccggcaat ggtgccgact gcctgatgcg acgcttgcgc gtcttatcag | 3600 |
| gcctacaaat tcccgcaccc tccgtaggcc ggataaggcg tttacgccgc atccggcaac | 3660 |
| agtgccgact gcctgatgcg acgctcgcgc gtcttatcag gccgcctctc atctgtataa | 3720 |
| atttcgaact acacttaact ggcttctctt aactgaggtc accatcatgc cgttaagtcc | 3780 |
| ctacctctct tttgccggta actgttccga cgcgattgcc tattatcaac gtacgttggg | 3840 |
| cgcggaactg ctctataaaa tcagcttcgg cgaaatgcca aaatcagcgc aggacagcgc | 3900 |
| cgagaactgc ccttccggaa tgcaatttcc cgataccgcc atcgctcatg ccaacgtgcg | 3960 |
| cattgccgga agcgacatca tgatgagcga tgccatgccg tcaggaaaag ccagctactc | 4020 |
| cggctttacg ctggtgctcg attcgcaaca ggtcgaagaa ggaaaacgct ggtttgacaa | 4080 |
| tcttgccgct aacggaaaaa tcgaaatggc ctggcaggaa actttctggg cgcatggctt | 4140 |
| tggcaaagtc accgataaat ttggcgtacc gtggatgatt aatgtcgtca acaacaacc | 4200 |
| aacgcaataa cccgccggga ggcccgcct cccgcactgt catcgaattc ccgttaactc | 4260 |
| ttcatctgtt agtcactttt aattaaccaa atcgtcacaa taatccgcca cgatggagcc | 4320 |
| acttttttag ggaggctgca tcatgcaaac gattatccgt gtcgagaagc tcgccaaaac | 4380 |
| cttcaatcag catcaggcgc tgcatgcggt tgatctgaac attcatcacg gtgaaatggt | 4440 |
| ggctctgctt gggccgtcgg gttccggcaa atccacccct ttacgtcact taagcggttt | 4500 |
| gattaccggc gataaatccg ccggcagcca tatcgagctg ctgggccgca cagtccagcg | 4560 |
| cgaaggccgt ctggcgcgcg atatccgcaa aagccgcgcc aacaccggct acatcttcca | 4620 |
| acaattcaac ctggtgaacc gcctgagcgt actggagaac gtgctgattg gcgcgctcgg | 4680 |
| cagcacgccg ttctggcgca cctgtttag ctggtttacc cgcgagcaga acaacgcgc | 4740 |
| gttacaggcg ctgacccgcg ttggcatggt gcattttgcc catcaacgcg tttccaccct | 4800 |
| ctccggcgga cagcagcagc gtgtggcgat tgcccgcgcg ctgatgcagc aggcgaaggt | 4860 |
| gattctggcc gatgaaccca tcgcctcgct ggacccggaa tccgcccgca tcgtgatgga | 4920 |
| caccctgcgc gacatcaatc agaacgacgg catcaccgtg gtcgtcacgc tgcatcaggt | 4980 |
| ggattacgcc ctgcgctact gcgaacgcat cgtcgccctg cgccagggc acgttttcta | 5040 |
| cgacggcagc agccaacagt ttgataacga acgttttgac catctctacc gcagcattaa | 5100 |
| tcgcatcgaa gagaacgcga aagctgcctg acatccccat cattgaggaa acgaatgaa | 5160 |
| cgctaagata attgcctcgc tggccttcac cagcatgttc agcctcagca ccctgttaag | 5220 |
| cccggcacac gccgaagagc aggaaaaggc gctgaatttc ggcattattt caacggaatc | 5280 |
| acagcaaaac ctgaaaccgc aatggacgcc attcttacag gatatggaga agaagctggg | 5340 |
| cgtgaaggtg aacgccttct ttgccccaga ctacgcaggc attatccagg gaatgcgctt | 5400 |
| caataaagtg gatatcgcct ggtacggcaa cctgtcggca atggaagcgg tggatcgcgc | 5460 |
| caacggccag gtcttcgccc agacggtcgc ggcggatgga tcgccaggtt actggagcgt | 5520 |

```
gttgatcgtc aacaaagata gtccgatcaa caacctgaac gatctgctgg cgaagcggaa    5580
agatctcacc ttcggcaatg gcgatcctaa ctccacctct ggcttcctcg tccccggtta    5640
ctacgtcttc gccaaaaaca atatctccgc cagcgacttc aagcgcaccg tcaacgccgg    5700
gcatgaaacc aacgcgctgg ccgtcgccaa caagcaggtg gatgtggcga ccaacaacac    5760
cgaaaacctc gacaagctga aacctccgc gccggagaag ctgaaagaac tgaaagtgat    5820
ctggaaatcg ccgctgatcc caggcgatcc gatcgtctgg cgtaaaaatc tttccgaaac    5880
caccaaagac aagatctacg acttctttat gaattacggc aaaacgccgg aagagaaagc    5940
ggtgctggaa cgcctgggct gggcgccgtt ccgcgcctcc agcgacctgc aactggtgcc    6000
gattcgccag ctcgcactgt ttaaagagat gcagggcgtg aaaagcaata aaggactgaa    6060
tgagcaggac aagctggcaa aaaccaccgc gattcaggcg caactggatg acctggaccg    6120
cctgaacaac gcgctaagcg cgatgagttc ggtgagtaaa gcggtgcagt aaatcgtagg    6180
tcggataaga cgccccggcg tcgcatccga caatgtgcag gcgttgatgc cggatgcggt    6240
gcaagcacct tatccggcct acagaccgga gccaaacatg caaaccatca ccatcgcccc    6300
acccaagcgc agctggttct cgcttctgag ctgggccgtt gttctcgccg tgctggtcgt    6360
ctcgtggcag ggcgcggaaa tggccccgct cacgctgatt aaagacgcg gcaacatggc    6420 aaccttcgct gccgacttct tcccgcccga tttcagccag tggcaggatt acctcaccga    6480
aatggccgtc acgctgcaaa tcgccgtctg gggcaccgcg ctggcggtgg ttctctccat    6540
cccctttggc ctgatgagcg ccgaaaacct ggtgccgtgg tgggtttacc agcccgttcg    6600
ccgcctgatg gacgcctgcc gcgccattaa cgaaatggtc ttcgccatgc tgttcgtggt    6660
cgccgtcggt ctcggaccgt tcgctggcgt gctggcgcta tttatccaca ccaccggcgt    6720
gctctccaag ctgctttccg aagcggtaga agcaattgaa cctggcccgg tggaaggcat    6780
tcgcgccacc ggtgccaaca agctcgaaga gatcctctac ggcgtgctgc gcaggtgat    6840 gccgctgctg atctcctact ccctctatcg cttcgaatcc aacgtccgct cggcgaccgt    6900
cgtcggcatg gtcggcgcgg gcgggatcgg cgtcaccctg tgggaagcga ttcgcggttt    6960
ccagttccaa caaacctgcg ccctgatggt gcttatcatc gtcacggtca gcctgctgga    7020
tttcctctct caacggttgc gtaagcactt tatctgataa gcgaggcatt gatatctatg    7080
cacttgtcta cacatccgac cagctaccca acacgctatc aagagatagc cgcaaaactt    7140
gagcaggagc ttcgtcaaca ctaccgctgc ggcgactatc ttcccgccga gcagcaactg    7200
gcagcgcgct ttgaggtgaa tcgccacacc ctgcgccgcg ccatcgacca actggtggaa    7260
aaaggctggg tacagcgccg tcagggcgtc ggcgtgctgg tgctgatgcg cccgttcgat    7320
tacccgctca acgcccaggc gcgttttagc cagaatctgc tggatcaggg cagccatccc    7380
accagcgaaa aactgctttc ggtattgcgc cccgcgtccg gccacgtcgc tgacgcactg    7440
gggattaccg aggggagaa cgtcatccac ctgcgcaccc tgcgtcgggt caacggcgtc    7500
gcgctctgtt taatcgacca ctacttgcg gacctcaccc tctggccgac gctgcaacgc    7560
ttcgacagcg gctcgctgca cgattttctg cgcgagcaaa ccggaattgc gctgcgccgc    7620
agccagacgc ggatcagcgc ccgccgcgcc caggccaaag agtgccagcg tcttgaaatc    7680
ccgaatatgt cgccgctgct gtgcgtgcgc acccttaacc accgtgacgg tgaaagcagc    7740
ccggcggagt actccgtcag cctgacgcgc gccgacatga ttgaattcac tatggagcac    7800
tgaatgcacg cagataccgc gacccgccag cactggatgt ccgtgctggc gcacagccaa    7860
ccggctgaac tggcagcacg cctgaacgcg ctaaacatca ccgccgacta tgaggtgatc    7920
```

-continued

```
cgcgccgctg aaactggcct ggtacagatt caggcgcgga tgggcggcac cggcgaacgt    7980
ttttttgccg gcgacgccac gctgacccgc gccgccgtgc gcctgactga cggcacgctc    8040
ggctacagct gggtgctggg gcgtgataaa cagcacgccg aacgctgcgc gctgattgac    8100
gcgctgatgc agcaatctcg ccactttcaa aacttatcag aaacccttat tgccccgctg    8160
gacgctgacc gtatggcacg cattgccgca cgccaggccg aagtgaacgc cagccgggtc    8220
gacttcttta cgatggttcg cggagacaac gcatgaccct ggaaaccgct tttatgcttc    8280
ccgtgcagga tgcccagcac agttttcgtc gcctgttaaa ggccatgagc gagccgggcg    8340
tgattgtcgc cctgcatcag ctcaaacgcg gctggcaacc gctgaatatc gccaccacca    8400
gcgtgctgct gacgctggcc gataacgaca cgccggtgtg gctttctacc ccattaaata    8460
acgatatcgt caaccagagc ctgcgttttc ataccaacgc gccgctggtc agccagccgg    8520
aacaggcgac cttcgcggtg acggatgagg cgatttccag cgaacagctc aacgcccttt    8580
ccaccggcac cgccgttgcg ccggaagcgg gcgcgacgct gattttacag gtcgccagcc    8640
tgagcggcgg gcgcatgttg cgtctcaccg gcgcgggtat tgccgaagaa cgaatgatcg    8700
ctccgcagct gccggagtgc attctgcacg aactcaccga gcgcccgcac ccgttcccgc    8760
tcggcatcga cctgatcctg acctgcggcg aacgcctgct ggctattccg cgaaccacgc    8820
atgtggaggt gtgctgatgt acgttgccgt aaaaggggc gaaaaggcga tcgacgccgc    8880
ccacgccctg caagagagcc gacgccgggg cgataccgat ttgcctgaac tgagcgtcgc    8940
ccagattgaa cagcagctta acctcgcggt agatcgcgtg atgaccgaag gcggcattgc    9000
cgaccgcgaa ctggcggcgc tggcgctgaa acaggccagc ggcgataacg ttgaagcgat    9060
tttcctgctg cgcgcctacc gcaccacgtt ggcgaagctg gcggtaagcg agccgctcga    9120
caccaccggg atgcgtctcg aacgccgtat ctccgccgtt tataaagaca ttcccggcgg    9180
ccagctgctt ggcccaacct acgactacac ccatcgcctg ctcgatttta ccctgctggc    9240
aaacggcgaa gcgccgacgc tgaccaccgc cgacagcgaa caacagccgt cgccgcacgt    9300
tttcagcctg ctggcgcgtc aggggctggc gaagtttgaa gaggatagcg gcgcacagcc    9360
ggatgacatc acccgcacgc cgccggtttta ccctgctca cgttcttccc gtttgcagca    9420
gttgatgcgc ggcgacgaag gctatttgct ggcgctggcc tactccaccc agcgtggtta    9480
cggacgcaat cacccgttcg cgggcgagat ccgcagtggt tacatcgacg tgtcgattgt    9540
gccggaagag ctgggatttg cggtaaacgt cggcgaacta ctgatgaccg agtgtgaaat    9600
ggtcaacggt tttatcgacc cgccggatga gccgccgcac ttcacgcgcg gctacgggct    9660
ggtattcggc atgagcgagc gcaaagcgat ggcaatggcg ctggtcgatc gtgcgttgca    9720
ggctccggaa tacggcgagc acgcgacagg cccggcgcag gatgaagagt ttgtgctggc    9780
acatgccgac aacgtcgaag ccgcaggctt tgtctcgcac ctcaaactcc cccactacgt    9840
cgatttccag gccgaactgg agctactcaa acgtctgcaa caggagaaga accatggcta    9900
atctgagcgg ctacaacttt gcctacctcg acgagcagac caaacgcatg atccgccgcg    9960
ccatcttaaa agcggtggcg atccccggtt atcaggtgcc gtttggcggg cgcgagatgc   10020
cgatgccata cggctgggga accggcggca tacagctcac cgccagcgtg attggcgaaa   10080
gcgacgtgct aaaggtgatt gaccagggtg cggatgacac caccaacgcc gtgtcgattc   10140
gcaacttctt taagcgcgtg accggggtaa acaccactga acgtacggac gatgcgacgc   10200
ttatccagac gcgtcaccgc atcccgaaa cgccgctgac cgaagatcag atcattatct   10260
tccaggtgcc aatcccggaa ccgctgcgct ttatcgagcc gcgcgaaacg gaaacccgca   10320
```

-continued

```
ccatgcacgc gctggaagag tacggcgtga tgcaggtgaa actgtatgaa gatatcgccc    10380
gcttcggtca tatcgccact acctacgcct atccggtgaa ggtgaacggg cgctacgtaa    10440
tggacccgtc gccgatcccg aaattcgata acccaaaaat ggacatgatg cccgccctgc    10500
aactgttcgg cgcggggcgc gagaagcgca tctatgcggt gccgccgttt acccgcgtgg    10560
aaagtctcga tttcgacgat cacccgttca ccgttcagca gtgggatgag ccatgcgcca    10620
tctgcggatc gacccacagc tatcttgatg aagtggtgct ggatgacgcc ggaaaccgca    10680
tgtttgtctg ctccgatacc gattattgcc gccaacagag cgaggcaaaa aaccaatgaa    10740
tcaaccgtta ctttcggtca ataacctgac ccacctttac gcgccgggca aaggctttag    10800
cgatgtctct tttgatttat ggccgggggga agtgctgggc attgtcgggg aatccggctc    10860
cgggaagacc acgctgctga agtcgatctc cgcgcgcctg acgccgcagc agggggaaat    10920
tcactacgag aaccgttcgc tgtatgcaat gagcgaggcc gaccgccgtc gcctgctgcg    10980
taccgaatgg ggcgtggtgc atcagcatcc actcgacggc ctgcgccgcc aggtgtcggc    11040
aggcggcaat atcggcgagc ggctgatggc gaccggggca cgtcattacg gcgatattcg    11100
tgccaccgcg cagaagtggc tggaagaggt ggagattccc gccaaccgga tcgacgacct    11160
gccgaccacc ttttccggcg gtatgcagca gcgtttgcag attgcccgca acctggtgac    11220
gcatccgaag ctggtgtttta tggatgaacc gaccggcggg ctggatgtgt cggtgcaggc    11280
ccgcctgctc gacctgctgc gcggcctggt ggtggagctg aacctcgcgg tggtgattgt    11340
cacccatgat ttaggcgtcg cccgcctgct ggcggaccgt ttgctggtga tgaagcaggg    11400
gcaagtggtg gagagtgggt taaccgaccg cgtgctcgac gacccgcatc atccgtatac    11460
acagctgctg gtgtcatcgg ttttgcagaa ttgagccggt gccggatgcg gcgtaaacgc    11520
cttatccggc ctacaaatgc gctccccgta ggtcggataa gacgcgtcag cgtcgcatcc    11580
gacacccgaa ccacgaggcg aaaaatgatt aacgtacaaa acgtcagtaa aaccttcatc    11640
ctgcaccagc aaaacggcgt gcgcctgccc gtcctcaatc gcgcctcgct caccgtcaac    11700
gcgggcgaat gcgtggtgct ccacggccat tccggcagcg gcaaatcaac tctgctacgc    11760
tcgctgtacg ccaactatct acccgacgaa ggtcaaatcc agatcaaaca cggtgacgag    11820
tgggtagacc tggtcaccgc gccagcgcgc aaagtggtgg aaatccgcaa accaccgtc    11880
ggctgggtga gccagtttct gcgcgtcatc ccgcgtatct cagcactgga agtggtgatg    11940
cagccgctgc tcgataccgg cgttccgcgt gaagcctgcg ccgctaaagc cgcgcgtctt    12000
ctcacccgcc tgaacgtgcc ggaacgcctg tggcacctgg caccatcgac attttccggt    12060
ggcgaacagc agcgcgtcaa catcgcccgc ggctttatcg tcgactaccc cattctgctg    12120
cttgacgaac ctaccgcctc gctggacgcc aaaaacagcg ccgcggtggt ggaactgatt    12180
cgcgaagcca aaacccgtgg cgcagccatc gtaggcatct ccatgacgaa agctgtacgt    12240
aatgacgtcg ccgaccgcct gcacccaatg ggagcctctt catgattatc aataacgtta    12300
agctggtgct ggaaaacgag gtggtaagcg gttcgctgga ggtgcagaac ggcgaaatcc    12360
gcgcctttgc cgaaagccag agccgcctgc cggaggcgat ggacggcgaa ggcggctggc    12420
tgctgccggg gctgattgag ctgcataccg ataatctgga taaattcttc accccgcgcc    12480
cgaaagttga ctggcctgcc cactcggcga tgagcagcca cgacgcgctg atggtggcga    12540
gcggcatcac caccgtactg gatgccgtgg caattggcga cgtgcgcgac ggcggcgatc    12600
ggctggagaa tctggagaag atgatcaacg ccatcgaaga gacgcagaaa cgcggcgtca    12660
accgcgccga gcaccgtctg catctgcgct gcgaactgcc gcatcacacc acgctgccgc    12720
```

-continued

```
tgtttgaaaa actggtgcag cgcgagccgg tgacgctggt gtcgctgatg gaccactcgc  12780
cgggccagcg ccagttcgcc aaccgcgaga gtatcgcga atattatcag ggcaaatact  12840
ccctcactga tgcgcagatg cagcagtacg aagaagagca actggcgctc gccgcacgct  12900
ggtcgcagcc gaatcgcgaa tccatcgccg ccctgtgccg cgcgcgaaaa attgcgcttg  12960
ccagccacga tgacgccacc cacgcccacg ttgctgaatc tcaccagctt ggcagcgtga  13020
tcgccgaatt tcccaccacg ttcgaagcgg cggaagcctc gcgcaagcat ggcatgaacg  13080
tgctgatggg cgcgccgaat attgtgcgcg cggctcgca ctccggcaac gtggcggcca  13140
gtgaactggc gcagcttggc ctgctggata tcctctcttc cgactactac cccgccagcc  13200
tgctcgatgc ggcatttcgc gtcgccgatg acgagagcaa ccgctttacg ctgccgcagg  13260
cggtgaagct ggtgactaaa aatccagcgc aggcgcttaa tctccaggat cgcggggtga  13320
ttggcgaggg caaacgcgcc gacctggtgc tggcgcatcg caaggacaat catattcata  13380
tcgaccacgt ctggcgtcag ggtaaaaggg tgttctgatg atgggaaaac tgatttggtt  13440
aatggggccg tccggctccg ggaaagacag cctgctggcg gaactccgcc tgcgggaaca  13500
aactcagtta ctggtggcgc atcgctacat cacgcgcgat gccagcgccg gaagtgaaaa  13560
ccatatcgcc ctgagcgagc aggagttttt tacccgcgcg gggcaaaatc tgttggcctt  13620
aagctggcac gctaacggtc tgtattatgg cgtcggcgtc gagattgatc tctggctgca  13680
cgccggattc gacgtgctgg tcaacggctc acgcgcccat ctgccgcagg cgcgggcgcg  13740
ctatcaatcg gcgctgctgc ccgtctgttt acaggtttcg ccggagatcc tccgccagcg  13800
cctggaaaac cgtggccgtg aaaacgccag tgaaattaac gcccgcctgg cgcgcgccgc  13860
ccgctatact ccacaggatt gccatacgct caacaatgac ggcagcctgc gccagtcggt  13920
cgacacgctg ctgacgctga tccatcagaa ggagaaacac catgcctgct tgtgagcttc  13980
gcccggccac gcagtacgac accgacgcgg tttacgcgct gatttgtgag ctaaaacagg  14040
cggagtttga ccaccacgcg tttcgcgtgg gttttaacgc caatctgcgc gacccaaaca  14100
tgcgctacca tctggcgctg cttgatgcg aagttgtcgg catgatcggc ctgcatttgc  14160
agtttcatct gcatcatgtc aactggatcg gcgaaattca ggagttggtg gtaatgccgc  14220 aggcgcgcg tctgaacgtc ggcagtaagt tactggcgtg ggcagaagaa gaagcccgcc  14280
aggccggggc cgaaatgacc gaactttcga ccaacgtgaa gcgccacgac gcgcaccgtt  14340
tctatctgcg cgaaggctac gagcagagcc acttccgctt caccaaggcg ctgtaacatg  14400
agcctgaccc tcacgctcac cggcaccggc ggcgcacagg gcgttccggc atgggctgc  14460 gagtgtgcgg cctgcgccag agcgcggcgc tcgccgcagt atcgccgcca accgtgcagc  14520
ggcgtagtga agtttaacga cgcaatcacc ctgatcgacg ccgggctgca cgatctcgcc  14580
gatcgctggt cgcccggatc gttccagcag ttttgctga cgcattatca tatggatcac  14640
gtccaggggc tgtttccgct cgcgctgggc gttggcgatc cgatcccggt ttacggcccg  14700
ccggatgaac agggctgcga cgatctgttt aaacatccgg gcctgcttga tttcagccac  14760
acggtggaac cgtttgtggt gtttgatttg caggggttac aggtcacgcc cctgccgctc  14820
aaccactcaa aactgacctt cggttatctg ctggaaacgg cacacagccg ggtggcgtgg  14880
ctgtctgaca ccgcaggctt gccggaaaaa acgctgaaat ttttacgcaa taatcagccg  14940
caggtaatgg tgatggattg cagtcacccg ccgcgcgcgg atgcaccgcg taatcactgt  15000
gatttaaata ccgtgcttgc gctgaatcag gttatccgct cgccacgggt gattctgacc  15060
catatcagcc accagtttga tgcgtggctg atggaaaacg cactaccgtc agggtttgag  15120
```

-continued

| | |
|---|---|
| gtggggtttg atgggatgga gattggggtg gcgtgatgag agggaatgtg cgcgctggcc | 15180 |
| ccctcaccct aaccctctcc ccagaggggc gaggggaccg attgtgctcg atattgaata | 15240 |
| ttgcgctcgt tttctccctc tccccattgg ggtgaggggc gatgcctgct ccatacccaa | 15300 |
| cctcatcgcc catactcatc ttccattctc cgctcttcat cctccagttg ccgacgctcc | 15360 |
| tgatcaagct ggcgctggcg atcgtccagc tgcctgcggc gatcttcaaa ctggcggcgg | 15420 |
| cggtcgtcat attgtctgcg ccgatcgtcg ctcacttcac gctgccagcc gtggtcgcgc | 15480 |
| gaatcttcat agttgaagcg gcgcacgaaa acgcgaaag cgtttcacga taatgcgaa | 15540 |
| aactttagct ttcgcgcttc aaatgaaaca gatgtattaa ttactgcttt ttattcatta | 15600 |
| catggggatc c | 15611 |

<210> SEQ ID NO 2
<211> LENGTH: 11672
<212> TYPE: DNA
<213> ORGANISM: Escherichia coli

<400> SEQUENCE: 2

| | |
|---|---|
| gaattcccgt taactcttca tctgttagtc acttttaatt aaccaaatcg tcacaataat | 60 |
| ccgccacgat ggagccactt ttttagggag gctgcatcat gcaaacgatt atccgtgtcg | 120 |
| agaagctcgc caaaaccttc aatcagcatc aggcgctgca tgcggttgat ctgaacattc | 180 |
| atcacggtga atggtggct ctgcttgggc cgtcgggttc cggaaaatcc accctttttac | 240 |
| gtcacttaag cggtttgatt accggcgata atctgtcgg tagccatatc gagctgctgg | 300 |
| gccgcacagt ccagcgcgaa ggccgcctgg cccgcgatat ccgcaaaagc cgcgcccata | 360 |
| ccggctacat attccaacaa ttcaacctgg tgaaccgcct gagcgtactg gagaacgtgc | 420 |
| tgattggcgc gctcggcagc acgccgttct ggcgcacctg ttttagctgg ttcaccggcg | 480 |
| agcagaaaca gcgcgcgtta caggcgctga cccgcgttgg catggtgcat tttgcccatc | 540 |
| agcgcgtttc caccctctcc ggcggccagc agcaacgtgt ggcgattgcc cgtgcgctga | 600 |
| tgcagcaggc gaaagtgatt ctggccgatg aacccatcgc ctcgctggac ccagaatcag | 660 |
| cgcgcatcgt gatggacacc ctgcgcgaca tcaaccagaa cgacggcatc accgtggtcg | 720 |
| tcacgctgca tcaggtggat tacgccctgc gctactgcga acgcatcgtc gccctgcgcc | 780 |
| agggcacgt cttctacgac ggcagcagcc aacagtttga taacgaacgt tttgaccatc | 840 |
| tctaccgcag cattaaccgc gtcgaagaga cgcgaaagc tgcctgacat ccccatcatt | 900 |
| gaggaaaacg aatgaacgct aagataattg cctcgctggc cttcaccagc atgttcagcc | 960 |
| tcagcaccct gttaagcccg gcgcacgccg aagagcagga aaaggcgttg aatttcggca | 1020 |
| ttatttcaac ggaatcacag caaaacctga accgcaatg gacgccgttc ttgcaggata | 1080 |
| tggagaagaa gctgggcgtg aaggtcaacg ccttctttgc cccggactac gcgggcatta | 1140 |
| tccaggggat gcgcttcaat aaagtggata tcgcctggta cggcaatctg tcggcgatgg | 1200 |
| aagcggtgga tcgcgccaat ggccaggtct tcgcccagac ggtcgcggcg gatggatcgc | 1260 |
| cgggttactg gagcgtgttg atcgtcaaca agacagtcc gatcaacaac ctgaacgatc | 1320 |
| tgctggcgaa gcgaaagat ctcacctttg gcaatgcga tcctaactcc acctctggct | 1380 |
| tcctcgtccc cggctactac gtcttcgcca aaaacaatat ctccgccagc gacttcaagc | 1440 |
| gcaccgtcaa cgccgggcat gaaaccaacg cgctggccgt cgccaacaag caggtggatg | 1500 |
| ttgccaccaa caacaccgaa aacctcgaca agctgaaaac ctccgcgcca gagaagctga | 1560 |
| aagaactgaa ggtgatctgg aagtcgccgc tgatcccagg cgatccgatc gtctggcgca | 1620 |

-continued

```
agaatctttc cgaaaccacc aaagacaaga tctacgactt ctttatgaac tacggcaaaa   1680
cgccggaaga aaaagcggtg ctggaacgcc tgggctgggc gccattccgc gcttccagcg   1740
acctgcaact ggtgccgatt cgccagctcg cgctgtttaa agagatgcag ggcgtgaaaa   1800
gcaataaagg actgaatgag caggacaagc tggcaaaaac caccgagatt caggcgcagc   1860
tggatgacct ggaccgcctg aacaacgcgc taagcgcgat gagttcggtg agtaaagcgg   1920
tgcagtaaat cgtaggtcgg ataagacgcc ccggcgtcgc atccgacaat gtgcaggcgt   1980
tgatgccgga tgcggtgcaa gcaccttatc cggcctacag accggagcca acatgcaaa   2040
ccatcaccat cgccccaccc aagcgcagct ggttctcgct tctgagctgg gccgttgtac   2100
tcgccgtgtt ggtcgtctcg tggcagggcg cggaaatggc cccgcttacg ctgatcaaag   2160
acggcggcaa catggcgacg ttcgccgccg acttcttccc gcccgatttc agccagtggc   2220
aggattacct caccgaaatg gccgtcacgc tgcaaatcgc cgtctggggc accgcgctgg   2280
cggtggttct ctccatcccc tttggcctga tgagcgccga aaacctggtg ccgtggtggg   2340
tttaccagcc cgttcgccgc ctgatggacg cctgccgcgc cattaacgaa atggtcttcg   2400
ccatgctgtt cgtggtcgcc gtcggcctcg gcccgttcgc tggcgtgctg gcgtgctggc   2460
gctgtttatc cacaccaccg gcgtgctctc caagctgctt ccgaagcgg tggaagcgat   2520
tgagcccggc ccggtggaag gcattcgcgc caccggtgcc aacaagctcg aagagatcct   2580
ctacggcgtg ctgccacagg tgatgccact gctgatctcc tactccctct atcgcttcga   2640
atccaacgtc cgctcggcga ccgtcgtcgg catggtcggc gcaggcggga tcggcgtcac   2700
cctgtgggaa gcgattcgcg gtttccagtt ccaacaaacc tgcgccctga tggtgcttat   2760
catcgtcacg gtcagcctgc tggatttcct ctctcaacgg ttgcgtaagc actttatctg   2820
ataagcgagg cattgatatc tatgcacttg tctacacatc cgaccagcta cccaacacgc   2880
tatcaagaga tagccgcaaa acttgagcag gagcttcgtc aacactaccg ctgcggcgac   2940
tatcttcccg ccgagcagca actggcagcg cgctttgagg tgaatcgcca caccctgcgc   3000
cgcgccatcg accaactggt ggaaaaaggc tgggtacagc gccgtcaggg cgtcggcgtg   3060
ctggtgctga tgcgcccgtt cgattacccg ctcaacgccc aggcgcgttt tagccagaat   3120
ctgctggatc agggcagcca tcccaccagc gaaaaactgc tttcggtatt gcgccccgcg   3180
tccggccacg tcgctgacgc actggggatt accgaggggg agaacgtcat ccacctgcgc   3240
accctgcgtc gtgtcaacgg cgtcgcgctc tgtttaatcg accactactt cgcggacctc   3300
accctctggc cgacgctgca acgcttcgac agcggctcgc tgcacgattt tctgcgcgag   3360
caaaccggaa ttgcgctgcg ccgcagccag acgcggatca cgcccgccg cgcccaggcc   3420
aaagagtgcc agcgtcttga aatcccgaat atgtcgccgc tgctgtgcgt gcgcaccctt   3480
aaccaccgtg acggtgaaag cagccgcgc gagtactccg tcagcctgac gcgcgccgac   3540
atgattgaat tcactatgga gcactgaatg cacgcagata ccgcgacccg ccagcactgg   3600
atgtccgtgc tggcgcacag ccaaccggct gaactggcag cacgcctgaa cgcgctaaac   3660
atcaccgccg actatgaggt gatccgcgcc gctgaaactg gcctggtaca gattcaggcg   3720
cggatgggcg gcaccggcga acgttttttt gccggcgacg ccacgctgac ccgcgccgcc   3780
gtgcgcctga ctgacggcac gctcggctac agctgggtgc aggggcgtga taaacagcac   3840
gccgaacgct gcgcgctgat tgacgcgctg atgcagcaat ctcgccactt tcaaaactta   3900
tcagaaaccc ttattgcccc gctggacgct gaccgtatgg cacgcattgc cgcacgccag   3960
gccgaagtga acgccagccg ggtcgacttc tttacgatgg ttcgcggaga caacgcatga   4020
```

-continued

```
ccctggaaac cgcttttatg cttcccgtgc aggatgccca gcacagtttt cgtcgcctgt    4080
taaaggccat gagcgagccg ggcgtgattg tcgccctgca tcagctcaaa cgcggctggc    4140
aaccgctgaa tatcgccacc accagcgtgc tgctgacgct ggccgataac gacacgccgg    4200
tgtggctttc taccccatta ataacgata tcgtcaacca gagcctgcgt tttcatacca     4260
acgcgccgct ggtcagccag ccggaacagg cgaccttcgc ggtgacggat gaggcgattt    4320
ccagcgaaca gctcaacgcc ctttccaccg gcaccgccgt tgcgccggaa gcgggtgcga    4380
cgctgatttt acaggtcgcc agcctgagcg cggacgcat gttgcgcctt actggtgcgg     4440
gtattgccga agaacgaatg atcgctccgc agctgccgga gtgcattctg cacgaactca    4500
ccgagcgccc gcatccgttc ccgctcggca tcgacctgat cctgacctgt ggcgagcgcc    4560
tgctggctat tccgcgaacc actcatgtgg aggtgtgctg atgtacgttg ccgtgaaagg    4620
gggcgagaag gcgatcgacg ccgcccacgc cctgcaagag agccgacgcc gaggcgatac    4680
cgatttgccc gaactgagcg tcgcccagat tgaacagcag cttaacctcg cggtagatcg    4740
cgtgatgacc gaaggcggca ttgccgaccg cgaactggcg cgctggcgc tgaaacaggc     4800 cagcggcgat aacgttgaag cgattttcct gctgcgcgcc taccgcacca cgttggcgaa    4860
gctggcggta agcgagccgc tcgacaccac cgggatgcgt ctcgaacgcc gtatctccgc    4920
cgtttataaa gacattcccg gcggccagct gcttggccca acctacgact acacccatcg    4980
cctgctcgat tttaccctgc tggcaaacgg cgaagcgccg acgctgacca ccgccgacag    5040
cgaacagcag ccgtcgccgc acgttttcag cctgctggcg cgtcagggc tggcgaagtt     5100 tgaagaggat agcggcgcac agccggatga catcacccgc acgccgccgg tttacccctg    5160
ctcacgctcc tcccgtttgc agcagttgat gcgcggcgac gaaggctatt tgctggcgct    5220
ggcctactcc acccaacgcg gttacgggcg caatcacccg ttcgcaggcg agatccgcag    5280
cggctatatc gacgtgtcga ttgtgccgga agagctggga tttgcggtga acgtcggcga    5340
actgctgatg actgagtgtg aaatggttaa cggttttatc gacccgccgg gtgagccgcc    5400
gcacttcacg cgcggctacg ggctggtgtt cggcatgagc gagcgcaaag cgatggcgat    5460
ggcgctggtc gaccgcgctc tgcaagcccc ggagtacggc gagcacgcga caggcccggc    5520
gcaggatgaa gagttcgtgc tggcacatgc cgacaacgtc gaagccgcag gctttgtctc    5580
acacctcaaa ctcccccact acgtcgattt ccaggccgaa ctggagctac tcaaacgtct    5640
gcaacaggag cagaaccatg gctaatctga gcggctacaa cttgcctac ctcgacgagc     5700 agaccaaacg catgatccgc cgcgccatct aaaagcggt ggcgatcccc ggttatcagg     5760
tgccgtttgg cggcgcgag atgccgatgc cgtacggctg gggaaccggc ggcattcagc     5820
ttaccgccag cgtgattggc gaaagcgacg tgctgaaggt gattgaccag ggcgcggatg    5880
acaccaccaa cgccgtgtcg attcgcaact tcttcaagcg cgtgaccggg gtaaacacca    5940
cggaacgtac ggacgatgcg acggttatcc agacgcgtca ccgcatcccc gaaacgccgc    6000
tgaccgaaga tcgataatt atcttccagg tgccaatccc cgagccgctg cgctttatcg     6060
agccgcgcga aacggaaacc cgcaccatgc acgcgctgga agagtacggc gtgatgcagg    6120
tgaaactgta tgaagatatc gcccgcttcg gtcatatcgc caccacctac gcctatccgg    6180
tgaaggtaaa tgggcgctac gtgatggacc cgtcgccgat cccgaaattc gataacccaa    6240
aaatggacat gatgcccgcc ctgcaactgt tcggcgcggg gcgcgagaag cgcatctatg    6300
cggtgccgcc gtttacccgc gtggaaagtc tcgatttcga cgatcacccg ttcaccgttc    6360
agcagtggga tgagccatgc gccatctgcg gatcgaccca cagctatctt gatgaagtgg    6420
```

-continued

```
tgctggatga cgccggaaac cgcatgtttg tctgctccga taccgattat tgccgccaac    6480
agagcgaggc aaaaaaccaa tgaatcaacc gttactttcg gtcaataacc tgacccacct    6540
ttacgcgccg ggcaaaggct ttagcgatgt ctcttttgat ttatggccgg gggaagtgct    6600
gggcattgtc ggggaatccg gctccgggaa gaccacgctg ctgaagtcga tctccgcgcg    6660
cctgacgccg cagcagggg aaattcacta cgagaaccgt tcgctgtatg caatgagcga    6720
ggccgaccgc cgtcgcctgc tgcgtaccga atggggcgtg gtgcatcagc atccactcga    6780
cggcctgcgc cgccaggtgt cggcaggcgg caatatcggc gagcggctga tggcgaccgg    6840
ggcacgtcat tacggcgata ttcgtgccac cgcgcagaag tggctggaag aggtggagat    6900
tcccgccaac cggatcgacg acctgccgac caccttttcc ggcggtatgc agcagcgttt    6960
gcagattgcc cgcaacctgg tgacgcatcc gaagctggtg tttatggatg aaccgaccgg    7020
cgggctggat gtgtcggtgc aggcccgcct gctcgacctg ctgcgcggcc tggtggtgga    7080
gctgaacctc gcggtggtga ttgtcaccca tgatttaggc gtcgcccgcc tgctggcgga    7140
ccgtttgctg gtgatgaagc aggggcaagt ggtggagagt gggttaaccg accgcgtgct    7200
cgacgacccg catcatccgt atacacagct gctggtgtca tcggttttgc agaattgagc    7260
cggtgccgga tgcggcgtaa acgccttatc cggcctacaa atgcgctccc cgtaggtcgg    7320
ataagacgcg tcagcgtcgc atccgacacc cgaaccacga ggcgaaaaat gattaacgta    7380
caaaacgtca gtaaaacctt catcctgcac cagcaaaacg gcgtgcgcct gcccgtcctc    7440
aatcgcgcct cgctcaccgt caacgcgggc gaatgcgtgg tgctccacgg ccattccggc    7500
agcggcaaat caactctgct acgctcgctg tacgccaact atctgcccga cgaaggtcaa    7560
atccagatca aacacggtga cgagtgggta gacctggtca ccgcgccagc gcgcaaagtg    7620
gtggaaatcc gcaaaaccac cgtcggctgg gtgagccagt ttctgcgcgt catcccgcgt    7680
atctcagcac tggaagtggt gatgcagccg ctgctcgata ccggcgttcc gcgtgaagcc    7740
tgcgccgcta agccgcgcg tcttctcacc cgcctgaacg tgccggaacg cctgtggcac    7800
ctggcaccat cgacattttc cggtggcgaa cagcagcgcg tcaacatcgc ccgcggcttt    7860
atcgtcgact accccattct gctgcttgac gaacctaccg cctcgctgga cgccaaaaac    7920
agcgccgcgg tggtggaact gattcgcgaa gccaaaaccc gtggcgcagc catcgtaggc    7980
atcttccatg acgaagctgt acgtaatgac gtcgccgacc gcctgcaccc aatgggagcc    8040
tcttcatgat tatcaataac gttaagctgg tgctggaaaa cgaggtggta agcggttcgc    8100
tggaggtgca gaacggcgaa atccgcgcct ttgccgaaag ccagagccgc ctgccggagg    8160
cgatggacgc cgaaggcggc tggctgctgc cggggctgat tgagctgcat accgataatc    8220
tggataaatt cttcaccccg cgcccgaaag ttgactggcc tgcccactcg gcgatgagca    8280
gccacgacgc gctgatggtg gcgagcggca tcaccaccgt actggatgcc gtggcaattg    8340
gcgacgtgcg cgacggcggc gatcggctgg agaatctgga gaagatgatc aacgccatcg    8400
aagagacgca gaaacgcggc gtcaaccgcg ccgagcaccg tctgcatctg cgctgcgaac    8460
tgccgcatca caccacgctg ccgctgtttg aaaaactggt gcagcgcgag ccggtgacgc    8520
tggtgtcgct gatggaccac tcgccggcc agcgccagtt cgccaaccgc gagaagtatc    8580
gcgaatatta tcagggcaaa tactccctca ctgatgcgca gatgcagcag tacgaagaag    8640
agcaactggc gctcgccgca cgctggtcgc agccgaatcg cgaatccatc gccgccctgt    8700
gccgcgcgcg aaaaattgcg cttgccagcc acgatgacgc cacccacgcc cacgttgctg    8760
aatctcacca gcttggcagc gtgatcgccg aatttcccac cacgttcgaa gcggcggaag    8820
```

-continued

```
cctcgcgcaa gcatggcatg aacgtgctga tgggcgcgcc gaatattgtg cgcggcggct    8880
cgcactccgg caacgtggcg gccagtgaac tggcgcagct tggcctgctg gatatcctct    8940
cttccgacta ctaccccgcc agcctgctcg atgcggcatt tcgcgtcgcc gatgaccaga    9000
gcaaccgctt tacgctgccg caggcggtga agctggtgac taaaaatcca gcgcaggcgc    9060
ttaatctcca ggatcgcggg gtgattggcg agggcaaacg cgccgacctg gtgctggcgc    9120
atcgcaagga caatcatatt catatcgacc acgtctggcg tcagggtaaa agggtgttct    9180
gatgatggga aaactgattt ggttaatggg ccgtccggc tccgggaaag acagcctgct    9240
ggcggaactc cgcctgcggg aacaaactca gttactggtg gcgcatcgct acatcacgcg    9300
cgatgccagc gccggaagtg aaaaccatat cgccctgagc gagcaggagt tttttacccg    9360 cgcgggcaa atctgttgg ccttaagctg gcacgctaac ggtctgtatt atggcgtcgg    9420
cgtcgagatt gatctctggc tgcacgccgg attcgacgtg ctggtcaacg gctcacgcgc    9480
ccatctgccg caggcgcggg cgcgctatca atcggcgctg ctgcccgtct gtttacaggt    9540
ttcgccggag atcctccgcc agcgcctgga aaaccgtggc cgtgaaaacg ccagtgaaat    9600
taacgcccgc ctggcgcgcg ccgcccgcta tactccacag gattgccata cgctcaacaa    9660
tgacggcagc ctgcgccagt cggtcgacac gctgctgacg ctgatccatc agaaggagaa    9720
acaccatgcc tgcttgtgag cttcgcccgg ccacgcagta cgacaccgac gcggtttacg    9780
cgctgatttg tgagctaaaa caggcggagt ttgaccacca cgcgtttcgc gtgggttta    9840 acgccaatct gcgcgaccca acatgcgct accatctggc gctgcttgat ggcgaagttg    9900
tcggcatgat cggcctgcat ttgcagtttc atctgcatca tgtcaactgg atcggcgaaa    9960
ttcaggagtt ggtggtaatg ccgcaggcgc gcggtctgaa cgtcggcagt aagttactgg    10020
cgtgggcaga agaagaagcc cgccaggccg gggccgaaat gaccgaactt cgaccaacg    10080 tgaagcgcca cgacgcgcac cgtttctatc tgcgcgaagg ctacgagcag agccacttcc    10140
gcttcaccaa ggcgctgtaa catgagcctg accctcacgc tcaccggcac cggcggcgca    10200
cagggcgttc cggcatgggg ctgcgagtgt cggcctgcg ccagagcgcg cgctcgccg    10260 cagtatcgcc gccaaccgtg cagcggcgta gtgaagttta acgacgcaat caccctgatc    10320
gacgccgggc tgcacgatct cgccgatcgc tggtcgcccg gatcgttcca gcagttttg    10380 ctgacgcatt atcatatgga tcacgtccag gggctgtttc cgctgcgctg gggcgttggc    10440
gatccgatcc cggtttacgg cccgccggat gaacagggct gcgacgatct gtttaaacat    10500
ccgggcctgc ttgatttcag ccacacggtg gaaccgtttg tggtgtttga tttgcagggg    10560
ttacaggtca cgcccctgcc gctcaaccac tcaaaactga ccttcggtta tctgctggaa    10620
acggcacaca gccgggtggc gtggctgtct gacaccgcag gtttgccgga aaaacgctg    10680 aaattttac gcaataatca gccgcaggta atggtgatgg attgcagtca cccgccgcgc    10740
gcggatgcac cgcgtaatca ctgtgattta ataccgtgc ttgcgctgaa tcaggttatc    10800
cgctcgccac gggtgattct gacccatatc agccaccagt tgatgcgtg gctgatggaa    10860 aacgcactac cgtcagggtt tgaggtgggg tttgatggga tggagattgg ggtggcgtga    10920
tgagagggaa tgtgcgcgct ggccccctca ccctaaccct ctcccagag gggcgagggg    10980 accgattgtg ctcgatattg aatattgcgc tcgttttctc cctctcccca ttgggtgag    11040 gggcgatgcc tgctccatac ccaacctcat cgcccatact catcttccat tctccgctct    11100
tcatcctcca gttgccgacg ctcctgatca agctggcgct ggcgatcgtc cagctgcctg    11160
cggcgatctt caaactggcg gcggcggtcg tcatattgtc tgcgccgatc gtcgctcact    11220
```

-continued

| | | | | | |
|---|---|---|---|---|---|
| tcacgctgcc | agccgtcgtc | gcgcgaatct | tcatagtctc | gcccacggtc | agggttataa | 11280 |
| gcgtcattaa | tcgcctgctg | aatattgcca | atggtgtcgt | cgataatatc | ggcctgggcc | 11340 |
| ggaacgtgga | cagcgtgagc | agggtgaata | aagaaatag | cggaaagcgt | tcattagcc | 11400 |
| aacctcaaaa | agaaactcta | tccacattaa | tcattactca | tccatgcaag | tagtggatga | 11460 |
| atctcaattt | ctccgctgct | ctattgccgt | aatcgcctcc | acgcgttgtt | gatgacgacc | 11520 |
| gccttcgtac | tgtgcgccca | gccacgcatc | cacaatcatt | tttgccagtt | cgaggccaac | 11580 |
| cactcgtgaa | ccaaaagcca | gcacgttggt | gtcgttatgc | tgccgcgaaa | gttgcgcgga | 11640 |
| ataaggttcg | ctacagacga | ccgcgcgaat | tc | | | 11672 |

<210> SEQ ID NO 3
<211> LENGTH: 435
<212> TYPE: DNA
<213> ORGANISM: Escherichia coli

<400> SEQUENCE: 3

| | | | | | |
|---|---|---|---|---|---|
| atgcctgctt | gtgagcttcg | cccggccacg | cagtacgaca | ccgacgcggt | ttacgcgctg | 60 |
| atttgtgagc | taaaacaggc | ggagtttgac | caccacgcgt | ttcgcgtggg | ttttaacgcc | 120 |
| aatctgcgcg | acccaaacat | gcgctaccat | ctggcgctgc | ttgatggcga | agttgtcggc | 180 |
| atgatcggcc | tgcatttgca | gtttcatctg | catcatgtca | actggatcgg | cgaaattcag | 240 |
| gagttggtgg | taatgccgca | ggcgcgcggt | ctgaacgtcg | gcagtaagtt | actggcgtgg | 300 |
| gcagaagaag | aagcccgcca | ggccggggcc | gaaatgaccg | aactttcgac | caacgtgaag | 360 |
| cgccacgacg | cgcaccgttt | ctatctgcgc | gaaggctacg | agcagagcca | cttccgcttc | 420 |
| accaaggcgc | tgtaa | | | | | 435 |

<210> SEQ ID NO 4
<211> LENGTH: 144
<212> TYPE: PRT
<213> ORGANISM: Escherichia coli

<400> SEQUENCE: 4

Met Pro Ala Cys Glu Leu Arg Pro Ala Thr Gln Tyr Asp Thr Asp Ala
 1               5                  10                  15

Val Tyr Ala Leu Ile Cys Glu Leu Lys Gln Ala Glu Phe Asp His His
                20                  25                  30

Ala Phe Arg Val Gly Phe Asn Ala Asn Leu Arg Asp Pro Asn Met Arg
            35                  40                  45

Tyr His Leu Ala Leu Leu Asp Gly Glu Val Val Gly Met Ile Gly Leu
        50                  55                  60

His Leu Gln Phe His Leu His Val Asn Trp Ile Gly Glu Ile Gln
 65                  70                  75                  80

Glu Leu Val Val Met Pro Gln Ala Arg Gly Leu Asn Val Gly Ser Lys
                85                  90                  95

Leu Leu Ala Trp Ala Glu Glu Glu Ala Arg Gln Ala Gly Ala Glu Met
            100                 105                 110

Thr Glu Leu Ser Thr Asn Val Lys Arg His Asp Ala His Arg Phe Tyr
        115                 120                 125

Leu Arg Glu Gly Tyr Glu Gln Ser His Phe Arg Phe Thr Lys Ala Leu
    130                 135                 140

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 5
aaacaccatg gctgcttgtg                                                   20

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 6
gtgacgaatt cgagctcatt acagcgcctt ggtga                                  35

<210> SEQ ID NO 7
<211> LENGTH: 435
<212> TYPE: DNA
<213> ORGANISM: Artificial Sequence
<220> FEATURE:
<223> OTHER INFORMATION: Description of Artificial Sequence:non-
      naturally occurring nucleotide sequence encoding modified
      PhnO protein P2A; g-c at nucleotide position 4
<220> FEATURE:
<221> NAME/KEY: CDS
<222> LOCATION: (1)..(432)

<400> SEQUENCE: 7 atg gct gct tgt gag ctt cgc ccg gcc acg cag tac gac acc gac gcg         48
Met Ala Ala Cys Glu Leu Arg Pro Ala Thr Gln Tyr Asp Thr Asp Ala
 1               5                  10                  15 gtt tac gcg ctg att tgt gag cta aaa cag gcg gag ttt gac cac cac         96
Val Tyr Ala Leu Ile Cys Glu Leu Lys Gln Ala Glu Phe Asp His His
                20                  25                  30 gcg ttt cgc gtg ggt ttt aac gcc aat ctg cgc gac cca aac atg cgc        144
Ala Phe Arg Val Gly Phe Asn Ala Asn Leu Arg Asp Pro Asn Met Arg
            35                  40                  45 tac cat ctg gcg ctg ctt gat ggc gaa gtt gtc ggc atg atc ggc ctg        192
Tyr His Leu Ala Leu Leu Asp Gly Glu Val Val Gly Met Ile Gly Leu
        50                  55                  60 cat ttg cag ttt cat ctg cat cat gtc aac tgg atc ggc gaa att cag        240
His Leu Gln Phe His Leu His His Val Asn Trp Ile Gly Glu Ile Gln
    65                  70                  75                  80 gag ttg gtg gta atg ccg cag gcg cgc ggt ctg aac gtc ggc agt aag        288
Glu Leu Val Val Met Pro Gln Ala Arg Gly Leu Asn Val Gly Ser Lys
                85                  90                  95 tta ctg gcg tgg gca gaa gaa gaa gcc cgc cag gcc ggg gcc gaa atg        336
Leu Leu Ala Trp Ala Glu Glu Glu Ala Arg Gln Ala Gly Ala Glu Met
            100                 105                 110 acc gaa ctt tcg acc aac gtg aag cgc cac gac gcg cac cgt ttc tat        384
Thr Glu Leu Ser Thr Asn Val Lys Arg His Asp Ala His Arg Phe Tyr
        115                 120                 125 ctg cgc gaa ggc tac gag cag agc cac ttc cgc ttc acc aag gcg ctg        432
Leu Arg Glu Gly Tyr Glu Gln Ser His Phe Arg Phe Thr Lys Ala Leu
    130                 135                 140 taa                                                                    435
```

```
<210> SEQ ID NO 8
<211> LENGTH: 144
<212> TYPE: PRT
<213> ORGANISM: Artificial Sequence

<400> SEQUENCE: 8

Met Ala Ala Cys Glu Leu Arg Pro Ala Thr Gln Tyr Asp Thr Asp Ala
 1               5                  10                  15

Val Tyr Ala Leu Ile Cys Glu Leu Lys Gln Ala Glu Phe Asp His His
             20                  25                  30

Ala Phe Arg Val Gly Phe Asn Ala Asn Leu Arg Asp Pro Asn Met Arg
         35                  40                  45

Tyr His Leu Ala Leu Leu Asp Gly Glu Val Val Gly Met Ile Gly Leu
     50                  55                  60

His Leu Gln Phe His Leu His His Val Asn Trp Ile Gly Glu Ile Gln
 65                  70                  75                  80

Glu Leu Val Val Met Pro Gln Ala Arg Gly Leu Asn Val Gly Ser Lys
                 85                  90                  95

Leu Leu Ala Trp Ala Glu Glu Gly Ala Arg Gln Ala Gly Ala Glu Met
            100                 105                 110

Thr Glu Leu Ser Thr Asn Val Lys Arg His Asp Ala His Arg Phe Tyr
        115                 120                 125

Leu Arg Glu Gly Tyr Glu Gln Ser His Phe Arg Phe Thr Lys Ala Leu
    130                 135                 140

<210> SEQ ID NO 9
<211> LENGTH: 264
<212> TYPE: DNA
<213> ORGANISM: Artificial Sequence
<220> FEATURE:
<223> OTHER INFORMATION: Description of Artificial Sequence:transit
      peptide coding sequence
<220> FEATURE:
<221> NAME/KEY: CDS
<222> LOCATION: (1)..(264)

<400> SEQUENCE: 9 atg gct tcc tct atg ctc tct tcc gct act atg gtt gcc tct ccg gct      48
Met Ala Ser Ser Met Leu Ser Ser Ala Thr Met Val Ala Ser Pro Ala
 1               5                  10                  15 cag gcc act atg gtc gct cct ttc aac gga ctt aag tcc tcc gct gcc      96
Gln Ala Thr Met Val Ala Pro Phe Asn Gly Leu Lys Ser Ser Ala Ala
             20                  25                  30 ttc cca gcc acc cgc aag gct aac aac gac att act tcc atc aca agc     144
Phe Pro Ala Thr Arg Lys Ala Asn Asn Asp Ile Thr Ser Ile Thr Ser
         35                  40                  45 aac ggc gga aga gtt aac tgc atg cag gtg tgg cct ccg att gga aag     192
Asn Gly Gly Arg Val Asn Cys Met Gln Val Trp Pro Pro Ile Gly Lys
     50                  55                  60 aag aag ttt gag act ctc tct tac ctt cct gac ctt acc gat tcc ggt     240
Lys Lys Phe Glu Thr Leu Ser Tyr Leu Pro Asp Leu Thr Asp Ser Gly
 65                  70                  75                  80 ggt cgc gtc aac tgc atg cag gcc                                     264
Gly Arg Val Asn Cys Met Gln Ala
                 85

<210> SEQ ID NO 10
<211> LENGTH: 88
<212> TYPE: PRT
<213> ORGANISM: Artificial Sequence
```

```
<400> SEQUENCE: 10

Met Ala Ser Ser Met Leu Ser Ser Ala Thr Met Val Ala Ser Pro Ala
  1               5                  10                  15

Gln Ala Thr Met Val Ala Pro Phe Asn Gly Leu Lys Ser Ser Ala Ala
             20                  25                  30

Phe Pro Ala Thr Arg Lys Ala Asn Asn Asp Ile Thr Ser Ile Thr Ser
         35                  40                  45

Asn Gly Gly Arg Val Asn Cys Met Gln Val Trp Pro Pro Ile Gly Lys
     50                  55                  60

Lys Lys Phe Glu Thr Leu Ser Tyr Leu Pro Asp Leu Thr Asp Ser Gly
 65              70                  75                  80

Gly Arg Val Asn Cys Met Gln Ala
                 85

<210> SEQ ID NO 11
<211> LENGTH: 696
<212> TYPE: DNA
<213> ORGANISM: Artificial Sequence
<220> FEATURE:
<223> OTHER INFORMATION: Description of Artificial Sequence: CTP-AMPA
      acetyltransferase  coding sequence and amino acid
      sequence translation
<220> FEATURE:
<221> NAME/KEY: CDS
<222> LOCATION: (1)..(696)

<400> SEQUENCE: 11 atg gct tcc tct atg ctc tct tcc gct act atg gtt gcc tct ccg gct      48
Met Ala Ser Ser Met Leu Ser Ser Ala Thr Met Val Ala Ser Pro Ala
  1               5                  10                  15 cag gcc act atg gtc gct cct ttc aac gga ctt aag tcc tcc gct gcc      96
Gln Ala Thr Met Val Ala Pro Phe Asn Gly Leu Lys Ser Ser Ala Ala
             20                  25                  30 ttc cca gcc acc cgc aag gct aac aac gac att act tcc atc aca agc     144
Phe Pro Ala Thr Arg Lys Ala Asn Asn Asp Ile Thr Ser Ile Thr Ser
         35                  40                  45 aac ggc gga aga gtt aac tgc atg cag gtg tgg cct ccg att gga aag     192
Asn Gly Gly Arg Val Asn Cys Met Gln Val Trp Pro Pro Ile Gly Lys
     50                  55                  60 aag aag ttt gag act ctc tct tac ctt cct gac ctt acc gat tcc ggt     240
Lys Lys Phe Glu Thr Leu Ser Tyr Leu Pro Asp Leu Thr Asp Ser Gly
 65              70                  75                  80 ggt cgc gtc aac tgc atg cag gcc atg gct gct tgt gag ctt cgc ccg     288
Gly Arg Val Asn Cys Met Gln Ala Met Ala Ala Cys Glu Leu Arg Pro
                 85                  90                  95 gcc acg cag tac gac acc gac gcg gtt tac gcg ctg att tgt gag cta     336
Ala Thr Gln Tyr Asp Thr Asp Ala Val Tyr Ala Leu Ile Cys Glu Leu
            100                 105                 110 aaa cag gcg gag ttt gac cac cac gcg ttt cgc gtg ggt ttt aac gcc     384
Lys Gln Ala Glu Phe Asp His His Ala Phe Arg Val Gly Phe Asn Ala
        115                 120                 125 aat ctg cgc gac cca aac atg cgc tac cat ctg gcg ctg ctt gat ggc     432
Asn Leu Arg Asp Pro Asn Met Arg Tyr His Leu Ala Leu Leu Asp Gly
    130                 135                 140 gaa gtt gtc ggc atg atc ggc ctg cat ttg cag ttt cat ctg cat cat     480
Glu Val Val Gly Met Ile Gly Leu His Leu Gln Phe His Leu His His
145                 150                 155                 160 gtc aac tgg atc ggc gaa att cag gag ttg gtg gta atg ccg cag gcg     528
Val Asn Trp Ile Gly Glu Ile Gln Glu Leu Val Val Met Pro Gln Ala
                165                 170                 175
```

```
cgc ggt ctg aac gtc ggc agt aag tta ctg gcg tgg gca gaa gaa gaa      576
Arg Gly Leu Asn Val Gly Ser Lys Leu Leu Ala Trp Ala Glu Glu Glu
            180                 185                 190 gcc cgc cag gcc ggg gcc gaa atg acc gaa ctt tcg acc aac gtg aag      624
Ala Arg Gln Ala Gly Ala Glu Met Thr Glu Leu Ser Thr Asn Val Lys
            195                 200                 205 cgc cac gac gcg cac cgt ttc tat ctg cgc gaa ggc tac gag cag agc      672
Arg His Asp Ala His Arg Phe Tyr Leu Arg Glu Gly Tyr Glu Gln Ser
210                 215                 220 cac ttc cgc ttc acc aag gcg ctg                                      696
His Phe Arg Phe Thr Lys Ala Leu
225                 230
```

<210> SEQ ID NO 12
<211> LENGTH: 232
<212> TYPE: PRT
<213> ORGANISM: Artificial Sequence

<400> SEQUENCE: 12

```
Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Gly Lys
    50                  55                  60

Lys Lys Phe Glu Thr Leu Ser Tyr Leu Pro Asp Leu Thr Asp Ser Gly
65                  70                  75                  80

Gly Arg Val Asn Cys Met Gln Ala Met Ala Ala Cys Glu Leu Arg Pro
                85                  90                  95

Ala Thr Gln Tyr Asp Thr Asp Ala Val Tyr Ala Leu Ile Cys Glu Leu
            100                 105                 110

Lys Gln Ala Glu Phe Asp His His Ala Phe Arg Val Gly Phe Asn Ala
        115                 120                 125

Asn Leu Arg Asp Pro Asn Met Arg Tyr His Leu Ala Leu Leu Asp Gly
    130                 135                 140

Glu Val Val Gly Met Ile Gly Leu His Leu Gln Phe His Leu His His
145                 150                 155                 160

Val Asn Trp Ile Gly Glu Ile Gln Glu Leu Val Val Met Pro Gln Ala
                165                 170                 175

Arg Gly Leu Asn Val Gly Ser Lys Leu Leu Ala Trp Ala Glu Glu Glu
            180                 185                 190

Ala Arg Gln Ala Gly Ala Glu Met Thr Glu Leu Ser Thr Asn Val Lys
        195                 200                 205

Arg His Asp Ala His Arg Phe Tyr Leu Arg Glu Gly Tyr Glu Gln Ser
    210                 215                 220

His Phe Arg Phe Thr Lys Ala Leu
225                 230
```

<210> SEQ ID NO 13
<211> LENGTH: 415
<212> TYPE: DNA
<213> ORGANISM: Zea mays
<220> FEATURE:
<221> NAME/KEY: N_region
<222> LOCATION: (15)..(163)
<220> FEATURE:
<221> NAME/KEY: intron
<222> LOCATION: (164)..(322)
<220> FEATURE:
<221> NAME/KEY: C_region
<222> LOCATION: (323)..(411)

<400> SEQUENCE: 13

```
tctagaggat cagcatggcg cccaccgtga tgatggcctc gtcggccacc gccgtcgctc    60
cgttcctggg gctcaagtcc accgccagcc tccccgtcgc ccgccgctcc tccagaagcc   120
tcggcaacgt cagcaacggc ggaaggatcc ggtgcatgca ggtaacaaat gcatcctagc   180
tagtagttct ttgcattgca gcagctgcag ctagcgagtt agtaatagga agggaactga   240
tgatccatgc atggactgat gtgtgttgcc catcccatcc catcccattt cccaaacgaa   300
ccgaaaacac cgtactacgt gcaggtgtgg ccctacggca acaagaagtt cgagacgctg   360
tcgtacctgc cgccgctgtc gaccggcggg cgcatccgct gcatgcaggc catgg        415
```

<210> SEQ ID NO 14
<211> LENGTH: 174
<212> TYPE: DNA
<213> ORGANISM: Artificial Sequence
<220> FEATURE:
<223> OTHER INFORMATION: Description of Artificial Sequence: chloroplast
   or plastid transit peptide coding sequence and amino
   acid sequence translation
<220> FEATURE:
<221> NAME/KEY: CDS
<222> LOCATION: (1)..(174)

<400> SEQUENCE: 14

```
atg gct tcc tct atg ctc tct tcc gct act atg gtt gcc tct ccg gct    48
Met Ala Ser Ser Met Leu Ser Ser Ala Thr Met Val Ala Ser Pro Ala
 1               5                  10                  15 cag gcc act atg gtc gct cct ttc aac gga ctt aag tcc tcc gct gcc    96
Gln Ala Thr Met Val Ala Pro Phe Asn Gly Leu Lys Ser Ser Ala Ala
             20                  25                  30 ttc cca gcc acc cgc aag gct aac aac gac att act tcc atc aca agc   144
Phe Pro Ala Thr Arg Lys Ala Asn Asn Asp Ile Thr Ser Ile Thr Ser
         35                  40                  45 aac ggc gga aga gtt aac tgc atg cag gcc                            174
Asn Gly Gly Arg Val Asn Cys Met Gln Ala
     50                  55
```

<210> SEQ ID NO 15
<211> LENGTH: 58
<212> TYPE: PRT
<213> ORGANISM: Artificial Sequence

<400> SEQUENCE: 15

```
Met Ala Ser Ser Met Leu Ser Ser Ala Thr Met Val Ala Ser Pro Ala
 1               5                  10                  15

Gln Ala Thr Met Val Ala Pro Phe Asn Gly Leu Lys Ser Ser Ala Ala
             20                  25                  30

Phe Pro Ala Thr Arg Lys Ala Asn Asn Asp Ile Thr Ser Ile Thr Ser
         35                  40                  45

Asn Gly Gly Arg Val Asn Cys Met Gln Ala
     50                  55
```

<210> SEQ ID NO 16
<211> LENGTH: 157
<212> TYPE: DNA
<213> ORGANISM: Artificial Sequence -continued

```
<220> FEATURE:
<223> OTHER INFORMATION: Description of Artificial Sequence: synthetic
      oligonucleotide representing base pairs 1 through
      157 of a 432 base pair AMPA acyltransferase gene

<400> SEQUENCE: 16
atggccgctt gcgagcttcg cccagccacg cagtacgaca ccgacgccgt gtacgcgctg     60
atctgcgagc tcaagcaggc ggagttcgac caccacgcct tccgcgtggg cttcaacgcc    120
aacctgcgcg accccaacat gcgctaccat ctggcgc                             157

<210> SEQ ID NO 17
<211> LENGTH: 187
<212> TYPE: DNA
<213> ORGANISM: Artificial Sequence
<220> FEATURE:
<223> OTHER INFORMATION: Description of Artificial Sequence: synthetic
      oligonucleotide sequence representing base pairs
      158 through 344 of a 432 base pair AMPA
      acyltransferase gene

<400> SEQUENCE: 17
tgcttgatgg cgaagtggtc ggcatgatcg gcctgcacct ccagttccac ctgcatcatg     60
tcaactggat cggcgagatc caggagctgg tcgtgatgcc acaggcgagg ggtctgaacg    120
tcggcagcaa gctcctggcg tgggccgagg aggaagccag gcaggccgga gccgagatga    180
ccgagct                                                              187

<210> SEQ ID NO 18
<211> LENGTH: 88
<212> TYPE: DNA
<213> ORGANISM: Artificial Sequence
<220> FEATURE:
<223> OTHER INFORMATION: Description of Artificial Sequence: synthetic
      oligonucleotide sequence representing base pairs
      345 through 432 of a 432 base pair AMPA
      acyltransferase gene

<400> SEQUENCE: 18
cagcaccaac gtgaagcgcc acgacgcgca ccgcttctac ctgcgcgaag gctacgagca     60
gagccacttc cgcttcacca aggcgctg                                       88

<210> SEQ ID NO 19
<211> LENGTH: 432
<212> TYPE: DNA
<213> ORGANISM: Artificial Sequence
<220> FEATURE:
<223> OTHER INFORMATION: Description of Artificial Sequence: synthetic
      oligonucleotide providing monocot optimized coding
      sequence for an AMPA acetyltransferase
<220> FEATURE:
<221> NAME/KEY: CDS
<222> LOCATION: (1)..(432)

<400> SEQUENCE: 19 atg gcc gct tgc gag ctt cgc cca gcc acg cag tac gac acc gac gcc       48
Met Ala Ala Cys Glu Leu Arg Pro Ala Thr Gln Tyr Asp Thr Asp Ala
  1               5                  10                  15 gtg tac gcg ctg atc tgc gag ctc aag cag gcg gag ttc gac cac cac       96
Val Tyr Ala Leu Ile Cys Glu Leu Lys Gln Ala Glu Phe Asp His His
             20                  25                  30 gcc ttc cgc gtg ggc ttc aac gcc aac ctg cgc gac ccc aac atg cgc      144
Ala Phe Arg Val Gly Phe Asn Ala Asn Leu Arg Asp Pro Asn Met Arg
         35                  40                  45
```

```
tac cat ctg gcg ctg ctt gat ggc gaa gtg gtc ggc atg atc ggc ctg       192
Tyr His Leu Ala Leu Leu Asp Gly Glu Val Val Gly Met Ile Gly Leu
     50                  55                  60 cac ctc cag ttc cac ctg cat cat gtc aac tgg atc ggc gag atc cag       240
His Leu Gln Phe His Leu His His Val Asn Trp Ile Gly Glu Ile Gln
 65                  70                  75                  80 gag ctg gtc gtg atg cca cag gcg agg ggt ctg aac gtc ggc agc aag       288
Glu Leu Val Val Met Pro Gln Ala Arg Gly Leu Asn Val Gly Ser Lys
                 85                  90                  95 ctc ctg gcg tgg gcc gag gag gaa gcc agg cag gcc gga gcc gag atg       336
Leu Leu Ala Trp Ala Glu Glu Glu Ala Arg Gln Ala Gly Ala Glu Met
             100                 105                 110 acc gag ctc agc acc aac gtg aag cgc cac gac gcg cac cgc ttc tac       384
Thr Glu Leu Ser Thr Asn Val Lys Arg His Asp Ala His Arg Phe Tyr
         115                 120                 125 ctg cgc gaa ggc tac gag cag agc cac ttc cgc ttc acc aag gcg ctg       432
Leu Arg Glu Gly Tyr Glu Gln Ser His Phe Arg Phe Thr Lys Ala Leu
     130                 135                 140

<210> SEQ ID NO 20
<211> LENGTH: 144
<212> TYPE: PRT
<213> ORGANISM: Artificial Sequence

<400> SEQUENCE: 20

Met Ala Ala Cys Glu Leu Arg Pro Ala Thr Gln Tyr Asp Thr Asp Ala
 1               5                  10                  15

Val Tyr Ala Leu Ile Cys Glu Leu Lys Gln Ala Glu Phe Asp His His
             20                  25                  30

Ala Phe Arg Val Gly Phe Asn Ala Asn Leu Arg Asp Pro Asn Met Arg
         35                  40                  45

Tyr His Leu Ala Leu Leu Asp Gly Glu Val Val Gly Met Ile Gly Leu
     50                  55                  60

His Leu Gln Phe His Leu His His Val Asn Trp Ile Gly Glu Ile Gln
 65                  70                  75                  80

Glu Leu Val Val Met Pro Gln Ala Arg Gly Leu Asn Val Gly Ser Lys
                 85                  90                  95

Leu Leu Ala Trp Ala Glu Glu Glu Ala Arg Gln Ala Gly Ala Glu Met
             100                 105                 110

Thr Glu Leu Ser Thr Asn Val Lys Arg His Asp Ala His Arg Phe Tyr
         115                 120                 125

Leu Arg Glu Gly Tyr Glu Gln Ser His Phe Arg Phe Thr Lys Ala Leu
     130                 135                 140

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide PHN1 for use as an amplification
      primer

<400> SEQUENCE: 21
atggctgctt gtgagcttcg                                                  20

<210> SEQ ID NO 22
<211> LENGTH: 20
<212> TYPE: DNA
<213> ORGANISM: Artificial Sequence
<220> FEATURE:
```

```
<223> OTHER INFORMATION: Description of Artificial Sequence: synthetic
      oligonucleotide PHN2 for use as an amplification
      primer

<400> SEQUENCE: 22
cagcgccttg gtgaagcgga                                                    20

<210> SEQ ID NO 23
<211> LENGTH: 1630
<212> TYPE: DNA
<213> ORGANISM: Artificial Sequence
<220> FEATURE:
<223> OTHER INFORMATION: Description of Artificial Sequence: expression
      cassette comprising plant operable promoter linked
      to a coding sequence encoding an AMPA
      acetyltransferase linked to a transcription
      termination sequence
<220> FEATURE:
<221> NAME/KEY: promoter
<222> LOCATION: (33)..(605)
<220> FEATURE:
<221> NAME/KEY: transit_peptide
<222> LOCATION: (627)..(892)
<220> FEATURE:
<221> NAME/KEY: CDS
<222> LOCATION: (893)..(1324)
<220> FEATURE:
<221> NAME/KEY: terminator
<222> LOCATION: (1350)..(1605)

<400> SEQUENCE: 23
```

| | | | | |
|---|---|---|---|---|
| gcggccgcgt | tcaagcttga | gctcaggatt | tagcagcatt | ccagattggg | ttcaatcaac | 60 |
| aaggtacgag | ccatatcact | ttattcaaat | tggtatcgcc | aaaaccaaga | aggaactccc | 120 |
| atcctcaaag | gtttgtaagg | aagaattctc | agtccaaagc | ctcaacaagg | tcagggtaca | 180 |
| gagtctccaa | accattagcc | aaaagctaca | ggagatcaat | gaagaatctt | caatcaaagt | 240 |
| aaactactgt | tccagcacat | gcatcatggt | cagtaagttt | cagaaaaaga | catccaccga | 300 |
| agacttaaag | ttagtgggca | tctttgaaag | taatcttgtc | aacatcgagc | agctggcttg | 360 |
| tggggaccag | acaaaaaagg | aatggtgcag | aattgttagg | cgcacctacc | aaaagcatct | 420 |
| ttgcctttat | tgcaaagata | aagcagattc | ctctagtaca | agtggggaac | aaaataacgt | 480 |
| ggaaaagagc | tgtcctgaca | gcccactcac | taatgcgtat | gacgaacgca | gtgacgacca | 540 |
| caaaagaatt | ccctctatat | aagaaggcat | tcattcccat | ttgaaggatc | atcagatact | 600 |
| gaaccaatcc | ttctagaaga | tctccacaat | ggcttcctct | atgctctctt | ccgctactat | 660 |
| ggttgcctct | ccggctcagg | ccactatggt | cgctcctttc | aacggactta | agtcctccgc | 720 |
| tgccttccca | gccacccgca | aggctaacaa | cgacattact | tccatcacaa | gcaacggcgg | 780 |
| aagagttaac | tgcatgcagg | tgtggcctcc | gattggaaag | aagaagtttg | agactctctc | 840 |
| ttaccttcct | gaccttaccg | attccggtgg | tcgcgtcaac | tgcatgcagg | cc atg gct | 898 |
| | | | | | Met Ala | |
| | | | | | 1 | |

| gct tgt gag ctt cgc ccg gcc acg cag tac gac acc gac gcg gtt tac | 946 |
|---|---|
| Ala Cys Glu Leu Arg Pro Ala Thr Gln Tyr Asp Thr Asp Ala Val Tyr | |
| 5 10 15 | |

| gcg ctg att tgt gag cta aaa cag gcg gag ttt gac cac cac gcg ttt | 994 |
|---|---|
| Ala Leu Ile Cys Glu Leu Lys Gln Ala Glu Phe Asp His His Ala Phe | |
| 20 25 30 | |

| cgc gtg ggt ttt aac gcc aat ctg cgc gac cca aac atg cgc tac cat | 1042 |
|---|---|
| Arg Val Gly Phe Asn Ala Asn Leu Arg Asp Pro Asn Met Arg Tyr His | |
| 35 40 45 50 | |

```
                                                            -continued ctg gcg ctg ctt gat ggc gaa gtt gtc ggc atg atc ggc ctg cat ttg        1090
Leu Ala Leu Leu Asp Gly Glu Val Val Gly Met Ile Gly Leu His Leu
            55                  60                  65 cag ttt cat ctg cat cat gtc aac tgg atc ggc gaa att cag gag ttg        1138
Gln Phe His Leu His His Val Asn Trp Ile Gly Glu Ile Gln Glu Leu
        70                  75                  80 gtg gta atg ccg cag gcg cgc ggt ctg aac gtc ggc agt aag tta ctg        1186
Val Val Met Pro Gln Ala Arg Gly Leu Asn Val Gly Ser Lys Leu Leu
    85                  90                  95 gcg tgg gca gaa gaa gaa gcc cgc cag gcc ggg gcc gaa atg acc gaa        1234
Ala Trp Ala Glu Glu Glu Ala Arg Gln Ala Gly Ala Glu Met Thr Glu
100                 105                 110 ctt tcg acc aac gtg aag cgc cac gac gcg cac cgt ttc tat ctg cgc        1282
Leu Ser Thr Asn Val Lys Arg His Asp Ala His Arg Phe Tyr Leu Arg
115                 120                 125                 130 gaa ggc tac gag cag agc cac ttc cgc ttc acc aag gcg ctg                1324
Glu Gly Tyr Glu Gln Ser His Phe Arg Phe Thr Lys Ala Leu
                135                 140 taatgagctc ggtaccggat ccaattcccg atcgttcaaa catttggcaa taaagttttct     1384 taagattgaa tcctgttgcc ggtcttgcga tgattatcat ataatttctg ttgaattacg     1444
ttaagcatgt aataattaac atgtaatgca tgacgttatt tatgagatgg gtttttatga     1504
ttagagtccc gcaattatac atttaatacg cgatagaaaa caaaatatag cgcgcaaact     1564
aggataaatt atcgcgcgcg gtgtcatcta tgttactaga tcgggatcg atccccgggc     1624 ggccgc                                                                 1630

<210> SEQ ID NO 24
<211> LENGTH: 144
<212> TYPE: PRT
<213> ORGANISM: Artificial Sequence

<400> SEQUENCE: 24

Met Ala Ala Cys Glu Leu Arg Pro Ala Thr Gln Tyr Asp Thr Asp Ala
  1               5                  10                  15
Val Tyr Ala Leu Ile Cys Glu Leu Lys Gln Ala Glu Phe Asp His His
            20                  25                  30
Ala Phe Arg Val Gly Phe Asn Ala Asn Leu Arg Asp Pro Asn Met Arg
        35                  40                  45
Tyr His Leu Ala Leu Leu Asp Gly Glu Val Val Gly Met Ile Gly Leu
    50                  55                  60
His Leu Gln Phe His Leu His His Val Asn Trp Ile Gly Glu Ile Gln
65                  70                  75                  80
Glu Leu Val Val Met Pro Gln Ala Arg Gly Leu Asn Val Gly Ser Lys
                85                  90                  95
Leu Leu Ala Trp Ala Glu Glu Glu Ala Arg Gln Ala Gly Ala Glu Met
            100                 105                 110
Thr Glu Leu Ser Thr Asn Val Lys Arg His Asp Ala His Arg Phe Tyr
        115                 120                 125
Leu Arg Glu Gly Tyr Glu Gln Ser His Phe Arg Phe Thr Lys Ala Leu
    130                 135                 140

<210> SEQ ID NO 25
<211> LENGTH: 2122
<212> TYPE: DNA
<213> ORGANISM: Artificial Sequence
<220> FEATURE:
<223> OTHER INFORMATION: Description of Artificial Sequence:expression
      cassette comprising plant promoter linked to
      sequence encoding AMPA acetyl transferase linked
      to termination sequence
<220> FEATURE:
<221> NAME/KEY: promoter
<222> LOCATION: (6)..(620)
<220> FEATURE:
<221> NAME/KEY: 5'UTR
<222> LOCATION: (645)..(715)
```

```
<220> FEATURE:
<221> NAME/KEY: intron
<222> LOCATION: (729)..(1178)
<220> FEATURE:
<221> NAME/KEY: transit_peptide
<222> LOCATION: (1179)..(1406)
<220> FEATURE:
<221> NAME/KEY: CDS
<222> LOCATION: (1407)..(1838)
<220> FEATURE:
<221> NAME/KEY: terminator
<222> LOCATION: (1849)..(2082)

<400> SEQUENCE: 25
```

| | | | | | |
|---|---|---|---|---|---|
| ctgcaggtcc | gatgtgagac | ttttcaacaa | agggtaatat | ccggaaacct | cctcggattc | 60 |
| cattgcccag | ctatctgtca | ctttattgtg | aagatagtgg | aaaaggaagg | tggctcctac | 120 |
| aaatgccatc | attgcgataa | aggaaaggcc | atcgttgaag | atgcctctgc | cgacagtggt | 180 |
| cccaaagatg | gaccccccacc | cacgaggagc | atcgtggaaa | aagaagacgt | tccaaccacg | 240 |
| tcttcaaagc | aagtggattg | atgtgatggt | ccgatgtgag | acttttcaac | aaagggtaat | 300 |
| atccggaaac | ctcctcggat | tccattgccc | agctatctgt | cactttattg | tgaagatagt | 360 |
| ggaaaaggaa | ggtggctcct | acaaatgcca | tcattgcgat | aaaggaaagg | ccatcgttga | 420 |
| agatgcctct | gccgacagtg | gtcccaaaga | tggaccccca | cccacgagga | gcatcgtgga | 480 |
| aaaagaagac | gttccaacca | cgtcttcaaa | gcaagtggat | tgatgtgata | tctccactga | 540 |
| cgtaagggat | gacgcacaat | cccactatcc | ttcgcaagac | ccttcctcta | tataaggaag | 600 |
| ttcatttcat | ttggagagga | cacgctgaca | agctgactct | agcagatcct | ctagaaccat | 660 |
| cttccacaca | ctcaagccac | actattggag | aacacacagg | acaacacac | cataagatcc | 720 |
| aagggaggcc | tccgccgccg | ccggtaacca | ccccgcccct | ctcctctttc | tttctccgtt | 780 |
| ttttttccg | tctcggtctc | gatctttggc | cttggtagtt | tgggtgggcg | agaggcggct | 840 |
| tcgtgcgcgc | ccagatcggt | gcgcgggagg | ggcgggatct | cgcggggaat | ggggctctcg | 900 |
| gatgtagatc | tgcgatccgc | cgttgttggg | ggagatgatg | gggcgtttaa | aatttcgccg | 960 |
| tgctaaacaa | gatcaggaag | aggggaaaag | ggcactatgg | tttatatttt | tatatatttc | 1020 |
| tgctgcttcg | tcaggcttag | atgtgctaga | tctttctttc | ttcttttgt | gggtagaatt | 1080 |
| taatccctca | gcattgttca | tcggtagttt | ttcttttcat | gatttcgtga | caaatgcagc | 1140 |
| ctcgtgcgga | gcttttttgt | aggtagaagt | gatcaaccat | ggcgcaagtt | agcagaatct | 1200 |
| gcaatggtgt | gcagaaccca | tctcttatct | ccaatctctc | gaaatccagt | caacgcaaat | 1260 |
| ctcccttatc | ggtttctctg | aagacgcagc | agcatccacg | agcttatccg | atttcgtcgt | 1320 |
| cgtggggatt | gaagaagagt | gggatgacgt | taattggctc | tgagcttcgt | cctcttaagg | 1380 |

| | | | | | | | | | | | | | | | | |
|---|---|---|---|---|---|---|---|---|---|---|---|---|---|---|---|---|
| tcatgtcttc | tgtttccacg | gcgtgc | atg | gcc | gct | tgc | gag | ctt | cgc | cca | gcc | | | | | 1433 |
| | | | Met | Ala | Ala | Cys | Glu | Leu | Arg | Pro | Ala | | | | | |
| | | | 1 | | | | 5 | | | | | | | | | |

| | | | | | | | | | | | | | | |
|---|---|---|---|---|---|---|---|---|---|---|---|---|---|---|
| acg | cag | tac | gac | acc | gac | gcc | gtg | tac | gcg | ctg | atc | tgc | gag | ctc | aag | 1481 |
| Thr | Gln | Tyr | Asp | Thr | Asp | Ala | Val | Tyr | Ala | Leu | Ile | Cys | Glu | Leu | Lys | |
| 10 | | | | 15 | | | | | 20 | | | | | 25 | | |

| | | | | | | | | | | | | | | | |
|---|---|---|---|---|---|---|---|---|---|---|---|---|---|---|---|
| cag | gcg | gag | ttc | gac | cac | cac | gcc | ttc | cgc | gtg | ggc | ttc | aac | gcc | aac | 1529 |
| Gln | Ala | Glu | Phe | Asp | His | His | Ala | Phe | Arg | Val | Gly | Phe | Asn | Ala | Asn | |
| | | 30 | | | | | 35 | | | | | 40 | | | | |

| | | | | | | | | | | | | | | | |
|---|---|---|---|---|---|---|---|---|---|---|---|---|---|---|---|
| ctg | cgc | gac | ccc | aac | atg | cgc | tac | cat | ctg | gcg | ctg | ctt | gat | ggc | gaa | 1577 |
| Leu | Arg | Asp | Pro | Asn | Met | Arg | Tyr | His | Leu | Ala | Leu | Leu | Asp | Gly | Glu | |
| | 45 | | | | | 50 | | | | | 55 | | | | | |

```
gtg gtc ggc atg atc ggc ctg cac ctc cag ttc cac ctg cat cat gtc      1625
Val Val Gly Met Ile Gly Leu His Leu Gln Phe His Leu His His Val
            60                  65                  70 aac tgg atc ggc gag atc cag gag ctg gtc gtg atg cca cag gcg agg      1673
Asn Trp Ile Gly Glu Ile Gln Glu Leu Val Val Met Pro Gln Ala Arg
 75                  80                  85 ggt ctg aac gtc ggc agc aag ctc ctg gcg tgg gcc gag gag gaa gcc      1721
Gly Leu Asn Val Gly Ser Lys Leu Leu Ala Trp Ala Glu Glu Glu Ala
 90                  95                 100                 105 agg cag gcc gga gcc gag atg acc gag ctc agc acc aac gtg aag cgc      1769
Arg Gln Ala Gly Ala Glu Met Thr Glu Leu Ser Thr Asn Val Lys Arg
                110                 115                 120 cac gac gcg cac cgc ttc tac ctg cgc gaa ggc tac gag cag agc cac      1817
His Asp Ala His Arg Phe Tyr Leu Arg Glu Gly Tyr Glu Gln Ser His
                125                 130                 135 ttc cgc ttc acc aag gcg ctg taaagatctg aattctgcat gcgtttggac         1868
Phe Arg Phe Thr Lys Ala Leu
            140 gtatgctcat tcaggttgga gccaatttgg ttgatgtgtg tgcgagttct tgcgagtctg    1928 atgagacatc tctgtattgt gtttctttcc ccagtgtttt ctgtacttgt gtaatcggct    1988 aatcgccaac agattcggcg atgaataaat gagaaataaa ttgttctgat tttgagtgca    2048 aaaaaaaagg aattagatct gtgtgtgttt tttggatccc cggggcggcc gccccgggtg    2108 gtgagcttct gcag                                                      2122

<210> SEQ ID NO 26
<211> LENGTH: 144
<212> TYPE: PRT
<213> ORGANISM: Artificial Sequence

<400> SEQUENCE: 26

Met Ala Ala Cys Glu Leu Arg Pro Ala Thr Gln Tyr Asp Thr Asp Ala
  1               5                  10                  15

Val Tyr Ala Leu Ile Cys Glu Leu Lys Gln Ala Glu Phe Asp His His
                 20                  25                  30

Ala Phe Arg Val Gly Phe Asn Ala Asn Leu Arg Asp Pro Asn Met Arg
             35                  40                  45

Tyr His Leu Ala Leu Leu Asp Gly Glu Val Val Gly Met Ile Gly Leu
         50                  55                  60

His Leu Gln Phe His Leu His Val Asn Trp Ile Gly Glu Ile Gln
 65                  70                  75                  80

Glu Leu Val Val Met Pro Gln Ala Arg Gly Leu Asn Val Gly Ser Lys
                 85                  90                  95

Leu Leu Ala Trp Ala Glu Glu Glu Ala Arg Gln Ala Gly Ala Glu Met
            100                 105                 110

Thr Glu Leu Ser Thr Asn Val Lys Arg His Asp Ala His Arg Phe Tyr
        115                 120                 125

Leu Arg Glu Gly Tyr Glu Gln Ser His Phe Arg Phe Thr Lys Ala Leu
    130                 135                 140

<210> SEQ ID NO 27
<211> LENGTH: 2378
<212> TYPE: DNA
<213> ORGANISM: Artificial Sequence
<220> FEATURE:
<223> OTHER INFORMATION: Description of Artificial Sequence:expression
      cassette comprising a plant promoter linked to an
      intron, a sequence encoding an AMPA acetyl
      transferase, and a termination sequence
```

```
<220> FEATURE:
<221> NAME/KEY: promoter
<222> LOCATION: (28)..(965)
<220> FEATURE:
<221> NAME/KEY: intron
<222> LOCATION: (966)..(1423)
<220> FEATURE:
<221> NAME/KEY: transit_peptide
<222> LOCATION: (1440)..(1667)
<220> FEATURE:
<221> NAME/KEY: CDS
<222> LOCATION: (1668)..(2099)
<220> FEATURE:
<221> NAME/KEY: terminator
<222> LOCATION: (2114)..(2369)

<400> SEQUENCE: 27
gatatcccta gggcggccgc gttaacaagc ttactcgagg tcattcatat gcttgagaag      60
agagtcggga tagtccaaaa taaacaaag gtaagattac ctggtcaaaa gtgaaaacat     120
cagttaaaag gtggtataaa gtaaaatatc ggtaataaaa ggtggcccaa agtgaaattt     180
actcttttct actattataa aaattgagga tgttttttgtc ggtactttga tacgtcattt    240
ttgtatgaat tggttttttaa gtttattcgc ttttggaaat gcatatctgt atttgagtcg    300
ggttttaagt tcgtttgctt ttgtaaatac agagggattt gtataagaaa tatctttaga    360
aaaacccata tgctaatttg acataatttt tgagaaaaat atatattcag gcgaattctc    420
acaatgaaca ataataagat taaaatagct ttcccccgtt gcagcgcatg ggtattttt     480 ctagtaaaaa taaagataa acttagactc aaaacattta caaaacaac ccctaaagtt     540 cctaaagccc aaagtgctat ccacgatcca tagcaagccc agcccaaccc aacccaaccc    600
agcccacccc agtccagcca actggacaat agtctccaca ccccccact atcaccgtga    660 gttgtccgca cgcaccgcac gtctcgcagc caaaaaaaa agaaagaaa aaaagaaaa      720 agaaaaaaca gcaggtgggt ccgggtcgtg ggggccggaa acgcgaggag gatcgcgagc    780
cagcgacgag gccggccctc cctccgcttc caaagaaacg ccccccatcg ccactatata    840 cataccccccc cctctcctcc catcccccca accctaccac caccaccacc accacctcca   900
cctcctcccc cctcgctgcc ggacgacgag ctcctccccc ctccccctcc gccgccgccg    960
cgccggtaac caccccgccc ctctcctctt tcttctcccg ttttttttc cgtctcggtc   1020 tcgatctttg gccttggtag tttgggtggg cgagaggcgg cttcgtgccg cccagatcgg   1080
tgcgcgggag gggcgggatc tcgcggctgg ctctcgcccc cgtggatccg gcccggatct   1140
cgcggggaat ggggctctcg gatgtagatc tgcgatccgc cgttgttggg gccgatgatg   1200
gggcccttaa aatttccgcc gtgctaaaca agatcaggaa gaggggaaaa gggcactatg   1260 gtttatatttt ttatatattt ctgctgcttc gtcaggctta gatgtgctag atctttcttt   1320 cttcttttttg tgggtagaat ttaatccctc agcattgttc atcggtagtt tttcttttca   1380
tgattcgtga caaatgcagc ctcgtgcgga cgttttttg taggtagaag tgatcaacca    1440
tggcgcaagt tagcagaatc tgcaatggtg tgcagaaccc atctcttatc tccaatctct   1500
cgaaatccag tcaacgcaaa tctcccttat cggtttctct gaagacgcag cagcatccac   1560
gagcttatcc gatttcgtcg tcgtggggat tgaagaagag tgggatgacg ttaattggct   1620
ctgagcttcg tcctcttaag gtcatgtctt ctgtttccac ggcgtgc atg gcc gct    1676
                                                    Met Ala Ala
                                                    1 tgc gag ctt cgc cca gcc acg cag tac gac acc gac gcc gtg tac gcg    1724
Cys Glu Leu Arg Pro Ala Thr Gln Tyr Asp Thr Asp Ala Val Tyr Ala
      5                  10                  15
```

```
ctg atc tgc gag ctc aag cag gcg gag ttc gac cac cac gcc ttc cgc    1772
Leu Ile Cys Glu Leu Lys Gln Ala Glu Phe Asp His His Ala Phe Arg
 20                  25                  30                  35 gtg ggc ttc aac gcc aac ctg cgc gac ccc aac atg cgc tac cat ctg    1820
Val Gly Phe Asn Ala Asn Leu Arg Asp Pro Asn Met Arg Tyr His Leu
             40                  45                  50 gcg ctg ctt gat ggc gaa gtg gtc ggc atg atc ggc ctg cac ctc cag    1868
Ala Leu Leu Asp Gly Glu Val Val Gly Met Ile Gly Leu His Leu Gln
                 55                  60                  65 ttc cac ctg cat cat gtc aac tgg atc ggc gag atc cag gag ctg gtc    1916
Phe His Leu His His Val Asn Trp Ile Gly Glu Ile Gln Glu Leu Val
             70                  75                  80 gtg atg cca cag gcg agg ggt ctg aac gtc ggc agc aag ctc ctg gcg    1964
Val Met Pro Gln Ala Arg Gly Leu Asn Val Gly Ser Lys Leu Leu Ala
 85                  90                  95 tgg gcc gag gag gaa gcc agg cag gcc gga gcc gag atg acc gag ctc    2012
Trp Ala Glu Glu Glu Ala Arg Gln Ala Gly Ala Glu Met Thr Glu Leu
100                 105                 110                 115 agc acc aac gtg aag cgc cac gac gcg cac cgc ttc tac ctg cgc gaa    2060
Ser Thr Asn Val Lys Arg His Asp Ala His Arg Phe Tyr Leu Arg Glu
                120                 125                 130 ggc tac gag cag agc cac ttc cgc ttc acc aag gcg ctg taaagatctg    2109
Gly Tyr Glu Gln Ser His Phe Arg Phe Thr Lys Ala Leu
            135                 140 aattcccgat cgttcaaaca tttggcaata agtttcttta gattgaatc ctgttgccgg   2169
tcttgcgatg attatcatat aatttctgtt gaattacgtt aagcatgtaa taattaacat   2229
gtaatgcatg acgttattta tgagatgggt ttttatgatt agagtcccgc aattatacat   2289
ttaatacgcg atagaaaaca aaatatagcg cgcaaactag gataaattat cgcgcgcggt   2349
gtcatctatg ttactagatc ggggatatc                                    2378

<210> SEQ ID NO 28
<211> LENGTH: 144
<212> TYPE: PRT
<213> ORGANISM: Artificial Sequence

<400> SEQUENCE: 28

Met Ala Ala Cys Glu Leu Arg Pro Ala Thr Gln Tyr Asp Thr Asp Ala
 1               5                  10                  15

Val Tyr Ala Leu Ile Cys Glu Leu Lys Gln Ala Glu Phe Asp His His
             20                  25                  30

Ala Phe Arg Val Gly Phe Asn Ala Asn Leu Arg Asp Pro Asn Met Arg
         35                  40                  45

Tyr His Leu Ala Leu Leu Asp Gly Glu Val Val Gly Met Ile Gly Leu
     50                  55                  60

His Leu Gln Phe His Leu His His Val Asn Trp Ile Gly Glu Ile Gln
 65                  70                  75                  80

Glu Leu Val Val Met Pro Gln Ala Arg Gly Leu Asn Val Gly Ser Lys
                 85                  90                  95

Leu Leu Ala Trp Ala Glu Glu Glu Ala Arg Gln Ala Gly Ala Glu Met
            100                 105                 110

Thr Glu Leu Ser Thr Asn Val Lys Arg His Asp Ala His Arg Phe Tyr
        115                 120                 125

Leu Arg Glu Gly Tyr Glu Gln Ser His Phe Arg Phe Thr Lys Ala Leu
    130                 135                 140
```

```
<210> SEQ ID NO 29
<211> LENGTH: 2107
<212> TYPE: DNA
<213> ORGANISM: Artificial Sequence
<220> FEATURE:
<223> OTHER INFORMATION: Description of Artificial Sequence:expression
      cassette comprising plant operable promoter linked
      to a leader, intron, a sequence encoding an AMPA
      acetyltransferase, and termination sequence
<220> FEATURE:
<221> NAME/KEY: promoter
<222> LOCATION: (26)..(590)
<220> FEATURE:
<221> NAME/KEY: 5'UTR
<222> LOCATION: (615)..(685)
<220> FEATURE:
<221> NAME/KEY: intron
<222> LOCATION: (699)..(1148)
<220> FEATURE:
<221> NAME/KEY: transit_peptide
<222> LOCATION: (1149)..(1426)
<220> FEATURE:
<221> NAME/KEY: CDS
<222> LOCATION: (1427)..(1858)
<220> FEATURE:
<221> NAME/KEY: terminator
<222> LOCATION: (1869)..(2102)
```

<400> SEQUENCE: 29

| | | | | | |
|---|---|---|---|---|---|
| gcggccgcgt | taacaagctt | ctgcaggtcc | gatgtgagac | ttttcaacaa | agggtaatat | 60 |
| ccggaaacct | cctcggattc | cattgcccag | ctatctgtca | ctttattgtg | aagatagtgg | 120 |
| aaaaggaagg | tggctcctac | aaatgccatc | attgcgataa | aggaaaggcc | atcgttgaag | 180 |
| atgcctctgc | cgacagtggt | cccaaagatg | accccccacc | cacgaggagc | atcgtggaaa | 240 |
| aagaagacgt | tccaaccacg | tcttcaaagc | aagtggattg | atgtgatggt | ccgatgtgag | 300 |
| acttttcaac | aaagggtaat | atccggaaac | ctcctcggat | tccattgccc | agctatctgt | 360 |
| cactttattg | tgaagatagt | ggaaaaggaa | ggtggctcct | acaaatgcca | tcattgcgat | 420 |
| aaaggaaagg | ccatcgttga | agatgcctct | gccgacagtg | gtcccaaaga | tgaccccca | 480 |
| cccacgagga | gcatcgtgga | aaaagaagac | gttccaacca | cgtcttcaaa | gcaagtggat | 540 |
| tgatgtgata | tctccactga | cgtaagggat | gacgcacaat | cccactatcc | ttcgcaagac | 600 |
| ccttcctcta | tataaggaag | ttcatttcat | ttggagagga | cacgctgaca | agctgactct | 660 |
| agcagatcct | ctagaaccat | cttccacaca | ctcaagccac | actattggag | aacacacagg | 720 |
| gacaacacac | cataagatcc | aagggaggcc | tccgccgccg | ccgtaaccca | cccgccccct | 780 |
| ctcctctttc | tttctccgtt | ttttttttccg | tctcggtctc | gatctttggc | cttggtagtt | 840 |
| tgggtgggcg | agaggcggct | tcgtgcgcgc | ccagatcggt | gcgcgggagg | ggcgggatct | 900 |
| cgcgggaat | gggctctcg | gatgtagatc | tgcgatccgc | cgttgttggg | ggagatgatg | 960 |
| gggcgtttaa | aatttcgccg | tgctaaacaa | gatcaggaag | aggggaaaag | ggcactatgg | 1020 |
| tttatatttt | tatatatttc | tgctgcttcg | tcaggcttag | atgtgctaga | tctttctttc | 1080 |
| ttcttttttgt | gggtagaatt | taatccctca | gcattgttca | tcgtagtttt | ttcttttcat | 1140 |
| gatttcgtga | caaatgcagc | ctcgtgcgga | gcttttttgt | aggtagaagt | gatcaaccat | 1200 |
| ggcgcaagtt | agcagaatct | gcaatggtgt | gcagaaccca | tctcttatct | ccaatctctc | 1260 |
| gaaatccagt | caacgcaaat | ctcccttatc | ggtttctctg | aagacgcagc | agcatccacg | 1320 |
| agcttatccg | atttcgtcgt | cgtgggggatt | gaagaagagt | gggatgacgt | taattggctc | 1380 |
| tgagcttcgt | cctcttaagg | tcatgtcttc | tgtttccacg | gcgtgc atg | gcc gct | 1435 |
| | | | | Met Ala Ala | |
| | | | | 1 | |

```
tgc gag ctt cgc cca gcc acg cag tac gac acc gac gcc gtg tac gcg    1483
Cys Glu Leu Arg Pro Ala Thr Gln Tyr Asp Thr Asp Ala Val Tyr Ala
      5                  10                  15 ctg atc tgc gag ctc aag cag gcg gag ttc gac cac cac gcc ttc cgc    1531
Leu Ile Cys Glu Leu Lys Gln Ala Glu Phe Asp His His Ala Phe Arg
 20                  25                  30                  35 gtg ggc ttc aac gcc aac ctg cgc gac ccc aac atg cgc tac cat ctg    1579
Val Gly Phe Asn Ala Asn Leu Arg Asp Pro Asn Met Arg Tyr His Leu
                 40                  45                  50 gcg ctg ctt gat ggc gaa gtg gtc ggc atg atc ggc ctg cac ctc cag    1627
Ala Leu Leu Asp Gly Glu Val Val Gly Met Ile Gly Leu His Leu Gln
             55                  60                  65 ttc cac ctg cat cat gtc aac tgg atc ggc gag atc cag gag ctg gtc    1675
Phe His Leu His His Val Asn Trp Ile Gly Glu Ile Gln Glu Leu Val
         70                  75                  80 gtg atg cca cag gcg agg ggt ctg aac gtc ggc agc aag ctc ctg gcg    1723
Val Met Pro Gln Ala Arg Gly Leu Asn Val Gly Ser Lys Leu Leu Ala
 85                  90                  95 tgg gcc gag gag gaa gcc agg cag gcc gga gcc gag atg acc gag ctc    1771
Trp Ala Glu Glu Glu Ala Arg Gln Ala Gly Ala Glu Met Thr Glu Leu
100                 105                 110                 115 agc acc aac gtg aag cgc cac gac gcg cac cgc ttc tac ctg cgc gaa    1819
Ser Thr Asn Val Lys Arg His Asp Ala His Arg Phe Tyr Leu Arg Glu
                120                 125                 130 ggc tac gag cag agc cac ttc cgc ttc acc aag gcg ctg taaagatctg    1868
Gly Tyr Glu Gln Ser His Phe Arg Phe Thr Lys Ala Leu
            135                 140 aattctgcat gcgtttggac gtatgctcat tcaggttgga gccaatttgg ttgatgtgtg    1928
tgcgagttct tgcgagtctg atgagacatc tctgtattgt gtttctttcc ccagtgtttt    1988
ctgtacttgt gtaatcggct aatcgccaac agattcggcg atgaataaat gagaaataaa    2048
ttgttctgat tttgagtgca aaaaaaaagg aattagatct gtgtgtgttt tttggatcc     2107

<210> SEQ ID NO 30
<211> LENGTH: 144
<212> TYPE: PRT
<213> ORGANISM: Artificial Sequence

<400> SEQUENCE: 30

Met Ala Ala Cys Glu Leu Arg Pro Ala Thr Gln Tyr Asp Thr Asp Ala
 1               5                  10                  15

Val Tyr Ala Leu Ile Cys Glu Leu Lys Gln Ala Glu Phe Asp His His
            20                  25                  30

Ala Phe Arg Val Gly Phe Asn Ala Asn Leu Arg Asp Pro Asn Met Arg
        35                  40                  45

Tyr His Leu Ala Leu Leu Asp Gly Glu Val Val Gly Met Ile Gly Leu
    50                  55                  60

His Leu Gln Phe His Leu His His Val Asn Trp Ile Gly Glu Ile Gln
 65                 70                  75                  80

Glu Leu Val Val Met Pro Gln Ala Arg Gly Leu Asn Val Gly Ser Lys
                85                  90                  95

Leu Leu Ala Trp Ala Glu Glu Glu Ala Arg Gln Ala Gly Ala Glu Met
           100                 105                 110

Thr Glu Leu Ser Thr Asn Val Lys Arg His Asp Ala His Arg Phe Tyr
       115                 120                 125

Leu Arg Glu Gly Tyr Glu Gln Ser His Phe Arg Phe Thr Lys Ala Leu
   130                 135                 140
```

<210> SEQ ID NO 31
<211> LENGTH: 2436
<212> TYPE: DNA
<213> ORGANISM: Artificial Sequence
<220> FEATURE:
<223> OTHER INFORMATION: Description of Artificial Sequence:monocot
      expression cassette comprising plant operable
      promoter linked to an intron, a sequence coding
      for an AMPA acetyltransferase, and a termination
      sequence
<220> FEATURE:
<221> NAME/KEY: promoter
<222> LOCATION: (26)..(640)
<220> FEATURE:
<221> NAME/KEY: intron
<222> LOCATION: (670)..(1473)
<220> FEATURE:
<221> NAME/KEY: transit_peptide
<222> LOCATION: (1498)..(1725)
<220> FEATURE:
<221> NAME/KEY: CDS
<222> LOCATION: (1726)..(2157)
<220> FEATURE:
<221> NAME/KEY: terminator
<222> LOCATION: (2172)..(2427)

<400> SEQUENCE: 31

| | | | | | |
|---|---|---|---|---|---|
| gcggccgcgt | taacaagctt | ctgcaggtcc | gatgtgagac | ttttcaacaa | agggtaatat | 60 |
| ccggaaacct | cctcggattc | cattgcccag | ctatctgtca | ctttattgtg | aagatagtgg | 120 |
| aaaaggaagg | tggctcctac | aaatgccatc | attgcgataa | aggaaaggcc | atcgttgaag | 180 |
| atgcctctgc | cgacagtggt | cccaaagatg | gaccccacc  | cacgaggagc | atcgtggaaa | 240 |
| aagaagacgt | tccaaccacg | tcttcaaagc | aagtggattg | atgtgatggt | ccgatgtgag | 300 |
| acttttcaac | aaagggtaat | atccggaaac | ctcctcggat | tccattgccc | agctatctgt | 360 |
| cactttattg | tgaagatagt | ggaaaaggaa | ggtggctcct | acaaatgcca | tcattgcgat | 420 |
| aaaggaaagg | ccatcgttga | agatgcctct | gccgacagtg | gtcccaaaga | tggaccccca | 480 |
| cccacgagga | gcatcgtgga | aaaagaagac | gttccaacca | cgtcttcaaa | gcaagtggat | 540 |
| tgatgtgata | tctccactga | cgtaagggat | gacgcacaat | cccactatcc | ttcgcaagac | 600 |
| ccttcctcta | tataaggaag | ttcatttcat | ttggagagga | cacgctgaca | agctgactct | 660 |
| agcagatcta | ccgtcttcgg | tacgcgctca | ctccgccctc | tgcctttgtt | actgccacgt | 720 |
| ttctctgaat | gctctcttgt | gtggtgattg | ctgagagtgg | tttagctgga | tctagaatta | 780 |
| cactctgaaa | tcgtgttctg | cctgtgctga | ttacttgccg | tcctttgtag | cagcaaaata | 840 |
| tagggacatg | gtagtacgaa | acgaagatag | aacctacaca | gcaatacgag | aaatgtgtaa | 900 |
| tttggtgctt | agcggtattt | atttaagcac | atgttggtgt | tatagggcac | ttggattcag | 960 |
| aagtttgctg | ttaatttagg | cacaggcttc | atactacatg | ggtcaatagt | atagggattc | 1020 |
| atattatagg | cgatactata | ataatttgtt | cgtctgcaga | gcttattatt | tgccaaaatt | 1080 |
| agatattcct | attctgtttt | tgtttgtgtg | ctgttaaatt | gttaacgcct | gaaggaataa | 1140 |
| atataaatga | cgaaattttg | atgtttatct | ctgctccttt | attgtgacca | taagtcaaga | 1200 |
| tcagatgcac | ttgttttaaa | tattgttgtc | tgaagaaata | agtactgaca | gtattttgat | 1260 |
| gcattgatct | gcttgtttgt | tgtaacaaaa | tttaaaaata | aagagtttcc | ttttgttgc  | 1320 |
| tctccttacc | tcctgatggt | atctagtatc | taccaactga | cactatattg | cttctcttta | 1380 |
| catacgtatc | ttgctcgatg | ccttctccct | agtgttgacc | agtgttactc | acatagtctt | 1440 |
| tgctcatttc | attgtaatgc | agataccaag | cggcctctag | aggatccagg | agcaaccatg | 1500 |
| gcgcaagtta | gcagaatctg | caatggtgtg | cagaacccat | ctcttatctc | caatctctcg | 1560 |

```
aaatccagtc aacgcaaatc tcccttatcg gtttctctga agacgcagca gcatccacga    1620
gcttatccga tttcgtcgtc gtggggattg aagaagagtg ggatgacgtt aattggctct    1680
gagcttcgtc ctcttaaggt catgtcttct gtttccacgg cgtgc atg gcc gct tgc    1737
                                                 Met Ala Ala Cys
                                                  1
```

| | | | | | | | | | | | | | | | | |
|---|---|---|---|---|---|---|---|---|---|---|---|---|---|---|---|---|
| gag | ctt | cgc | cca | gcc | acg | cag | tac | gac | acc | gac | gcc | gtg | tac | gcg | ctg | 1785 |
| Glu | Leu | Arg | Pro | Ala | Thr | Gln | Tyr | Asp | Thr | Asp | Ala | Val | Tyr | Ala | Leu | |
| | 5 | | | | 10 | | | | 15 | | | | | 20 | | |
| atc | tgc | gag | ctc | aag | cag | gcg | gag | ttc | gac | cac | cac | gcc | ttc | cgc | gtg | 1833 |
| Ile | Cys | Glu | Leu | Lys | Gln | Ala | Glu | Phe | Asp | His | His | Ala | Phe | Arg | Val | |
| | | | | 25 | | | | | 30 | | | | | 35 | | |
| ggc | ttc | aac | gcc | aac | ctg | cgc | gac | ccc | aac | atg | cgc | tac | cat | ctg | gcg | 1881 |
| Gly | Phe | Asn | Ala | Asn | Leu | Arg | Asp | Pro | Asn | Met | Arg | Tyr | His | Leu | Ala | |
| | | 40 | | | | | 45 | | | | | 50 | | | | |
| ctg | ctt | gat | ggc | gaa | gtg | gtc | ggc | atg | atc | ggc | ctg | cac | ctc | cag | ttc | 1929 |
| Leu | Leu | Asp | Gly | Glu | Val | Val | Gly | Met | Ile | Gly | Leu | His | Leu | Gln | Phe | |
| | | 55 | | | | 60 | | | | | 65 | | | | | |
| cac | ctg | cat | cat | gtc | aac | tgg | atc | ggc | gag | atc | cag | gag | ctg | gtc | gtg | 1977 |
| His | Leu | His | His | Val | Asn | Trp | Ile | Gly | Glu | Ile | Gln | Glu | Leu | Val | Val | |
| | 70 | | | | 75 | | | | | 80 | | | | | | |
| atg | cca | cag | gcg | agg | ggt | ctg | aac | gtc | ggc | agc | aag | ctc | ctg | gcg | tgg | 2025 |
| Met | Pro | Gln | Ala | Arg | Gly | Leu | Asn | Val | Gly | Ser | Lys | Leu | Leu | Ala | Trp | |
| 85 | | | | 90 | | | | | 95 | | | | | 100 | | |
| gcc | gag | gag | gaa | gcc | agg | cag | gcc | gga | gcc | gag | atg | acc | gag | ctc | agc | 2073 |
| Ala | Glu | Glu | Glu | Ala | Arg | Gln | Ala | Gly | Ala | Glu | Met | Thr | Glu | Leu | Ser | |
| | | | 105 | | | | | 110 | | | | | 115 | | | |
| acc | aac | gtg | aag | cgc | cac | gac | gcg | cac | cgc | ttc | tac | ctg | cgc | gaa | ggc | 2121 |
| Thr | Asn | Val | Lys | Arg | His | Asp | Ala | His | Arg | Phe | Tyr | Leu | Arg | Glu | Gly | |
| | | 120 | | | | | 125 | | | | | 130 | | | | |
| tac | gag | cag | agc | cac | ttc | cgc | ttc | acc | aag | gcg | ctg | taaagatctg | | | | 2167 |
| Tyr | Glu | Gln | Ser | His | Phe | Arg | Phe | Thr | Lys | Ala | Leu | | | | | |
| | 135 | | | | | 140 | | | | | | | | | | |

```
aattcccgat cgttcaaaca tttggcaata agtttcttta agattgaatc ctgttgccgg    2227
tcttgcgatg attatcatat aatttctgtt gaattacgtt aagcatgtaa taattaacat    2287
gtaatgcatg acgttattta tgagatgggt ttttatgatt agagtcccgc aattatacat    2347
ttaatacgcg atagaaaaca aaatatagcg cgcaaactag gataaattat cgcgcgcggt    2407
gtcatctatg ttactagatc ggggatatc                                      2436

<210> SEQ ID NO 32
<211> LENGTH: 144
<212> TYPE: PRT
<213> ORGANISM: Artificial Sequence

<400> SEQUENCE: 32

Met Ala Ala Cys Glu Leu Arg Pro Ala Thr Gln Tyr Asp Thr Asp Ala
 1               5                  10                  15

Val Tyr Ala Leu Ile Cys Glu Leu Lys Gln Ala Glu Phe Asp His His
                20                  25                  30

Ala Phe Arg Val Gly Phe Asn Ala Asn Leu Arg Asp Pro Asn Met Arg
            35                  40                  45

Tyr His Leu Ala Leu Leu Asp Gly Glu Val Val Gly Met Ile Gly Leu
        50                  55                  60

His Leu Gln Phe His Leu His His Val Asn Trp Ile Gly Glu Ile Gln
 65                  70                  75                  80

Glu Leu Val Val Met Pro Gln Ala Arg Gly Leu Asn Val Gly Ser Lys
                85                  90                  95
```

-continued

```
Leu Leu Ala Trp Ala Glu Glu Glu Ala Arg Gln Ala Gly Ala Glu Met
            100                 105                 110

Thr Glu Leu Ser Thr Asn Val Lys Arg His Asp Ala His Arg Phe Tyr
        115                 120                 125

Leu Arg Glu Gly Tyr Glu Gln Ser His Phe Arg Phe Thr Lys Ala Leu
    130                 135                 140
```

PLANTS AND PLANT CELLS TRANSFORMATION TO EXPRESS AN AMPA-N-ACETYLTRANSFERASE

REFERENCE TO PRIOR APPLICATIONS

This application claims the benefit of priority to U.S. Provisional Application Serial No. 60/108,763 filed Nov. 17, 1998.

FIELD OF THE INVENTION

The present invention relates in general to herbicide resistance in plants, and more particularly to a new class of phosphonate metabolizing genes and methods of using these genes for improving plant tolerance to phosphonate herbicides.

DESCRIPTION OF THE PRIOR ART

Phosphorous containing organic molecules can be naturally occurring or synthetically derived. Organic molecules containing phosphorous-carbon (C—P) bonds are also found naturally or as synthetic compounds, and are often not rapidly degraded, if at all, by natural enzymatic pathways. Synthetic organophosphonates and phosphinates, compounds that contain a direct carbon-phosphorous (C—P) bond in place of the better known carbon-oxygen-phosphorous linkage of phosphate esters (Metcalf et al., Gene 129:27–32, 1993), have thus been widely used as insecticides, antibiotics, and as herbicides (Chen et al., J. Biol. Chem. 265:4461–4471, 1990; Hilderbrand et al., *The role of phosphonates in living systems*, Hilderbrand, R. L., ed, pp. 5–29, CRC Press, Inc., Boca Raton, Fla., 1983). Phosphonates are ubiquitous in nature, and are found alone and in a diversity of macromolecular structures in a variety of organisms (Jiang et al., J. Bacteriol. 177:6411–6421, 1995). Degradation of phosphonate molecules proceeds through a number of known routes, a C—P lyase pathway, a phosphonatase pathway, and a C—N hydrolysis pathway (Wanner, Biodegradation 5:175–184, 1994; Barry et al., U.S. Pat. No. 5,463,175, 1995). Bacterial isolates capable of carrying out these steps have been characterized (Shinabarger et al., J. Bacteriol. 168:702–707, 1986; Kishore et al., J. Biol. Chem. 262:12,164–12,168, 1987; Pipke et al., Appl. Environ. Microbiol. 54:1293–1296,1987; Jacob et al., Appl. Environ. Microbiol. 54:2953–2958, 1988; Lee et al., J. Bacteriol. 174:2501–2510, 1992; Dumora et al., Biochim. Biophys. Acta 997:193–198, 1989; Lacoste et al., J. Gen. Microbiol. 138:1283–1287, 1992). However, with the exception of phosphonatase and glyphosate oxidase (GOX), other enzymes capable of carrying out these reactions have not been characterized.

Several studies have focused on the identification of genes required for C—P lyase degradation of phosphonates. Wackett et al. (J. Bacteriol. 169:710–717, 1987) disclosed broad substrate specificity toward phosphonate degradation by *Agrobacterium radiobacter* and specific utilization of glyphosate as a sole phosphate source. Shinabarger et al. and Kishore et al. disclosed C—P lyase degradation of the phosphonate herbicide, glyphosate, to glycine and inorganic phosphate through a sarcosine intermediate by Pseudomonas species.

*E. coli* B strains had previously been shown to be capable of phosphonate utilization (Chen et al.), whereas *E. coli* K-12 strains were incapable of phosphonate degradation. However, K-12 strains were subsequently shown to contain a complete, though cryptic, set of genes (psiD or phn) capable of phosphonate utilization (Makino et al.), as mutants were easily selected by growth on low phosphate media containing methyl- or ethyl-phosphonate as sole phosphorous sources. Such K-12 strains adapted for growth on methyl- or ethylphosphonate were subsequently shown to be able to utilize other phosphonates as sole phosphorous sources (Wackett et al., J. Bacteriol. 169:1753–1756, 1987).

Avila et al. (J. Am. Chem. Soc. 109:6758–6764, 1987) were interested in the mechanistic appraisal of biodegradative and detoxifying processes as related to aminomethylphosphonates, including elucidating the intermediates, products, and mechanisms of the degradative dephosphorylation process. Avila et al. studied the formation of dephosphorylated biodegradation products from a variety of aminophosphonate substrates in *E. coli* K-12 cultures previously adapted to growth on ethylphosphonate. Furthermore, Avila et al. utilized N-acetyl-AMPA (N-acetyl-amino-methyl-phosphonate) as a sole phosphate source in some of their studies in order to show that acetylated AMPA was not inhibitory to C—P bond cleavage. In addition, Avila et al. noted that N-acetyl-AMPA was able to serve as a sole phosphate source during *E. coli* K-12 growth, however, they did not observe N-acetyl-AMPA formation when AMPA was used as a sole phosphate source. Their results indicated that AMPA was not a substrate for acetylation in *E. coli*.

Chen et al. identified a functional psiD locus from *E. coli* B by complementation cloning into an *E. coli* K-12 strain deficient for phosphonate utilization, which enabled the K-12 strain to utilize phosphonate as a sole phosphate source (J. Biol. Chem. 265:4461–4471, 1990). Chen et al. thus disclosed the DNA sequence of the psiD complementing locus, identified on a 15.5 kb BamHI fragment containing 17 open reading frames designated phnA-phnQ, comprising the *E. coli* B phn operon. The cryptic phn (psiD) operon from *E. coli* K-12 was subsequently found to contain an 8-base pair insertion in phnE. The resulting frameshift in phnE not only results in defective phnE gene product, but also apparently causes polar effects on the expression of downstream genes within the operon, which prevent phosphonate utilization (Makino et al., J. Bacteriol. 173:2665–2672, 1991). The operon has been more accurately described to contain the genes phnC-phnP by the work of Makino et al. Further research has been directed to understanding the nature of the function of each of the genes within this operon (Chen et al., J. Biol. Chem. 265:4461–4471, 1990; Makino et al., J. Bacteriol. 173:2665–2672, 1991; Wanner et al., FEMS Microbiol. Lett. 100:133–140, 1992; Metcalf et al., Gene 129:27–32, 1993; Ohtaki et al., Actinomyceteol. 8:66–68, 1994). In all of these efforts, the phnO gene has been implicated as a regulatory protein based on its similarity to other nucleotide binding proteins containing structural helix-turn-helix motifs. Furthermore, mutagenesis of genes in the phn operon demonstrated that phnO was not required for phosphonate utilization, further supporting the proposed regulatory function for this gene (Metcalf et al., J. Bacteriol. 173:587–600, 1991), at least for the phosphonates tested. Homologous phn sequences have been identified from other bacteria, including a gene substantially similar to *E. coli* phnO, isolated from *S. griseus*, using nucleotide sequences deduced from those in the *E. coli* phnO gene (Jiang et al., J. Bacteriol. 177:6411–6421, (1995); McGrath et al., Eur. J. Biochem. 234:225–230, (1995); Ohtaki et al., Actinomyceteol. 8:66–68, (1994)). However, no function other than as a regulatory factor has been proposed for phnO. A regulatory role for phnO in the CP lyase operon has been cited again in a recent review (Berlyn, Microbiol. Molec. Biol. Rev. 62:814–984, 1998).

Advances in molecular biology, and in particular in plant sciences in combination with recombinant DNA technology, have enabled the construction of recombinant plants which contain nonnative genes of agronomic importance. Furthermore, when incorporated into and expressed in a plant, such genes desirably confer some beneficial trait or characteristic to the recombinant plant. One such trait is herbicide resistance. A recombinant plant capable of growth in the presence of a herbicide has a tremendous advantage over herbicide-susceptible species. In addition, herbicide tolerant plants provide a more cost effective means for agronomic production by reducing the need for tillage to control weeds and volunteers.

Chemical herbicides have been used for decades to inhibit plant metabolism, particularly for agronomic purposes as a means for controlling weeds or volunteer plants in fields of crop plants. A class of herbicides which have proven to be particularly effective for these purposes are known as phosphonates or phosphonic acid herbicides. Perhaps the most agronomically successful phosphonate herbicide is glyphosate (N-phosphono-methyl-glycine).

Recombinant plants have been constructed which are tolerant to the phosphonate herbicide glyphosate. When applied to plants, glyphosate is absorbed into the plant tissues and inhibits aromatic amino acid formation, mediated by an inhibition of the activity of the plastid-localized 5-enolpyruvyl-3-phosphoshikimic acid synthase enzyme, also known as EPSP synthase or EPSPS, an enzyme generally thought to be unique to plants, bacteria and fungi. Recombinant plants have been transformed with a bacterial EPSPS enzyme which is much less sensitive to glyphosate inhibition. Therefore, plants expressing this bacterial EPSPS are less sensitive to glyphosate, and are often characterized as being glyphosate tolerant. Therefore, greater amounts of glyphosate can be applied to such recombinant plants, ensuring the demise of plants which are susceptible or sensitive to the herbicide. However, other genes have been identified which, when transformed into a plant genome, encoding enzymes which also provide glyphosate tolerance. One such enzyme has been described as GOX, or glyphosate-oxidoredutase. GOX functions in providing protection to plants from the phosphonate herbicide glyphosate by catalyzing the degradation of glyphosate to aminomethyl phosphonic acid (AMPA) and glyoxylate. AMPA produced as a result of glyphosate degradation can cause bleaching and stunted or depressed plant growth, among other undesireable characteristics. Many plant species are also sensitive to exogeneously applied AMPA, as well as to endogenous AMPA produced as a result of GOX mediated glyphosate herbicide degradation. No method has been described which discloses the protection of plants from applications of phosphonate herbicides such as AMPA.

Barry et al. (U.S. Pat. No. 5,633,435) disclose genes encoding EPSP synthase enzymes which are useful in producing transformed bacteria and plants which are tolerant to glyphosate as a herbicide, as well as the use of such genes as a method for selectively controlling weeds in a planted transgenic crop field. Barry et al. (U.S. Pat. No. 5,463,175) disclose genes encoding glyphosate oxidoreductase (GOX) enzymes useful in producing transformed bacteria and plants which degrade glyphosate herbicide as well as crop plants which are tolerant to glyphosate as a herbicide. Barry et al. (U.S. Pat. No. 5,463,175) disclosed the formation of AMPA as a product of GOX mediated glyphosate metabolism. AMPA has been reported to be much less phytotoxic than glyphosate for most plant species (Franz, 1985) but not for all plant species (Maier, 1983; Tanaka et al., 1986).

Co-expression of a gene encoding a protein capable of neutralizing or metabolizing AMPA produced by glyphosate degradation would provide a substantial improvement over the use of GOX alone. Thus, a method for overcoming sensitivity to AMPA formation as a result of glyphosate degradation, or a method for resistance to AMPA when used as a herbicide or as a selective agent in plant transformation methods, would be useful for providing enhanced or improved herbicide tolerance in transgenic plants and in other organisms sensitive to such compounds.

The use of glyphosate as a chemical gametocide has been described (U.S. Pat. No. 4,735,649). Therein, it is disclosed that glyphosate can, under optimal conditions, kill about 95% of male gametes, while leaving about 40–60% of the female gametes capable of fertilization. In addition, a stunting effect was typically observed at the application levels disclosed, shown by a reduction in the size of the plant and by a minor amount of chlorosis. Thus, a major drawback of using glyphosate as a gametocide, as is generally true with most gametocides, is the phytotoxic side effects resulting from lack of sufficient selectivity for male gametes. These phytotoxic manifestations may be effectuated by AMPA production in transgenic plants expressing GOX after treatment with glyphosate. Therefore, it would be advantageous to provide a method for preventing the stunting effect and chlorosis as side effects of using glyphosate as a gametocide in transgenic plants expressing GOX. Furthermore, a more effective method would optimally kill more than 95% of male gametes or prevent male gametes from maturing and would leave greater than 60% of female gametes substantially unaffected. It is believed that tissue specific co-expression of GOX with a transacylase gene encoding an enzyme capable of N-acylation of AMPA would achieve this goal.

It has now been discovered that the *E. coli* phnO gene encodes an enzyme having transacylase, acyltransferase, or Acyl-CoA transacylase activity in which a preferred substrate is a phosphonate displaying a terminal amine, and in particular amino-methyl-phosphonic acid (AMPA). The transfer of an acyl group from an Acyl-CoA to the free terminal amine of AMPA results in the formation of an N-acylated AMPA. Plants are not known to acylate AMPA to any great extent, and some plants have been shown to be sensitive to AMPA and insensitive to acyl-AMPA. Thus, expression of phnO in plants would be useful in enhancing the phosphonate herbicide tolerance, particularly when AMPA is used as a herbicide or selective agent in plant transformation, and more particularly when glyphosate is used as a herbicide in combination with recombinant plants expressing a GOX gene.

SUMMARY OF THE INVENTION

Briefly therefore the present invention is directed to a composition of matter comprising a novel class of genes which encode proteins capable of N-acylation of phosphonate compounds and to methods of using these genes and encoded proteins for improving plant tolerance to phosphonate herbicides. The present invention is also directed to a method for selecting recombinant plants and microbes transformed with genes encoding proteins which are capable of N-acylation of phosphonate compounds, and to peptides which are capable of N-acylation of the compound N-amino-methyl-phosphonic acid (N-AMPA) and other related phosphonate compounds. In addition, the present invention is also directed to a method for using plants transformed with transacylase genes to prevent self-fertilization or to a method for enhancing hetero-fertilization in plants.

Among the several advantages found to be achieved by the present invention, therefore, may be noted the provision of producing stably transformed herbicide tolerant recombinant plants which have inserted into their genomes a polynucleotide sequence encoding a desired gene product, preferably an N-acyl-transferase enzyme. The polynucleotide sequence preferably is composed of a cassette containing a promoter sequence which is functional in plants and which is operably linked 5' to a structural DNA sequence which, when transcribed into an RNA sequence, encodes an N-acyl-transferase enzyme peptide. The promoter sequence can be heterologous with respect to the structural DNA sequence and causes sufficient expression of the transferase enzyme in plant tissue to provide herbicide tolerance to the plant transformed with the polynucleotide sequence. The structural sequence is preferably operably linked 3' to a 3' non-translated polyadenylation sequence which functions in plants, and which when transcribed into RNA along with the structural sequence causes the addition of a polyadenylated nucleotide sequence to the 3' end of the transcribed RNA. Expression of the structural DNA sequence produces sufficient levels of the acyltransferase enzyme in the plant tissue to enhance the herbicide tolerance of the transformed plant.

As a further embodiment, the structural DNA sequence may also contain an additional 5' sequence encoding an amino-terminal peptide sequence which functions in plants to target the peptide produced from translation of the structural sequence to an intracellular organelle. This additional coding sequence is preferably linked in-frame to the structural sequence encoding the acyltransferase enzyme. The amino terminal peptide sequence can be either a signal peptide or a transit peptide. The intracellular organelle can be a chloroplast, a mitochondrion, a vacuole, endoplasmic reticulum, or other such structure. The structural DNA sequence may also be linked to 5' sequences such as untranslated leader sequences (UTL's), intron sequences, or combinations of these sequences and the like which may serve to enhance expression of the desired gene product. Intron sequences may also be introduced within the structural DNA sequence encoding the acyltransferase enzyme. Alternatively, chloroplast or plastid transformation can result in localization of an acyltransferase coding sequence and enzyme to the chloroplast or plastid, obviating the requirement for nuclear genome transformation, expression from the nuclear genome, and subsequent targeting of the gene product to a subcellular organelle.

Preferably, the recombinant plant expresses a gene encoding an enzyme which catalyzes the formation of AMPA. AMPA formation can result from the metabolism of a naturally occurring precursor, from a precursor such as glyphosate provided to the plant, or can result from the formation of AMPA through some catabolic pathway. Co-expression of GOX along with AMPA acyltransferase expression provides a plant which is surprisingly more resistant to certain phosphonate herbicides. However, one embodiment allowing plants transformed with only an N-acyltransferase to grow in the presence of AMPA or similar or related compounds would provide a useful selective method for identifying genetically transformed plants, callus, or embryogenic tissues.

In accordance with another aspect of the present invention is the provision of a method for selectively enhancing or improving herbicide tolerance in a recombinant plant which has inserted into its nuclear, chloroplast, plastid or mitochondrial genome a cassette comprised of a polynucleotide sequence which encodes an N-acyl-transferase enzyme.

A further embodiment encompasses the improvement of a method for selectively enhancing herbicide tolerance in a transformed plant expressing a GOX gene which encodes a glyphosate oxidoreductase enzyme expressed in the same plants in which an acyltransferase enzyme is produced.

In accordance with another aspect of the present invention is the provision of a method for producing a genetically transformed herbicide tolerant plant by inserting into a genome of a plant cell a cassette comprising a polynucleotide sequence which encodes an N-acyl-transferase enzyme.

A further embodiment encompasses the improvement of a method for producing a genetically transformed herbicide tolerant plant from a plant cell expressing a GOX gene which encodes a glyphosate oxidoreductase enzyme expressed in the same plant cell in which an acyltransferase enzyme is produced.

In any of the foregoing embodiments, the herbicide tolerant plant or plant cell can be selected from the group consisting of corn, wheat, cotton, rice, soybean, sugarbeet, canola, flax, barley, oilseed rape, sunflower, potato, tobacco, tomato, alfalfa, lettuce, apple, poplar, pine, eucalyptus, acacia, poplar, sweetgum, radiata pine, loblolly pine, spruce, teak, alfalfa, clovers and other forage crops, turf grasses, oilpalm, sugarcane, banana, coffee, tea, cacao, apples, walnuts, almonds, grapes, peanuts, pulses, petunia, marigolds, vinca, begonias, geraniums, pansy, impatiens, oats, sorghum, and millet.

In accordance with another aspect of the present invention is the provision of a peptide capable of N-acylation of the compound N-aminomethylphosphonic acid (N-AMPA or AMPA) or other such compounds which are capable of causing phytotoxic effects when applied to, introduced into, or produced by plant metabolisms. One such peptide is N-aminomethylphosphonic acid transacylase (AAT) derived from expression of an *E. coli* phnO structural gene sequence. Other peptides similar in structure and function to the *E. coli* phnO gene product are also contemplated.

Another aspect of the present invention is the provision of a method for selecting cells transformed with a vector containing an acyltransferase gene expressing an enzyme capable of N-acylation of AMPA and like compounds. The method includes the steps of transforming a population of cells with the vector, and isolating and purifying the transformed cells from non-transformed cells in the population after selecting for the transformed cells by incubation in the presence of amounts of AMPA sufficient to be inhibitory to the growth or viability of any non-transformed cells. The transformed cells can be bacterial, plant or fungal cells. Bacterial cells can be members of any of the families encompassed by Enterobacteraceae, Mycobacteraceae, Agrobacteraceae, and Actinobacteraceae, among others. Fungal cells can be members of Ascomycota, Basidiomycota, etc. Plant cells can be derived from any member of the Plantae family.

A further embodiment of the present invention provides for a method for producing a plant from a tissue, a cell, or other part of a plant which was derived from a plant transformed with an acyltransferase gene, a phnO gene, a gox gene, a gene in which GOX and acyltransferase peptides are produced from a translational fusion or a transcriptional fusion, or a polycistronic gene which encodes GOX and acyltransferase peptides.

A further embodiment of the present invention provides for a method for producing plants which express all or a portion of a phnO gene or similar acyltransferase gene, or a GOX gene as an antisense gene in a tissue specific manner.

Other aspects also include reagents such as antibodies directed to AMPA acyltransferase, and polynucleotides for use in identifying acyltransferase gene sequences. These reagents can be included in kits containing AMPA acyltransferase, polynucleotides which are or are complimentary to an AMPA acyltransferase gene sequence, polynucleotides for use in thermal amplification of an AMPA acyltransferase gene sequence, antibodies directed to AMPA acyltransferase for the detection of AMPA acyltransferase in the laboratory or in the field, and any other reagents necessary for use in kit form as well as for use in other assays contemplated herein.

A further object of the present invention is to provide a method for using phosphonate herbicides as chemical hybridizing agents. The method allows for selective gametocidal effects and for the production of male sterile plants. Such plants may be engineered so that gox or phnO, or gox and phnO fail to be expressed in plant tissues required for reproduction, causing sensitivity to applied phytotoxic compounds which inhibit formation of mature gamete structures.

DETAILED DESCRIPTION OF THE INVENTION

Figure 1:
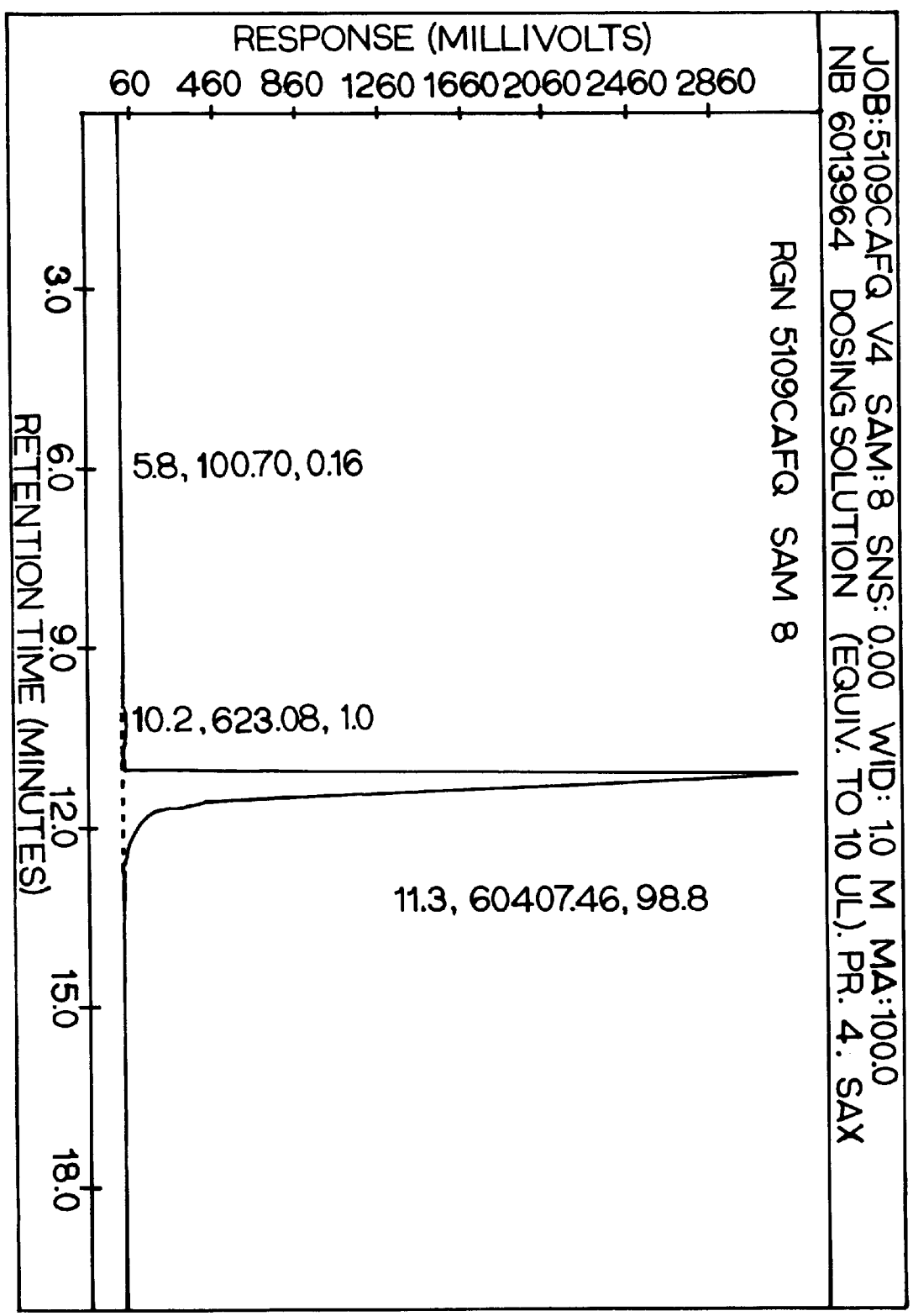
FIG. 1 illustrates a [$^{14}$C] isotope detection HPLC chromatogram representing a sample of a dosing solution containing only [$^{14}$C] glyphosate (11.3 minutes, 98.8%), and trace amounts of [$^{14}$C] AMPA (5.8 minutes, 0.16%) and an unidentified [$^{14}$C] material (10.2 minutes, 1%).

The following detailed description of the invention is provided to aid those skilled in the art in practicing the present invention. Even so, the following detailed description should not be construed to unduly limit the present invention as modifications and variations in the embodiments discussed herein may be made by those of ordinary skill in the art without departing from the spirit or scope of the present inventive discovery.

Many words and phrases are well known in the art of molecular biology, microbiology, protein chemistry, and plant sciences and generally have their plain and ordinarily understood meaning, otherwise to be taken in context. However, the following words and phrases as used herein have the meanings generally set forth below.

AMPA Acyltransferase

As used herein, AMPA acyltransferase refers to an enzyme which functions in transferring an acyl chemical group from an acylcarrier compound such as coenzyme A, which is well known and abbreviated in the biological and chemical arts as CoA. In particular, an AMPA acyltransferase transfers an acyl chemical group from an acylcarrier to the free amino group of aminomethylphosphonate, well known to be a byproduct of glyphosate oxidoreductase mediated glyphosate metabolism. AMPA acyltransferase (AAT), which herein may also be known as AMPA acetyltransferase, AMPA transacylase, or acetyl-AMPA synthase (AAS), has been shown herein to be capable of acetyl transferase activity, propionyl transferase activity, malonyl transferase activity, and succinyl transferase activity. Thus, any biologically functional equivalent of these compounds (acetyl, propionyl, malonyl, or succinyl) which serves as an acyl-carrier form of substrate capable of functioning with an AMPA acyltransferase enzyme is within the scope of the present invention. One AMPA acyltranferase which has been identified, and shown by example herein to function according to the description contained herein, has previously been referred to in the art as PhnO, a protein encoded by the phnO gene within the E. coli phn operon.

Biological Functional Equivalents

As used herein such equivalents with respect to the AMPA-acyltransferase proteins of the present invention are peptides, polypeptides and proteins that contain a sequence or moiety exhibiting sequence similarity to the novel peptides of the present invention, such as PhnO, and which exhibit the same or similar functional properties as that of the polypeptides disclosed herein, including transacylase activity. Biological equivalents also include peptides, polypeptides and proteins that react with, i.e. specifically bind to antibodies raised against PhnO and that exhibit the same or similar transacylase activity, including both monoclonal and polyclonal antibodies.

Biological functional equivalents as used herein with respect to genes encoding acyltransferases are polynucleotides which react with the polynucleotide sequences contemplated and described herein, i.e. which are capable of hybridizing to a polynucleotide sequence which is or is complementary to a polynucleotide encoding an acyltransferase which functions in transacylation of AMPA or which encode substantially similar acyltransferase proteins contemplated and described herein. A protein which is substantially similar to the proteins described herein is a biological functional equivalent and exhibits the same or similar functional properties as that of the polypeptides disclosed herein, including improved herbicide tolerance or improved herbicide resistance. Biological equivalent peptides contain a sequence or moiety such as one or more active sites which exhibit sequence similarity to the novel peptides of the present invention, such as PhnO. Biological equivalents also include peptides, polypeptides, and proteins that react with, i.e. which specifically bind to antibodies raised against PhnO and PhnO-like peptide sequences and which exhibit the same or similar improvement in herbicidal tolerance or resistance, including both monoclonal and polyclonal antibodies.

Chloroplast or plastid localized, as used herein, refers to a biological molecule, either polynucleotide or polypeptide, which is positioned within the chloroplast or plastid such that the molecule is isolated from the cellular cytoplasmic milieu, and functions within the chloroplast or plastid cytoplasm to provide the effects claimed in the instant invention. Localization of a biological molecule to the chloroplast or plastid can occur, with reference to polynucleotides, by artificial mechanical means such as electroporation, mechanical microinjection, or by polynucleotide coated microprojectile bombardment, or with reference to polypeptides, by secretory or import means wherein a natural, non-naturally occurring, or heterologous plastid or chloroplast targeting peptide sequence is used which functions to target, insert, assist, or localize a linked polypeptide into a chloroplast or plastid.

Event refers to a transgenic plant or plant tissue derived from the insertion of foreign DNA into one or more unique sites in the nuclear, mitochondrial, plastid or chloroplast DNA.

Expression

The combination of intracellular processes, including transcription, translation, and other intracellular protein and RNA processing and stabilization functions, which a coding DNA molecule such as a structural gene is subjected to in order to produce a gene product.

Non-naturally Occurring Gene

A non-naturally occurring acyl-transferase gene of the present invention contains genetic information encoding a plant functional RNA sequence, but preferably is a gene encoding an acyl-transferase protein, whether naturally occurring or a variant of a naturally occurring protein, prepared in a manner involving any sort of genetic isolation or manipulation. This includes isolation of the gene from its naturally occurring state, manipulation of the gene as by codon modification, site specific mutagenesis, truncation, introduction or removal of restriction endonuclease cleavage sites, synthesis or resynthesis of a naturally occurring sequence encoding an acyltransferase of the present invention by in vitro methodologies such as phosphoramidite chemical synthesis methods, etc., thermal amplification methods such as polymerase chain reaction, ligase chain reaction, inverted polymerase reaction, and the like etc., and any other manipulative or isolative method.

Operably Linked

Nucleic acid segments connected in frame so that the properties of one influence the expression of the other. For example, a promoter sequence having properties of polymerase loading, binding, and initiation of transcription functions influences the expression of sequences which are linked to the promoter.

Plant-Expressible Coding Regions

Coding regions which are expressible, i.e can be transcribed and/or translated in planta, because they contain typical plant regulatory elements to facilitate the expression of a gene of interest.

Plastid Transit Peptide

Any amino acid sequence useful in targeting or localizing a linked amino acid, such as a protein fusion, to a subcellular compartment or organelle such as a plastid or chloroplast. Amino acid sequences which facilitate entry into a mitochondria are not altogether unlike or dissimilar from plastid transit peptides, and are also described as transit peptides, but fail to function for targeting peptide sequences to plastid or chloroplast organelles.

Progeny of a transgenic plant includes any offspring or descendant of the transgenic plant which contains at least one heterologous or trans-gene, or any subsequent plant derived from the transgenic plant which has the transgene in its lineage. Progeny is not limited to one generation, but rather encompasses the descendants of the transgenic plant so long as they contain or express the desired transgene. Seeds containing transgenic embryos as well as seeds from the transgenic plants and their offspring or descendants are also important parts of the invention. Transgenic cells, tissues, seeds or plants which contain a desired transgene are progeny of the original transgenic cells, tissue, or plant.

Promoter

A recognition site on a DNA sequence or group of DNA sequences that provides an expression control element for a structural gene and to which RNA polymerase specifically binds and initiates RNA synthesis (transcription) of that gene.

$R_0$ is the primary regenerant plant derived from transformation of plant tissue or cells in culture. Subsequent progeny or generations derived from the $R_0$ are referred to as $R_1$ (first generation), $R_2$ (second generation), etc.

Regeneration

The process of producing a whole plant by growing a plant from a plant cell or plant tissue (e.g., plant protoplast or explant).

Structural Coding Sequence refers to a DNA sequence that encodes a peptide, polypeptide, or protein that is produced following transcription of the structural coding sequence to messenger RNA (mRNA), followed by translation of the mRNA to produce the desired peptide, polypeptide, or protein product.

Structural Gene

A gene that is expressed to produce a polypeptide.

Substantial Homology

As this term is used herein, substantial homology refers to nucleic acid sequences which are from about 40 to about 65 percent homologous, from about 66 percent homologous to about 75 percent homologous, from about 76 percent homologous to about 86 percent homologous, from about 87 percent homologous to about 90 percent homologous, from about 91 percent homologous to about 95 percent homologous, and from about 96 percent homologous to about 99 percent homologous to a reference polynucleotide sequence, such as either an *E. coli* phnO gene sequence. A first polynucleotide molecule which is substantially homologous to a second polynucleotide molecule is or is complimentary to the second polynucleotide such that the first polynucleotide molecule hybridizes to the second polynucleotide molecule or its complementary sequence under stringent hybridization conditions, with stringency being defined as the optimum concentration of salt and temperature required to bring about hybridization of a first polynucleotide to a second polynucleotide. Methods for varying stringency are well known in the art but may be referenced in Sambrook et al., Eds., Molecular Cloning: A Laboratory Manual, Second Edition, 1989, Cold Spring Harbor Press; or Ausubel et al, Eds., Short Protocols in Molecular Biology, Third Edition, 1995, John Wiley and Sons, Inc. Polypeptides which are believed to be within the scope if the present invention are those which are from about 40 to about 65 percent similar, from about 66 percent similar to about 75 percent similar, from about 76 percent similar to about 86 percent similar, from about 87 percent similar to about 90 percent similar, from about 91 percent similar to about 95 percent similar, and from about 96 percent similar to about 99 percent similar to a reference polypeptide sequence, preferably to an *E. coli* PhnO peptide sequence.

Terminator

As used herein with respect to plant specific sequences intended for in planta expression, the 3' end transcription termination and polyadenylation sequence.

Transformation is a process of introducing an exogenous polynucleotide sequence, such as a plasmid or viral vector or a recombinant polynucleotide molecule, into a cell, protoplast, plastid or chloroplast, or mitochondria in which the exogenous polynucleotide sequence is either incorporated into an endogenous polynucleotide sequence contained within the cell, or is capable of autonomous replication. A transformed cell is a cell which has been altered by the introduction of one or more exogenous polynucleotide molecules into that cell. A stably transformed cell is a transformed cell which has incorporated all or a portion of the exogenous polynucleotide into the cells' nuclear, mitochondrial, or plastid or chloroplast genomic material such that the exogenous polynucleotide confers some genotypic or phenotypic trait or traits to that cell and to the progeny of the transformed cell, measured by the detection of the exogenously introduced polynucleotide, the mRNA or protein product of the exogenous polynucleotide, a metabolite not normally produced by or found within the cell in the absence of the exogenous polynucleotide, or a visual inspection of the cell, plant tissue, or plants derived from the transformed cell.

Transgene

A transgene is a polynucleotide sequence which has been transferred to a cell and comprises an expression cassette containing a structural gene sequence encoding a desired polypeptide. The transgene is capable of being expressed when in a recipient transformed cell, tissue, or organism. This may include an entire plasmid or other vector, or may simply include the plant functional coding sequence of the transferred polynucleotide. A transgenic cell is any cell derived from or regenerated from a transformed cell, including the initially transformed cell. Exemplary transgenic cells include plant callus tissue derived from a transformed plant cell and particular cells such as leaf, root, stem, meristem, and other somatic tissue cells, or reproductive or germ line and tapetal cells obtained from a stably transformed transgenic plant. A transgenic event is a plant or progeny thereof derived from the insertion of at least one exogenous polynucleotide into the nuclear, plastidic, or mitochondrial genome of a plant cell or protoplast. A transgenic plant is a plant or a progeny thereof which has been genetically modified to contain and express heterologous polynucleotide sequences as proteins or as RNA or DNA molecules not previously a part of the plant composition. As specifically exemplified herein, a transgenic cotton plant, for example, is genetically modified to contain and express at least one heterologous DNA sequence operably linked to and under the regulatory control of transcriptional and translational control sequences which function in plant cells or tissue or in whole plants. A transgenic plant may also be referred to as a transformed plant. A transgenic plant also refers to progeny of the initial transgenic plant where those progeny contain and are capable of expressing the heterologous coding sequence under the regulatory control of the plant expressible transcriptional and translational control sequences described herein. A transgenic plant can produce transgenic flowers, seeds, bulbs, roots, tubers, fruit, and pollen and the like and can be crossed by conventional breeding means with compatible lines of plants to produce hybrid transgenic plants.

Vector

A DNA or other polynucleotide molecule capable of replication in a host cell and/or to which another DNA or other polynucleotide sequence can be operatively linked so as to bring about replication of the linked sequence. A plasmid is an exemplary vector.

In accordance with the present invention, it has been discovered that plants can produce a phytotoxic compound when transformed with certain genes encoding enzymes capable of degrading glyphosate. In particular, glyphosate oxidoreductase (GOX) mediated metabolism of glyphosate produces a phytotoxic compound identified as N-aminomethyl-phosphonate (AMPA). Other studies have shown that an N-acylated derivative of AMPA, N-acyl-aminomethyl-phosphonate (N-acyl-AMPA or acyl-AMPA), is much less phytotoxic to most plant species. Enzymes have been identified which are able to covalently modify AMPA through an acylation mechanism, resulting in the formation of N-acyl-AMPA. One enzyme in particular causes exogeneously applied AMPA to be N-acetylated. In plants expressing this enzyme along with GOX, phytotoxic AMPA effects are not observed.

The inventions contemplated herein take advantage of recombinant polynucleotide cassettes comprised of elements for regulating gene expression into which sequences, such as structural genes encoding useful proteins, can be inserted. Insertion of such sequences into an expression cassette is preferably accomplished using restriction endonucleases well known in the art, however other methods for insertion are known. For example, site specific recombination methods are effective for inserting desired sequences into such expression cassettes. Expression cassettes contain at least a plant operable promoter for use in initiating the production of a messenger RNA molecule from which the useful protein is translated. Cassettes also contain plant operable sequences, identified as 3' sequences, which function in terminating transcription and provide untranslated sequences which are 3' polyadenylated. Thus, an expression cassette intended for use in plants should contain at least a promoter sequence linked at its 3' end to a 3' transcription termination and polyadenylation sequence. Preferably, a polycloning sequence or linker sequence containing one or more unique restriction endonuclease cleavage sites is present bridging the promoter and 3' sequence for convenient insertion of structural gene sequences and other elements. An expression cassette intended for use in plants also preferably contains a 5' untranslated sequence inserted between the promoter and the 3' sequence. 5' untranslated sequences (UTL's) have been shown to enhance gene expression in plants. Introns are also contemplated as sequences which may be present in such expression cassettes of the present invention. The presence of plant operable introns has also been shown, in maize in particular, to enhance gene expression in certain plant species. Introns may be present in an expression cassette in any number of positions along the sequence of the cassette. This can include positions between the promoter and the 3' termination sequence and/or within a structural gene. There may be more than one intron present in an expression cassette, however for the purposes of the contemplated inventions herein, it is preferred that introns be present when expression cassettes are used in monocotyledonous plants and plant tissues. Enhancer sequences are also well known in the art and may be present, although not necessarily as a part of an expression cassette, as enhancer sequences are known to function when present upstream or downstream or even at great distances from a promoter driving expression of a gene of interest.

The expression of a gene localized to the plant nuclear genome and which exists in double-stranded DNA form involves transcription to produce a primary messenger RNA transcript (mRNA) from one strand of the DNA by RNA polymerase enzyme, and the subsequent processing of the mRNA primary transcript inside the nucleus. This processing involves a 3' non-translated polynucleotide sequence which adds polyadenylate nucleotides to the 3' end of the RNA. Transcription of DNA into mRNA is regulated by a sequence of DNA usually referred to as the "promoter". The promoter comprises a sequence of bases that signals RNA polymerase to associate with the DNA and to initiate the transcription of mRNA using the template DNA strand to make a corresponding complementary strand of RNA.

Those skilled in the art will recognize that there are a number of promoters which are active in plant cells, and have been described in the literature. Such promoters may be obtained from plants, plant viruses, or plant commensal, saprophytic, symbiotic, or pathogenic microbes and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), the rice Act1 promoter, the Figwort Mosaic Virus (FMV) 35S promoter, the sugar cane bacilliform DNA virus promoter, the ubiquitin promoter, the peanut chlorotic streak virus promoter, the comalina yellow virus promoter, the chlorophyll a/b binding protein promoter, and meristem enhanced promoters Act2, Act8, Act11 and EF1a and the like. All of these promoters have been used to create various types of DNA constructs which have been expressed in plants (see e.g., McElroy et al., 1990; Barry and Kishore, U.S. Pat. No. 5,463,175) and which are within the scope of the present invention. Chloroplast and plastid specific promoters, chloroplast or plastid functional promoters, and chloroplast or plastid operable promoters are also envisioned. It is preferred that the particular promoter selected should be capable of causing sufficient in-planta expression to result in the production of an effective amount of acyltransferase to render a plant substantially tolerant to phosphonate herbicides and products of phosphonate herbicide metabolism. The amount of acyltransferase required to provide the desired tolerance may vary with the plant species.

One set of preferred promoters are constitutive promoters such as the CaMV35S or FMV35S promoters that yield high levels of expression in most plant organs. Enhanced or duplicated versions of the CaMV35S and FMV35S promoters are particularly useful in the practice of this invention (Kay et al, 1987; Rogers, U.S. Pat. No. 5,378,619). In addition, it may also be preferred to bring about expression of the acyltransferase gene in specific tissues of the plant, such as leaf, stem, root, tuber, seed, fruit, etc., and the promoter chosen should have the desired tissue and developmental specificity. Therefore, promoter function should be optimized by selecting a promoter with the desired tissue expression capabilities and approximate promoter strength and selecting a transformant which produces the desired herbicide tolerance in the target tissues. This selection approach from the pool of transformants is routinely employed in expression of heterologous structural genes in plants since there is variation between transformants containing the same heterologous gene due to the site of gene insertion within the plant genome. (Commonly referred to as "position effect"). In addition to promoters which are known to cause transcription (constitutive or tissue-specific) of DNA in plant cells, other promoters may be identified for use in the current invention by screening a plant cDNA library for genes which are selectively or preferably expressed in the target tissues and then determine the promoter regions.

It is preferred that the promoters utilized have relatively high expression in all meristematic tissues in addition to other tissues inasmuch as it is now known that phosphonate herbicides can be translocated and accumulated in this type of plant tissue. Alternatively, a combination of chimeric genes can be used to cumulatively result in the necessary overall expression level of acyltransferase enzyme to result in the herbicide tolerant phenotype. A promoter which provides relatively high levels of expression can cause the production of a desired protein to in planta levels ranging from 0.1 milligrams per fresh weight gram of plant tissue, to 0.5 milligrams per fresh weight gram of plant tissue, to 1.0 milligrams per fresh weight gram of plant tissue, to 2.0 or more milligrams per fresh weight gram of plant tissue. The in planta levels of a desired protein in genetically isogenic crops in a field can range across a spectrum, but generally the levels fall within 70% of a mean, more preferably within 50% of a mean, and even more preferably within 25% of a mean for all plants analyzed in a given sample.

The promoters used in the DNA constructs (i.e. chimeric plant genes) of the present invention may be modified, if desired, to affect their control characteristics. For example, the CaMV35S promoter may be ligated to the portion of the *Arabidopsis thaliana* ribulose-1,5-bisphosphate carboxylase small subunit gene (ssRUBISCO) that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, et cetera. Furthermore, the promoters may be altered to contain multiple "enhancer sequences" to assist in elevating gene expression. Examples of such enhancer sequences have been reported by Kay et al. (1987).

One RNA produced by a DNA construct of the present invention also contains a 5' non-translated leader sequence. This sequence can be derived from the promoter selected to express the gene, and can be specifically modified so as to increase translation of the mRNA. The nontranslated or 5' untranslated leader sequence (NTR or UTR) can be derived from an unrelated promoter or coding sequence. For example, the 5' non-translated regions can also be obtained from viral RNA's, from suitable eucaryotic genes, or from a synthetic gene sequence. The present invention is not limited to constructs, as presented in one of the following examples, wherein the non-translated region is derived from the 5' non-translated sequence that accompanies the promoter sequence. Examples of plant gene leader sequences which are useful in the present invention are the wheat chlorophyll a/b binding protein (cab) leader and the petunia heat shock protein 70 (hsp70) leader (Winter et al., 1988).

For optimal expression in monocotyledonous plants, an intron should also be included in the DNA expression construct. This intron would typically be placed near the 5' end of the mRNA in untranslated sequence. This intron could be obtained from, but not limited to, a set of introns consisting of the maize hsp70 intron (Brown et al., U.S. Pat. No. 5,424,412; 1995) or the rice Act1 intron (McElroy et al., 1990).

Where more than one expression cassette in included within a plasmid or other polynucleotide construct, a first expression cassette comprising a DNA molecule typically contains a constitutive promoter, a structural DNA sequence encoding a glyphosate oxidoreductase enzyme (GOX), and a 3' non-translated region. A second expression cassette comprising a DNA molecule typically contains a constitutive promoter, a structural DNA sequence encoding an N-acyl-transferase enzyme which is capable of reacting with AMPA to produce N-acyl-AMPA, and a 3' non-translated region. Additional expression cassettes comprising a DNA molecule are also envisioned. For example, genes encoding insecticidal or fungicidal activities, drought or heat tolerance, antibiotic compounds, pharmaceutical compounds or reagents such as tumor suppressor proteins or antibody components, biopolymers, other commercially useful compounds and the like may also be expressed in the plants envisioned by the present invention, along with genes which provide increased herbicide tolerance. A number of constitutive promoters which are active in plant cells have been described. Suitable promoters for constitutive expression of either GOX or an N-acyl-transferase include, but are not limited to, the cauliflower mosaic virus (CaMV) 35S promoter (Odell et al. 1985), the Figwort mosaic virus (FMV) 35S (Sanger et al. 1990), the sugarcane bacilliform DNA virus promoter (Bouhida et al., 1993), the commelina yellow mottle virus promoter (Medberry and Olszewski 1993), the light-inducible promoter from the small subunit of the ribulose-1,5-bis-phosphate carboxylase (ssRUBISCO) (Coruzzi et al., 1984), the rice cytosolic triosephosphate isomerase (TPI) promoter (Xu et al. 1994), the adenine phosphoribosyltransferase (APRT) promoter of Arabidopsis (Moffatt et al. 1994), the rice actin 1 gene promoter (Zhong et al. 1996), and the mannopine synthase and octopine synthase promoters (Ni et al. 1995). All of these promoters have been used to create various types of plant-expressible recombinant DNA constructs. Comparative analysis of constitutive promoters by the expression of reporter genes such as the uidA (β-glucuronidase) gene from E. coli has been performed with many of these and other promoters (Li et al. 1997; Wen et al. 1993).

Promoters used in the second cassette comprising a DNA molecule can be selected to control or limit specific expression where cell lethality is desired. In a preferred embodiment, the promoter will be capable of directing expression exclusively or primarily in tissues critical for plant survival or plant viability, while limiting expression of the second cassette comprising a DNA molecule in other nonessential tissues. For example, tissues which differentiate into pollen development or terminal tissues such as the pollen itself, the tapetal cell layer of the anther, or the anther tissues. Alternatively, plant promoters capable of regulating the expression of genes in particular cell and tissue types are well known. Those that are most preferred in the embodiments of this invention are promoters which express specifically during the development of the male reproductive tissue or in pollen at levels sufficient to produce inhibitory RNA molecules complementary to the sense RNA transcribed by the constitutive promoter of the first expression cassette comprising a DNA molecule. Examples of these types of promoters include the TA29 tobacco tapetum-specific promoter (Mariani et al. 1990), the PA1 and PA2 chalcone flavonone isomerase promoters from petunia (van Tunen et al. 1990), the SLG gene promoter from Brassica oleracea (Heizmann et al. 1991), and LAT gene promoters from tomato (Twell et al. 1991).

Anther and pollen-specific promoters from rice have been isolated. Examples include the Osg6B promoter, which was shown to drive expression of the β-glucuronidase gene in transgenic rice in immature anthers. No activity was detected in other tissues of spikelets, leaves or roots (Yokoi et al. 1997). The PS1 pollen-specific promoter from rice has been shown to specifically express the β-glucuronidase gene in rice pollen (Zou et al. 1994). Additional rice genes have been identified that specifically express in the anther tapetum of rice (Tsuchiya et al. 1994, Tsuchiya et al. 1997). The isolation of additional genes expressed predominantly during anther development in rice can be performed, for example, by construction of a cDNA library to identify anther specific clones (Qu et al.).

Those skilled in the art are aware of the approaches used in the isolation of promoters which function in plants, and from genes or members of gene families that are highly expressed in particular plant tissues such as in roots, shoots, meristem, leaves, flowers, fruits, in pollen, or in plant cell types involved in the production of pollen (Stinson et al. 1987; Brown and Crouch. 1990; McCormick et al. 1989). Further examples of tissue specific promoters include the promoter for the exopolygalacturonase gene of maize (Dubald, et al. 1993) and the promoter for the Zmc13 mRNA (Hanson, et al. 1989). Promoters which have been shown to preferentially express in tomato pollen are the LAT52 and LAT59 promoters (Twell et al. 1991). A portion of the maize pZtap promoter sequence (psgB6-1) was disclosed in U.S. Pat. No. 5,470,359.

A recombinant DNA molecule of the present invention typically comprises a promoter operably or operatively linked to a DNA sequence encoding a 5' non-translated region, a DNA sequence of a plant intron, a structural sequence encoding a chloroplast transit peptide (CTP), a DNA coding sequence for a gene encoding improved herbicide tolerance, and a 3' non-translated region.

The 5' non-translated leader sequence can be derived from the promoter selected to express the heterologous DNA sequence, and can be specifically modified if desired so as to increase translation of mRNA. A 5' non-translated region can also be obtained from viral RNAs, from suitable eukaryotic genes, or from a synthetic gene sequence. The present invention is not limited to constructs wherein the non-translated region is derived from the 5' non-translated sequence which accompanies the promoter sequence. The leader sequence could also be derived from an unrelated promoter or coding sequence.

The 3' non-translated region of a plant operable recombinant DNA molecule contains a polyadenylation signal which functions in plants to cause the addition of adenylate nucleotides to the 3' end of the RNA. The 3' non-translated region can be obtained from various genes which are expressed in plant cells. The nopaline synthase 3' untranslated region (Fraley et al. 1983), the 3' untranslated region from pea ssRUBISCO (Coruzzi et al. 1994), the 3' untranslated region from soybean 7S seed storage protein gene (Schuler et al. 1982) and the pea small subunit of the pea ssRUBISCO gene are commonly used in this capacity. The 3' transcribed, non-translated regions containing the polyadenylate signal of Agrobacterium tumor-inducing (Ti) plasmid genes are also suitable.

Examples of plant introns suitable for expression in monocots includes, for example, maize hsp70 intron, rice actin 1 intron, maize ADH 1 intron, Arabidopsis SSU intron, Arabidopsis EPSPS intron, petunia EPSPS intron and others known to those skilled in the art.

It may be particularly advantageous to direct the localization of proteins conferring herbicide tolerance to subcellular compartment, for example, to the mitochondrion, endoplasmic reticulum, vacuoles, chloroplast or other plastidic compartment. Proteins can be directed to the chloroplast by including at their amino-terminus a chloroplast transit peptide (CTP). Naturally occurring chloroplast targeted proteins, synthesized as larger precursor proteins containing an amino-terminal chloroplast targeting peptide directing the precursor to the chloroplast import machinery, have been previously identified and are well known in the art. Chloroplast targeting peptides are generally cleaved by specific endoproteases located within the chloroplast organelle, thus releasing the targeted mature and preferably active enzyme from the precursor into the chloroplast melieu. Examples of sequences encoding peptides which are suitable for directing the targeting of the herbicide tolerance gene or transacylase gene product to the chloroplast or plastid of the plant cell include the petunia EPSPS CTP, the Arabidopsis EPSPS CTP2 and intron, and others known to those skilled in the art. Such targeting sequences provide for the desired expressed protein to be transferred to the cell structure in which it most effectively functions, or by transferring the desired expressed protein to areas of the cell in which cellular processes necessary for desired phenotypic function are concentrated. Chloroplast targeting peptides have been found to be particularly useful in the selection of glyphosate resistant plants (Barry et al., U.S. Pat. No. 5,463,175; Barry et al., U.S. Pat. No. 5,633,435). Glyphosate functions to kill the cell by inhibiting aromatic amino acid biosynthesis which takes place within the chloroplast. Therefor, concentrating the resistance gene product within the chloroplast provides increased resistance to the herbicide. The examples herein provide for a transacylase which is also targeted to or localized to and concentrated within the chloroplast. Specific examples of chloroplast targeting peptides are well known in the art and include the Arabidopsis thaliana ribulose bisphosphate carboxylase small subunit ats1A transit peptide, an Arabidopsis thaliana EPSPS transit peptide, and a Zea maize ribulose bisphosphate carboxylase small subunit transit peptide. One CTP that has functioned herein to localize heterologous proteins to the chloroplast was derived from the Arabidopsis thaliana ribulose bisphosphate carboxylase small subunit ats1A transit peptide. A polynucleotide sequence encoding a variant of this transit peptide used herein provides the native transit peptide amino acid sequence plus a reiteration of the transit peptide cleavage site, and has been shown herein to be useful for deploying active recombinant transacylase enzyme to the chloroplast (SEQ ID NO:9).

An alternative means for localizing plant operable herbicide tolerance or herbicide resistance genes to a chloroplast or plastid includes chloroplast or plastid transformation. Recombinant plants can be produced in which only the mitochondrial or chloroplast DNA has been altered to incorporate the molecules envisioned in this application. Promoters which function in chloroplasts have been known in the art (Hanley-Bowden et al., Trends in Biochemical Sciences 12:67–70, 1987). Methods and compositions for obtaining cells containing chloroplasts into which heterologous DNA has been inserted have been described, for example by Daniell et al. (U.S. Pat. No. 5,693,507; 1997) and Maliga et al. (U.S. Pat. No. 5,451,513; 1995).

The accumulation of AMPA in plants can cause phytotoxic symptoms which are manifested phenotypically as chlorosis of the leaves, stunted growth, infertility, and death, although not all of these symptoms are evidenced in every species of plant. It has been discovered herein that enzymatic modification of the AMPA molecule by transacylation to produce N-acyl-AMPA provides a means for overcoming the phytotoxic effects of AMPA. A method for assaying the conversion of AMPA to N-acyl-AMPA involves providing [$^{14}$C] labeled AMPA as one substrate for the transacylase enzyme, and acyl-CoA as another substrate for the enzyme in an aqueous reaction volume, and separating the [$^{14}$C] labeled AMPA substrate from N-acyl-[$^{14}$C]-AMPA product by HPLC on an anion exchange column as described in the examples herein. Surprisingly, the transacylase enzyme has been shown to be capable of utilizing other acylated-CoA compounds as substrates for transacylating the AMPA substrate. In particular, propionyl-CoA was shown to be a particularly reactive substrate for the transacylation reaction in vitro, producing N-propionyl-[$^{14}$C]-AMPA. Larger acylated-CoA compounds, i.e. butyryl-CoA or methylmalonyl-CoA and other organic molecules covalently linked to CoA which have a carbon chain length greater than $C_3$ proved to be less effective in the transacylation reaction when using AMPA as the acyl-group recipient substrate. Notwithstanding this information, one skilled in the art would recognize that other transacylases which are substantially related by amino acid sequence homology to a PhnO or PhnO-like enzyme as characterized herein would have a similar substrate specificity in the AMPA transacylase reaction as compared to that encompassed by PhnO. These other enzymes too are conceptually within the scope and spirit of the invention described herein. For example, fatty acid biosynthesis is mediated by a wide range of acyl-CoA and acyl-carrier protein compounds which may be useful as substrates in transacylating phytotoxic compounds such as AMPA. A transacylase capable of AMPA transacylation using a fatty acid intermediate could conceivably provide plant protection by eliminating AMPA phytotoxicity. An enzyme such as PhnO, which is capable of transacylation, may be useful in detoxifying a wide range of toxic compounds which contain CP bonds and which additionally contain a CN linkage.

Methods and compositions for transforming a bacterium, a yeast or fungal cell, a plant cell, or an entire plant with one or more expression vectors comprising a phnO- or phnO-like gene sequence are further aspects of this disclosure. A transgenic bacterium, yeast or fungal cell, plant cell, or plant derived from such a transformation process or the progeny and seeds from such a transgenic plant are also further embodiments of this invention.

Methods for transforming bacteria and yeast or fungal cells are well known in the art. Typically, means of transformation are similar to those well known means used to transform other bacteria, such as E. coli, or yeast, such as Saccharomyces cerevisiae. Methods for DNA transformation of plant cells include, but are not limited to Agrobacterium-mediated plant transformation, protoplast transformation, gene transfer into pollen, injection into reproductive organs, injection into immature embryos, plastid or chloroplast transformation, and particle bombardment. Each of these methods has distinct advantages and disadvantages. Thus, one particular method of introducing genes into a particular plant species may not be the most effective for another plant species, but it is well known by those skilled in the art which methods are useful for a particular plant species.

There are many methods for introducing transforming DNA segments into cells, but not all are suitable for delivering DNA to plant cells. Suitable methods are believed to include virtually any method by which DNA can be introduced into a cell, such as by Agrobacterium infection, binary bacterial artificial chromosome (BIBAC) vectors (Hamilton et al., 1996), direct delivery of DNA such as, for example by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neuman, 1982; Fromm et al., 1985; U.S. Pat. No. 5,384,253) and the gene gun (Johnston and Tang, 1994; Fynan et al., 1993; Luthra et al., 1997); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992)

Methods for transforming dicots, primarily by use of *Agrobacterium tumefaciens*, and obtaining transgenic plants have been published for cotton (U.S. Pat. Nos. 5,004,863; 5,159,135; 5,518,908), soybean (U.S. Pat. Nos. 5,569,834; 5,416,011; McCabe et al. (1988); Christou et al. (1988)), Brassica (U.S. Pat. No. 5,463,174), peanut (Cheng et al. (1996); De Kathen and Jabobsen (1990)).

Transformation of monocots using electroporation, particle bombardment, and Agrobacterium have also been reported. Transformation and plant regeneration have been achieved in asparagus (Bytebier et al. (1987)), barley (Wan and Lemaux (1994)), maize (Rhodes et al. (1988); Ishida et al. (1996); Gordon-Kamm et al. (1990); Fromm et al. (1990); Koziel et al. (1993); Armstrong et al. (1995), oat (Somers et al. (1992)), orchardgrass (Horn et al. (1988)), rice (Toriyama et al. (1988); Park et al. (1996); Abedinia et al. (1997); Zhang and Wu (1988); Zhang et al. (1988); Battraw and Hall (1990); Christou et al. (1991); Park et al. (1996)), rye (De la Pena et al. (1987)), sugar cane (Bower and Birch (1992)), tall fescue (Wang et al. (1992)), and wheat (Vasil et al. (1992); Weeks et al. (1993)). Techniques for monocot transformation and plant regeneration are also discussed in Davey et al. (1986).

Recombinant plants could also be produced in which only the mitochondrial or chloroplast DNA has been altered to incorporate the molecules envisioned in this application. Promoters which function in chloroplasts have been known in the art (Handley-Bowden et al., Trends in Biochemical Sciences 12:67–70, 1987). Methods and compositions for obtaining cells containing chloroplasts into which heterologous DNA has been inserted has been described by Daniell et al., U.S. Pat. No. 5,693,507 (1997) and Maliga et al. (U.S. Pat. No. 5,451,513; 1995). Recombinant plants which have been transformed using heterologous DNA, altering both nuclear and chloroplast or plastidic genomes is also within the scope of this invention.

The present invention discloses DNA constructs comprising polynucleotide sequences encoding AMPA-transacylase. Methods for identifying and isolating heterologous genes encoding peptides which function in N-acylation of AMPA are disclosed herein. Methods for the construction and expression of synthetic genes in plants are well known by those of skill in the art and are described in detail in U.S. Pat. No. 5,500,365, and in monocotyledonous plants in particular in U.S. Pat. No. 5,689,052. The present invention contemplates the use of AMPA acyltransferase genes alone or in combination with genes encoding GOX mediated glyphosate degradation enzymes in the transformation of both monocotyledonous and dicotyledonous plants. To potentiate the expression of these genes, the present invention provides DNA constructs comprising polynucleotide sequences encoding these types of proteins which are localized to the plant cell cytoplasm as well as sequences encoding plastid targeting peptides positioned upstream of the polynucleotide sequences encoding the AMPA transacylase and/or GOX proteins.

In one aspect, nucleotide sequence information provided by the invention allows for the preparation of relatively short DNA sequences having the ability to specifically hybridize to gene sequences of the selected polynucleotides disclosed herein. In these aspects, nucleic acid probes of an appropriate length are prepared based on a consideration of selected polynucleotide sequences encoding AMPA transacylase polypeptides, e.g., sequences such as are shown in SEQ ID NO: 1, SEQ ID NO:2, and SEQ ID NO:3. Such nucleic acid probes may also be prepared based on a consideration of selected polynucleotide sequences encoding a plastid targeting peptide, such as those shown in SEQ ID NO:9, SEQ ID NO:11, SEQ ID NO:13, and SEQ ID NO:14. The ability of such nucleic acid probes to specifically hybridize to a gene sequence encoding an AMPA transacylase polypeptide or a plastid targeting peptide sequence lends to them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined sequence of a AMPA transacylase gene from any suitable organism using PCR™ technology. The process may also be used to detect, amplify or mutate a defined sequence of the polynucleotide encoding a plastid targeting peptide. Segments of genes related to the polynucleotides encoding the AMPA transacylase polypeptides and plastid targeting peptides of the present invention may also be amplified by PCR™ using such primers.

To provide certain of the advantages in accordance with the present invention, a preferred nucleic acid sequence employed for hybridization studies or assays includes sequences that are substantially complementary to at least a length of 14 to 30 or so consecutive nucleotides of a polynucleotide sequence flanking, in cis with, or encoding an AMPA transacylase, such as that shown in SEQ ID NO:5 or SEQ ID NO:6, or sequences that are substantially complementary to at least a length of 14 to 30 or so consecutive nucleotides of a sequence encoding a plastid targeting peptide. By "substantially complimentary", it is meant that a polynucleotide is preferably about 70% complimentary, or more preferably about 80% complimentary, or even more preferably about 90% complimentary, or most preferably about 99–100% complimentary in sequence to a target polynucleotide sequence.

A size of at least 14 nucleotides in length helps to ensure that the fragment will be of sufficient length to form a duplex molecule that is both stable and selective. Molecules having complementary sequences over segments greater than 14 bases in length are generally preferred. In order to increase stability and selectivity of the hybrid, and thereby improve the quality and degree of specific hybrid molecules obtained, one will generally prefer to design nucleic acid molecules having gene-complementary sequences of 14 to 20 nucleotides, or even longer where desired. Such fragments may be readily prepared by, for example, directly synthesizing the fragment by chemical means, such as phosphoramidite chemistries for example; by application of nucleic acid reproduction technology, such as the PCR™ technology of U.S. Pat. Nos. 4,683,195, and 4,683,202 (each specifically incorporated herein by reference); or by excising selected DNA fragments from recombinant plasmids containing appropriate inserts and suitable restriction sites.

The present invention also contemplates an expression vector comprising a polynucleotide of the present invention. Thus, in one embodiment an expression vector is an isolated and purified DNA molecule comprising a promoter operably linked to a coding region that encodes a polypeptide of the present invention, which coding region is operatively linked to a transcription-terminating region, whereby the promoter drives the transcription of the coding region. The coding region may include a segment or sequence encoding a AMPA transacylase and a segment or sequence encoding a plastid targeting peptide. The DNA molecule comprising the expression vector may also contain a plant functional intron, and may also contain other plant functional elements such as sequences encoding untranslated sequences (UTL's) and sequences which act as enhancers of transcription or translation.

As used herein, the terms "operatively linked" or "operably linked" mean that a sequence which functions as a promoter is connected or linked to a coding region in such a way that the transcription of that coding region is controlled and regulated by that promoter. Means for operatively linking a promoter to a coding region to regulate both upstream and downstream are well known in the art.

Preferred plant transformation vectors include those derived from a Ti plasmid of *Agrobacterium tumefaciens*, as well as those disclosed, e.g., by Herrera-Estrella (1983), Bevan (1983), Klee (1985) and Eur. Pat. Appl. No. EP 0120516 (each specifically incorporated herein by reference). In addition, plant preferred transformation vectors directed to chloroplast or plastid transformation include those disclosed in U.S. Pat. No. 5,693,507 (1997), U.S. Pat. No. 5,451,513 (1995), McBride et al. (1995), Staub et al. (1995a), Staub et al. (1995b), and WO 95/24492 (each specifically incorporated herein by reference).

Where an expression vector of the present invention is to be used to transform a plant, a promoter is selected that has the ability to drive expression in that particular species of plant. Promoters that function in different plant species are also well known in the art. Promoters useful in expressing the polypeptide in plants are those which are inducible, viral, synthetic, or constitutive as described (Odell et al., 1985), and/or temporally regulated, spatially regulated, and spatio-temporally regulated. Preferred promoters include the enhanced CaMV35S promoters, and the FMV35S promoter.

The expression of a gene which exists in double-stranded DNA form localized to the plant nuclear genome involves transcription of messenger RNA (mRNA) from the coding strand of the DNA by an RNA polymerase enzyme, and the subsequent processing of the mRNA primary transcript inside the nucleus. Genes expressed from within a chloroplast or plastid also produce an mRNA transcript which is not processed further prior to translation. In any event, transcription of DNA into mRNA is regulated by a region of DNA referred to as the "promoter". The DNA comprising the promoter is represented by a sequence of bases that signals RNA polymerase to associate with the DNA and to initiate the transcription of mRNA using one of the DNA strands as a template to make a corresponding strand of RNA. The particular promoter selected should be capable of causing sufficient expression of an AMPA acyltransferase enzyme coding sequence to result in the production of an herbicide tolerance effective or herbicide resistance effective amount of the transacylase protein localized to the desired intracellular location.

Structural genes can be driven by a variety of promoters in plant tissues. Promoters can be near-constitutive (i.e. they drive transcription of the transgene in all tissue), such as the CaMV35S promoter, or tissue-specific or developmentally specific promoters affecting dicots or monocots. Where the promoter is a near-constitutive promoter such as CaMV35S or FMV35S, increases in polypeptide expression are found in a variety of transformed plant tissues and most plant organs (e.g., callus, leaf, seed, stem, meristem, flower, and root). Enhanced or duplicate versions of the CaMV35S and FMV35S promoters are particularly useful in the practice of this invention (Kay et al., 1987; Rogers, U.S. Pat. No. 5,378,619).

Those skilled in the art will recognize that there are a number of promoters which are active in plant cells, and have been described in the literature. Such promoters may be obtained from plants or plant viruses and include, but are not limited to, the nopaline synthase (NOS) and octopine synthase (OCS) promoters (which are carried on tumor-inducing plasmids of *A. tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), the rice Act1 promoter and the Figwort Mosaic Virus (FMV) 35S promoter. All of these promoters have been used to create various types of DNA constructs which have been expressed in plants (see e.g., McElroy et al., 1990, U.S. Pat. No. 5,463,175).

In addition, it may also be preferred to bring about expression of genes such as an AMPA acyltransferase which improve herbicide tolerance or herbicide resistance in specific tissues of a plant by using plant integrating vectors containing a tissue-specific promoter. Specific target tissues may include the leaf, stem, root, tuber, seed, fruit, etc., and the promoter chosen should have the desired tissue and developmental specificity. Therefore, promoter function should be optimized by selecting a promoter with the desired tissue expression capabilities and approximate promoter strength, and selecting a transformant which produces the desired transacylase activity in the target tissues. This selection approach from the pool of transformants is routinely employed in expression of heterologous structural genes in plants since there is variation between transformants containing the same heterologous gene due to the site of gene insertion within the plant genome (commonly referred to as "position effect"). In addition to promoters which are known to cause transcription (constitutive or tissue-specific) of DNA in plant cells, other promoters may be identified for use in the current invention by screening a plant cDNA library for genes which are selectively or preferably expressed in the target tissues, then determining the promoter regions. Chloroplast or plastid functional promoters are known in the art (Hanley-Bowden et al., Daniell et al., Maliga et al.).

Other exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (McBride and Summerfelt, 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989) promoters. Preferred promoters are the cauliflower mosaic virus (CaMV 35S) promoter and the S-E9 small subunit RuBP carboxylase promoter.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al. (1987). Chloroplast or plastid specific promoters are known in the art (Daniell et al., U.S. Pat. No. 5,693,507; herein incorporated by reference). Promoters obtainable from chloroplast genes, for example, such as the psbA gene from spinach or pea, the rbcL and atpB promoter regions from maize, and rRNA promoters. Any chloroplast or plastid operable promoter is within the scope of the present invention.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

The RNA produced by a DNA construct of the present invention may also contain a 5' non-translated leader sequence (5'UTL). This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs wherein the non-translated region is derived from the 5' non-translated sequence that accompanies the promoter sequence. One plant gene leader sequence for use in the present invention is the petunia heat shock protein 70 (hsp70) leader (Winter et al., 1988).

5' UTL's are capable of regulating gene expression when localized to the DNA sequence between the transcription initiation site and the start of the coding sequence. Compilations of leader sequences have been made to predict optimum or sub-optimum sequences and generate "consensus" and preferred leader sequences (Joshi, 1987). Preferred leader sequences are contemplated to include those which comprise sequences predicted to direct optimum expression of the linked structural gene, i.e. to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in maize in particular, will be most preferred. One particularly useful leader may be the petunia HSP70 leader.

In accordance with the present invention, expression vectors designed to specifically potentiate the expression of the polypeptide in the transformed plant may include certain regions encoding plastid or chloroplast targeting peptides, herein abbreviated in various forms as CTP, CTP1, CTP2, etc., each representing a different or variant targeting peptide sequence. These regions allow for the cellular processes involved in transcription, translation and expression of the encoded protein to be fully exploited when associated with certain GOX or AMPA transacylase protein sequences. Such targeting peptides function in a variety of ways, such as for example, by transferring the expressed protein to the cell structure in which it most effectively operates, or by transferring the expressed protein to areas of the cell in which cellular processes necessary for expression are concentrated. The use of CTP's may also increase the frequency of recovery of morphologically normal plants, and the frequency at which transgenic plants may be recovered.

Chloroplast targeting peptides have been found particularly useful in the glyphosate resistant selectable marker system. In this system, plants transformed to express a protein conferring glyphosate resistance are transformed along with a CTP that targets the peptide to the plant cell's chloroplasts. Glyphosate inhibits the shikimic acid pathway which leads to the biosynthesis of aromatic compounds including amino acids and vitamins. Specifically, glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS). Introduction of a transgene encoding EPSPS allows the plant cell to resist the effects of glyphosate, especially when the transgene encodes a glyphosate insensitive EPSPS enzyme. Thus, as the herbicide glyphosate functions to kill the cell by interrupting aromatic amino acid biosynthesis, particularly in the cell's chloroplast, the CTP allows increased resistance to the herbicide by concentrating what glyphosate resistance enzyme the cell expresses in the chloroplast, i.e. in the target organelle of the cell. Exemplary herbicide resistance enzymes include EPSPS and glyphosate oxido-reductase (GOX) genes (see Comai, 1985, U.S. Pat. No. 4,535,060, specifically incorporated herein by reference in its entirety).

CTPs can target proteins to chloroplasts and other plastids. For example, the target organelle may be the amyloplast. Preferred CTP's of the present invention include those targeting both chloroplasts as well as other plastids. Specific examples of preferred CTP's include the maize RUBISCO SSU protein CTP, and functionally related peptides such as the *Arabidopsis thaliana* RUBISCO small subunit CTP and the *Arabidopsis thaliana* EPSPS CTP. These CTP's are exemplified by the polynucleotide and amino acid sequences shown in SEQ ID NO:9, SEQ ID NO:11, SEQ ID NO:13, and SEQ ID NO: 14 respectively.

Recombinant plants, cells, seeds, and other plant tissues could also be produced in which only the mitochondrial or chloroplast DNA has been altered to incorporate the molecules envisioned in this application. Promoters which function in chloroplasts have been known in the art (Hanley-Bowden et al., Trends in Biochemical Sciences 12:67–70, 1987). Methods and compositions for obtaining cells containing chloroplasts into which heterologous DNA has been inserted has been described in U.S. Pat. No. 5,693,507 (1997). McBride et al. (WO 95/24492) disclose localization and expression of genes encoding Cry1A δ-endotoxin protein in tobacco plant chloroplast genomes.

An exemplary embodiment of the invention involves the plastid or chloroplast targeting or plastid or chloroplast localization of genes encoding enzymes or proteins conferring herbicide tolerance or herbicide resistance in plants. Plastid or chloroplast targeting sequences have been isolated from numerous nuclear encoded plant genes and have been shown to direct importation of cytoplasmically synthesized proteins into plastids or chloroplasts (reviewed in Keegstra and Olsen, 1989). A variety of plastid targeting sequences, well known in the art, including but not limited to ADPGPP, EPSP synthase, or ssRUBISCO, may be utilized in practicing this invention. In addition, plastidic targeting sequences (peptide and nucleic acid) for monocotyledonous crops may consist of a genomic coding fragment containing an intron sequence as well as a duplicated proteolytic cleavage site in the encoded plastidic targeting sequences.

The preferred CTP sequence for dicotyledonous crops is referred to herein as (SEQ ID NO:9), and consists of a genomic coding fragment containing the chloroplast targeting peptide sequence from the EPSP synthase gene of *Arabidopsis thaliana* in which the transit peptide cleavage site of the pea ssRUBISCO CTP replaces the native EPSP synthase CTP cleavage site (Klee et al., 1987).

For optimized expression in monocotyledonous plants, an intron may also be included in the DNA expression construct. Such an intron is typically placed near the 5' end of the mRNA in untranslated sequence. This intron could be obtained from, but not limited to, a set of introns consisting of the maize heat shock protein (HSP) 70 intron (U.S. Pat. No. 5,424,412; 1995), the rice Act1 intron (McElroy et al., 1990), the Adh intron 1 (Callis et al., 1987), or the sucrose synthase intron (Vasil et al., 1989).

The 3' non-translated region of the genes of the present invention which are localized to the plant nuclear genome also contain a polyadenylation signal which functions in plants to cause the addition of adenylate nucleotides to the 3' end of the mRNA. RNA polymerase transcribes a nuclear genome coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Examples of preferred 3'0 regions are (1) the 3' transcribed, non-translated regions containing the polyadenylation signal of Agrobacterium tumor-inducing (Ti) plasmid genes, such as the nopaline synthase (NOS) gene and (2) the 3' ends of plant genes such as the pea ribulose-1,5-bisphosphate carboxylase small subunit gene, designated herein as E9 (Fischhoff et al., 1987). Constructs will typically include the gene of interest along with a 3' end DNA sequence that acts as a signal to terminate transcription and, in constructs intended for nuclear genome expression, allow for the poly-adenylation of the resultant mRNA. The most preferred 3' elements are contemplated to be those from the nopaline synthase gene of *A. tumefaciens* (nos 3'end) (Bevan et al., 1983), the terminator for the T7 transcript from the octopine synthase gene of *A. tumefaciens*, and the 3' end of the protease inhibitor I or II genes from potato or tomato. Regulatory elements such as TMV Ω element (Gallie, et al., 1989), may further be included where desired.

According to the present invention and as noted above, chloroplast or plastid localized genes encoding enzymes conferring herbicide tolerance or herbicide resistance characteristics to plants do not require sequences which confer transcription termination and polyadenylation signals, but instead may only require transcription termination information at the 3' end of the gene. For coding sequences introduced into a chloroplast or plastid, or into a chloroplast or plastid genome, mRNA transcription termination is similar to methods well known in the bacterial gene expression art. For example, either in a polycistronic or a monocistronic sequence, transcription can be terminated by stem and loop structures or by structures similar to rho dependent sequences.

Transcription enhancers or duplications of enhancers could be used to increase expression. These enhancers often are found 5' to the start of transcription in a promoter that functions in eukaryotic cells, but can often be inserted in the forward or reverse orientation 5' or 3' to the coding sequence. Examples of enhancers include elements from the CaMV 35S promoter, octopine synthase genes (Ellis et al., 1987), the rice actin gene, and promoter from non-plant eukaryotes (e.g., yeast; Ma et al., 1988).

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

Constructs intended for expression from within a chloroplast or plastid utilizing chloroplast or plastid specific transcriptional and translational machinery can contain either mono- or polycistronic sequences.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *A. tumefaciens* described (Rogers et al., 1987). However, several other plant integrating vector systems are known to function in plants including pCaMVCN transfer control vector described (Fromm et al., 1985). pCaMVCN (available from Pharmacia, Piscataway, N.J.) includes the CaMV35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e. the chimeric gene containing the nopaline synthase promoter, Tn5 neomycin phosphotransferase II (nptII) and nopaline synthase 3' non-translated region described (Rogers et al., 1988).

Means for preparing expression vectors are well known in the art. Expression (transformation) vectors used to transform plants and methods of making those vectors are described in U.S. Pat. Nos. 4,971,908, 4,940,835, 4,769,061 and 4,757,011 (each of which is specifically incorporated herein by reference). Those vectors can be modified to include a coding sequence in accordance with the present invention.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer enhanced herbicide resistance enzymatic activity to a cell is preferably a polynucleotide encoding an AMPA transacylase or a functional equivalent, alone or in combination, with a gene encoding a GOX enzyme or a functional equivalent of GOX. In accordance with such embodiments, a coding region comprising the DNA sequence of SEQ ID NO:3, SEQ ID NO:7, or SEQ ID NO:19 is also preferred.

Specific genes encoding AMPA transacylase that have been shown to successfully transform plants in conjunction with plastid targeting peptide-encoding genes, to express the AMPA transacylase at sufficient herbicidally protective levels are those genes comprised within the plasmid vectors. Preferred plasmids containing plastid targeting sequences include pMON17261, pMON10151, pMON10149, pMON32570, pMON32571, pMON32572, pMON32573, pMON32926, pMON32931, pMON32932, pMON32936, pMON32938, pMON32946, pMON32947, pMON32948, and pMON32950. These plasmids contain polynucleotide sequences which encode node targeting sequences as shown in SEQ ID NO:9, SEQ ID NO:11, SEQ ID NO:13, SEQ ID NO: 14. Expression cassettes comprising plant operable promoters linked to coding sequences, some with and some without 5' untranslated sequences and/or intron sequences, wherein the coding sequences contain at least an AMPA transacylase or transacetylase, linked to plant operable termination sequences are disclosed in particular as set forth in SEQ ID NO:23, SEQ ID NO:25, SEQ ID NO:27, SEQ ID NO:29, and SEQ ID NO:31.

The work described herein has identified methods of potentiating in planta expression of an AMPA transacylase, which confer protection from glyphosate and related herbicides to plants when incorporated into the nuclear, plastid, or chloroplast genome of susceptible plants which also express a GOX or similar gene. U.S. Pat. No. 5,500,365 (specifically incorporated herein by reference) describes a method for synthesizing plant genes to optimize the expression level of the protein for which the synthesized gene encodes. This method relates to the modification of the structural gene sequences of the exogenous transgene, to make them more "plant-like" and therefore more likely to be translated and expressed by the plant. A similar method for enhanced expression of transgenes, preferably in monocotyledonous plants, is disclosed in U.S. Pat. No. 5,689,052 (specifically incorporated herein by reference). Agronomic, horticultural, ornamental, and other economically or commercially useful plants can be made in accordance with the methods described herein.

Such plants may co-express the AMPA transacylase gene and/or a GOX gene along with other antifungal, antibacterial, or antiviral pathogenesis-related peptides, polypeptides, or proteins; insecticidal proteins; other proteins conferring herbicide resistance; and proteins involved in improving the quality of plant products or agronomic performance of plants. Simultaneous co-expression of multiple heterologous proteins in plants is advantageous in that it can exploits more than one mode of action to control plant damage or improve the quality of the plant or products produced by the plants metabolism.

It is contemplated that introduction of large DNA sequences comprising more than one gene may be desirable. Introduction of such sequences may be facilitated by use of bacterial or yeast artificial chromosomes (BACs or YACs, respectively), or even plant artificial chromosomes. For example, the use of BACs for Agrobacterium-mediated transformation was disclosed by Hamilton et al. (1996).

Ultimately, the most desirable DNA sequences for introduction into a monocot genome may be homologous genes or gene families which encode a desired trait (for example, increased yield), and which are introduced under the control of novel promoters or enhancers, etc., or perhaps even homologous or tissue specific (e.g., root-collar/sheath-, whorl-, stalk-, earshank-, kernel- or leaf-specific) promoters or control elements. Indeed, it is envisioned that a particular use of the present invention may be the production of transformants comprising a transgene which is targeted in a tissue-specific manner. For example, herbicide resistance or herbicide tolerance genes may be expressed specifically or specifically regulated in a negative manner in the plants reproductive tissues which can provide a means for enhancing herbicide tolerance or sensitivity to those tissues. Such regulatory control means can provide methods for regulating the escape of transgenes into the environment or for controlling the illicit use of proprietary or licensed intellectual or commercialized property.

Vectors for use in tissue-specific targeting of gene expression in transgenic plants typically will include tissue-specific promoters and also may include other tissue-specific control elements such as enhancer sequences. Promoters which direct specific or enhanced expression in certain plant tissues will be known to those of skill in the art in light of the present disclosure.

It also is contemplated that tissue specific expression may be functionally accomplished by introducing a constitutively expressed gene (all tissues) in combination with an antisense gene that is expressed only in those tissues where the gene product is not desired. For example, a gene coding for the AMPA transacylase from *E. coli* may be introduced such that it is expressed in all tissues using the 35S promoter from Cauliflower Mosaic Virus. Alternatively, a rice actin promoter or a histone promoter from a dicot or monocot species also could be used for constitutive expression of a gene. Furthermore, it is contemplated that promoters combining elements from more than one promoter may be useful. For example, U.S. Pat. No. 5,491,288 discloses combining a Cauliflower Mosaic Virus promoter with a histone promoter. Therefore, expression of an antisense transcript of the AMPA transacylase gene in a maize kernel, using for example a zein promoter, would prevent accumulation of the transacylase in seed. Thus, in a plant expressing both GOX and the transacylase, application of glyphosate herbicide would result in seed tissues which fail to mature. Conversely, antisense suppression of the GOX gene would effectuate the same result. Preferably, suppression of the transacylase in specific tissues would be more advantageous, particularly where specific tissues have demonstrated an intolerance to AMPA or related compounds. It is specifically contemplated by the inventor that a similar strategy could be used with the instant invention to direct expression of a screenable or selectable marker in seed tissue.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may this be localized using the techniques of molecular biology known to those of skill in the art.

It is contemplated that expression of some genes in transgenic plants will be desired only under specified conditions. For example, it is proposed that expression of certain genes that confer resistance to environmentally stress factors such as drought will be desired only under actual stress conditions. It further is contemplated that expression of such genes throughout a plants development may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver and Mundy, 1990). It also is expected that expression of genes conferring resistance to applications of herbicides would be desired only under conditions in which herbicide is actually present. Therefore, for some desired traits, inducible expression of genes in transgenic plants will be desired.

It is proposed that, in some embodiments of the present invention, expression of a gene in a transgenic plant will be desired only in a certain time period during the development of the plant. Developmental timing frequently is correlated with tissue specific gene expression. For example expression of zein storage proteins is initiated in the endosperm about 15 days after pollination.

It also is contemplated that it may be useful to specifically target DNA insertion within a cell. For example, it may be useful to target introduced DNA to the nucleus, and in particular into a precise position within one of the plant chromosomes in order to achieve site specific integration. For example, it would be useful to have a gene introduced through transformation which acts to replace an existing gene in the cell, or to complement a gene which is not functional or present at all.

A plant transformed with an expression vector of the present invention is also contemplated. A transgenic plant derived from such a transformed or transgenic cell is also contemplated. Those skilled in the art will recognize that a chimeric plant gene containing a structural coding sequence of the present invention can be inserted into the genome of a plant by methods well known in the art. Such methods for DNA transformation of plant cells include Agrobacterium-mediated plant transformation, the use of liposomes, transformation using viruses or pollen, electroporation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as infection by A. tumefaciens and related Agrobacterium strains, direct delivery of DNA such as, for example, by PEG-mediated transformation of protoplasts (Omirulleh et al., 1993), by desiccation/inhibition-mediated DNA uptake, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation is well-known to those of skill in the art. To effect transformation by electroporation, one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner, rendering the cells more susceptible to transformation. Such cells would then be recipient to DNA transfer by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like. Using these particles, DNA is carried through the cell wall and into the cytoplasm on the surface of small metal particles as described (Klein et al., 1987; Klein et al., 1988; Kawata et al., 1988). The metal particles penetrate through several layers of cells and thus allow the transformation of cells within tissue explants. The microprojectile bombardment method is preferred for the identification of chloroplast or plastid directed transformation events.

An advantage of microprojectile bombardment, in addition to it being an effective means of reproducibly stably transforming plant cells, is that neither the isolation of protoplasts (Cristou et al., 1988) nor the susceptibility to Agrobacterium infection is required. An illustrative embodiment of a method for delivering DNA into plant cells by acceleration is a Biolistics Particle Delivery System, which can be used to propel particles coated with DNA or cells through a screen, such as a stainless steel or Nytex screen, onto a filter surface covered with the plant cultured cells in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature plant embryos.

Accordingly, it is contemplated that one may desire to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

The methods of particle-mediated transformation is well-known to those of skill in the art. U.S. Pat. No. 5,015,580 (specifically incorporated herein by reference) describes the transformation of soybeans using such a technique.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). The genetic engineering of cotton plants using Agrobacterium-mediated transfer is described in U.S. Pat. No. 5,004,863 (specifically incorporated herein by reference); like transformation of lettuce plants is described in U.S. Pat. No. 5,349,124 (specifically incorporated herein by reference); and the Agrobacterium-mediated transformation of soybean is described in U.S. Pat. No. 5,416,011 (specifically incorporated herein by reference). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant varieties where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al., 1987). Other monocots recently have also been transformed with Agrobacterium. Included in this group are corn (Ishida et al.) and rice (Cheng et al.).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

An independent segregant may be preferred when the plant is commercialized as a hybrid, such as corn. In this case, an independent segregant containing the gene is crossed with another plant, to form a hybrid plant that is heterozygous for the gene of interest.

An alternate preference is for a transgenic plant that is homozygous for the added structural gene; i.e. a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for gene of interest activity and mendelian inheritance indicating homozygosity relative to a control (native, non-transgenic) or an independent segregant transgenic plant.

Two different transgenic plants can be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see e.g., Potrykus et al., 1985; Lorz et al., 1985; Fromm et al., 1985; Uchimiya et al, 1986; Callis et al., 1987; Marcotte et al, 1988).

Application of these systems to different plant germplasm depends upon the ability to regenerate that particular plant variety from protoplasts. Illustrative methods for the regeneration of cereals from protoplasts are described (see, e.g., Fujimura et al, 1985; Toriyama et al, 1986; Yamada et al, 1986; Abdullah et al, 1986).

To transform plant germplasm that cannot be successfully regenerated from protoplasts, other ways to introduce DNA into intact cells or tissues can be utilized. For example, regeneration of cereals from immature embryos or explants can be effected as described (Vasil, 1988).

Unmodified bacterial genes are often poorly expressed in transgenic plant cells. Plant codon usage more closely resembles that of humans and other higher organisms than unicellular organisms, such as bacteria. Several reports have disclosed methods for improving expression of recombinant genes in plants (Murray et al., 1989; Diehn et al., 1996; Iannacone et al., 1997; Rouwendal et al., 1997; Futterer et al., 1997; and Futterer and Hohn, 1996). These reports disclose various methods for engineering coding sequences to represent sequences which are more efficiently translated based on plant codon frequency tables, improvements in codon third base position bias, using recombinant sequences which avoid suspect polyadenylation or A/T rich domains or intron splicing consensus sequences.

U.S. Pat. No. 5,500,365 (specifically incorporated herein by reference) describes the preferred method for synthesizing plant genes to optimize the expression level of the protein for which the synthesized gene encodes. This method relates to the modification of the structural gene sequences of the exogenous transgene, to make them more "plant-like" and therefore more likely to be translated and expressed by the plant, monocot or dicot. However, the method as disclosed in U.S. Pat. No. 5,689,052 provides for enhanced expression of transgenes, preferably in monocotyledonous plants, which is herein incorporated in its entirety by reference. Briefly, according to Brown et al., the frequency of rare and semi-rare monocotyledonous codons in a polynucleotide sequence encoding a desired protein are reduced and replaced with more preferred monocotyledonous codons. Enhanced accumulation of a desired polypeptide encoded by a modified polynucleotide sequence in a monocotyledonous plant is the result of increasing the frequency of preferred codons by analyzing the coding sequence in successive six nucleotide fragments and altering the sequence based on the frequency of appearance of the six-mers as to the frequency of appearance of the rarest 284, 484, and 664 six-mers in monocotyledenous plants. Furthermore, Brown et al. disclose the enhanced expression of a recombinant gene by applying the method for reducing the frequency of rare codons with methods for reducing the occurrence of polyadenylation signals and intron splice sites in the nucleotide sequence, removing self-complementary sequences in the nucleotide sequence and replacing such sequences with nonself-complementary nucleotides while maintaining a structural gene encoding the polypeptide, and reducing the frequency of occurrence of 5'-CG-3' di-nucleotide pairs in the nucleotide sequence. These steps are performed sequentially and have a cumulative effect resulting in a nucleotide sequence containing a preferential utilization of the more-preferred monocotyledonous codons for monocotyledonous plants for a majority of the amino acids present in the desired polypeptide.

Thus, the amount of a gene coding for a polypeptide of interest can be increased in plants by transforming those plants using transformation methods such as those disclosed herein. In particular, chloroplast or plastid transformation can result in desired coding sequences being present in up to about 10,000 copies per cell in tissues containing these subcellular organelle structures (McBride et al., Bio/Technology 13:362–365, 1995).

DNA can also be introduced into plants by direct DNA transfer into pollen as described (Zhou et al., 1983; Hess, 1987). Expression of polypeptide coding genes can be obtained by injection of the DNA into reproductive organs of a plant as described (Pena et al., 1987). DNA can also be injected directly into the cells of immature embryos and introduced into cells by rehydration of desiccated embryos as described (Neuhaus et al., 1987; Benbrook et al., 1986).

After effecting delivery of exogenous DNA to recipient cells, the next step to obtain a transgenic plant generally concern identifying the transformed cells for further culturing and plant regeneration. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

An exemplary embodiment of methods for identifying transformed cells involves exposing the transformed cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing. One example of a preferred marker gene confers resistance to glyphosate. When this gene is used as a selectable marker, the putatively transformed cell culture is treated with glyphosate. Upon treatment, transgenic cells will be available for further culturing while sensitive, or non-transformed cells, will not. This method is described in detail in U.S. Pat. No. 5,569,834, which is specifically incorporated herein by reference. Another example of a preferred selectable marker system is the neomycin phosphotransferase (nptII) resistance system by which resistance to the antibiotic kanamycin is conferred, as described in U.S. Pat. No. 5,569,834 (specifically incorporated herein by reference). Again, after transformation with this system, transformed cells will be available for further culturing upon treatment with kanamycin, while non-transformed cells will not. Yet another preferred selectable marker system involves the use of a gene construct conferring resistance to paromomycin. Use of this type of a selectable marker system is described in U.S. Pat. No. 5,424,412 (specifically incorporated herein by reference).

Another preferred selectable marker system involves the use of the genes contemplated by this invention. In particular, a phnO gene or a substantially similar gene encoding an AMPA transacylase can be utilized as a selectable marker. Plant cells which have had a recombinant DNA molecule introduced into their genome can be selected from a population of cells which failed to incorporate a recombinant molecule by growing the cells in the presence of AMPA. One skilled in the art will recognize the particular advantages that this selectable marker system has over previous selectable marker systems. The selectable marker used in the recombinant DNA integrated into a plant genome reduces the amount of DNA targeted for integration because the selectable marker will also be used for improved herbicide tolerance or improved herbicide resistance in plants generated from transformed plant cells. This selectable marker also provides an additional marker system not known before, particularly in a field in which there are often only a limited number of selectable markers available.

Transplastonomic selection (selection of plastid or chloroplast transformation events) is simplified by taking advantage of the sensitivity of chloroplasts or plastids to spectinomycin, an inhibitor of plastid or chloroplast protein synthesis, but not of protein synthesis by the nuclear genome encoded cytoplasmic ribosomes. Spectinomycin prevents the accumulation of chloroplast proteins required for photosynthesis and so spectinomycin resistant transformed plant cells may be distinguished on the basis of their difference in color: the resistant, transformed cells are green, whereas the sensitive cells are white, due to inhibition of plastid-protein synthesis. Transformation of chloroplasts or plastids with a suitable bacterial aad gene, or with a gene encoding a spectinomycin resistant plastid or chloroplast functional ribosomal RNA provides a means for selection and maintenance of transplastonomic events (Maliga, Trends in Biotechnology 11:101–106, 1993).

It is further contemplated that combinations of screenable and selectable markers will be useful for identification of transformed cells. In some cell or tissue types a selection agent, such as glyphosate or kanamycin, may either not provide enough killing activity to clearly recognize transformed cells or may cause substantial nonselective inhibition of transformants and nontransformants alike, thus causing the selection technique to not be effective. It is proposed that selection with a growth inhibiting compound, such as glyphosate at concentrations below those that cause 100% inhibition followed by screening of growing tissue for expression of a screenable marker gene such as kanamycin would allow one to recover transformants from cell or tissue types that are not amenable to selection alone. It is proposed that combinations of selection and screening may enable one to identify transformants in a wider variety of cell and tissue types. The availability of the transacylases of the present invention may obviate the necessity for combination selection and screening by providing an additional selection means.

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

In one embodiment, a transgenic plant of this invention thus has an increased amount of a coding region encoding an AMPA transacylase polypeptide which may also be expressed along with a plastid targeting peptide. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for expression of the transacylase transgene as well as for improved herbicide tolerance, particularly when the transacylase transgene is co-expressed along with a gene encoding a GOX enzyme.

The genes and acyltransferases according to the subject invention include not only the full length sequences disclosed herein but also fragments of these sequences, or fusion proteins, which retain the characteristic improved herbicidal protective activity of the sequences specifically exemplified herein.

It should be apparent to a person of skill in this art that AMPA transacylase genes and peptides can be identified and obtained through several means. The specific genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of such transacylases.

Equivalent AMPA transacylases and/or genes encoding these transacylases can also be isolated from *E. coli* strains and/or DNA libraries using the teachings provided herein. For example, antibodies to the transacylases disclosed and claimed herein can be used to identify and isolate other transacylases from a mixture of proteins. Specifically, antibodies may be raised to the transacylases disclosed herein and used to specifically identify equivalent AMPA transacylases by immunoprecipitation, column immunopurification, enzyme linked immunoassay (ELISA), or Western blotting.

A further method for identifying the peptides and genes of the subject invention is through the use of oligonucleotide probes. These probes are nucleotide sequences having a detectable label. As is well known in the art, if the probe molecule and sequences in a target nucleic acid sample hybridize by forming a strong bond between the two molecules, it can be reasonably assumed that the probe and target sample contain essentially identical polynucleotide sequences. The probe's detectable label provides a means for determining in a known manner whether hybridization has occurred. Such a probe analysis provides a rapid method for identifying AMPA transacylase genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxin, as well as enzymes such as hydrolyses or peroxidases, or the various chemiluminescers such as luciferin, or fluorescent compounds like fluorescein, rhodamine, Texas Red, and derivatives and the like. The probe may also be labeled at both ends with different types of labels for ease of separation, as, for example, by using an isotopic label at the end mentioned above and a biotin label at the other end, or with different fluorescent emitters which have overlapping absorption and emission spectra.

Duplex formation and stability depend on substantial complementary between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, more than one coding nucleotide triplet (codon) can be used for most of the amino acids used to make proteins. Therefore different nucleotide sequences can code for a particular amino acid. Thus, the amino acid sequence of the *E. coli* AMPA transacylase and peptide, and the plastid targeting peptides and the polynucleotides which code for them, can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of a gene encoding an AMPA acyltransferase and/or gene encoding a plastid targeting peptide, as discussed in the present invention. Such mutants can be made by techniques well known to persons skilled in the art. For example, UV irradiation can be used to prepare mutants of host organisms. Likewise, such mutants may include asporogenous host cells which also can be prepared by procedures well known in the art.

Site-specific or site-directed mutagenesis is a technique useful in the preparation of individual, novel and unique useful peptides, or biologically functional equivalent proteins or peptides, through specific mutagenesis of structural genes encoding such peptides. The technique further provides a ready ability to prepare and test sequence variants by altering the coding sequence of a gene, for example, by introducing one or more nucleotide sequence changes into the DNA for the purpose of creating a new or useful restriction endonuclease cleavage recognition sequence or for the purpose of altering the coding sequence so that a gene's codons and percent G/C represent those more commonly used by a particular genus or species. Site-specific mutagenesis allows the production of deletion, insertion, or replacement mutations through the use of specific mutagenesis oligonucleotide sequences comprising the DNA sequence of the desired mutation. Mutagenesis oligonucleotides typically provide a primer sequence of sufficient size and sequence complexity to form a stable duplex on both sides of the desired mutation target site. Typically, a primer of about 17 to 25 nucleotides in length is preferred, with about 5 to 10 residues overlapping either side of the desired mutation target site.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis, and often contain a filamentous phage origin of replication which, in the presence of a helper phage, allows synthesis of single stranded DNA from the plasmid vector.

In general, site-directed mutagenesis in accordance herewith is performed by first obtaining a single-stranded vector or melting apart of two strands of a double stranded vector which includes within its sequence a mutation target site. A mutagenesis oligonucleotide primer bearing the desired mutant sequence is prepared, generally synthetically. The mutagenesis primer is then annealed with the single-stranded vector at the mutation target site, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors containing the mutation represented by the mutagenesis primer sequence.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Such procedures may favorably change the protein's biochemical and biophysical characteristics or its mode of action. These include, but are not limited to: 1) improved AMPA transacylase formation, 2) improved protein stability or reduced protease degradation, 3) improved substrate recognition and binding, 4) improved enzyme kinetics, and 5) improved N-acyl-AMPA formation due to any or all of the reasons stated above.

Modification and changes may be made in the structure of the peptides of the present invention and DNA segments which encode them and still obtain a functional molecule that encodes a protein or peptide with desirable characteristics. The biologically functional equivalent peptides, polypeptides, and proteins contemplated herein should possess at least from about 40% to about 65% sequence similarity, preferably from about 66% to about 75% sequence similarity, more preferably from about 76% to about 85% similarity, and most preferably from about 86% to about 90% or greater sequence similarity to the sequence of, or corresponding moiety within, the AMPA acyltransferase amino acid sequences disclosed herein.

The following is a discussion based upon changing the amino acids of a protein to create an equivalent, or even an improved, second-generation molecule. In particular embodiments of the invention, mutated AMPA transacylase proteins are contemplated to be useful for improving or enhancing the in planta expression of the protein, and consequently increasing or improving the AMPA transacylase activity and/or expression of the recombinant transgene in a plant cell. The amino acid changes may be achieved by changing the codons of the DNA sequence, according to the codons given in Table 1, in dicotyledonous, and more particularly in monocotyledonous plants.

TABLE 1

| Amino Acid | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventor that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−7); serine (−8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Polynucleotides encoding heterologous proteins are known by those skilled in the art, to often be poorly expressed when incorporated into the nuclear DNA of transgenic plants (reviewed by Diehn et al., 1996). Preferably, a nucleotide sequence encoding a heterologous protein of interest is designed essentially as described in U.S. Pat. Nos. 5,500,365 and 5,689,052 (each specifically incorporated herein by reference). Examples of nucleotide sequences useful for expression include but are not limited to, SEQ ID NO:3, SEQ ID NO:7, SEQ ID NO:11, and SEQ ID NO:19.

Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within a fundamental polypeptide sequence can be made by substituting one amino acid within one of these groups with another amino acid within the same group. The encoding nucleotide sequence (gene, plasmid DNA, cDNA, or synthetic DNA) will thus have corresponding base substitutions, permitting it to encode biologically functional equivalent forms of an AMPA transacylase.

The following examples describe preferred embodiments of the invention. Other embodiments within the scope of the claims herein will be apparent to one skilled in the art of endeavor from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLES

Example 1

This example illustrates the growth inhibitory effects of N-aminomethyl phosphonic acid (AMPA) on plant callus tissue, and the lack of inhibition of N-acetyl-aminomethyl phosphonic acid on plant callus tissue in in vitro culture conditions.

Certain recombinant plant species which express a bacterial GOX gene, and which were also exposed to glyphosate, can exhibit phytotoxic effects manifested through such symptoms as chlorosis, flower abscission, and reduced fertility. The basis for these symptoms had not previously been determined. Previous studies had indicated that plants expressing GOX metabolized glyphosate to AMPA and glyoxylate (U.S. Pat. No. 5,463,175). Glyoxylate is readily metabolized by plants, however AMPA persists in plant tissues and may be the cause of phytotoxic effects such as chlorosis, stunting, or other undesireable effects. It had previously been shown that Achromobacter species LBAA was able to enzymatically modify AMPA to N-acetyl AMPA (U.S. Pat. No. 5,463,175). The Achromobacter data, coupled with the plant phytotoxicity data, indicated that N-acylation of AMPA in planta may provide effective relief from chlorosis and other undesireable effects. Thus, tobacco callus tissue was exposed to AMPA and to N-acetyl AMPA in order to determine if either of these compounds exhibited cytotoxic effects similar to those observed in plants expressing GOX and exposed to glyphosate.

Tobacco callus was generated from leaf pieces of wild type *Nicotiana tabacum* cv. "Samsun" tobacco on MS104 plates (MS salts 4.3 g/l, sucrose 30 g/l, B5 vitamins 500× 2 ml/l, NAA 0.1 mg/l, and Bacto Agar 1.0 mg/l). Callus tissue was applied to plates with or without AMPA and with or without N-acetyl AMPA. Plates contained AMPA or N-acetyl AMPA at concentrations of 0.1 mM or 0.4 mM. Plates were incubated for up to three weeks and monitored periodically.

Callus tissue on control plates containing no AMPA or N-acetyl AMPA grew at normal rates, regenerating roots and shoots as expected. Callus tissue in the presence of AMPA was severely inhibited. No growth was observed, showing the phytotoxic effect of AMPA at these concentrations. Callus tissue on plates containing N-acetyl AMPA was not inhibited, and formed roots and shoots similar to control callus tissue growth. This result indicated that AMPA, as a byproduct of GOX mediated metabolism of glyphosate, could be responsible for the observed phototoxicity in plants. This result also indicated the possibility of an improved method for selecting plants from genetically transformed callus tissue, as well as a possible method for enhancing glyphosate herbicide resistance.

Example 2

This example illustrates that degradation of glyphosate by GOX enzyme hydrolysis in the bacterium Achromobacter sp. strain LBAA results in the production of AMPA and N-acetyl AMPA.

It has been previously shown that GOX mediated glyphosate degradation produced glyoxylate and AMPA (Barry et al., U.S. Pat. No. 5,463,175). Achromobacter sp. strain LBAA was also shown to produce AMPA and glyoxylate as a result of glyphosate degradation. The glyphosate degradation pathway was characterized in resting cells of glyphosate-grown Achromobacter sp. strain LBAA according to the following procedure. Cells from a 100 ml culture of LBAA, grown in DF3S medium containing glucose, gluconate and citrate as carbon sources and with thiamine and Yeast Extract (0.01%) to supply trace requirements and with glyphosate at 0.2 mM as a phosphorous source, were harvested at a cell density of 200 Klett units, washed twice with 20 ml of DF3S medium and the equivalent of 20 ml of cells were resuspended in 100 µl of the same medium containing [$^{14}$C]glyphosate (2.5 ml of 52 mCi/mmol, Amersham; CFA.745). The cell mix was incubated at 30° C. with shaking and 20 ml samples were withdrawn at various intervals. The samples were centrifuged to separate the cells from the broth supernatant. Both the supernatant and cell pellets were analyzed by HPLC.

Samples prepared in this way were analyzed by strong anion exchange (SAX) HPLC with radioisotope label detection to determine their levels of [$^{14}$C]-AMPA and N-acetyl-[$^{14}$C]-AMPA. Samples were injected using a Waters WISP autoinjector. Chromatographic profiles and quantitative data were collected using MACS2, Monsanto's automated chromatography data collection system. A Spherisorb S5 SAX, 250 mm×10 mm column, or an Alltech 5 micron, 250 mm×10 mm SAX column was used for the analyses. Solvents used were designated as solution A and solution B. Solution A contained 0.005M $KH_2PO_4$ adjusted to pH 2.0 with $H_3PO_4$ in 4% methanol. Solution B contained 0.10 M $KH_2PO_4$ adjusted to pH 2.0 with $H_3PO_4$ in 4% methanol. Each sample run time consisted of a step gradient program with an eluent flow rate of 3 ml per minute and a scintillation fluid (tradename ATOMFLOW, No. NEN-995 obtained from Packard Instruments) flow rate of 9 ml per minute. The HPLC solvent profile for distinguishing [$^{14}C$]-AMPA from N-acetyl-[$^{14}C$]-AMPA in each sample analyzed was represented by 100% solvent A at times zero through 5 minutes, then solvent B at 100% at time 5 minutes through 15 minutes, then 100% solvent A through 20 minutes at which time the column is prepared to receive another sample.

Cell pellets were first resuspended in DF3S medium made acidic by addition of 0.65N HCl, boiled for 5 minutes, then centrifuged briefly to provide a solution phase for HPLC analysis. Supernatants were treated similarly prior to HPLC analysis. An acidified glyphosate control was also subjected to HPLC analysis, and the glyphosate retention time (RT) was determined to be 10.8 minutes. The amount of radioactivity in the glyphosate peak remaining in the supernatant after two hours incubation had decreased to about 33% of the initial levels, indicating that the glyphosate was extensively metabolized. About 3% of the glyphosate was found to be within the cell. Material co-eluting with the methylamine standard with an RT of 6 minutes accounted for about 5% of the initial amount of radioactivity in the supernatant and for about 1.5% of the initial amount of radioactivity identified in the cell contents.

The GOX mediated glyphosate degradation pathway was elucidated further in a subsequent experiment where the metabolism of [$^{14}C$]AMPA was compared to that of [$^{14}C$] glyphosate as indicated above in resting cells harvested at 165 Klett units and resuspended at the equivalent of 15 ml cells per 100 ml DF3S medium. The samples were analyzed by HPLC and consisted of whole cultures acidified and treated as described above. Cultures exposed to [$^{14}C$] glyphosate for two hours were found to have 25% of the label in the methylamine/N-acetyl-methylamine peak with a retention time of 14.7 minutes, 12.5% as AMPA with a retention time of 6 minutes, 30% in a peak with a retention time of 13.2 minutes, and 30% as glyphosate with a retention time of 10.8 minutes. Analysis of cultures exposed to [$^{14}C$]-AMPA for two hours indicated that 15% of the label was found as N-acetyl-methylamine/methylamine, 59% as AMPA, and 18% in the 13.2 minute peak. The material eluting at 13.2 minutes was identified as N-acetyl-AMPA by negative ion electrospray mass spectrometry. The result showed strong ions at m/e 152 and m/e 154, as expected for this compound, which has a molecular weight of 153 Daltons. The m/e 154 ion was due to the isotopic $^{14}C$ atom. N-acetyl-methyl-[$^{14}C$]-AMPA arises from N-methyl-[$^{14}C$]-AMPA, which is a known impurity in preparations of [$^{14}C$]-AMPA.

These data indicated that the glyphosate degradation pathway in Achromobacter strain LBAA proceeds from hydrolysis of glyphosate to AMPA, which is then converted to the products methylamine presumably through a dephosphorylation step, and N-acetyl-AMPA presumably through some previously unknown transacylation step. A small amount of N-acetyl-AMPA is then converted to N-acetyl-methylamine. A similar acylation step has been inferred from the products identified in E. coli when aminomethylphosphonates are utilized as sole sources of phosphate (Avila et al., 1987).

Example 3

This example illustrates the identification of an AMPA acyltransferase activity in E. coli.

Avila et al. (1987) identified dephosphorylated biodegradation products from the metabolism of a variety of aminophosphonate substrates used as sole phosphate sources in vivo in E. coli while studying C—P bond scission. Their studies indicated that AMPA was not a substrate for acylation in E. coli K-12. In addition, Avila et al. were interested in the effect of N-linked chemical substitutions on C—P bond scission of phosphonates in E. coli, and identified N-acetylated products derived from the metabolism of some aminophosphonates. Avila et al. also demonstrated that 'wild type' E. coli K12 strains, unlike wild type E. coli B strains, are unable to use phosphonates as a source of phosphate. Thus, in consideration of the phytotoxic effects of AMPA on callus tissue as shown in Example 1 and the generation of AMPA from GOX mediated glyphosate degradation as shown in Example 2, the E. coli data in Avila et al. indicated that there may be an enzyme or pathway present in some bacterial species which is capable of converting aminomethylphosphonate (AMPA) to N-acetyl-AMPA. An enzyme or pathway with those characteristics would, if expressed in plants, confer a significant advantage to plants expressing GOX when treated with glyphosate.

To test this, an i E. coliK-12 strain adapted for growth on AMPA was grown on low phosphate containing medium in order to obtain cell lysates to be assayed for the presence of an enzyme capable of AMPA N-acylation. The phn (mpu) operon is cryptic in E. coli K-12 due to an 8 base pair insertion which causes a frameshift mutation in the phnE gene. The frameshift inactivates PhnE and creates a polar effect on translation of other genes downstream of phnE within the operon, resulting in the inability of such mutants to use phosphonates as phosphate sources (Makino et al., J. Bacteriol. 173:2665–2672, 1991). Selection of a spontaneously derived mutation restores the function of the phn operon (phn+or mpu+). Thus, K-12 strains adapted for growth on AMPA, methyl-phosphonate, or ethyl-phosphonate contain such effective spontaneously derived mutations.

Briefly, an aliquot of a fresh L-broth culture of E. coli K-12 strain JM101 (mpu–) was plated onto MOPS (Neidhardt et al., 1974) complete agar medium containing amino acids at 25 mg/ml, vitamin B1 [thiamine] at 10 mg/ml, 0.2% glucose, and 1.5% DIFCO "Purified" agar along with aminomethylphosphonate (AMPA; 0.2 mM; Sigma Chemical Co., St. Louis, Mo.) as the sole phosphate source, and incubated at 37° C. for three days. Colonies arising on this media were picked and streaked onto MOPS complete agar containing either AMPA or methylphosphonate (Alfa) as the sole phosphate source. One colony, designated E. coli JM101 mpu+, was chosen from those that grew equally and uniformly on both phosphonate containing media, and was further designated as E. coli strain GB993.

The phn operon is induced when E. coli is grown in media lacking or limited in a phosphate source. Therefore, E. coli GB993 was compared to the parental JM101 strain when grown in MOPS minimal media. GB993 and its mpu– parent strain, JM101, were grown under identical conditions, varying only the amount of phosphate available or supplemented with AMPA. 50 ml cultures were grown in duplicate in 250 ml sidearm-Erlenmeyer flasks with continuous shaking at 37° C. in MOPS medium (5 mls of 10× MOPS salts, 0.5 ml 1 mg/ml thiamin, 0.5 ml 20% glucose, to 50 mls with $dH_2O$) containing 0.1 or 5 mM phosphate, or 0.1 mM phosphate supplemented with approximately 0.2 mM AMPA, pH 7.0. The cultures were generally grown to about 220 Klett units and the cells were pelleted by centrifugation, resuspended in 1.5 mls of 10 mM Tris/l mM DTT, and lysed with two passes through a French press at 1,000 psi. Lysates were centrifuged to remove debris and the supernatant passed through a G-50 column equilibrated with 50 mM Tris pH 7.0. Table 2 shows the results of cell cultures grown in this manner.

TABLE 2

Effects of Phosphate Substrate on Cell Growth

| | Strain | | | | | |
|---|---|---|---|---|---|---|
| | JM101 0.1 mM Phosphate | JM101 5 mM Phosphate | JM101 0.2 mM AMPA | GB993 0.1 mM Phosphate | GB993 5 mM Phosphate | GB993 0.2 mM AMPA |
| Growth Period (hrs) | 48 | 29 | 54 | 48 | 29 | 54 |
| Harvest Density (Klett Units) | 155 | 240 | — | 140 | 244 | 185 |

— indicates no measurable growth

An HPLC assay was used to determine the presence or absence of any AMPA acyltransferase activity in the media and cell lysates. The assay monitors the conversion of [$^{14}$C]AMPA to N-acetyl-[$^{14}$C] AMPA. Generally, 100 µl of a 2× assay solution consisting of 16.5 mg acetyl-CoA, 250 µl of 2M Tris, pH 7.5, 4.5 mls dH$_2$O and [$^{14}$C]AMPA (30 mM) was mixed with 25–75 pl of lysate and 1 µl each of 0.5 M MgCl$_2$ and MnCl$_2$, and brought to 200 µl with dH$_2$O. The assay was incubated for 30 minutes at 37° C., and quenched with 200 µl 90–100 mM NaOAc (sodium acetate) pH 4.4 in ethanol and then analyzed immediately by HPLC as described above, or stored at −20° C. Only GB993 lysate samples derived from cultures grown in the presence of AMPA or 0.1 mM phosphate supplemented media demonstrated appreciable AMPA acyltransferase activity. This result indicated that a gene encoding an acyltransferase enzyme capable of AMPA N-acylation was present in GB993 and was regulated for expression when grown under low phosphate conditions. Thus, the coding sequence for the enzymatic activity appears to be part of the pho regulon and may reside in the phn operon.

Example 4

This example illustrates the identification of an *E. coli* phn operon gene encoding an enzyme capable of AMPA acylation.

Example 3 indicated that the AMPA acyltransferase activity observed in lysates of *E. coli* may be encoded by a gene in the phn operon. The entire phn operon in *E. coli* B and in *E. coli* K-12 has previously been cloned and sequenced (Wanner et al., Chen et al.). The *E. coli* K-12 phn operon DNA sequence has been shown to be identical to the published DNA sequence of the phn operon from *E. coli* B with the exception of an eight base pair insertion in the phnE gene (Wanner et al). Clones containing various amounts of the phn operon genes from either bacterial genetic background are readily available (Wanner et al., Chen et al., Dr. J. W. Frost at Purdue University). Plasmids containing differing amounts of the JM101 phn operon DNA were used to transform JM101(mpu−) in order to test for a plasmid localized phn gene that, when expressed, confers upon JM 101 the ability to utilize AMPA as a sole phosphate source.

A plasmid obtained from J. Frost (Dr. J. W. Frost, Department of Chemistry, Purdue University, West Lafayette, Ind. 47907), designated herein as pF, contains an *E. coli* K-12 8 kb EcoRI fragment which encodes the phn operon genes phnG through phnQ. A single NcoI site is present at the 5' end of the phnG coding region. Plasmid pF was digested with EcoRI and NcoI, releasing a 2 kb NcoI-EcoRI fragment containing the genes phnG through phnI, and a second NcoI-EcoRI fragment about 6 kb in length containing the genes phnJ through phnQ. Each fragment was gel purified and ligated into a cloning and expression vector in an orientation which would allow for expression of the phn operon genes present within each of the NcoI-EcoRI fragments from a plasmid borne inducible promoter. The 2 kb fragment was inserted into the NcoI-EcoRI sites within the vector pMON7258, a positive selection cloning vector identical to pUC118 with the exception of polylinker domain (Viera et al., Methods Enzymol. 153:3, 1987), the resulting plasmid being designated as p58-1. The orientation of the 2 kb fragment in p58-1 allows for the expression of the phnG-phnI genes from the lac promoter within the vector. The 6 kb EcoRI-NcoI fragment was inserted into the NcoI and EcoRI sites in a similar positive selection vector, pMON7259, producing the plasmid designated as pMON17195. pMON7259 is identical to pUC119 except for the polylinker domain, which contains a multiple cloning site opposite in orientation to that within pMON7258, and which also allows for expression of the phnJ-phnQ genes from a lac promoter. p58-1 and pMON7259 were transformed into *E. coli* K12 (mpu−) strain JM101, and maintained with ampicillin antibiotic resistance selection. pMON7259 and pF were also transformed into JM 101 as negative and positive controls, respectively.

Cultures of each transformant were grown overnight in M9 liquid broth media supplemented with 2% casamino acids, thiamine, and 0.2% glucose with shaking at 37° C., and then diluted 1:50 into 50 ml of fresh pre-warmed media of the same composition in a 250 ml side-armed Erlenmeyer flask. Cultures were incubated with shaking at 37° C. until reaching a cell density of about 80–100 Klett Units as measured on a Klett-Summerson spectrophotometer through a #2 green filter. Expression from the plasmid lac promoter was induced by the addition of 100 microliters of 500 mM IPTG so that the final IPTG concentration was about 1 mM. The induction phase growth period was allowed to progress for two hours. Table 3 shows the cell density profile of each culture from 1:50 dilution through the two hour induction period.

TABLE 3

Induction Profile of JM101 Cultures Harboring Various phn Plasmids

| Culture/Plasmid | IPTG | $I_0$ | $I_1$ | $I_2$ |
|---|---|---|---|---|
| pMON7259 | + | 13 | 75 | 222 |
| p58-1 | + | 15 | 70 | 212 |
| pMON17195 | + | 15 | 90 | 220 |

TABLE 3-continued

Induction Profile of JM101 Cultures Harboring Various phn Plasmids

| Culture/<br>Plasmid | IPTG | $I_0$ | $I_1$ | $I_2$ |
|---|---|---|---|---|
| pF | + | 17 | 97 | 290 |
| pF | — | 15 | — | 260 |

$I_0$ indicates the cell culture density at the 1:50 dilution time point; $I_1$ indicates the cell culture density at the time of IPTG addition; and $I_2$ indicates the cell culture density at the time of harvest.

The cells in each culture were harvested by centrifugation at 10,000 rpm for 10 minutes at 4° C. in a Beckman J2 centrifuge. The cell pellet was washed one time in ice cold 154 mM NaCl solution, and then resuspended in 1.5 ml extraction buffer (50 mM Tris-HCl pH 7.5, 1 mM DTT, 50 mM Tris-HCl pH 7.5). Cell suspensions were ruptured with two passes through a French Press at 1000 psi. The resulting lysate was centrifuged for 15 minutes at 14,000 rpm at 4° C. in an EPPENDORF™ model 5402 microcentrifuge in order to remove debris. Each cleared lysate was transferred to a fresh pre-chilled tube and the volume of the extract was adjusted to 2.5 ml with 50 mM Tris-HCl pH 7.5. A PD10 column was equilibrated with 25 ml 50 mM Tris-HCl, pH 7.5 and then each sample was applied to the desalting column. Each eluted sample was adjusted to 3.5 ml with 50 mM Tris-HCl, pH 7.5. Each sample was distributed to assay tubes and mixed with reagents in order to assay for the presence of AMPA acyltransferase activity as shown in Table 4.

TABLE 4

Assay Conditions for Bacterial Lysates Expressing phn Genes

| Sample | IPTG | Extract Volume* | 50 mM Tris Volume* | 2X Assay Mix Volume* | Total Volume* |
|---|---|---|---|---|---|
| pMON7259 | + | 25 | 75 | 100 | 200 |
| pMON7259 | + | 100 | 0 | 100 | 200 |
| p58-1 | + | 25 | 75 | 100 | 200 |
| p58-1 | + | 100 | 0 | 100 | 200 |
| pMON17195 | + | 25 | 75 | 100 | 200 |
| pMON17195 | + | 100 | 0 | 100 | 200 |
| pF | + | 25 | 75 | 100 | 200 |
| pF | + | 100 | 0 | 100 | 200 |
| pF | — | 25 | 75 | 100 | 200 |
| pF | — | 100 | 0 | 100 | 200 |
| — | na | 0 | 100 | 100 | 200 |

*all volumes are in microliters
Composition of mixtures of each sample, designated by plasmid content, as prepared for AMPA acyltransferase assay.

Each mixture was incubated at 37° C. for 30 minutes, and quenched with an equal volume (200 microliters) of 90–100 mM NaOAc (sodium acetate), pH 4.4 in ethanol and if not analyzed immediately by HPLC as described above, then stored overnight at −20° C.

Unused portions of each lysate were stored either at 4° C., or mixed with glycerol to 10% by volume, and stored at −20° C.

Samples of each lysate subjected to the AMPA transacylase assay were analyzed by HPLC for the presence of [$^{14}$C]AMPA and acylated [$^{14}$C]AMPA, as described above. The results are shown in Table 5.

TABLE 5

HPLC Analysis of Bacterial Lysate
Conversion of AMPA to Acetyl-AMPA

| Sample | % Acetyl AMPA | % AMPA |
|---|---|---|
| pMON7259 | no data | no data |
| pMON7259 | 8 | 92 |
| p58-1 | 5 | 95 |
| p58-1 | 13 | 87 |
| pMON17195 | 100 | 0 |
| pMON17195 | 100 | 0 |
| pF | 61 | 39 |
| pF | 97 | 3 |
| pF | 52 | 48 |
| pF | 90 | 10 |
| — | — | 100 |

Results of HPLC analysis of each sample, indicating the relative amount of [$^{14}$C] AMPA or acetyl-[$^{14}$C] AMPA as a percentage of the total amount of [$^{14}$C] in both peaks combined.

This data indicated that the plasmid containing the 6 kb NcoI-EcoRI fragment isolated from pF in pMON17195 contained one or more genes which, upon IPTG induction of the lac promoter in an mpu− strain of E. coli, elicited the production of an acyltransferase activity capable of converting all of the [$^{14}$C]AMPA available in the assay mix to acetyl-[$^{14}$C]AMPA. The gene or genes required for AMPA N-acylation were further defined by restriction deletion analysis.

Plasmids containing various segments of the phn operon from either E. coli B or E. coli K-12 were constructed to further delineate the nature of the phn operon gene or genes involved in conferring AMPA acyltransferase activity when expressed in an mpu− E. coli JM101. pMON7333 contains the pMON17195 equivalent E. coli DNA insertion, but in pUC 119, and is a single E. coli B strain HindIII fragment containing the wild type phn operon genes phnG through phnQ. pMON15020 was constructed by cloning a 5,713 base pair NcoI to EcoRI E. coli B DNA fragment from pMON7333 into pMON7259, and contains the genes phnJ through phnQ. pMON15022 was constructed by inserting a 1,686 base pair EcoRI to SalI fragment from pMON17195 into the positive selection cloning and expression vector pBlueScriptSP (Invitrogen), which contains the E. coli K-12 genes phnO, P and Q. pMON15023 was constructed by deleting an 1,820 base pair SalI fragment from pMON17195, leaving behind the E. coli K-12 phn operon genes phnJ and phnK, the 5' end of phnL, and all of phnO, P and Q.

The plasmids pMON17195, pMON15020, pMON15022, pMON15023, and pMON7259 were transformed into the mpu−0 E. coli K-12 strain JM101 and were maintained by ampicillin antibiotic selection. Overnight cultures of each of these transformants were grown with antibiotic selection and were diluted 1:50 into fresh M9 media as described above, and incubated at 37° C. with shaking in 250 ml sidearm-Erlenmeyer flasks to a cell density of about 100 Klett units. Each culture was induced with IPTG as in example 3, and incubated for two additional hours with shaking. The cells were harvested by centrifugation in a Beckman J2 centrifuge at 4,000 RPM for 10 minutes at 4° C. Cell pellets were washed once with 50 ml of 154 mM NaCl, and stored at −20° C.

Cell pellets were resuspended in 1.5 ml Extraction Buffer as in example 3 and ruptured by two passes through a French Press at 1000 psi. The ruptured cell suspensions were centrifuged in an Eppindorf microcentrifuge Model 5402 for 15 minutes at 14,000 rpm and at 4° C. The cleared lysates were decanted into new tubes pre-chilled on ice, and the total volume was adjusted to 2.5 ml with addition of Extraction Buffer. These samples were desalted over a PD10 column pre-equilibrated with 25 ml of 50 mM Tris-HCl, pH 7.5, and eluted with 3.5 ml of 50 mM Tris HCl pH 7.5. Samples were then subjected to an AMPA acylation assay as described above, incubated for 30 minutes at 37° C., and quenched with 200 microliters of 90.9 mM NaOAc pH 4.4. The volumes of each sample used in the assay are noted in Table 6. All volumes represent microliters of each solution used.

TABLE 6

Assay Conditions for Bacterial Lysates Expressing phn Genes from Plasmids

| Plasmid | Extract | 50 mM Tris | 2X Assay Mix | Total Volume |
|---|---|---|---|---|
| — | — | 100 | 100 | 200 |
| pMON 17195 | 25 | 75 | 100 | 200 |
| pMON 17195 | 100 | — | 100 | 200 |
| pMON 15020 | 75 | 75 | 100 | 200 |
| pMON 15020 | 100 | — | 100 | 200 |
| pMON 15022 | 75 | 75 | 100 | 200 |
| pMON 15022 | 100 | — | 100 | 200 |
| pMON 15023 | 75 | 75 | 100 | 200 |
| pMON 15023 | 100 | — | 100 | 200 |
| pMON 7259 | 75 | 75 | 100 | 200 |
| pMON 7259 | 100 | — | 100 | 200 |

Composition of mixtures of each sample, designated by plasmid content, as prepared for AMPA acyltransferase assay Quenched samples were subjected to HPLC analysis as described above. Table 7 illustrates the results of HPLC analysis of each sample, indicating the relative amount of [$^{14}$C) AMPA or acetyl-[$^{14}$C]AMPA as a percentage of the total amount of [$^{14}$C] in both peaks combined.

TABLE 7

HPLC Analysis of Bacterial Lysate [$^{14}$C]-AMPA Conversion to Acetyl-[$^{14}$C]-AMPA

| Sample | Extract Volume | % [$^{14}$C]-AMPA | % Acetyl-[$^{14}$C]-AMPA | Total % [$^{14}$C] |
|---|---|---|---|---|
| — | — | 100 | — | 100 |
| pMON17195 | 25 | 66 | 34 | 100 |
| pMON17195 | 100 | 26 | 74 | 100 |
| pMON15020 | 75 | — | 100 | 100 |
| pMON15020 | 100 | — | 100 | 100 |
| pMON15022 | 75 | — | 100 | 100 |
| pMON15022 | 100 | — | 100 | 100 |
| pMON15023 | 75 | — | 100 | 100 |
| pMON15023 | 100 | — | 100 | 100 |
| pMON 7259 | 75 | 87 | 13 | 100 |
| pMON 7259 | 100 | 72 | 28 | 100 |

HPLC analysis of each sample, indicating the relative amount of [$^{14}$C] AMPA or acetyl-[$^{14}$C]AMPA as a percentage of the total amount of [$^{14}$C] in both peaks combined The data in Table 7 indicates that AMPA acylation activity is derived from the phn operon open reading frames consisting of phnO, phnP, and phnQ, which are the only phn genes present in pMON15022. Other plasmids conferring AMPA acylation activity upon induction also contained at least the phnO, P, and Q genes, providing strong evidence that the observed activity was the result of one or more of these gene products. Therefore, additional plasmids were constructed based on the phnO, P, and Q gene sequences in order to determine which gene or genes were required for the acylation function.

Bacterial acylase, transacylase, and acyltransferase genes have been known in the literature for some time. Most are small 15–25 K Da proteins. Therefore, on the basis of size comparison, only the phnO and phnQ gene products would fall into this category. However, based on similarity comparisons with other proteins in the GENBANK, SWISSPROT, and EMBL databases, the predicted phnO gene product appeared to most closely resemble other proteins having acylase activity. For example, the E. coli PhnO protein aligned well with a gentamicin acetyltransferase-3-I described in Wohlleben et al. (Mol. Gen. Genet. 217:202–208, 1989). pMON15020 containing the E. coli B phn operon genes phnJ through phnP on a single 6.0 kb NcoI-EcoRI fragment was digested with SalI and EcoRI to release a 2.0 kb fragment containing the phnO, P and Q genes. This 2 kb fragment was excised and purified from a 0.7% TAE Agarose gel, treated with T4 DNA polymerase to excise the 3' overhanging ends, then with Klenow and deoxynucleotide triphosphates (dXTP's) to provide blunt ends, and then ligated into the EcoRV site of pBlueScriptSP to produce plasmid pMON15024. pMON15024 was digested with NdeI and EcoRI, deleting a 1200 base pair fragment containing most of the phnP and all of the phnQ coding sequences. The remaining pMON15024 plasmid fragment still containing the phnO gene was treated with Klenow fragment DNA polymerase in the presence of dideoxynucleotides according to the manufacturer's instructions in order to fill in the 3' ends exposed by restriction enzyme digestion, then ligated together to produce the plasmid pMON15027. pMON15027 contains only the phnO gene flanked 3' by a small portion of phnP. The 1200 base pair NdeI to EcoRI fragment obtained from pMON15024 was cloned into pMON2123 to produce pMON15026, which contains the 3' two thirds of the phnP gene flanked 3' by phnQ. Plasmids pMON15024, 15026, and 15027 were introduced into mpu– JM101, and cell lysates of transformants were analyzed as above after growth and induction for the presence of AMPA acyltransferase activity. Only pMON15024 and pMON15027 exhibited acyltransferase activity, indicating that the phnO gene product was responsible for AMPA acylation.

A DNA fragment containing only the phnO gene with convenient flanking restriction endonuclease sites for use in further cloning manipulations was produced using thermal cycling methods. Synthetic oligonucleotide primers were synthesized by Midland Certified Reagents, Co. (Midland Tex.) based on the published phnO gene and flanking sequence in order to amplify the phnO gene (Chen et al., J. Biol. Chem. 256: 4461–4471, 1990). The sequence AAA-CACCATGGCTGCTTGTG (SEQ ID NO: 5), designated AATPCR6, represents a synthetic oligonucleotide which is homologous to the template strand of the phnO gene. The 5' adenosine residue of SEQ ID NO: 5 corresponds to base pair 13,955 of the published phn operon sequence, immediately 5' of the phnO ATG initiation codon at position 13,962–13, 964 (Chen et al., J. Biol. Chem. 256: 4461–4471, 1990). SEQ ID NO: 5 incorporates a single base pair mismatch from the published phnO sequence at position 13,965 represented by a C to G inversion, which generates an alanine codon in place of a proline codon at position 2 and also creates a unique NcoI restriction site spanning the ATG initiation codon. The sequence GTGACGAATTCGAGCT-CATTACAGCGCCTTGGTGA (SEQ ID NO: 6), designated AATPCR7, represents a synthetic oligonucleotide which is homologous to the coding strand of the phnO gene. The 3' adenosine residue of SEQ ID NO: 6 corresponds to base pair 14,380 of the published phn operon (Chen et al., J. Biol. Chem. 256: 4461–4471, 1990). The thymidine at position number nineteen of SEQ ID NO: 6 corresponds to the adenosine at position 14,396 of the published phnO sequence (Chen et al.). A portion of SEQ ID NO: 6 overlaps the native phnO termination codon, introduces a second in frame termination codon immediately 3' of and adjacent to the native termination codon, and also introduces unique EcoRI and SacI restriction sites 3' of these termination codons.

pMON15024 was used as a template for amplification of the phnO gene in a standard thermal amplification reaction. Briefly, a 100 microliter reaction sample was prepared which contained 0.1 ng template DNA, reaction buffer, 200 pM each primer, 200 mM dNTP, 1.25 U Taq DNA polymerase and was overlayed with mineral oil. This reaction sample was subjected to thirty five cycles at 94° C. for one minute, 50° C. for two minutes, and 72° C. for three minutes which resulted in the amplification of a 459 base pair DNA product as determined by analysis of five microliters of the reaction sample on a ethidium bromide stained 0.7% TAE agarose gel. A 444 base pair product was purified using standard methods from a 1% TAE agarose gel after digestion of a sample of the 459 base pair amplification product with NcoI and EcoRI restriction endonucleases. The 444 base pair product was ligated into compatible sites in pMON7259 to generate pMON15028. Cell lysates prepared as above from IPTG induced cultures of JM101 containing pMON15028 were analyzed for the presence of AMPA acyltransferase activity and compared to cultures containing pMON15027. The results were indistinguishable, thus confirming that phnO encoded an enzyme capable of AMPA acylation. In addition, this result indicated that the P2A mutation in the protein, which was introduced into the gene coding sequence as a result of thermal amplification using the AATPCR6 oligonucleotide primer (SEQ ID NO: 5), was without effect on the acyltransferase activity of the resulting PhnO protein when expressed in E. coli.

Example 5

This example illustrates the production of polyclonal antibodies directed to the PhnO peptide.

Further studies of the phnO gene product required the use of antibodies directed to the PhnO protein. Therefore, PhnO was overproduced in E. coli JM101 for for use as an immunogen in stimulating the production of antibodies upon injection into a goat. The phnO gene containing the P2A mutation in plasmid pMON15028 was introduced into plasmid pMON17061 on an NcoI to EcoRI DNA fragment, producing pMON15032. phnO expression in pMON15032 is under the control of the E. coli recA promoter adjacent to the bacteriophage T7 gene 10L ribosome binding sequence. Cells were grown to mid log phase and induced by addition of nalidixic acid to the culture to approximately 50 parts per million, from a stock solution of 50 mg nalidixic acid powder dissolved in 1 ml 0.1 N NaOH. The culture was maintained under inducing conditions for twelve hours at 37° C. Cells were harvested as described in example 3, and sonicated in phosphate buffered saline. About 23% of the total soluble protein in the induced E. coli lysates was determined to be PhnO and approximately 60% of the total PhnO protein was released into the soluble phase as judged by SDS-PAGE and Coomassie blue staining. The protein was further purified by preparative SDS-PAGE providing a sufficient quantity of PhnO for use in producing antibody which binds to or reacts antigenically with PhnO or related AMPA transacylase proteins. Briefly, the PhnO protein was separated by size from other proteins in a 15% SDS-PAGE gel. A gel slice containing the PhnO protein was excised, weighed, and homogenized using a polytron in a volume of phosphate buffered saline (PBS, pH 7.0) equal to the mass of the gel slice. The homogenate was mixed with an equal volume of complete Freund's media until a colloidal mixture was obtained. An 8-ml inoculum of this mixture was used for the first injection into a goat. Two weeks post-injection, a 50-ml bleed was collected and serum was separated from blood solids by centrifugation. A booster injection of gel purified PhnO protein was administered in a colloidal mixture of 50% incomplete Freund's adjuvant at four weeks, and at six weeks a second bleed was obtained.

The serum from the second bleed was used to screen for the presence of sufficient antibody titers specific for PhnO protein. Extracts from JM101 cells containing pMON15032 were subjected to western blot analysis. The concentration of protein in the extract was determined to be about 55 mg/ml by Bradford assay, and a prior Coomassie stained gel using this same extract was subjected to a densitometer scan which indicated that about 23% of the total cell protein was PhnO. The extract was desalted over a PD10 column, eluted with 10 mM Tris pH 7.5, and diluted with an equal volume of 2× SDS sample buffer. Serial dilutions were prepared using 1× sample buffer and loaded into wells of a 15% SDS PAGE gel. Additional samples were mixed with a tobacco leaf protein extract containing 10 additional micrograms of protein per lane in addition to the E. coli PhnO extracts. The tobacco leaf protein extracts were used to screen for the presence of cross reactive antibody to plant proteins. Proteins were separated according to size by electrophoresis at 7.5 mA constant for fourteen hours at 4° C., and the gel was electroblotted onto a MSI 0.45 micron nitrocellulose filter at 0.5 Ampere in Tris-Glycine transfer buffer for one hour. The membrane was then blocked with TBST (Tris, BSA, NaCl, Tween-20, Short Protocols in Molecular Biology, 3rd Ed., Wiley and Sons, Pub.) for two hours at room temperature, incubated forty-five minutes with a 1:500 dilution of the second bleed serum at room temperature, washed two times in TBST, incubated another forty-five minutes with alkaline phosphatase conjugated rabbit anti-goat IgG (Boehringer Mannheim Biochemicals, Inc.), washed three times with TBST and one time with alkaline phosphatase buffer, and finally incubated for two and one half minutes with a standard color development solution containing NBT and BCIP. The reaction was terminated by washing the membrane with ample quantities of distilled water. The antibody was able to detect PhnO protein in as little as 50 nanograms of E. coli extract independent of the presence of additional plant proteins in one half of the samples. In addition, very few cross reactive bands were detected in either set of samples, indicating that the serum sample contains very little IgG which cross reacts with either E. coli or tobacco plant proteins when tested using this western blot method.

An alternative source for generating antibody which is capable of specific binding to or reacting antigenically with PhnO protein was also utilized. A phnO gene was placed into a commercial vector (Invitrogen) containing a metal binding amino acid coding sequence (His6) upstream of and in frame with the phnO coding sequence. The His6-phnO DNA sequence was inserted into the E. coli expression vector pMON6235 on an NcoI to EcoRI fragment, under the control of an E. coli arabinose operon araBAD promoter, producing plasmid pMON32909. His6-PhnO protein was produced upon arabinose induction of E. coli W3110 cells containing pMON32909, and purified over a metal affinity column according to the manufacturers' instructions.

His-tagged purified His6-PhnO protein standard was injected into 6 New Zealand White rabbits using an immunization procedure similar to that used for the goat, described above. Antiserum raised in these rabbits was also shown to be specific for binding PhnO protein and non-cross reactive with other E. coli bacteria] or tobacco plant proteins.

Example 6

This example illustrates properties of an AMPA transacylase enzyme using aminomethylphosphonate and acetyl-CoA as substrates in an enzyme assay as measured by endpoint kinetic analysis.

The apparent Km ($K_m$) and Vmax ($V_{max}$) of PhnO enzyme were determined for the substrates aminomethlyphosphonate and acetyl-CoA. Determination of the PhnO $K_m$ and $V_{max}$ were made by endpoint kinetic analyses, determining the enzyme velocity in consuming each substrate at varying substrate concentrations, and plotting the inverse of the enzyme velocity versus the inverse of the substrate concentration to produce a Lineweaver-Burk plot of enzyme kinetics. The conversion of [$^{14}$C]-AMPA to N-acetyl-[$^{14}$C]-AMPA was monitored as in example 2, using enzyme in a desalted crude lysate of E. coli expressing phnO from pMON15032, produced as in example 4. Total protein per ml of extract was determined by the method of Bradford which indicated approximately 22.5 mg/ml. Densitometric scanning of Coomassie stained SDS-polyacrylamide gels resolving PhnO protein from these lysates indicated that PhnO represents about 23% of total protein, thus the cell extract was determined to contain about 5.2 mg PhnO protein per ml. In a first assay to determine the apparent $K_m$ and $V_{max}$ of PhnO for AMPA, [$^{14}$C]-AMPA concentrations ranged from 2 to 38 mM. Enzyme reactions were incubated at 37° C. for 5 minutes and quenched with 1 volume of 100 mM sodium acetate (NaOAc), pH 4.4, in ethanol. Samples were analyzed by HPLC to determine the amount of [$^{14}$C]-AMPA converted to N-acetyl-[$^{14}$C]-AMPA. The assay conditions and output for each set of reactions are shown in Table 8.

TABLE 8

PhnO Enzyme Kinetics for AMPA Substrate

| Sample | $S^1$ | % Turnover$^2$ | Velocity$^3$ | 1/S | 1/V | V/S |
|---|---|---|---|---|---|---|
| 1 | 200 | 39.5 | 79 | 1.0 | 0.0127 | 79.00 |
| 2 | 400 | 35.1 | 140 | 0.5 | 0.0071 | 70.00 |
| 3 | 800 | 32.9 | 263 | 0.25 | 0.0038 | 65.75 |
| 4 | 1200 | 26.8 | 322 | 0.166 | 0.0031 | 53.67 |
| 5 | 1600 | 26.2 | 426 | 0.125 | 0.0023 | 53.25 |
| 6 | 2000 | 22.1 | 442 | 0.100 | 0.0023 | 44.20 |
| 7 | 2400 | 19.2 | 461 | 0.083 | 0.0022 | 38.42 |
| 8 | 2800 | 17.6 | 493 | 0.071 | 0.0020 | 35.21 |
| 9 | 3200 | 17.3 | 554 | 0.063 | 0.0018 | 34.63 |
| 10 | 3600 | 14.5 | 522 | 0.056 | 0.0019 | 29.00 |
| 11 | 4000 | 13.6 | 544 | 0.050 | 0.0018 | 27.20 |
| 12 | 6000 | 12.7 | 762 | 0.033 | 0.0013 | 25.15 |
| 13 | 7600 | 10 | 760 | 0.026 | 0.0013 | 19.76 |

[1]AMPA substrate concentration in reaction in nm (nanomoles)
[2]% turnover measured by the percent of N-acetyl-[$^{14}$C]-AMPA formed in relation to the amount of [$^{14}$C]-AMPA remaining in the sample
[3]enzyme velocity in units of AMPA (nm) converted to N-acetyl-AMPA per minute per mg of protein A Lineweaver-Burk plot of the 1/V vs 1/S data from Table 8 indicates that the apparent $K_m$ of PhnO for AMPA as a substrate is about 9 mM, and the apparent $V_{max}$ is about 824 U/mg protein.

The apparent $K_m$ of PhnO for the substrate acetyl-CoA was determined in similar experiments. After several attempts to obtain end point kinetics, it was determined that the turnover number was too low to be reliable at AMPA concentrations of about 30 mM and enzyme amounts of about 1–10 ng. An alternative approach was tried using tritium labeled acetyl-CoA. The specific activity of the label was about 40× higher than with [$^{14}$C], providing a gain in sensitivity that allowed for the determination of the apparent $K_m$ of PhnO for Acetyl-CoA. The [$^3$H]-acetyl-CoA (Amersham, Inc.) specific activity was 360 mCi/mg or 250 μCi/ml. The transacylation mediated by PhnO from [$^3$H]-acetyl-CoA to [$^3$H]-acetyl-AMPA was monitored by weak anion exchange HPLC chromatography, with the retention times of acetyl-CoA and acetyl-AMPA adjusted so that these compounds were separated by about three minutes. This was accomplished by adjusting the concentration of $KH_2PO_4$ buffer (pH 5.5) to 40 mM with a flow rate of 1 ml per minute over an AX100 weak anion exchange column. Each sample was reacted with PhnO and 30 mM AMPA for five minutes at 37° C. and quenched with 100 mM NaOAc pH 4.4 in ethanol, then analyzed by HPLC. [$^3$H]-acetyl-CoA substrate ranged from 25 micromolar to 1.3 mM in each reaction along with about 5ng PhnO, 50 mM Tris pH 7.5, 1 mM $MnCl_2$, 1 mM $MgCl_2$, and 30 mM AMPA. Samples were analyzed by HPLC to determine the amounts of N-[$^3$H]-acetyl-AMPA produced, and [$^3$H]-acetyl-CoA remaining. The assay conditions and results for these reactions are shown in Table 9.

TABLE 9

PhnO Enzyme Kinetics for Acetyl-CoA Donor Substrate

| Sample No. | [Acetyl-CoA]$^1$ | Velocity$^2$ | 1/[S]$^3$ | 1/V$^4$ | V/S$^5$ |
|---|---|---|---|---|---|
| 1 | 25 | 34 | 0.0400 | 0.0294 | 1.3600 |
| 2 | 50 | 66 | 0.0200 | 0.0152 | 1.3200 |
| 3 | 75 | 94 | 0.0133 | 0.0106 | 1.2533 |
| 4 | 100 | 125 | 0.0100 | 0.0080 | 1.2500 |
| 5 | 125 | 150 | 0.0080 | 0.0067 | 1.2000 |
| 6 | 150 | 173 | 0.0066 | 0.0058 | 1.1533 |
| 7 | 175 | 193 | 0.0057 | 0.0052 | 1.1029 |
| 8 | 200 | 219 | 0.0050 | 0.0046 | 1.0950 |
| 9 | 225 | 240 | 0.0044 | 0.0042 | 1.0667 |
| 10 | 250 | 259 | 0.0040 | 0.0039 | 1.0360 |
| 11 | 375 | 339 | 0.0027 | 0.0030 | 0.9040 |
| 12 | 390 | 287 | 0.0026 | 0.0035 | 0.7359 |
| 13 | 520 | 331 | 0.0019 | 0.0030 | 0.6365 |
| 14 | 650 | 352 | 0.0015 | 0.0028 | 0.5415 |
| 15 | 780 | 372 | 0.0013 | 0.0027 | 0.4769 |
| 16 | 910 | 397 | 0.0011 | 0.0025 | 0.4363 |
| 17 | 1040 | 411 | 0.0009 | 0.0024 | 0.3952 |
| 18 | 1170 | 425 | 0.0008 | 0.0024 | 0.3632 |
| 19 | 1300 | 434 | 0.0007 | 0.0023 | 0.3338 |

[1]substrate concentration in micromolar units
[2]enzyme velocity as measured by amount of [$^3$H] incorporated into [$^3$H]-acetyl-AMPA per unit time
[3]inverse substrate concentration
[4]inverse velocity
[5]ratio of velocity to substrate concentration A Lineweaver-Burk plot of the 1/V vs 1/S data from Table 9 indicates that the apparent $K_m$ of PhnO for acetyl-CoA as a substrate is between 375–390 micromolar, and the apparent $V_{max}$ is about 824 U/mg protein.

An approximate pH range of activity for the PhnO enzyme was determined using enzyme in crude lysate of E. coli expressing phnO from pMON15032. The ability of the enzyme to produce N-acetyl AMPA from a mixture containing acetyl-CoA and AMPA across a range of pH values was determined. The reactions were carried out in MES/MOPS/Tricine buffer equilibrated to a pH value from 4.5 to 9.0, with actual pH values ranging from 5.2 through 9.0. Briefly, 95 microliters of an appropriate buffer was mixed with 100 microliters of 2× assay mix as described in example 4, and 5 microliters of desalted E. coli lysate containing approximately 400 ng/microliter PhnO protein. The reaction was incubated at 37° C. for five minutes and quenched with 100 mM NaOAc pH 4.4 in ethanol, and analyzed by HPLC as described in example 4. The results are shown in Table 10.

TABLE 10

PhnO Enzyme pH Profile

| Buffer pH | [1]Mock Reaction pH | [2]% Turnover | N-Acetyl CoA (nmole) | [3]Velocity (nmole/min/ microgram) |
|---|---|---|---|---|
| 5.0 | 5.23 | 3.7 | 222 | 22.2 |
| 5.5 | 5.62 | 3.9 | 234 | 23.4 |
| 6.0 | 5.92 | 4.2 | 252 | 25.2 |
| 6.5 | 6.47 | 13.3 | 798 | 79.8 |
| 7.0 | 7.0 | 27.0 | 1620 | 162.0 |
| 7.5 | 7.48 | 32.0 | 1920 | 192.0 |
| 8.0 | 8.05 | 34.3 | 2058 | 205.8 |
| 8.5 | 8.46 | 33.5 | 2010 | 201.0 |
| 9.0 | 9.0 | 33.9 | 2034 | 203.4 |

[1]indicates true pH value after combining all reagents for each initial buffer pH value given
[2]determined as in Table 9 for Km and Vmax
[3]determined as in Table 9 for Vmax The results indicate that optimum PhnO transacylase activity using AMPA and acetyl-CoA as substrates is about pH 8.0. However PhnO efficiently converts AMPA to N-acetyl-AMPA using acetyl-CoA as the acetyl donor across a pH range from about 6.5 to at least 9.0.

Additional experiments were carried out with purified PhnO protein to further characterize the scope of the enzyme's substrate preference for acyl-CoA acyl donor compounds. It has been established herein that at least one substrate acyl-donor or leaving group can be a two carbon acid compound such as the acetyl-moiety in the compound Acetyl-CoA. It was not known what range of acyl-molecules comprised of different carbon chain lengths would or could function as a leaving group from the acyl-CoA acyl donor when reacted with PhnO transacylase and AMPA as the acyl-receptor molecule. Therefor, an HPLC assay similar to that described in Example 2 was developed to determine the scope of the enzymes' ability to transfer an acyl-group from an acyl-CoA acyl donor to [$^{14}$C]-AMPA.

PhnO was purified from a one liter Luria Bertani broth culture of *E. coli* JM101 expressing a recombinant phnO gene from pMON15032 after nalidixic acid induction for three hours at 37° C. Cells were harvested by centrifugation and resuspended in 40 ml cold Tris buffer (0.1 M Tris-HCl pH 8) and placed on ice. The cell suspension was brought to 1 mM DTT and 0.5 mM PMSF. The suspension was lysed by 2 passages through a prechilled French pressure cell at 1,100 psi, centrifuged at 12,000 g (10,000 rpm in an Sorvall SA600 rotor) for 40 min at 4° C., then placed on ice. The cleared supernatants were poured into fresh 15 ml polypropylene tubes. The samples were split again into two equal portions and maintained at −80° C. until used further for purification of PhnO protein. 20 microliters of the soluble fraction was assayed for enzyme activity using the HPLC method described above in Example 2, except after terminating the assay with acid addition, the sample was stored at −80° C. A Sephacryl S200 column was prepared according to the manufacturers' instructions and equilibrated with a solution containing 20 mM Tris pH 8.0 and 0.5 mM $MgCl_2$. The entire total soluble extract was layered over the top of the column bed after thawing on ice. Forty 9 ml fractions were collected from the column eluate, and thirty microliters of each fraction was analyzed by western blot using anti-PhnO antiserum after resolution on a 15% SDS-PAGE gel.

Also, thirty microliters of each fraction was analyzed for AMPA acyl transferase activity using the method described in Example 2. Samples which exhibited acyl transferase activity and which corresponded to positive western blot data were pooled. These were represented by fractions 7 through 19 in this example, and were combined into a 100 ml volume, distributed into ten 10 tubes each containing 10 ml volumes, and stored at −80° C. for further use.

Anion exchange chromatography was used to determine the elution pattern of PhnO away from other contaminating proteins that co-elute during the Sephacryl S200 fractionation. One tube from the combined PhnO positive fractions was thawed on ice and injected into a 5/5 Mono-Q column pre-equilibrated with buffers A (one liter of 20 mM Tris-HCl pH 8.0 Mili-Q distilled deionized water) and B (one liter of 20 mM Tris-HCl pH 8.0, 1 M NaCl). The sample containing PhnO active protein was injected into the column and one milliliter fractions were collected. The column was washed for five minutes with a flow rate of 1.8 ml per minute Buffer A after loading the PhnO containing sample. At five minutes, Buffer B was added to the flow volume at 0.5 ml per minute for four minutes. Buffer B was ramped up to 22% of the flow volume at 10 minutes, 30% at 12 minutes, 36% at 13 minutes, 41% at 14 minutes, 46% at 15 minutes, 74% at 16 minutes, and 100% at 16 minutes through 22 minutes, at which point Buffer B flow was terminated and Buffer A was reinitiated at 100% to equilibrate the column. Ten microliter volumes from individual fractions collected from the Mono-Q column were analyzed by western blot and for transacylase activity as described in Example 2. Fractions which exhibited positive AMPA acyltransferase activity and which correlated with the Western blot data were pooled and maintained as a purified protein sample. Samples of this purified PhnO protein were used to determine enzyme's acyl donor substrate specificity.

Enzyme reactions were prepared as follows. 100 microliter reactions consisted of 50 mM Tris-HCl pH 8.0, 1 mM $MgCl_2$, 3 microliters of 1.3 mM [$^{14}$C]-AMPA (115,392 dpm per microliter), 0.1 mM or 1 mM acyl-CoA acyl donor, and 2.5 microliter purified enzyme sample. A assay premix was prepared from which 45 microliters was used in each 100 microliter reaction. This 45 microliter premix sample consisted of 40 microliters distilled and deionized water, 2 microliters of 50 mM $MgCl_2$, and 3 microliters of 1.3 mM [$^{14}$C]-AMPA (115,392 dpm per microliter). Reactions were initiated by mixing 40 microliters of 125 mM Tris-HCl pH 8.0, 2.5 microliters protein sample and 10 microliters acyl-CoA acyl donor compound in a microcentrifuge tube at room temperature. Each acyl-CoA acyl donor compound was prepared as a stock solution of 1 mM, 5 mM or 10 mM stocks. Each tube was then mixed with 45 microliters of the assay premix containing the [$^{14}$C]-AMPA receptor substrate, mixed gently and transferred to a 30° C. water bath for 5 minutes. Each reaction was terminated with the addition of 4 microliters of 1M HCl, mixed by vortexing, and placed on ice or stored at −20° C. until assayed for the presence of [$^{14}$C]-AMPA or related compounds by HPLC.

HPLC analysis was carried out using a Waters 510 dual pump HPLC system with a 481 wavelength max UV detector and a scintillation pump, a Phenomenex PHENOSPHERE 5 micrometer 80 Å SAX-silica HPLC column (250×4.6 mm, 3500 PSI max pressure), Buffer A consisting of 5 mM $KH_2PO_4$, 4% methanol, adjusted to pH 2.0 with $H_3PO_4$, and Buffer B consisting of 200 mM $KH_2PO_4$, 4% methanol adjusted to pH 2.0 with $H_3PO_4$, and HAZARD Atomflow (Packard) containing 64% 1, 2, 4 trimethylbenzene, 7.5% sodium-dicotyl sulfosuccinate, 3.5% sodium diamylsulfosuccinate, and 6% polyoxyethylene(4)lauryl ether. HPLC gradient conditions for each sample analysis were similar to those described in Example 2, with minor variations. The flow rates are provided in Table 11.

TABLE 11

HPLC Gradient Conditions

| Time (min) | Flow (ml/min) | % A | % B | Flow Rate[1] |
|---|---|---|---|---|
| 0.0 | 1 | 100 | 0 | 3 |
| 2.0 | 1 | 100 | 0 | 3 |
| 5.0 | 1 | 50 | 50 | 3 |
| 15.0 | 1 | 0 | 100 | 3 |
| 17.0 | 1 | 0 | 100 | 3 |
| 17.3 | 1 | 100 | 0 | 3 |
| 21.0 | 1 | 100 | 0 | 3 |
| 21.3 | 0.1 | 100 | 0 | 0 |

[1]Scintillation fluid flow rate in milliliters per minute

Stock solutions of Acyl-CoA acyl donor compounds were prepared as described above, and these are listed here: Na Acetyl-CoA, Li n-propionyl-CoA, Li glutaryl-CoA, Li methylmalonyl CoA, Li crotonoyl-CoA, Li isobutyryl-CoA, Na succinyl-CoA, Li tiglyl-CoA, Li n-valeryl-CoA, and Li desulfo-CoA. All compounds were obtained from Sigma Chemical Company, St. Louis, Mo. The percent activity of the purified enzyme for transfer of the CoA associated acyl-moiety to [$^{14}$C]-AMPA was determined by measuring the percentage of [$^{14}$C]-AMPA HPLC chromatogram peak area converted to some other [$^{14}$C]-compound, such as N-acetyl-[$^{14}$C]-AMPA, with the amount of N-acetyl-[$^{14}$C]-AMPA produced during the reaction in which [$^{14}$C]-AMPA and 1 mM acetyl-CoA are substrates for PhnO being established as the 100% reference. The results are shown in Table 12.

TABLE 12

AMPA Transacylase Enzyme Efficiency for Acyl-CoA Acyl Donor Substrate

| Acyl-CoA Acyl Donor | [$^{14}$C]-AMPA % Conversion[1] | % Activity |
|---|---|---|
| Acetyl-CoA 0.1 mM | 79.2 | 79.2 |
| Acety-CoA 0.5 mM | 98.7 | 98.7 |
| Acety-CoA 1 mM | 100.00 | 100.00 |
| Propionyl-CoA 0.1 mM | 78.2 | 78.2 |
| Propionyl-CoA 0.5 mM | 97.8 | 97.8 |
| Propionyl-CoA 1 mM | 100.00 | 100.00 |
| Glutaryl-CoA 0.1 mM | 0.81 | 0.81 |
| Glutaryl-CoA 0.5 mM | 0.00 | 0.00 |
| Glutaryl-CoA 1 mM | 0.57 | 0.57 |
| Methylmalonyl-CoA 0.1 mM | 1.11 | 1.11 |
| Methylmalonyl-CoA 0.5 mM | 2.08 | 2.08 |
| Methylmalonyl-CoA 1 mM | 2.21 | 2.21 |
| Crotonoyl-CoA 0.1 mM | 0.80 | 0.80 |
| Crotonoyl-CoA 0.5 mM | 0.00 | 0.00 |
| Crotonoyl-CoA 1 mM | 0.00 | 0.00 |
| Isobutyryl-CoA 0.1 mM | 2.10 | 2.10 |
| Isobutyryl-CoA 0.5 mM | 0.20 | 0.20 |
| Isobutyryl-CoA 1 mM | 0.00 | 0.00 |
| Succinyl-COA 0.1 mM | 5.06 | 5.06 |
| Succinyl-CoA 0.5 mM | 3.38 | 3.38 |
| Succinyl-CoA 1 mM | 1.56 | 1.56 |
| Tiglyl-CoA 0.1 mM | 0.00 | 0.00 |
| Tiglyl-CoA 0.5 mM | 0.00 | 0.00 |
| Tiglyl-CoA 1 mM | 0.99 | 0.99 |
| Valeryl-CoA 0.1 mM | 0.24 | 0.24 |
| Valeryl-CoA 0.5 mM | 0.00 | 0.00 |
| Valeryl-CoA 1 mM | 0.33 | 0.33 |
| Desulfo-CoA 0.1 mM | 0.95 | 0.95 |
| Desulfo-CoA 0.5 mM | 1.25 | 1.25 |
| Desulfo-CoA 1 mM | 0.52 | 0.52 |

[1]percentage of [$^{14}$C]-AMPA HPLC chromatogram peak area converted to some other [$^{14}$C]-compound, such as N-acetyl-[$^{14}$C]-AMPA, with the amount of N-acetyl-[$^{14}$C]-AMPA produced during the reaction in which [$^{14}$C]-AMPA and 1 mM acetyl-CoA are substrates for PhnO being established as the 100% reference These results indicate that PhnO enzyme is capable of efficiently utilizing acyl-CoA associated compounds which have an acyl group with a carbon chain length of not more than three for transacylating AMPA. Other compounds which have a longer carbon chain length than propionyl- and which are not broad or bulky, such as methylmalonly-, isobutyryl-, and succinyl-CoA compounds are also effective acyl-CoA acyl donors, but at a lower enzyme efficiency.

Example 7

This example illustrates the in vitro expression and targeting of an AMPA acyltransferase protein into isolated chloroplasts.

Many chloroplast-localized proteins are expressed from nuclear genes as precursors and are targeted to the chloroplast by a chloroplast transit peptide (CTP). The CTP is removed during steps involved in import of the targeted protein into the chloroplast. Examples of such chloroplast proteins include the small subunit (SSU) of ribulose-1,5-bisphosphate carboxylase (RUBISCO), 5-enolpyruvylshikimate-3-phosphate (EPSPS), ferredoxin, ferredoxin oxidoreductase, the light-harvesting-complex protein I and protein II, and thioredoxin F. It has been demonstrated in vivo and in vitro that non-chloroplast proteins may be targeted to the chloroplast by use of fusions with a CTP and that a CTP sequence is sufficient to target a protein to the chloroplast (Della-Cioppa et al., 1987). 5-enolpyruvylshikimate-3-phosphate synthetase (EPSPS) enzyme is located in the chloroplast and is the glyphosate target in plants. Targeting glyphosate oxidoreductase to the chloroplast has been found to provide tolerance to plants to glyphosate, although GOX localized to the cytoplasm is also able to provide such tolerance. Generally, recombinant GOX enzyme is localized to the chloroplast. GOX mediated glyphosate metabolism produces AMPA, which has been shown to be phytotoxic. It has been shown herein that PhnO is capable of AMPA N-acylation and that N-acetyl-AMPA is not phytotoxic. Therefore, it may be necessary to inactivate AMPA in plants. This assumes that AMPA acyltransferase can be expressed in plants as an active enzyme, and that such acyltransferases are capable of being imported into the chloroplast and retain enzymatic activity. In view of the AMPA phytotoxicity as described in example 1, an AMPA acyltransferase gene was introduced into plant expression vectors to test expression in plants. In addition, import of acyltransferase into chloroplasts was also tested.

A DNA sequence encoding a chloroplast targeting peptide was linked 5' to and in frame with a DNA sequence encoding an AMPA acyltransferase. A DNA sequence encoding an arabidopsis ribulose-1-bis-phosphate carboxylase small subunit chloroplast transit peptide (CTP, SEQ ID NO:9) was excised from pMON17058 using BglII and NcoI restriction endonucleases, and inserted into complementary restriction sites in pMON15028 to produce pMON15029, so that the CTP coding sequence was linked 5' to and in frame with the phnO coding sequence in pMON15028. The resulting chimeric phnO gene in pMON15029 is capable of producing a chloroplast targeted PhnO protein. An EcoRI to BglII DNA cassette containing the CTP-PhnO coding sequence, SEQ ID NO:11, from pMON15029 was inserted into EcoRI and BamHI sites in pBlueScript KS(−) to produce pMON15036. The CTP-PhnO coding sequence in pMON15036 can be expressed in an in vitro transcription/translation system from a phage T3 promoter. A similar plant transient expression plasmid, pMON15035, was constructed, but without the chloroplast targeting sequence. An EcoRI to BglII DNA fragment containing only the phnO coding sequence was excised from pMON15028 and inserted into EcoRI and BamHI sites in pBlueScript KS(+) so that PhnO could be produced from a phage T7 promoter in an in vitro transcription/translation system. An NcoI to EcoRI DNA sequence encoding PhnO was excised from pMON15028 and inserted into pMON17061, producing pMON15032. pMON15032 provides for expression of phnO from an $E.\ coli$ recA promoter. A BglII to EcoRI DNA fragment encoding PhnO was excised from pMON15028 and inserted into pBlueScript SK(−) to produce pMON15033. pMON15033 provides for expression of phnO from an $E.\ coli$ lac promoter. A BglII to EcoRI DNA fragment encoding CTP-PhnO was excised from pMON15029 and inserted into compatible sites in pBlueScript SK(−), providing for expression of chloroplast targeted PhnO protein from an $E.\ coli$ lac promoter from pMON15034.

pMON15032, pMON15033, and pMON15034 were introduced into $E.\ coli$ JM101. Cultures were grown and induced as described above, except that expression from cells containing pMON15032 was induced with addition of 50 parts per million nalidixic acid in 0.1 M NaOH. Cleared lysates were prepared from each culture and subjected to an AMPA acyltransferase assay as described above in order to determine the presence of AMPA acyltransferase activity. All lysates contained substantial amounts of acyltransferase activity above control levels. More importantly, the CTP-PhnO peptide (SEQ ID NO: 12) expressed from pMON15034 appeared to retain full enzymatic acyltransferase activity.

pMON15035 (PhnO) and pMON15036 (CTP-PhnO) were used in vitro to generate [$^{35}$S]-methionine labeled PhnO protein for use in a chloroplast import assay. Briefly, the procedure used for in vitro transcription and translation was as described in *Short Protocols In Molecular Biology, Third Edition*, Ed. Ausubel et al., Wiley & Sons Pub., (1995), which is herein incorporated by reference. About 20 micrograms of plasmid DNA was digested to completion with HindIII restriction endonuclease in a 100 microliter reaction. 20 microliters of the plasmid digest, or about 4 micrograms of linearized plasmid DNA, was used in an in vitro transcription reaction to generate mRNA for producing PhnO or CTP-PhnO protein product in later translation reactions. Transcription reactions consisted of 20 microliters of linearized plasmid DNA, 20 microliters of a 5× transcription buffer (200 mM TrisHCl pH 8.0, 40 mM $MgCl_2$, 10 mM spermidine and 250 mM NaCl), 20 microliters of 5× ribonucleoside triphosphate mix (5 mm each ATP, CTP, UTP, 5 mM diguanosine triphosphate (G-5'ppp5'-G)TP, 5 mM GTP), 10 microliters 0.1 M dithiothreitol (DTT), 10 microliters RNasin™ (a pancreatic ribonuclease inhibitor mixture from Promega), 4 microliters RNA polymerase (T7 or T3, New England Biolabs, Inc.), and distilled, deionized water to 100 microliters. Each reaction was incubated at 37° C. for one hour. 4.5 microliters of each reaction was analyzed on a 1.4% agarose formaldehyde gel to ensure that each reaction produced adequate RNA template for the following translation step.

20 microliters of the transcription reactions were used for producing [$^{35}$S]-methionine labeled PhnO proteins for use in a chloroplast import assay. Briefly, RNA was mixed with 6 microliters of an aqueous amino acid mixture without methionine, 15 microliters of [$^{35}$S]-methionine (1400 Ci/mmol, Amersham), and 200 microliters of a rabbit reticulocyte lysate. These reactions were incubated at 37° C. for two hours and placed on dry ice for storage. A 10 microliter sample of each reaction was analyzed on a 15% SDS-PAGE gel. Gels were vacuum dried and placed directly onto the emulsion side of KODAK™ X-O-MAT™ film for autoradiography. The results indicated that each plasmid produced respective peptides of predicted molecular mass for PhnO (pMON15035) and CTP-PhnO (pMON15036) in sufficient quantity to test for uptake into chloroplasts in an import assay.

Intact chloroplasts were isolated from one head of deveined Romaine lettuce according to Edelman et al., *Methods in Chloroplast Molecular Biology*, Elsevier Biomedical Press, Chap. 86, 1982. One liter of grinding buffer (GR-buffer) stock was prepared (2 mM NaEDTA, 1 mM MgCl2, 1 mM MnCl2, 50 mM Hepes-KOH pH 7.5, and 0.33 mM sorbitol). Immediately before use, 890 mg of ascorbic acid was added to 900 ml of GR-buffer stock solution. One head of torn, deveined Romaine lettuce was mixed with 900 ml GR-buffer and emacerated by mixing in a Waring blender three times for three seconds each time at high speed. The slurry was filtered through four layers of Miracloth, and the filtrate was centrifuged at 5,000 RPM for 10 minutes at 4° C. in a SORVALL™ GS-3 rotor. The supernatant was decanted and the pellet resuspended with a glass rod in 4 milliliters of GR-buffer. Chloroplasts were isolated by centrifugation through a Percoll gradient. 80% Percoll was prepared by mixing 16 mls of PBF-Percoll with 4 mls of 5× Buffer (10 mM EDTA, 5 mM $MgCl_2$, 5 MM $MnCl_2$, 250 MM Hepes-KOH, 30 grams sorbitol, 490 mg NaAscorbate, 85.5 mg glutathione to 100 mls with dd$H_2$O). A 40% Percoll solution was prepared by combining 8 mls PBF-Percoll with 4 mils 5× Buffer and 8 mls of dd$H_2$O. A Percoll gradient was prepared in a 30 ml Corex tube by layering 10 mls of 40% Percoll onto 10 mls of 80% Percoll. Chloroplasts were isolated by layering the resuspended chloroplasts onto the percoll gradient, spinning at 9,500 RPM for ten minutes in an SS-34 SORVALL™ swinging bucket rotor at 4° C. for ten minutes with the brake on. Broken chloroplasts remain in the upper layer and were pipetted off. The intact chloroplasts were located at the interface of the 40/80% Percoll gradient and were removed to a new 30 ml COREX™ tube. The isolated chloroplasts were washed two times with GR-buffer and centrifuged for collection after each wash in a SS-34 rotor at 6,000 RPM for ten minutes at 4° C. with the brake off. Isolated, washed chloroplasts were resuspended in 1 ml sterile 50 mM Hepes-KOH pH 7.7, 330 mM sorbitol by gently stirring with a glass rod, and the chlorophyll concentration of the slurry was determined. 5 mls of an 80% acetone solution was added to 20 microliters of the chloroplast slurry and vortexed gently. The resulting mixture was filtered through a Whatman™ #1 filter paper into a culture tube. The absorbance of the filtrate was determined at 645 nm and 663 nm against an 80% acetone blank. The chlorophyll concentration in micrograms per ml was determined according to equation #1 as [chlorophyll $\mu$g/ml]=[$A_{645}$+ [$A_{663}$*(8.02)]. The mass of the chlorophyll in $\mu$g is calculated by taking the amount of chlorophyll measured in $\mu$g/l and multiplying by the volume into which the chloroplasts were resuspended (equation #2), which is 5 mls in this example. Thus, the concentration of chlorophyll in μg/μl in the measured sample is equivalent to the value determined in equation #2 divided by the volume of the sample measured, which in this example is 20 μl. In this example, $A_{645}$ was determined to be 0.496, and $A_{663}$ was determined to be 1.0814. Thus, the concentration of chlorophyll in the measured sample was 4.67 μg/μl. The concentration of chlorophyll in the chloroplast slurry was adjusted to 4.0 μg/μl with Hepes-KOH pH 7.7, 330 mM sorbitol solution and the resulting chloroplast suspension was stored on ice in the dark.

A typical 300 microliter uptake experiment contained 5 mM ATP, 8.3 mM unlabeled methionine, 322 mM sorbitol, 58.3 mM Hepes-KOH (pH 8.0), 50 microliters reticulocyte lysate translation products, and intact chloroplasts (about 200 microgram chlorophyll). The uptake mixtures were gently rocked at room temperature in 10×75 mm glass tubes, directly in front of a fiber optic illuminator set at maximum light intensity using a 150 Watt bulb. Two separate 70 microliter samples of each uptake mix were removed at 0, 5, 10 and 15 minutes. One sample was centrifuged over 100 microliter silicone-oil gradients in 150 microliter polyethylene tubes by centrifugation at 11,000×g for 30 seconds, and immediately frozen in dry ice. Under these conditions, the intact chloroplasts form a pellet under the silicone-oil layer and the incubation medium containing the reticulocyte lysate remains floating on the surface of the interface. The other sample was treated with protease (one tenth volume or 7 microliters of 0.25 mg/ml each trypsin and chymotrypsin protease mixture) for thirty minutes on ice, then subjected to silicone-oil separation and frozen on dry ice. The chloroplast pellets were then resuspended in 50–100 microliters of a lysis buffer (10 mM Hepes-KOH pH 7.5, 1 mM PMSF, 1 mM benzamidine, 5 mM ε-amino-n-caproic acid, and 30 micrograms per ml aprotinin) and centrifuged at 15,000×g for 20 minutes to pellet the thylakoid membranes. The cleared supernatant (stromal proteins) from this spin, and an aliquot of the reticulocyte lysate incubation medium from each uptake experiment, were mixed with an equal volume of 2× SDS-PAGE sample buffer and analyzed on a 15% SDS-PAGE gel, dried, and exposed to film as described above. Chloroplasts exposed to [$^{35}$S]-methionine labeled CTP-PhnO contained [$^{35}$S]-labeled protein of a size consistent with the predicted CTP-processed form of PhnO, while chloroplasts exposed to methionine labeled PhnO were devoid of labeled protein. Labeled protein imported into the chloroplasts was also protease resistant. These results indicated that PhnO could be targeted to chloroplasts when fused to a plastid targeting peptide sequence.

Example 8

This example illustrates the identification and characterization of plants transformed with an AMPA acyltransferase.

A wide variety of plant species have been successfully transformed using any number of plant transformation methodologies well known in the art. In particular, *Agrobacterium tumefaciens* mediated plant transformation is the preferred method presently in use, however, ballistic methods which increase delivery of naked DNA directly to plant cells through microprojectile bombardment are also very effective in producing recombinantly transformed plants. In addition, methods which involve the use of liposomes, electroporation, chemicals that increase free DNA uptake, and transformation using viruses or pollen are alternatives which can be used to insert DNA constructs of this invention into plant cells. Plants which can be transformed by the practice of the present invention include but are not limited to corn, wheat, cotton, rice, soybean, sugarbeet, canola, flax, barley, oilseed rape, sunflower, potato, tobacco, tomato, alfalfa, lettuce, apple, poplar, pine, eucalyptus, acacia, poplar, sweetgum, radiata pine, loblolly pine, spruce, teak, alfalfa, clovers and other forage crops, turf grasses, oilpalm, sugarcane, banana, coffee, tea, cacao, apples, walnuts, almonds, grapes, peanuts, pulses, petunia, marigolds, vinca, begonias, geraniums, pansy, impatiens, oats, sorghum, and millet. DNA molecules for use in the present invention can be native or naturally occurring genes or chimeric genes constructed from useful polynucleotide sequences including promoters, enhancers, translated or non-translated leaders, sequences encoding signal peptides, sequences encoding transit peptides, structural genes, fusions of structural genes, terminators, introns, inverted repeats or direct repeats, linkers, and polyadenylation sequences. DNA sequences contemplated in this invention include single and double stranded polynucleotide sequences, linear sequences, and covalently closed circular polynucleotide sequences, plasmids, bacmids, cosmids, bacterial artificial chromosomes (BAC's), yeast artificial chromosomes (YAC's), and viral DNA and RNA sequences. In consideration of Agrobacterium mediated plant transformation, suitable plant transformation vectors include those derived from a Ti plasmid of *Agrobacterium tumefaciens*, as well as those disclosed, for example by Herrera-Estrella (1983), Bevan (1984), Klee (1985) and EPO publication 120,516 (Schilperoort et al.). In addition to plant transformation vectors derived from the Ti or root-inducing (Ri) plasmids of Agrobacterium, alternative methods as described above can be used to insert the DNA constructs of this invention into plant cells.

Plasmids used for plant transformation generally were constructed from vectors which have been described elsewhere, particularly in U.S. Pat No. 5,463,175 (Barry et al., 1995), which is herein incorporated by reference. Plasmids were constructed and maintained in *E. coli* using Tn7 aminoglycoside adenylyltransferase resistance (aad gene, commonly referred to as streptomycin/spectinomycin or Spc/Str resistance), which is also a determinant for selection and maintenance in Agrobacterium. Other plasmid maintenance and selectable markers well known in the art for use in *E. coli* were also used, consisting essentially of neomycin phosphotransferase, gentamycin acetyltransferase, and beta lactamase genes alone or present in combination on a single replicon or vector. Plasmids generally contain oriV, a replication origin derived from the broad host range plasmid RK2, and ori322 and bom (origin of replication for maintenance in *E. coli*, and basis of mobility for conjugational transfer respectively) sequences derived from plasmid pBR322.

A phnO gene encoding an AMPA acyltransferase was inserted into expression cassettes in plant transformation vectors. These cassettes generally contain the following elements in sequential 5' to 3' order: a sequence comprising a plant operable promoter, a sequence encoding a chloroplast or plastid transit peptide, a cloning site or sites contained within a polylinker, and a plant functional 3' non-translated region. Expression cassettes often are constructed to contain unique restriction sites flanking the cassette domain so that the entire cassette can be excised from one plasmid and placed into other similarly constructed plasmid vectors. Restriction sites comprised of eight base pair recognition sequences are preferred, and most cassettes in the present invention are flanked at least on one end by a NotI restriction endonuclease recognition site. Preferred promoters are the figwort mosaic virus promoter, P-FMV (Gowda et al., 1989), the cauliflower mosaic virus 35S promoter CaMV 35S (Odell et al., 1985), or the enhanced CaMV 35S promoter (U.S. Pat. No. 5,196,525; Kay et al., 1987). A number of other promoters which are active in plant cells have been described in the literature. Such promoters may be obtained from plants or plant viruses and include, but are not limited to the nopaline synthase (NOS) and octopine synthase (OCS) promoters which are carried on tumor-inducing plasmids generally found within virulent and non-virulent strains of *Agrobacterium tumefaciens*, the cauliflower mosaic virus (CaMV) 19S promoter, the comalina yellow mottle virus promoter, the sugar cane bacilliform DNA virus promoter, the peanut chlorotic streak virus promoter, the rice actin promoter, and the light-inducible ribulose 1,5-bisphosphate carboxylase small subunit promoter (ssRUBISCO). These promoters can used to create various types of DNA constructs useful for gene expression in plants (see for example Barry et al. U.S. Pat. No. 5,463,175). Particularly desirable promoters which are contemplated because of their constitutive nature are the Cauliflower Mosaic Virus 35S (CaMV35S) and the Figwort Mosaic Virus 35S (FMV35S) promoters which have previously been shown to produce high levels of expression in most plant organs. Other promoters which would direct tissue specific or targeted expression are also contemplated, for example in tissue such as leaves, meristem, flower, fruit and organs of reproductive character. In addition, chimeric promoters are also envisioned. Nopaline synthase gene (NOS 3') and the pea ribulose bisphosphate carboxylase synthase E9 gene (E9 3') 3' nontranslated termination and polyadenylation sequences were also used.

Expression cassettes consisting of a AMPA acyltransferase structural gene inserted downstream of a promoter and between a sequence encoding a chloroplast targeting peptide and a 3' nontranslated sequence were generally present on a plant transformation vector. Expression cassettes were generally flanked on either end of the cassette by a nopaline type T-DNA right border region on one end and a left border region on the other end, both border regions derived from pTiT37 (Fraley et al., 1985). Some plant transformation vectors only contained the right border region, required for initiation of T-DNA transfer from Agrobacterium to the host cell. Most plant transformation vectors also contained a GOX (glyphosate oxidoreductase) gene, as described above, and in U.S. Pat. No. 5,463,175. GOX enzyme expressed from these vectors was generally targeted to the chloroplast when inserted into the plant genome.

Plant transformation vectors were mobilized into the ABI Agrobacterium strain A208 carrying the disarmed Ti plasmid pTiC58 (pMP9ORK)(Koncz and Schell, 1986). The Ti plasmid does not carry the T-DNA phytohormone genes which induce crown gall formation. Mating of the plant vector into ABI was done by the triparental conjugation system using the helper plasmid pRK2013 (Ditta et al., 1980). Alternatively, the plant transformation plasmid can be introduced into the ABI strain by electroporation as described by Mattanovich et al. (Efficient transformation of Agrobacterium spp. by electroporation., Nucleic Acids Res. (1989), 17(16), 6747), which is herein incorporated by reference. When plant tissue is incubated with the ABI::plant vector conjugate, the recombinant vector is transferred to the plant cells by the vir functions encoded by the disarmed pTiC58 plasmid. Ideally, the recombinant vector opens at the T-DNA right border region, and the DNA between the right and left border sequences is transferred directionally and inserted into the host plant genome, although the entire recombinant plant transformation vector sequence may be transferred and inserted. The pTiC58 Ti plasmid does not transfer to the plant cells but remains in the Agrobacterium donor.

Recombinant plants can be regenerated from plant cells or plant tissue which has been transformed with a functional AMPA acyltransferase structural gene. The choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers), and various floral crops. See for example, Ammirato, 1984; Shimamoto, 1989; Fromm, 1990; and Vasil, 1990). Recombinant plants which have been transformed with an AMPA acyltransferase can also be selected on medium containing AMPA. The appropriate inhibitory concentration of AMPA can readily be determined by one of ordinary skill in the art for any particular host by screening for AMPA toxicity as described in example 1. Alternatively, when AMPA acyltransferase is transformed into plants previously transformed with GOX and selected for growth on glyphosate, either AMPA or glyphosate can be used as the selective ingredient for selecting for transformation events which express sufficient levels of AMPA acyltransferase enzyme. Glyphosate must be applied at levels which would otherwise be inhibitory to a recombinant plant expressing GOX and selected for growth on glyphosate, due to the increased level of AMPA which may be produced as a result of GOX mediated glyphosate degradation. In plants which express recombinant GOX enzyme, exposure to increasing levels of glyphosate has been shown to induce yellowing or chlorosis of the leaves, stunted growth characteristics, and infertility. AMPA acyltransferase expressed coordinately or in combination with GOX expression can overcome these detrimental effects. It is also possible to use AMPA as a plant transformation selectable marker as an alternative to glyphosate selection.

Tobacco

Tobacco plants were transformed with a phnO gene. A tobacco leaf disc transformation procedure employed healthy tissue from a leaf of about one month old. After a 15–20 minute surface sterilization with 10% CLOROX™ plus a surfactant, leaves were rinsed three times in sterile water. Leaf discs were punched with a sterile paper punch, and placed upside down on MS 104 media (4.3 g/l MS salts, 30 µl sucrose, 2 ml/l 500× B5 vitamins, 0.1 mg/l NAA, and 1.0 mg/l BA), and pre-cultured for one day. Discs were then inoculated with an 1:5 diluted overnight culture of disarmed Agrobacterium ABI containing the subject vector (final culture density about 0.6 OD as determined at 550 nm). The inoculation was done by placing the discs in sterile centrifuge tubes along with the culture. After thirty to sixty seconds, the liquid was drained off and the discs were blotted between sterile filter paper. The discs were then placed upside down on a filter disc on MS 104 feeder plates and incubated for 2–3 days. After this co-culture period, the discs were transferred, still upside down, to selection plates containing MS 104 media. After 2–3 weeks, callus formed, and individual clumps were separated from the leaf discs. Shoots were cleanly cut from the callus when they were large enough to distinguish from stems. The shoots were placed on hormone-free rooting media (MSO: 4.3 µ/l MS salts, 30 g/l sucrose, and 2 ml/l 500× B5 vitamins) with selection. Roots formed in 1–2 weeks. Any leaf callus assays are preferably done on rooted shoots while still sterile.

Rooted shoots were placed in soil and were maintained in a high humidity environment (ie: plastic containers or bags). The shoots were hardened off by gradually exposing them to ambient humidity conditions.

Three tobacco transformation events, designated as lines 33476, 36779, and 37235 were selected for further analysis. pMON17226 (Barry et al., U.S. Pat. No. 5,463,175, 1995) was used to produce plant line 33476 which contains an FMV-CTP-GOX gene construct. Lines 36779 and 37235 were produced using pMON17261, which is a plasmid derived from pMON17226 which contains NotI cassette containing an FMV-CTP-PhnO gene sequence (SEQ ID NO: 11) in addition to FMV-CTP-GOX. The NotI cassette was constructed as follows. The sequence encoding CTP, represented by SEQ ID NO:9, was excised from pMON17058 as a BglII to NcoI fragment and inserted into pMON15028, forming a sequence represented by SEQ ID NO: 11 in which the CTP coding sequence was upstream of and in frame with the PhnO coding sequence represented within SEQ ID NO:7. The resulting construct was designated as pMON15029. The CTP-PhnO coding sequence was excised from pMON15029 on a BglII to SacI fragment and combined with pMON17063 fragments to produce pMON15038. pMON17063 was disassembled using restriction digestion to provide parts necessary for pMON15038 construction. pMON17063 was digested with SacI and HindIII to produce a vector backbone into which a promoter fragment and the CTP-PhnO sequence were inserted. pMON17063 was also digested in a separate reaction with HindIII and BglII to produce a fragment containing an FMV promoter sequence. The promoter fragment and the CTP-PhnO fragment were ligated together in a reaction along with the vector backbone fragment to produce pMON15038, containing a NotI cassette harboring a sequence encoding a chloroplast targeted PhnO peptide expressed from an FMV promoter and flanked downstream by a NOS E9 3' transcription termination and polyadenylation sequence. This NotI sequence was excised from pMON15038 and inserted into the unique NotI site in pMON17241 to produce pMON17261, containing a chloroplast targeted GOX coding sequence expressed from an FMV promoter and flanked downstream by an E9 3' sequence, along with the CTP-PhnO coding sequence and expression cassette. Transformation events derived from this vector are expected not only to be resistant to glyphosate, but to provide resistance to AMPA phytotoxicity as well. Lines 36779 and 37235 derived from pMON17261 were analyzed for the presence of genes encoding glyphosate oxidoreductase and AMPA acyltransferase by PCR, for the presence of GOX and PhnO enzymes by western blot, and for the presence of metabolites produced as a result of GOX mediated [$^{14}$C]-glyphosate degradation by HPLC.

Line 33476, obtained as a transformation event derived from pMON17226, was selected as a "GOX only" control. Lines 36779 and 37235 demonstrated different phenotypes upon exposure to glyphosate and were selected as glyphosate resistant events arising after transformation with pMON17261. Line 37235 became bleached or yellowed upon exposure to glyphosate, similar in phenotype to the GOX only line 33476. However, line 36779 displayed no such bleaching effect. DNA was extracted from leaf tissue for each of these events as well as from wt Samsun tobacco leaf, and subjected to PCR to determine the presence or absence of the transforming phnO gene.

Genomic DNA isolated from transformed tobacco lines was used as the template DNA in a PCR reaction and reaction products were compared to wild type Samsun tobacco. PCR reactions consisted of 50 microliters total volume containing 10x amplification buffer, 1.5 mM $MgCl_2$, deoxynucleotide mix with each at 1 mM, 50–100 ng genomic DNA, primers each at a final concentration of 16.8 pM, and 1.5 units of AmpliTaq DNA polymerase (Cetus/Perkin Elmer). Primers (synthesized to order by GENOSYS) consisted of the sequences as set forth in SEQ ID NO:21 and SEQ ID NO:22. SEQ ID NO:21 is a 20 base pair sequence capable of priming the synthesis of the P2A phnO gene sequence (SEQ ID NO:7) and hybridizes to the first twenty nucleotides of the coding sequence in that gene. SEQ ID NO:22 is also a 20 base pair sequence, but is capable of priming synthesis of a phnO gene from the terminal coding sequence into the structural coding region and hybridizes to the terminal twenty nucleotides of the sequence encoding PhnO. Amplification conditions consisted of three cycles of 97° C. for one minute, 60° C. for two minutes, and 72° C. for two minutes, followed by 37 cycles of 94° C. for one minute, 60° C. for two minutes, and 72° C. for two minutes, followed generally by a 4° C. soak. 10 microliter samples were generally analyzed by 1% TAE agarose gel electrophoresis to resolve the relevant bands from residual primers. Upon ethidium bromide staining of the product gels, a phnO gene amplification product about 432 base pairs as judged by the migration position versus HindIII digested lambda molecular weight markers appeared only in the line 33779 extracts, indicating the presence of the phnO gene in that line.

Seed from Ro transformation events were obtained after self crossing in growth chamber conditions. Ro seed were cured and planted to generate R1 progeny. Source leaves of R1 progeny at the five leaf stage were exposed to [$^{14}$C]-glyphosate by spotting a 2 microliter sample onto each vein(50 microliters of [$^{14}$C]-glyphosate Na+salt, 517,000 dpm/microgram, 0.42 microgram/microliter mixed with 10 microliters of glycerol). Each leaf received several spots depending on the number of veins on that leaf. Three days later 15 additional 2 microliter spots were applied to each leaf. Two weeks later, five 2 microliter spots were applied to each of two leaves on each plant. These were new leaves and were not the older leaves to which glyphosate was initially applied. Five days after this last application, about 300 milligrams of tissue was sampled from two sink leaves on each plant. The samples from each plant were homogenized in separate 1 ml volumes of deionized water, centrifuged at 9,000 RPM in a microcentrifuge, and the aqueous volumes were collected and stored on ice. Extracts were analyzed by HPLC for the presence of [$^{14}$C] labeled metabolites as in Example 2. The extract obtained from line 33476 (GOX) contained only [$^{14}$C]-AMPA. The extract obtained from line 37235 contained non-metabolized [$^{14}$C]-glyphosate as well as a trace but measurable amount of [$^{14}$C]-AMPA. Only N-acetyl-[$^{14}$C]-AMPA was observed in the extract obtained from line 36779. These results are consistent with the PCR data which indicated that line 36779 contained at least one copy of the phnO gene. In addition, the lack of a bleaching effect in line 36779 after exposure to glyphosate is consistent with the presence of functional GOX and PhnO enzymes and the absence of detectable [$^{14}$C]-AMPA.

Cotton

A recombinant phnO gene was transformed into Coker 312 variety cotton (*Gossypium hirsutum L.*). Glyphosate tolerant cotton lines were produced by Agrobacterium mediated plant transformation using double border binary plasmid vectors containing either (1) gox, an Achromobacter sp. strain LBAA gene encoding a glyphosate-metabolizing enzyme glyphosate oxidoreductase (GOX), (2) the gox gene and an *E. coli* phnO gene encoding PhnO, or (3) the gox/phnO double gene construct along with an Agrobacterium strain CP4 gene encoding 5-enolpyruvylshikimate-3-phosphate synthase (EPSPS). All vectors are capable of replication in both *Agrobacterium tumefaciens* and *E. coli* hosts, and contain an aminoglycoside adenylyltransferase gene (aad) conferring resistance to aminoglycosides such as spectinomycin or streptomycin and providing a method for plasmid maintenance.

pMON17241 contains a recombinant gene consisting of a 35S FMV promoter linked 5' to an *Arabidopsis thaliana* ribulose-1,5-bisphosphate carboxylase small subunit (SSU1A) gene sequence encoding a plastid or chloroplast targeting peptide (Timko et al., 1988) which is translationally fused to a gox gene coding sequence, which is linked 3' to a 3' untranslated region, designated E9, from a pea ribulose-1,5-bisphosphate carboxylase gene.

pMON17213 is a double gene plant transformation vector containing expression cassettes comprising (1) a 35S FMV promoter linked to a sequence encoding an *Arabidopsis thaliana* EPSPS chloroplast targeting peptide linked in-frame to a strain CP4 EPSPS coding sequence, which is linked 3' to an E9 3' untranslated region; and (2) a 35S FMV promoter linked to an SSU1A gene sequence encoding a plastid targeting peptide linked in-frame to a GOX coding sequence, which is linked 3' to a NOS 3' termination sequence.

pMON17261, described above, is a double gene plant transformation vector containing expression cassettes comprising (1) an FMV 35S promoter linked to an SSU1A chloroplast targeting peptide coding sequence linked in-frame to a GOX coding sequence, which is flanked downstream by the E9 3' untranslated region; and (2) an FMV 35S promoter linked to an SSU1A chloroplast targeting peptide coding sequence (SEQ ID NO:9) linked in-frame to a PhnO coding sequence (SEQ ID NO:7), which is linked 3' to a NOS 3' sequence.

pMON10151 is a double gene plant transformation vector containing expression cassettes comprising (1) an FMV 35S promoter linked to an SSU1A chloroplast targeting peptide coding sequence (SEQ ID NO:9) linked in-frame to a PhnO coding sequence (SEQ ID NO:7), which is flanked downstream by a NOS 3' sequence; and (2) an enhanced 35S promoter linked to an SSU1A chloroplast targeting peptide coding sequence linked in-frame to a GOX coding sequence which is flanked downstream by a NOS 3' sequence.

pMON10149 is a triple gene plant transformation vector containing expression cassettes comprising (1) an FMV 35S promoter and a petunia HSP70 5' untranslated leader sequence linked to an SSU1A chloroplast targeting peptide coding sequence linked in-frame to an EPSPS coding sequence, which is flanked downstream by the E9 3' termination and polyadenylation sequence; (2) an FMV 35S promoter linked to an SSU1A chloroplast targeting peptide coding sequence (SEQ ID NO:9) linked in-frame to a PhnO coding sequence (SEQ ID NO:7), which is flanked downstream by a NOS 3' sequence; and (3) an enhanced 35S CaMV promoter linked to an SSU1A chloroplast targeting peptide coding sequence linked in-frame to a GOX coding sequence, which is flanked downstream by a nopaline synthase 3' polyadenylation sequence (NOS 3').

Plasmid vectors were assembled in *E. coli* K12 strains and mated into a disarmed ABI Agrobacterium strain. Aminoglycoside resistant Agrobacterium strains were used to transform Coker 312 derived hypocotyl sections with modifications as described by Umbeck et al. (1987) and Umbeck (U.S. Pat. No. 5,159,135 (1992), incorporated herein by reference), except that plants were regenerated with modifications described by Trolinder and Goodin (1987). Selection for glyphosate resistance produced several lines of cotton callus, which were subsequently determined by PCR of genomic DNA to contain the respective genes encoding EPSPS, GOX or PhnO transferred from Agrobacterium. Additionally, these same callus lines were determined by Western blot analysis to express the desired genes. After plant regeneration, whole cotton plants which contained the indicated coding sequences were recovered.

Previously identified plants transformed with a double gene glyphosate resistance cassette comprised of EPSPS and GOX encoding genes were determined to be resistant to glyphosate when applied at 48 ounces per acre through the 6–7 leaf stage, however severe bleaching of the leaves was observed. This phytotoxic effect was presumed to be due to the formation of AMPA as a result of GOX mediated glyphosate degradation. To test this, AMPA was sprayed at three different rates onto wild type Coker 312 plants. Leaf chlorosis and stunted growth was observed in plants at four days post-application of glyphosate at 640 ounces per acre and at eight days post-application of 64 ounces per acre. These results suggested that the phytotoxic effect observed in EPSPS/GOX transformed cotton plant lines was a result of GOX mediated AMPA production in plants, and that the phytotoxic effect may be obviated by co-expression of an AMPA acyltransferase along with GOX. To test this, cotton plants expressing GOX or GOX plus EPSPS alone or in combination with PhnO expression were treated with [$^{14}$C]-glyphosate, and the metabolism of the isotope labeled glyphosate was monitored in leaf tissue seven days after application.

Coker 312 glyphosate resistant recombinant cotton line 4416 was selected as a glyphosate resistant cotton line after transformation with pMON10149, a triple gene *Agrobacterium tumefaciens* mediated double border plant transformation vector containing chloroplast targeted EPSPS, GOX, and PhnO, each expressed independently from separate 35S promoters. Several 4416 R3 plants were raised from R2 seed. One leaf of each plantlet at the three or four stage was treated with a mixture of ROUNDUP ULTRA™ commercial herbicide mixture (Lot No. GLP-9701-7428-F) which had been fortified with [$^{14}$C]-glyphosate (Code No. C-2251). The ROUNDUP ULTRA™ was shown to be 30.25% glyphosate acid by weight and the [$^{14}$C]-glyphosate had a /radiochemical purity of 97.3% and a specific activity of 36.36 mCi/mmol. The treatment solution consisted of approximately 38 µL containing $1.60 \times 10^6$ dpm with a [$^{14}$C]-glyphosate specific activity of $1.713 \times 10^3$ dpm/µg glyphosate acid. Three or seven days after topical application the treated leaves were rinsed with water, frozen in liquid nitrogen, fractured with a spatula and then ground using a TEKMAR™ tissuemizer in 10 mL of water. The leaf extracts were adjusted to pH 3.5–4.0 with 1N HCl and approximately 4–8000 dpm were analyzed for the presence of [$^{14}$C]-metabolites by HPLC with liquid scintillation vial collection and detection (HPLC/LSC) as described in example 2. The new growth including the meristem and new leaves that emerged following topical application were also extracted and analyzed for [$^{14}$C]-metabolites. The results are shown in Table 13.

TABLE 13

[14C]-Glyphosate Metabolism In Glyphosate Resistant Cotton

| Line 4416 Plant# | % [14C] metabolite in Glyphosate Treated Leaf Extract . . . * | | | % [14C] metabolite in New Growth Extract . . . * | | |
|---|---|---|---|---|---|---|
| | Glyphosate | AMPA | N-Acetyl-AMPA | Glyphosate | AMPA | N-Acetyl-AMPA |
| MD03 | 55.2 | 2.5 | 37.4 | nd** | nd | 93.4 |
| MD04 | 94.6 | 2.1 | 1.7 | 97.9 | nd | nd |
| A01 | 48.6 | 2.1 | 44.7 | 0.9 | 0.2 | 95.8 |
| A02 | 67.3 | 2.0 | 29.1 | 0.7 | 0.2 | 96.5 |
| A03 | 48.8 | 2.0 | 43.4 | 1.2 | nd | 94.0 |
| A04 | 19.4 | 1.6 | 73.9 | 1.5 | nd | 94.0 |
| A05 | 59.9 | 2.2 | 31.1 | 2.2 | 0.2 | 95.2 |
| A06 | 38.2 | nd | 60.9 | 1.5 | 0.2 | 93.5 |
| A07 | 64.1 | nd | 26.8 | 1.4 | 0.5 | 93.9 |
| A08 | 90.9 | 2.0 | 1.9 | 91.2 | 2.5 | 1.9 |

*[14C]-Glyphosate, [14C]-AMPA, and N-Acetyl-[14C]-AMPA as a percentage of total [14C] isotope observed by HPLC/LSC in each sample.
**nd indicates that the metabolite was not detected by HPLC/LSC Analysis of the water rinsed glyphosate treated leaves indicated the presence of significant levels of N-acetyl-[14C]-AMPA in eight of the ten plants tested. These levels represented 27–74% of the isotope extracted from the treated leaves. The remaining activity was almost entirely [14C]-glyphosate. Very little of the [14C] isotope was present as [14C]-AMPA. The remaining two plants had very limited ability to metabolize glyphosate as indicated by the high levels of [14C]-glyphosate remaining on or in the leaves.

ROUNDUP ULTRA fortified with [14C]-glyphosate to a single leaf on each plant at the three to four leaf stage. Treated leaves were harvested and rinsed with water, then ground and extracted, and extracts were analyzed by HPLC as described above for the presence of [14C]-glyphosate, [14C]-AMPA, and N-acetyl-[14C]-AMPA. New growth, including the meristem and new leaves that emerged following application were also extracted and analyzed. The results are shown in Table 14.

TABLE 14

[14C]-Glyphosate Metabolism In Glyphosate Resistant Cotton

| Plant | *% [14C] metabolite in Glyphosate Treated Leaf Extract . . . | | | *% [14C] metabolite in New Growth Extract . . . | | |
|---|---|---|---|---|---|---|
| | Glyphosate | AMPA | N-Acetyl-AMPA | Glyphosate | AMPA | N-Acetyl-AMPA |
| GOX/PhnO Plants | | | | | | |
| B01 | 76.7 | 3.0 | 14.0 | 3.4 | 1.0 | 89.9 |
| B02 | 63.9 | 4.8 | 25.0 | 1.1 | 1.5 | 91.5 |
| B03 | 54.4 | 3.2 | 36.4 | 0.8 | nd | 94.7 |
| B04 | 58.3 | 5.7 | 28.9 | 1.1 | 1.2 | 91.0 |
| EPSPS/GOX Plants | | | | | | |
| C01 | 59.8 | 26.6 | nd | 3.72 | 85.7 | nd |
| C02 | 92.7 | 2.1 | 0.8 | 92.8 | 0.8 | nd |
| C03 | 81.2 | 10.7 | nd | 13.5 | 72.0 | 1.9 |
| C04 | 86.2 | 6.4 | 1.0 | 13.9 | 76.2 | nd |

*[14C]-Glyphosate, [14C]-AMPA, and N-Acetyl-[14C]-AMPA as a percentage of total [14C] isotope labeled metabolites observed after HPLC/LSC analysis in each sample.
**nd indicates that the metabolite was not detected by HPLC/LSC.

One of these plants also showed signs of stunting seven days after treatment, indicating glyphosate phytotoxicity.

Analysis of new growth in the ten plants tested showed that the predominant form of [14C] labeled metabolite present was N-acetyl-[14C]-AMPA at greater than 90% of the total radioisotope in the samples. In contrast, more than 90% of the isotope in the remaining two plants was in the form of [14C]-glyphosate, consistent with the analysis of the extract from the treatment leaf for these two plants.

The metabolism of [14C]-glyphosate in recombinant cotton lines 4268 (GOX/PhnO) and 3753 (EPSPS/GOX) was also studied. Plants in this study were treated as indicated above for cotton line 4416, by applying droplets of Significant levels of N-acetyl-[14C]-AMPA were present in the treated leaves of all four line 4268 plants (GOX/PhnO; B01–B04). In contrast, N-acetyl-[14C]-AMPA was not detectable in extracts obtained from line 3753 plants (EPSPS/GOX; C01–C04). Three of these plants contained significant levels of [14C]-AMPA in treated leaf extracts, ranging from 6–27%. One line 3753 plant was deficient in the conversion of [14C]-glyphosate to N-acetyl-[14C]-AMPA, and this plant also appeared to be stunted.

90–95% of the [14C] isotope in extracts of new growth from line 4268 plants was determined to be in the form of N-acetyl-[14C]-AMPA. However, 72–86% of the [14C] isotope in extracts of new growth from three of the line 3753 plants was determined to be [$^{14}$C]-AMPA, with [$^{14}$C]-glyphosate accounting for the remainder of the isotope in these tissues. 93% of the isotope obtained from line 3753 plant number C02 was determined to be [$^{14}$C]-glyphosate, consistent with the lack of glyphosate metabolism in the application leaf as well as the observed stunting. In addition, growth regions of all line 3753 plants were discolored and yellow following treatment, but improved with time. By harvest, new growth leaves became mottled.

These results are consistent with the presence of active gox and phnO gene products in the indicated plants. The GOX and PhnO proteins are metabolizing glyphosate to AMPA and N-acetyl-AMPA in the predicted manner, and line 4268 plant extracts provide a similar metabolic pattern to that observed with line 4416 plant extracts as judged by HPLC and by phenotypic observation. In both lines, the predominant [$^{14}$C] product in new growth tissue extracts after [$^{14}$C]-glyphosate application is N-acetyl-[$^{14}$C]-AMPA. The phytotoxicity as observed by discoloration of plant leaves in line 3753 after glyphosate application is associated with the lack of an AMPA N-acyltransferase activity. In contrast, the presence of an AMPA N-acyltransferase activity in both the 4416 and the 4268 plant lines resulted in a lack of phytotoxic effects observed in line 3753 plants.

Canola

Canola plants were transformed with the vectors pMON17138 and pMON17261 and a number of plant lines of the transformed canola were obtained which exhibited glyphosate tolerance. Plants were transformed according to the method described in Barry et al. (U.S. Pat. No. 5,633, 435). Briefly, *Brassica napus* cv Westar plants were grown in controlled growth chamber conditions as described. Four terminal internodes from plants just prior to bolting or plants in the process of bolting but before flowering were removed and surface sterilized in 70% v/v ethanol for one minute, then in 2% w/v sodium hypochlorite for twenty minutes, then rinsed three times with sterile distilled deionized water. Stems with leaves attached could be refrigerated in moist plastic bags for up to three days prior to sterilization. Six to seven stem segments were cut into 5 mm discs with a Redco Vegetable Slicer 200 maintaining orientation of basal end. Stem discs (explants) were inoculated with 1 milliliter of ABI *Agrobacterium tumefaciens* strain A208 containing a recombinant plant transformation plasmid prepared as described above. Explants were placed basal side down in petri plates containing 0.1× standard MS salts, B5 vitamins, 3% sucrose, 0.8% agar, pH 5.7, 1 mg/l BA (6-benzyladenine). The plates were layered with 1.5 ml of media containing MS salts, B5 vitamins, 3% sucrose, pH 5.7, 4 mg/l p-chlorophenoxyacetic acid, 0.005 mg/l kinetin and covered with sterile filter paper.

Following a 2.3 day co-culture, explants were transferred to deep dish petri plates (seven explants per plate) containing MS salts, B5 vitamins, 3% sucrose, 0.8% agar, pH 5.7, 1 mg/l BA, 500 mg/l carbenicillin, 50 mg/l cefotaxime, 200 mg/l kanamycin or 175 mg/l gentamicin for selection, and transferred after three weeks to fresh media, five explants per plate. Explants were cultured in a growth room at 25° C. with continuous light (Cool White). After an additional three weeks, shoots were excised from the explants, and leaf recallusing assays were initiated to confirm modification of $R_0$ shoots. Three tiny pieces of leaf tissue were placed on recallusing media containing MS salts, B5 vitamins, 3% sucrose, 0.8% agar, pH 5.7, 5 mg/l BA, 0.5 mg/l naphthalene acetic acid (NAA), 500 mg/l carbenicillin, 50 mg/l cefotaxime, 200 mg/l kanamycin or gentamicin or 0.5 mM glyphosate. The leaf assays were incubated in a growth room under the same conditions as explant culture. After an additional three weeks, the leaf recallusing assays were scored for herbicide tolerance (callus or green leaf tissue) or sensitivity (bleaching).

Each shoot stem was dipped in ROOTONE at the time of excision, placed in a two inch pot containing Metro-MIX 350, and maintained in a closed humid environment in a growth chamber at 24° C., 16/8 hour photoperiod, 400 uE per square meter per second (HID lamps) for a hardening-off period of approximately three weeks.

Plasmid pMON17138 is an Agrobacterium mediated single border plant transformation vector maintained in the bacterium by selection on streptomycin or spectinomycin. pMON17138 contains a single right Ti border flanking the 3' end of the genetic elements desired to be transferred into the plant genome. This vector contains two plant operable expression cassettes. One cassette is comprised of a cauli-movirus 35S promoter driving expression of a neomycin phosphotransferase gene (nptII), flanked downstream by a nopaline synthase 3' transcription termination and polyadenylation sequence (NOS 3'). The other cassette is comprised of a figwort mosaic virus promoter (described in Rogers, U.S. Pat. No. 5,678,319) upstream of a pea ribulose bisphosphate carboxylase small subunit transcription termination and polyadenylation sequence. A chloroplast targeted glyphosate oxidoreductase (GOX) coding sequence is inserted between the promoter and pea 3' sequence.

Plasmid pMON17261 is an Agrobacterium mediated double border plant transformation vector similar to pMON17138. A chloroplast targeted GOX encoding cassette identical to that in pMON17138 is present downstream from a Ti right border, and upstream of an additional plant operable expression cassette comprised of a figwort mosaic virus promoter (P-FMV) linked to a NOS 3' sequence. A chloroplast targeted PhnO coding sequence is inserted between the second P-FMV and NOS3' sequences.

$R_1$ plants derived from transformation events using pMON17261 and pMON17138 were evaluated using a glyphosate spray test described in Barry et al. (U.S. Pat. No. 5,633,435).

Corn

An AMPA acyltransferase gene has also been introduced into Black Mexican Sweet corn cells with expression of the gene and glyphosate resistance detected in callus. Callus tissue was transformed according to the method described in Barry et al. (U.S. Pat. No. 5,463,175). Various plasmids were used to introduce glyphosate resistance genes encoding GOX and EPSPS in combination with an AMPA acyltransferase gene into corn cells. These plasmids differed from each other with respect to promoters used, chloroplast or plastid targeting peptide sequences used, untranslated leader sequences used, presence or absence of an intron, and type of 3' terminator used, however all plasmids contained a synthetically derived AMPA acyltransferase gene encoding PhnO containing the P2A mutation. The synthetic gene was constructed from three smaller polynucleotide sequences synthesized for Monsanto and characterized for the presence of the desired DNA coding sequence and amino acid sequence translation by Stratagene, Inc., La Jolla, Calif. The non-naturally occurring gene was assembled from three smaller sequences comprised of SEQ ID NO: 16, SEQ ID NO: 17, and SEQ ID NO: 18, wherein the fully assembled gene is represented by SEQ ID NO: 19, and is present in each of the plasmids used for the corn callus transformation. The non-naturally occurring gene coding sequence was established based on the method described in Fishhoff et al. in U.S. Pat. No. 5,500,365 in which monocot preferred codons were used in place of those preferred by *E. coli*. The fully assembled gene encodes a full length PhnO protein identical to the native protein sequence with the exception of the P2A mutation introduced by PCR using SEQ ID NO:5 and SEQ ID NO:6 to engineer appropriate restriction endonuclease recognition sites into the flanking ends of the coding sequence. Plasmids which were used in generating the corn callus data are shown in Table 15 along with differences with respect to genetic elements flanking the AMPA acyltransferase encoding sequence.

TABLE 15

Corn Callus Transformation Plasmids and Relevant Genetic Elements

| Plasmid | Relevant Genetic Elements* |
|---|---|
| pMON32926 | [Pe35S / I-Zm.Hsp70 / CTP / phnO / T-At.Nos] → GOX → EPSPS |
| pMON32931 | [Pe35S / I-Zm.Hsp70 / phnO / T-At.Nos] → GOX → EPSPS |
| pMON32932 | [Pe35S / I-Zm.Hsp70 / CTP / phnO / T-At.Nos] → GOX → EPSPS |
| pMON32936 | [P-Os.Act1 / I-Os.Act1 / CTP / phnO / T-At.Nos] → GOX → EPSPS |
| pMON32938 | [P-Os.Act1 / I-Os.Act1 / CTP / phnO / T-At.Nos] → GOX → EPSPS |
| pMON32946 | [Pe35S / L-Ta.Cab / CTP / phnO / T-Ta.Hsp70]] → GOX → EPSPS |
| pMON32947 | [Pe35S / L-Ta.Hsp70 / CTP/ phnO / T-Ta.Hsp70] → GOX → EPSPS |
| pMON32948 | EPSPS → [Pe35S / I-Zm.Hsp70 / CTP / phnO / T-At.Nos] → GOX |
| pMON32950 | EPSPS → [Pe35S / I-Zm.Hsp70 / CTP / phnO / T-At.Nos] → GOX |
| pMON32570 | EPSPS → [Pe35S / L-Ta.Cab / I-Os.Act1 / CTP / phnO / T-Ta.Hsp70] → GOX |
| pMON32571 | EPSPS → [Pe35S / L-Ta.Cab / I-Os.Act1 / CTP / phnO / T-Ta.Hsp70] → GOX |
| pMON32572 | EPSPS → [Pe35S / L-Zm.Hsp70 / I-Os.Act1 / CTP / phnO / T-Ta.Hsp70] → GOX |
| pMON32573 | EPSPS → [Pe35S / L-Ta.Cab / I-Os.Act1 / CTP / phnO / T-Ta.Hsp70] → GOX |

*Genetic elements contained within PhnO expression cassettes as indicated in each plasmid. Elements are shown in the order in which they appear in the plasmid, along with the presence of other genes encoding herbicide resistance, if present, flanking the PhnO expression cassette.
→ indicates the direction of transcription of each gene or genes flanking the PhnO expression cassette. Individual elements are described in the text.

Promoters which were used included the CaMV e35 S promoter and the rice actin promoter (P-Os.Act1). Introns which were used included those obtained from plant genes such as corn Hsp70 (I-Zm.Hsp70) and rice actin (I-Os.Act1). Non-translated leader sequences which were used included wheat chlorophyll a/b binding protein (L-Ta.Cab) and corn Hsp70 (L-Zm.Hsp70). Termination and polyadenylation sequences which were used included *Agrobacterium tumefaciens* NOS 3' (T-At.Nos) and wheat Hsp70 (T-Ta.Hsp70). The same chloroplast targeting sequence was used in all PhnO expression cassettes, represented by SEQ ID NO: 9.

A [$^{14}$C]-glyphosate metabolism assay was used for determining whether transformed corn callus tissues contain functioning forms of these enzymes. The assay was developed to screen large numbers of corn callus samples. Callus was obtained from Monsanto Company and Dekalb Seed Company corn transformation groups. The Monsanto callus samples, individually designated as callus lines "19nn-nn-nn" in Table 16, were produced from HI II X B73 corn embryos. Callus samples were bombarded with complete covalently closed circular recombinant plant transformation vector plasmid DNA or with linear DNA fragments isolated from such plasmids 25–50 days after embryo isolation. Transformed lines were identified 8–14 weeks after bombardment. These lines were sub-cultured on fresh media every 2 weeks and were 5–7 months old when used in the metabolism assay. The Dekalb callus lines OO, OR, OW, OX, and OY were obtained from HI II x AW embryos. All line designations correspond to the recombinant plasmid or linear fragment used for ballistic transformation of callus tissue as noted in the legend to Table 16.

4.5 mCi of N-phosphono-[$^{14}$C]-methylglycine ([$^{14}$C]-glyphosate) was obtained from the Monsanto Radiosynthesis group in a 1.5 mM aqueous solution, having a specific radioactivity of 39.4 mCi/mM (5.2×10$^5$ dpm/microgram).

The sample was identified with code number C-2182.2. A stock solution sterilized by filtration through a 0.2-micron Acrodisk (Gelman no. 4192) was prepared by combining 2.5 mL [$^{14}$C]-glyphosate (3.3×10$^8$ dpm) with 2.5 mL of corn callus growth medium (N6 medium) and 5.0 mg of Mon 0818 surfactant. [$^{14}$C]-glyphosate in the resulting dose solution was 0.75 mM. The N6 medium was described by Chu et al. (1975) and was prepared using salts and vitamins obtained from Sigma Chemical Company, St. Louis, Mo. Mon 0818 surfactant is ethoxylated tallowamine, the surfactant used in Roundup herbicide. The dose solution was subjected to HPLC analysis as described in Example 2. The results are shown in a chromatogram illustrated in FIG. 1. Three radioactive peaks were resolved, the largest of which corresponded to glyphosate (11.3 min, 98.8%). Impurity peaks corresponding to [$^{14}$C]-AMPA (5.8 min, 0.16%) and an unidentified material (10.2 min, 1.0%) were also present in the dose solution. No peaks corresponding to N-acetyl-[$^{14}$C]-AMPA were present in the dose solution. Two additional dose solutions were prepared using these reagents, each of which were scaled three fold to 15 ml volumes based on the preparation method described above.

N-acetyl-[$^{14}$C]-AMPA was synthesized for use as a retention time HPLC standard. 1 mL of pyridine and 2 mL of acetic anhydride was added to a 20-mL screw cap culture tube and chilled on ice. 0.1 mL of an aqueous solution of [$^{14}$C]-AMPA (6.2×10$^6$ dpm, code C-2127.2) was added to the chilled solution. The tube was then removed from the ice bath and warmed to about 50–60° C. A 10-$\mu$L sample was removed after about 30 minutes and combined with 0.5 mL of water and analyzed according to the HPLC method set forth above. [$^{14}$C]-AMPA was not detected, however two new radioactive peaks were identified; one peak at 13.9 minutes (68%) and the other at 15.4 minutes (32%). A sample of the material eluting at 13.9 minutes was isolated and analyzed by negative ion electrospray mass spectrometry. The result showed strong ions at m/e 152 and 154, as expected for this compound, which has a molecular weight of 153 Daltons; the ml/z 154 ion was due to the isotopic [$^{14}$C]atom. The radioactive peak eluting at 15.4 minutes was not isolated. However, in a separate HPLC experiment, it was shown to co-elute with synthetic N-acetyl-N-methyl-AMPA. N-methyl-[$^{14}$C]-AMPA has previously been shown to be an impurity in the initial [$^{14}$C]-AMPA material.

Figure 2:
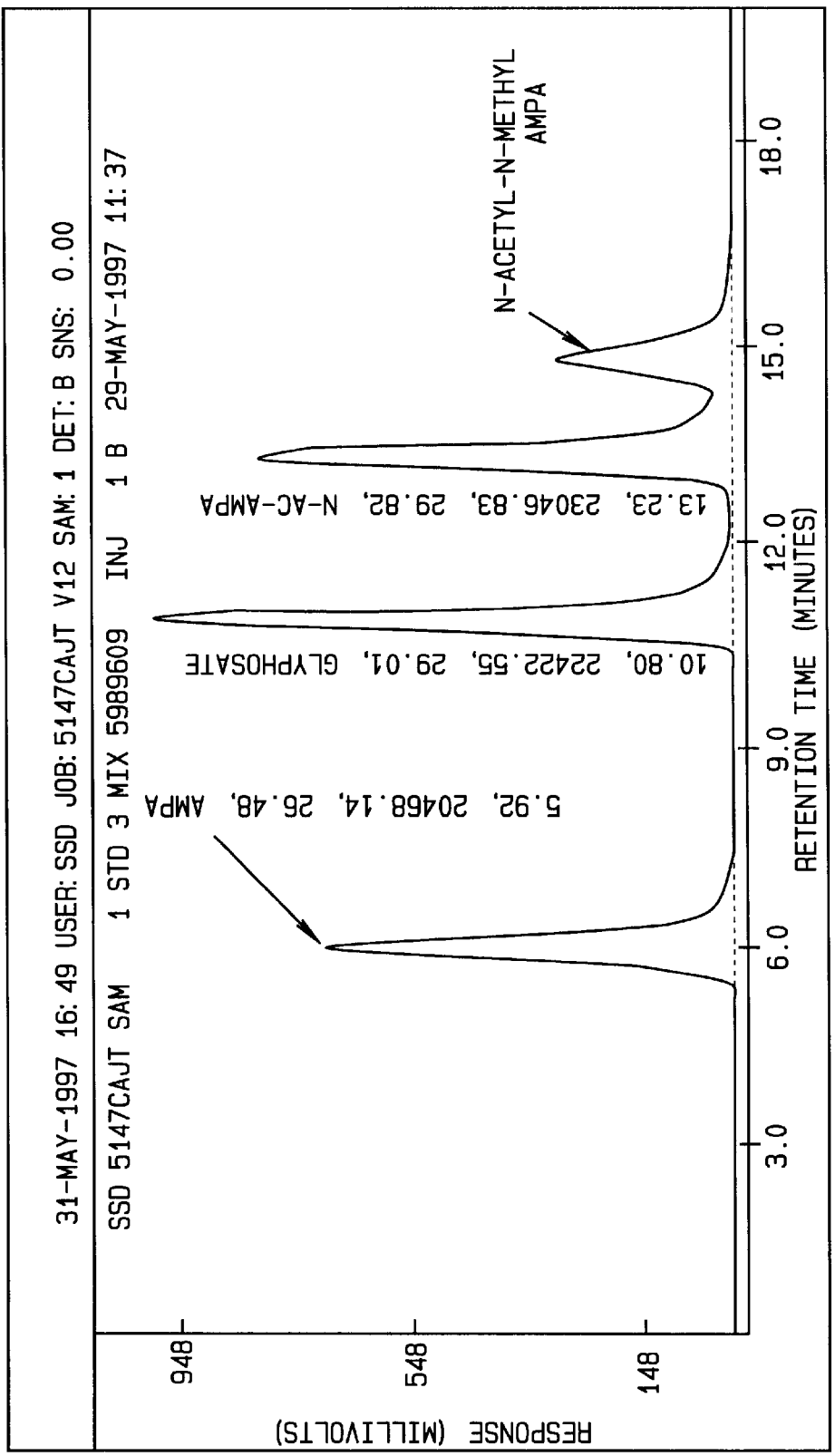
FIG. 2 illustrates an HPLC profile of a mixture of standards of the observed radioactive metabolites [$^{14}$C] AMPA, [$^{14}$C] glyphosate, and N-acetyl-[$^{14}$C]-AMPA, as well as the impurity indentified as N-acetyl-N-methyl-[$^{14}$C]-AMPA.

Under aseptic conditions, corn callus samples were transferred to individual wells of sterile 48-well COSTAR™ cell culture clusters (cat. No. 3548). The individual callus samples were not weighed. However, in several cases the total weight of the callus samples in a 48-well plate was determined. Typically, the average weight of individual callus samples was approximately 200–250 mg. In each assay, a nontransformed callus sample, HI II X B73, was included as a control. 50 µl of dose solution containing $3.3 \times 10^6$ dpm of $[^{14}C]$-glyphosate was added to each callus sample. 48-well plates were sealed with parafilm and placed in a plastic bag containing a wet paper towel to provide a moist atmosphere. Bags were closed and placed in a dark drawer at 25° C. for 10 days. Each callus sample was subsequently transferred to a labeled microcentrifuge tube (VWR, 1.7-mL, cat. No. 20170-620). 1.0 mL of de-ionized water was added to each tube, and the tubes were closed and placed in round 20-tube floating microcentrifuge racks (Nalge cat. no. 5974-1015). These microfuge tubes were floated in boiling water for 30 minutes, shaken using a vortex mixer, and centrifuged for 5 minutes using a Fisher brand microcentrifuge. 120-µL supernatant samples were removed for analysis by HPLC as described below. The samples were injected using a Waters WISP autoinjector. Chromatographic profiles were obtained for each sample analyzed, and quantitative information was obtained by extrapolating the area under the radioactive elution peaks to total $[^{14}C]$ in each sample. FIG. 2 shows an HPLC profile of a mixture of standards of the observed radioactive metabolites $[^{14}C]$ AMPA, $[^{14}C]$ glyphosate, and N-acetyl-$[^{14}C]$-AMPA and the impurity identified as N-acetyl-N-methyl-$[^{14}C]$-AMPA.

HPLC analysis was typically completed using a SPHER-ISORB™ S5 SAX 250 mm×10 mm column for most analyses. Some samples were analyzed on an ALLTECH™ 5-micron, 250×10 mm SAX column, which provided similar performance. Two solvents were prepared. Solvent A consisted of 0.005 M $KH_2PO_4$, adjusted to pH 2.0 with $H_3PO_4$ and contained 4% methanol. Solvent B consisted of 0.10 M $KH_2PO_4$, adjusted to pH 2.0 with $H_3PO_4$ and also contained 4% methanol. The eluent flow rate was set at 3 mL/min, and the scintillation fluid flow rate was set at 9 mL/min using ATOMFLOW™ scintillation fluid (No. NEN-995, from Packard Instruments). All column solvent steps were linear, with the injection and column solvent flow rates as indicated in example 2. The column is prepared for an additional injection at 20 minutes.

Figure 3:
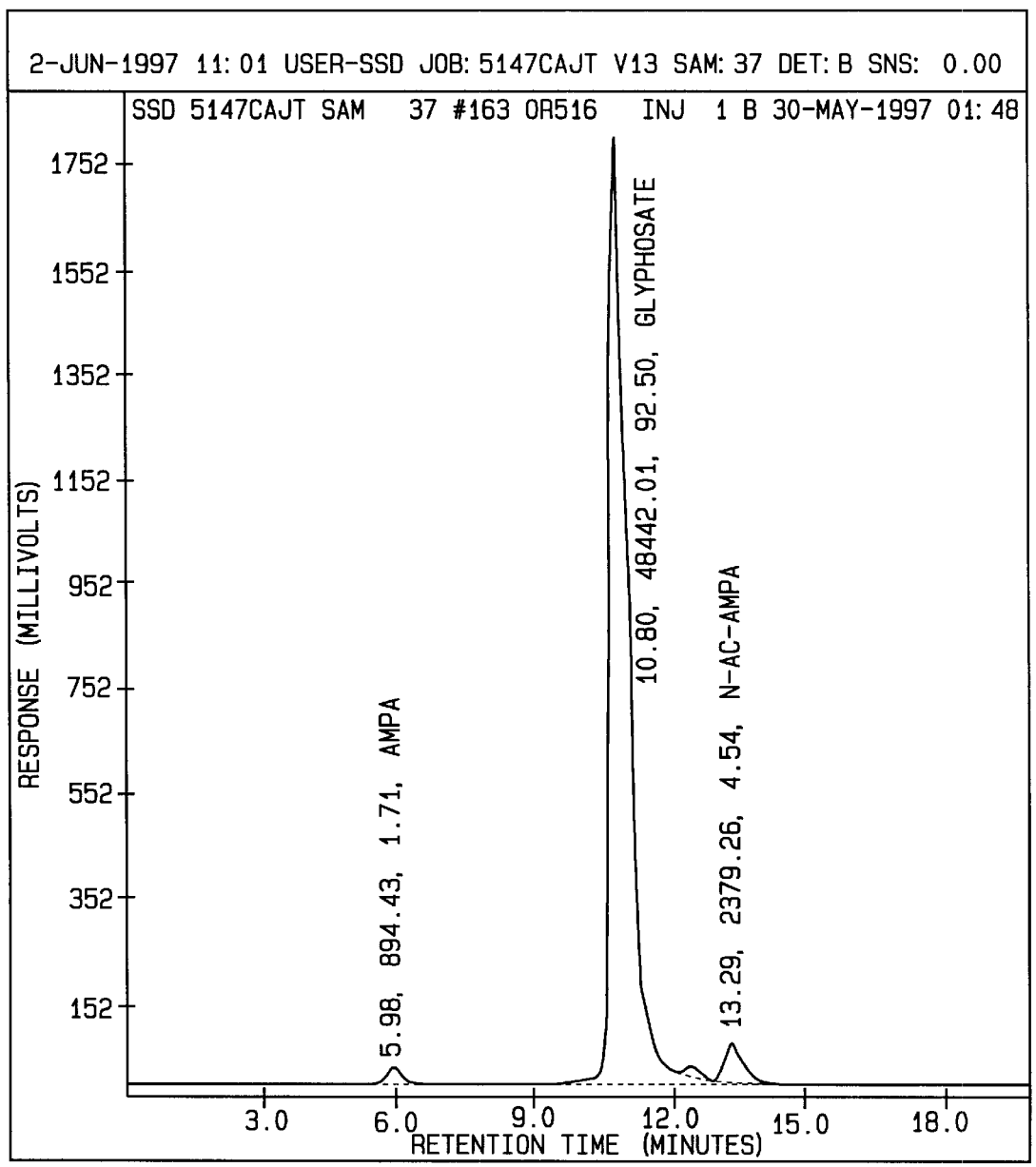
FIG. 3 illustrates a representative HPLC profile of an extract from a corn callus tissue transformed with GOX and AMPA acetyltransferase, and treated with [$^{14}$C] glyphosate. The peaks indicate [$^{14}$C] glyphosate (10.8 minutes, 92.5% of total observed [$^{14}$C]), [$^{14}$C] AMPA primarily generated by GOX mediated glyphosate degradation (5.98 minutes, 1.71% of total observed [$^{14}$C], and N-acetyl-[$^{14}$C]AMPA produced from acylation of [$^{14}$C] AMPA mediated by recombinant AMPA acyltransferase expressed within callus tissue (13.29 minutes, 4.54% total observed [$^{14}$C]).
Figure 4:
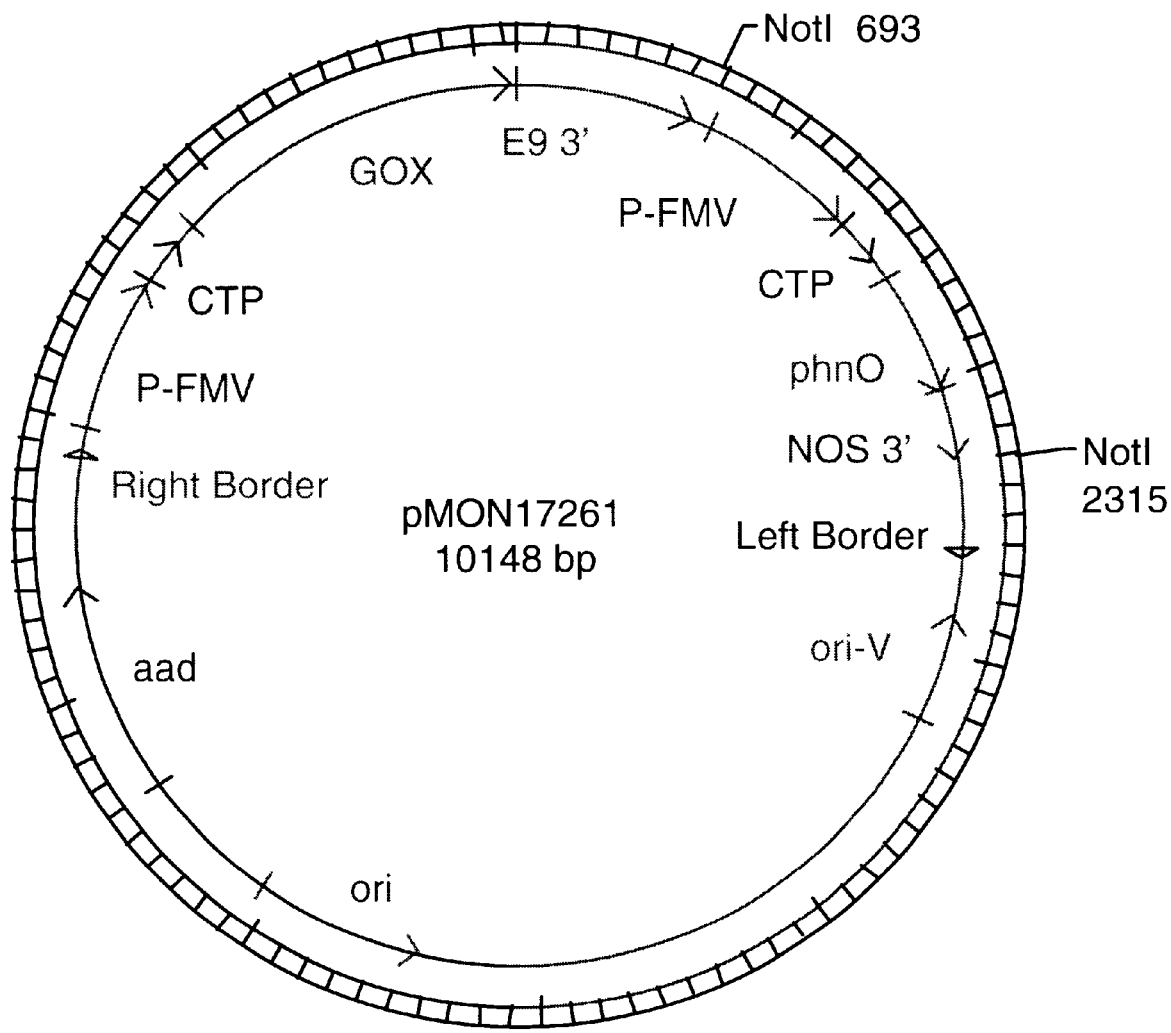
FIG. 4 illustrates plasmid pMON17261.
Figure 5:
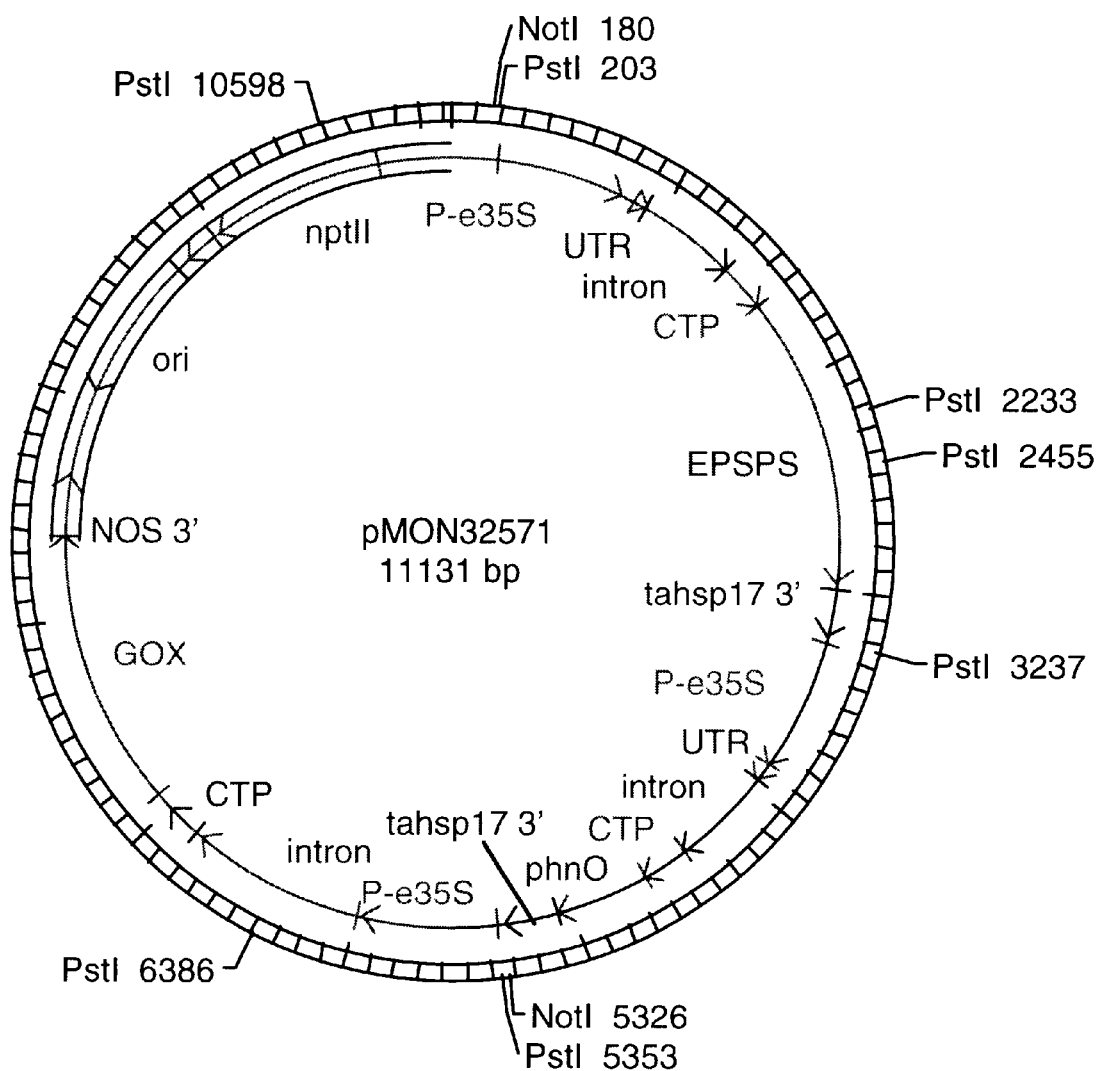
FIG. 5 illustrates plasmid pMON32571.
Figure 6:
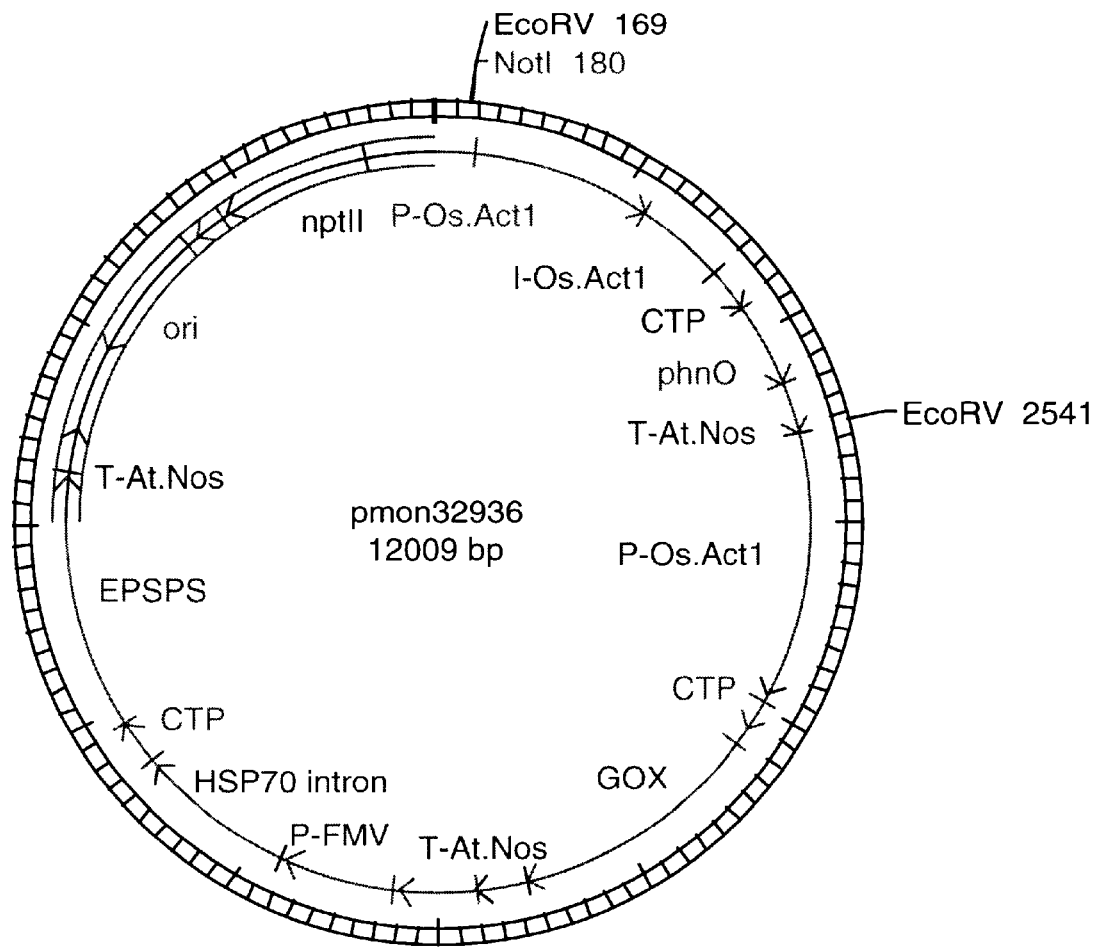
FIG. 6 illustrates plasmid pMON32936.
Figure 7:
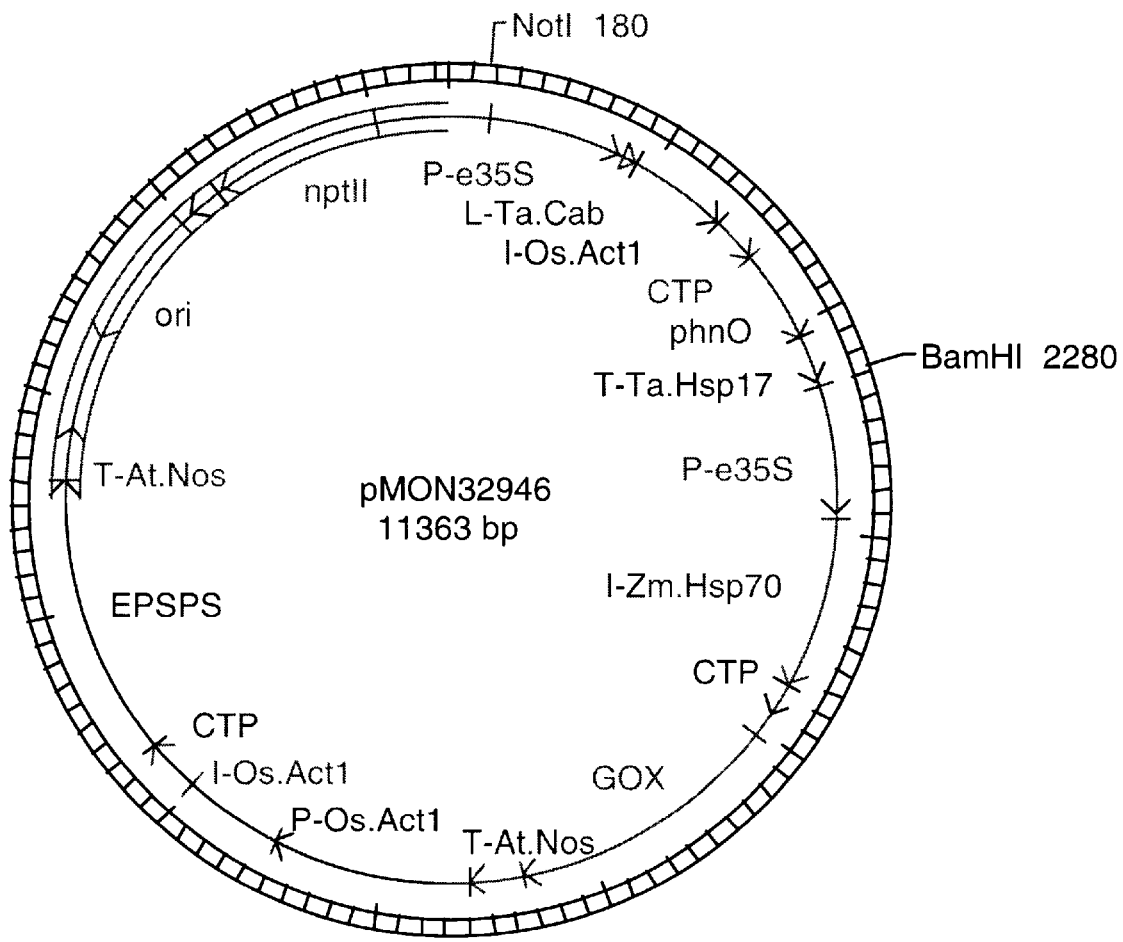
FIG. 7 illustrates plasmid pMON32946.
Figure 8:
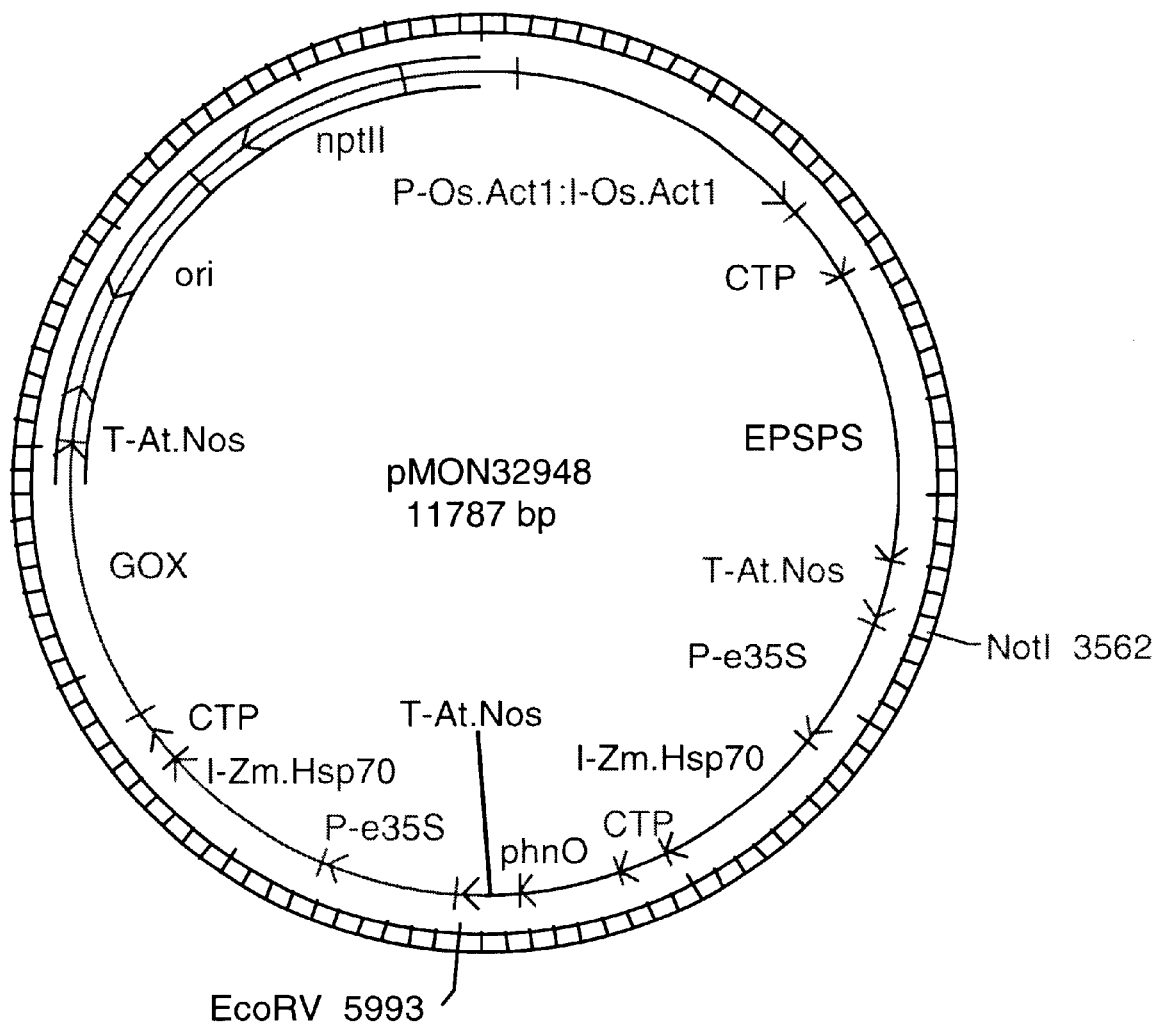
FIG. 8 illustrates plasmid pMON32948.

Callus samples from 359 transformed corn lines were combined with 50-µL aliquots of $[^{14}C]$-glyphosate dose solution and incubated for 10 days in the dark. Each post-incubation callus sample, together with its clinging dose material, was transferred to a 1.7-mL microcentrifuge tube along with 1 mL of water, and each tube was placed in boiling water. This step causes cell lysis, releasing soluble intracellular compounds including any isotope labeled compounds such as glyphosate, AMPA, and N-acetyl-AMPA. It was determined during method development that if the post-incubation calli were rinsed thoroughly with water, 85–95% of the radioactivity was rinsed off, and HPLC analysis showed that virtually all of the radioactivity in the rinses was due to $[^{14}C]$-glyphosate and none was attributable to $[^{14}C]$-metabolites. In these experiments, the rinsed calli gave extracts containing $[^{14}C]$-metabolites in addition to $[^{14}C]$-glyphosate. This indicated that the radioactivity in the rinses was due mainly, if not exclusively, to unabsorbed surface $[^{14}C]$-glyphosate. It is important to take this into account when considering the rather low percentages of the dose converted to metabolites, because the percentage calculation includes large amounts of unabsorbed surface radioactivity. The method development work also showed that simply boiling the incubated calli in water released as much radioactivity as could be released by a conventional grinding/extracting procedure. Experiments were conducted to show that oiling did not alter the metabolite profiles. The streamlined procedures made it possible to analyze large numbers of samples (e.g., 96) at one time. Table 16 shows representative data of the callus samples producing the highest levels of N-acetyl-$[^{14}C]$-AMPA or $[^{14}C]$-AMPA obtained after HPLC analysis. A representative chromatogram of a GOX plus AMPA acyltransferase transformed, glyphosate treated, callus extract sample is shown in FIG. 3.

TABLE 16

Transformed Corn Callus Lines Producing Amounts of AMPA or N-Acetyl-AMPA

| Callus Producing N-Acetyl-$[^{14}C]$-AMPA | | | Callus Producing $[^{14}C]$-AMPA | | |
| --- | --- | --- | --- | --- | --- |
| Callus* | Transformed with . . . | Percent** N-Acetyl-$[^{14}C]$-AMPA | Callus* | Transformed with . . . | Percent** $[^{14}C]$-AMPA |
| 1978-05-02 | pMON32570 | 0.27 | 1980-28-03 | pMON32571 | 2.89 |
| 1978-08-01 | pMON32570 | 0.94 | OR523 | pMON32926 | 2.00 |
| 1978-20-02 | pMON32570 | 0.57 | OR534 | pMON32926 | 5.00 |
| 1978-21-02 | pMON32570 | 0.23 | OR537 | pMON32926 | 2.00 |
| 1978-22-01 | pMON32570 | 0.90 | OR539 | pMON32926 | 5.08 |
| 1978-24-02 | pMON32570 | 1.80 | 1971-08-01 | pMON32932 | 2.64 |
| 1978-35-01 | pMON32570 | 0.22 | 1971-27-03 | pMON32932 | 3.63 |
| 1980-01-01 | pMON32570 | 0.27 | OO505 | pMON32932 | 2.73 |
| 1980-03-01 | pMON32571 | 0.22 | OO509 | pMON32932 | 2.86 |
| 1981-28-01 | pMON32571 | 0.25 | OO510 | pMON32932 | 2.34 |
| 1981-02-01 | pMON32572 | 0.65 | OO512 | pMON32932 | 2.31 |
| 1981-03-01 | pMON32572 | 0.74 | OO514 | pMON32932 | 1.98 |
| 1981-18-01 | pMON32572 | 0.22 | OO535 | pMON32932 | 2.88 |
| 1981-23-01 | pMON32572 | 0.48 | OO538 | pMON32932 | 2.70 |
| 1981-24-02 | pMON32572 | 0.29 | OO539 | pMON32932 | 1.97 |
| 1981-32-02 | pMON32572 | 1.08 | OO553 | pMON32932 | 3.56 |
| 1977-05-03 | pMON32573 | 0.39 | OO576 | pMON32932 | 3.49 |
| OR516 | pMON32926 | 1.91 | OO579 | pMON32932 | 2.85 |
| 1972-14-01 | pMON32931 | 0.40 | 1986-17-01 | pMON32936 | 2.29 |
| 1972-32-01 | pMON32931 | 0.75 | 1986-18-03 | pMON32936 | 3.05 |
| 1972-33-01 | pMON32931 | 0.55 | 1986-18-04 | pMON32936 | 2.15 |

TABLE 16-continued

Transformed Corn Callus Lines Producing Amounts of AMPA or N-Acetyl-AMPA

| Callus Producing N-Acetyl-[$^{14}$C]-AMPA | | | Callus Producing [$^{14}$C]-AMPA | | |
|---|---|---|---|---|---|
| Callus* | Transformed with . . . | Percent** N-Acetyl-[$^{14}$C]-AMPA | Callus* | Transformed with . . . | Percent** [$^{14}$C]-AMPA |
| OO544 | pMON32932 | 0.28 | 1986-28-02 | pMON32936 | 2.06 |
| 1986-06-01 | pMON32936 | 0.30 | 1983-12-02 | pMON32938 | 2.41 |
| 1986-08-01 | pMON32936 | 1.13 | 1983-31-01 | pMON32938 | 2.90 |
| 1986-08-03 | pMON32936 | 0.70 | 1985-03-02 | pMON32946 | 2.51 |
| 1986-12-01 | pMON32936 | 0.33 | 1985-38-01 | pMON32947 | 1.99 |
| 1986-18-02 | pMON32936 | 0.40 | OX512 | pMON32948 | 2.43 |
| 1986-18-03 | pMON32936 | 0.51 | OX533 | pMON32948 | 3.91 |
| 1986-18-04 | pMON32936 | 1.09 | OX556 | pMON32948 | 12.11 |
| 1986-22-04 | pMON32936 | 0.64 | OY504 | pMON32950 | 2.25 |
| 1983-11-01 | pMON32938 | 0.21 | OY511 | pMON32950 | 2.53 |
| OW534 | pMON32946 | 0.77 | OY528 | pMON32950 | 2.58 |
| OW542 | pMON32946 | 0.85 | OY532 | pMON32950 | 2.24 |
| 1985-26-01 | pMON32947 | 0.60 | OY534 | pMON32950 | 4.02 |
| 1985-26-03 | pMON32947 | 0.71 | OY535 | pMON32950 | 2.34 |
| 1985-11-04 | pMON32952 | 0.37 | OY540 | pMON32950 | 5.57 |

*All lines were transformed using ballistic methods. Lines designated by 19xx-yy-zz were transformed with isolated linear fragments of plasmids. Linear fragments were isolated so as to be separate from plasmid backbone structure.
**percent radioactivity detected for N-Acetyl-[$^{14}$C]-AMPA or [$^{14}$C]-AMPA peaks determined as a fraction of the total amount of radioactivity in the sample, including residual [$^{14}$C]-glyphosate as described in the text.

19 of the 359 callus samples tested produced extracts containing N-acetyl-[$^{14}$C]-AMPA at a level distinctly higher than the other callus samples. Callus OR516 was the strongest in this respect and was analyzed five times during a period of two months, providing values ranging from 0.50–4.54% (average 1.91%). The basis for the relatively large spread in the percentage of N-acetyl-[$^{14}$C]-AMPA formed at various times is unknown. In four of the five analyses of OR516, the percentage of N-acetyl-[$^{14}$C]-AMPA present was higher than that of [$^{14}$C]-AMPA, indicating an efficient conversion of [$^{14}$C]-AMPA to N-acetyl-[$^{14}$C]-AMPA. The callus next most efficient in producing N-acetyl-[$^{14}$C]-AMPA was 1978-24-02, which was the only other callus besides OR516 that contained more N-acetyl-[$^{14}$C]-AMPA than [$^{14}$C]-AMPA in its extract. One hundred of the 359 callus samples tested produced extracts containing [$^{14}$C]-AMPA at a level distinctly higher than other callus samples. OX556 was a superlative producer of [$^{14}$C]-AMPA, yielding more than twice as much of the metabolite as any other callus in the study. The control callus, HI II X B73, which contained no inserted genes, produced no detectable levels of N-acetyl-[$^{14}$C]-AMPA and only background levels of [$^{14}$C]-AMPA. This result indicates that expression of an AMPA acyltransferase in corn is effective in conversion of AMPA produced as a result of GOX mediated glyphosate degradation to N-acetyl-AMPA.

Wheat

GOX mediated glyphosate degradation has been shown to produce AMPA, and AMPA has previously been shown to be the source of phytotoxic effects. Therefor, effects of wheat plant exposure to the compounds AMPA or N-acetyl-AMPA was determined as in example 2 in order to observe any wheat sensitivity or insensitivity to either of these compounds. The observation of any phytotoxic effects would indicate that GOX mediated glyphosate metabolism would be detrimental to Triticum species.

Wheat immature embryos were exposed to different concentrations of AMPA and N-acetyl-AMPA in a wheat embryo germination assay. MMSO base media was prepared containing 40 grams per liter maltose, 2 grams per liter GELRITE™, MS salts, and vitamins. Salts, vitamins, and maltose were dissolved in 3500 ml water and the pH was adjusted to 5.8. 500 ml was dispensed into a separate bottle along with 1 gram of GELRITE™ and autoclaved for 17 minutes. After the medium had cooled to about 45° C., AMPA or N-acetyl-AMPA was added to a defined concentration. The mixture was poured into six square Sundae cups under sterile conditions and allowed to solidify.

Immature wheat embryos were isolated from twenty day old seedlings (after anther formation) and inoculated into each MMSO media. Each Sundae cup contained nine immature embryo's. Three separate plates were used for each concentration of AMPA (0, 0.1, 0.15, 0.2, 0.25, 0.3, and 1.0 mM) or N-acetyl-AMPA (0, 0.1, 0.3, 1.0, and 3.0 mM). Sundae cups were incubated for ten days and the length of roots and shoots were determined and compared. The results are shown in Table 17.

TABLE 17

Comparison of AMPA and N-acetyl AMPA on Germinating Shoot and Root Length

| Phosphonate Compound | Shoot (cm) | Root (cm) |
|---|---|---|
| AMPA (mM) | | |
| 0.00 | 12.6 ± 2.6 | 7.0 ± 1.9 |
| 0.10 | 11.7 ± 2.5 | 8.0 ± 2.0 |
| 0.15 | 11.3 ± 2.1 | 6.3 ± 1.7 |
| 0.20 | 9.2 ± 1.8 | 4.6 ± 2.1 |
| 0.25 | 8.5 ± 1.8 | 3.1 ± 1.6 |
| 0.30 | 6.6 ± 1.8 | 2.6 ± 1.6 |
| 1.00 | 0.9 ± 0.1 | 0.4 ± 0.1 |
| N-Acetyl-AMPA | | |
| 0.00 | 12.6 ± 2.6 | 7.0 ± 1.9 |
| 0.10 | 12.0 ± 2.4 | 5.9 ± 1.4 |
| 0.30 | 11.7 ± 3.5 | 5.2 ± 1.2 |
| 1.00 | 12.2 ± 3.2 | 5.4 ± 1.5 |
| 3.00 | 11.2 ± 2.6 | 5.9 ± 1.6 |

AMPA was not substantially inhibitory to growth and elongation of immature embryo's at concentrations under 0.2 mM. However, concentrations above 0.2 mM were severely inhibitory to both shoot and root elongation, indicating that AMPA may also be phytotoxic to wheat and, considering the nature of the monocot crop species as a whole, phytotoxic to other monocotyledonous crops as well as turf grasses. Germination of immature embryo's was significantly affected when the AMPA level was higher than 0.20 mM. 1.00 mM AMPA eliminated the germination of immature embryo's in wheat. In contrast, N-acetyl-AMPA was not inhibitory to shoots and only mildly inhibitory to root elongation at any concentrations tested in this experiment. The highest N-acetyl-AMPA concentration tested was greater than ten times the minimal non-inhibitory concentration determined for AMPA. There are no significant effects to immature embryo germination when the N-acetyl-AMPA concentration is less than 3.0 mM. This result indicates that N-acetylation of AMPA in wheat would prevent AMPA phytotoxicity arising as a result of GOX mediated glyphosate herbicide metabolism.

Recombinant glyphosate tolerant wheat plants were generated according to the method of Zhou et al. (Plant Cell Reports 15:159–163, 1995). Briefly, spring wheat, *Triticum aestivum* cv Bobwhite, was used as the target transformation line. Stock plants were grown in an environmentally controlled growth chamber with a 16 hour photoperiod at 800 microJoule per square meter per second provided by high-intensity discharge lights (Sylvania, GTE Products Corp., Manchester, N.H.). The day/night temperatures were 18/16° C. Immature caryopses were collected from the plants 14 days after anthesis. Immature embryos were dissected aseptically and cultured on MMS2 medium, a Murashige and Skoog (Physiol. Plant 15:473–497, 1962) basal medium supplemented with 40 grams per liter maltose and 2 milligrams per liter 2,4-D. In some experiments, CM4 medium was used. CM4 medium contains is MMS2 medium, but contains only 0.5 milligrams per liter 2,4-D and includes 2.2 milligrams per liter picloram. The immature embryos were cultured at 26° C. in the dark.

Immature embryos were transferred five days after culture initiation to an osmotic treatment CM4 medium containing 0.35 M mannitol four hours prior to bombardment according to the method of Russell et al. (In Vitro Cell Devel. Biol., 28P:97–105, 1992). Thirty to forty embryos were placed in the center of each plate and bombarded in a DuPont PDS1000 apparatus. Plasmid DNA was adsorbed onto 1 $\mu$m tungsten particles according to the method of Sanford et al. (Particle Sci. Technol., 5:27–37, 1987). Embryos were bombarded twice at a distance of 13 mm from the stopping plate. A 100 $\mu$m stainless steel screen was placed immediately below the stopping plate.

After a 16 hour post bombardment treatment on the osmotic medium, the embryos were transferred to MMS2 or CM4 medium. Following a one week delay, the embryos were transferred to the MMS2 or CM4 medium containing 2 mM glyphosate. After 9–12 weeks of callus proliferation on the selection medium, calli were transferred to a MMS0.2 regeneration medium containing 0.2 mg/l 2,4-D and 0.1 mM glyphosate. Shoots obtained from the regeneration medium were transferred to MMSO without 2,4-D but containing 0.02 mM glyphosate.

Glyphosate tolerant $R_0$ plants as well as $R_1$ progeny were transferred to 15 centimeter diameter pots and grown in an environmentally controlled chamber as described above. Two weeks later, the plants were sprayed with 3 ml/liter ROUNDUP (41% active ingredient, Monsanto Company) in a spray chamber, which was designed to mimic a field dose application of 0.6 kilograms glyphosate per hectare. Damage symptoms were observed and recorded at different stages following the spraying.

Genomic DNA was isolated from leaf tissue of $R_0$ and $R_1$ progeny following the method of Shure et al. (Cell 35:225–233, 1983). Fifteen micrograms of genomic DNA was digested with BglII restriction endonuclease and fractionated on a 0.8% agarose gel. The DNA was transferred to Hybond N membranes (Amersham) according to the standard procedure described in Sambrook et al. (Molecular Cloning: A Laboratory Manual, Cold Spring Harbor Laboratory Press, 1989). The membranes were probed independently for the presence of genes encoding EPSPS and GOX. A 3.4 kb DNA fragment containing the EPSPS gene and a 4.8 kb DNA fragment containing the GOX gene were released from pMON19574 by BglII restriction endonuclease digestion, isolated by 0.7% agarose gel electrophoresis, and labeled with [$^{32}$P] dCTP using a Stratagene PRIME-IT II random primer labeling kit. Probes were labeled to a specific activity of $3\times10^9$ counts per minute per microgram and $1.3\times10^9$ counts per minute per microgram, respectively. Membranes were hybridized for 14 hours at 42° C. in a solution containing 50% formamide, 5× SSC, 5× Denhardt's, 0.5% SDS, and 100 microgram per milliliter tRNA. The condition of the final wash was 0.1% SSC and 0.1% SDS at 60° C. for fifteen minutes.

EPSPS and GOX protein assays were conducted using crude protein extracts from leaf tissue of $R_0$ plants and total proteins were quantified following the method of Bradford (Anal. Biochem. 72:248–256, 1976). The percentage of EPSPS and GOX protein represented in the extracts was quantified using an ELISA method and calculated as percent total extractable protein.

Immature embryos from the $R_0$ transgenic and Bobwhite control plants were isolated twenty days after anthesis and cultured on the MMSO medium with 0.02 mM glyphosate for a germination test. Germinated and non-germinated embryos were recorded ten days later and the data was analyzed by $\chi^2$ test for 3:1 segregation. Tolerant plants from the germination test were transferred to soil and sprayed with three milliliters per liter of ROUNDUP as described above.

Five plasmids harboring glyphosate resistance genes were used to transform immature wheat embryos as described above. pMON19338 contains a nucleotide cassette encoding a petunia EPSPS chloroplast transit peptide in frame with an Agrobacterium strain CP4 EPSPS enzyme sequence. The nucleotide cassette is inserted downstream of a cauliflower mosaic virus enhanced 35S promoter linked 3' to a maize HPS70 intron sequence and upstream of a nopaline synthase 3' transcription termination and polyadenylation sequence. Convenient restriction sites are positioned between the intron sequence and the 3' termination sequence for insertion of genetic elements. pMON19643 is identical to pMON19338 except that a GOX enzyme encoding sequence is used in place of the Agrobacterium EPSPS enzyme encoding sequence. pMON19574 is identical to pMON19338 but additionally contains a chloroplast targeted glyphosate-oxidoreductase expression cassette identical to that in pMON19643 downstream of and immediately adjacent to the EPSPS expression cassette. pMON32570 is similar to pMON19574 in that expression cassettes encoding a chloroplast targeted EPSPS and chloroplast targeted GOX are present, however, an expression cassette encoding a chloroplast targeted AMPA acyltransferase enzyme is also present between the EPSPS and GOX expression cassettes. Other elements which are present in pMON19574 and not in the other plasmids are also worthy of mention. For example, a wheat major chlorophyll a/b binding protein gene 5' untranslated leader is present between the enhanced 35S promoter and intron in both the EPSPS and AMPA acyltransferase expression cassettes (McElroy et al., Plant Cell 2:163–171, 1990). Also, a wheat hsp17 gene 3' transcription termination and polyadenylation sequence is present in place of the nopaline synthase 3' sequence for both EPSPS and AMPA acyltransferase expression cassettes. All plasmids produced recombinant glyphosate tolerant wheat plants using the ballistic transformation method described above. However, plasmids which were capable of expressing GOX only or GOX along with an AMPA acyltransferase either did not produce recombinant glyphosate tolerant wheat plants or produced plants which experienced problems with stunted growth, aberrant segregation of phenotypes, and infertility and were not analyzed further. The data obtained after biolistic transformation using the described plasmids is shown in Table 18.

TABLE 18

Wheat Biolistic Transformation Data

| Glyphosate Tolerance Gene(s) | # Explants | #Transgenic Events | Transformation Efficiency[1] |
|---|---|---|---|
| GOX | 120 | 0 | 0 |
| GOX + PhnO | 434 | 6 | 1.4 |
| EPSPS | 120 | 6 | 5.0 |

TABLE 18-continued

Wheat Biolistic Transformation Data

| Glyphosate Tolerance Gene(s) | # Explants | #Transgenic Events | Transformation Efficiency[1] |
|---|---|---|---|
| EPSPS + GOX | 120 | 1 | 0.8 |
| EPSPS + PhnO + GOX | 10,068 | 314 | 3.1 |

[1]transformation efficiency based on percentage of transgenic events identified from a total population of explants arising from a combination of experiments in which a particular vector construct has been bombarded into immature embryo's.

Transformed glyphosate tolerant plants arising out of these transformations were self crossed and allowed to produce R1 seed, which were used to generate R1 plants. Glyphosate tolerance generally segregated in the expected ratio of 3:1 in R1 plants as judged by R1 plant sensitivities after spraying with glyphosate at the three leaf stage. Glyphosate tolerant R 1 plants were self crossed and allowed to produce R2 seed. R2 seed was germinated from a number of different glyphosate tolerant lines to produce R2 glyphosate tolerant plants to which [$^{14}$C]-glyphosate was applied as described above. Plant leaf and stem tissues were harvested at 48 hours after glyphosate application, and water soluble compounds were extracted as described above and analyzed by HPLC as in example 2 for the presence of [$^{14}$C]-glyphosate metabolites. The total area under the [$^{14}$C] isotope labeled peaks eluting from the column was summed to provide a baseline of 100% [$^{14}$C]-compound identification for each sample analyzed. The results are shown in Table 19.

TABLE 19

Glyphosate Metabolism In Wheat Plant Extracts[1]

| Sample & Glyphosate Tolerance Gene(s) | Plant Line No. | [$^{14}$C]-Glyphosate | [$^{14}$C]-AMPA | Acetyl-[$^{14}$C]-AMPA | [$^{14}$C]-Other[4] |
|---|---|---|---|---|---|
| Standard[2] | na | 30 | 26 | 31 | 13 |
|  | na | 29 | 24 | 29 | 18 |
|  | na | 35 | 29 | 36 | 0 |
| Growth Medium[3] | na | 60 | 32 | 0.2 | 8 |
|  | na | 48 | 25 | 2 | 25 |
|  | na | 87 | 7 | 0 | 6 |
| EPSPS | 24756 | 43 | 25 | 1 | 31 |
|  | 24756 | 53 | 46 | 0 | 1 |
|  | 25397 | 61 | 38 | 0 | 1 |
|  | 25397 | 37 | 19 | 1.2 | 43 |
|  | 25397 | 64 | 20 | 0 | 16 |
| EPSPS + PhnO + GOX | 27249 | 6 | 7 | 85 | 2 |
|  | 27249 | 14 | 12 | 61 | 13 |
|  | 27249 | 5 | 24 | 33 | 38 |
|  | 25462 | 48 | 21 | 0 | 31 |
|  | 25462 | 44 | 5 | 0 | 51 |
|  | 25462 | 54 | 35 | 0 | 11 |
|  | 26281 | 48 | 14 | 17 | 21 |
|  | 26281 | 64 | 11 | 13 | 12 |
|  | 26281 | 38 | 7 | 7 | 48 |
|  | 28598 | 20 | 7 | 5 | 68 |
|  | 28598 | 25 | 7 | 5 | 63 |
| Bobwhite | na | 74 | 26 | 0 | 0 |
|  | na | 17 | 15 | 0 | 32 |
|  | na | 34 | 24 | 0 | 42 |

[1]plant tissue extracts were analyzed by HPLC after [$^{14}$C]-glyphosate application as in Example 1, and the area under the plots for each peak were summed to provide a base of 100% [$^{14}$C]-compound identification for each sample.
[2]standard solution containing approximately equal [$^{14}$C] molar ratios of each known glyphosate metabolism related compound.
[3]growth medium including [$^{14}$C]-glyphosate; glyphosate has previously been shown to be degraded by a photolytic process to AMPA, which can be autoacylated in the presence of certain acyl compounds (MSL-0598).
[4]uncharacterized [$^{14}$C]-labeled compounds which are resolved using the disclosed chromatographic method. Retention time of glyphosate is about 9.6 minutes, AMPA is about 5.4 minutes, N-acetyl-AMPA is about 12.5 minutes, and the major [$^{14}$C]-labeled impurity in the [$^{14}$C]-glyphosate sample is about 4.7 minutes.

The standard solution contains approximately equal molar ratios of each of the compounds glyphosate, AMPA and N-acetyl-AMPA, as well as a number of impurities which are present as a result of the chemical synthesis of these isotope labeled compounds. Growth medium to which [14C]-glyphosate was added was treated to the same conditions as wheat plants, ie, the medium was exposed to incident light intensities which plants received. As expected, photodegradation of glyphosate to AMPA was observed, and a small percentage of AMPA appeared to be converted to acetyl-AMPA, probably as a result of exposure in the growth medium to other acylated compounds. Photodegradation of glyphosate by visible light exposure to AMPA as the major degradation product has been observed previously (Lund-Hoeie et al., *Photodegradation of the herbicide glyphosate in water*. Bull. Environ. Contam. Toxicol. 36:723–729, 1986). Recombinant wheat plants transformed with an EPSPS-only plasmid did not produce [$^{14}$C]-AMPA or acetyl-[$^{14}$C]-AMPA from [$^{14}$C]-glyphosate. [$^{14}$C]-AMPA and trace amounts of acetyl-[$^{14}$C]-AMPA which were observed were within the limits observed as a result of photodegradation in the growth medium control. Non-recombinant Bobwhite control plants treated with [$^{14}$C]-glyphosate also did not produce AMPA or acetyl-AMPA. Plants transformed with the triple gene construct plasmid containing genes capable of expressing EPSPS, PhnO and GOX produced variable results. About one third of these plants appeared to efficiently convert glyphosate to acetyl-AMPA, indicating that the GOX and PhnO enzymes were present and functional. Southern blot analyses demonstrated that the transgenes were integrated into the wheat genomes and transmitted to the following generations. Western blot analysis using anti-EPSPS, anti-GOX, or anti-PhnO antiserum to detect these proteins in the triple gene transformed plant extracts provided further insight into the basis for the variable [$^{14}$C]-glyphosate metabolism observation. Western blot analysis indicated that all of the lines were producing EPSPS, however only line 27249 was producing GOX and PhnO protein. This result is consistent with the data in Table 19, which shows that line 27249 efficiently metabolizes [$^{14}$C]-glyphosate to acetyl-[$^{14}$C]-AMPA. This plant line also did not demonstrate stunting, partial fertility, or altered segregation phenotypes associated with other lines. These results indicate that co-expression of GOX and AMPA acyltransferase in wheat plants expressing recombinant EPSPS provides improved herbicide tolerance.

Example 9

This example illustrates the transformation of tobacco chloroplasts with a phnO gene.

Recombinant plants can be produced in which only the mitochondrial or chloroplast DNA has been altered to incorporate the molecules envisioned in this application. Promoters which function in chloroplasts have been known in the art (Hanley-Bowden et al., Trends in Biochemical Sciences 12:67–70, 1987). Methods and compositions for obtaining cells containing chloroplasts into which heterologous DNA has been inserted have been described, for example by Daniell et al. (U.S. Pat. No. 5,693,507; 1997) and Maliga et al. (U.S. Pat. No. 5,451,513; 1995). A vector can be constructed which contains an expression cassette from which an acyltransferase protein could be produced. A cassette could contain a chloroplast operable promoter sequence driving expression of, for example, a phnO gene, constructed in much the same manner as other polynucleotides herein, using PCR methodologies, restriction endonuclease digestion, and ligation etc. A chloroplast expressible gene would provide a promoter and a 5' untranslated region from a heterologous gene or chloroplast gene such as psbA, which would provide for transcription and translation of a DNA sequence encoding an acyltransferase protein in the chloroplast; a DNA sequence encoding an acyltransferase protein; and a transcriptional and translational termination region such as a 3' inverted repeat region of a chloroplast gene that could stabilize an expressed mRNA coding for an acyltransferase protein. Expression from within the chloroplast would enhance gene product accumulation. A host cell containing chloroplasts or plastids can be transformed with the expression cassette and then the resulting cell containing the transformed chloroplasts can be grown to express the acyltransferase protein. A cassette may also include an antibiotic, herbicide tolerance, or other selectable marker gene in addition to the acyltransferase gene. The expression cassette may be flanked by DNA sequences obtained from a chloroplast DNA which would facilitate stable integration of the expression cassette into the chloroplast genome, particularly by homologous recombination. Alternatively, the expression cassette may not integrate, but by including an origin of replication obtained from a chloroplast DNA, would be capable of providing for replication of, for example, a heterologous phnO or other acyltransferase gene within the chloroplast.

Plants can be generated from cells containing transformed chloroplasts and can then be grown to produce seeds, from which additional plants can be generated. Such transformation methods are advantageous over nuclear genome transformation, in particular where chloroplast transformation is effected by integration into the chloroplast genome, because chloroplast genes in general are maternally inherited. This provides environmentally "safer" transgenic plants, virtually eliminating the possibility of escapes into the environment. Furthermore, chloroplasts can be transformed multiple times to produce functional chloroplast genomes which express multiple desired recombinant proteins, whereas nuclear genomic transformation has been shown to be rather limited when multiple genes are desired. Segregational events are thus avoided using chloroplast or plastid transformation. Unlike plant nuclear genome expression, expression in chloroplasts or plastids can be initiated from only one promoter and continue through a polycistronic region to produce multiple peptides from a single mRNA.

The expression cassette would be produced in much the same way that other plant transformation vectors are constructed. Plant chloroplast operable DNA sequences can be inserted into a bacterial plasmid and linked to DNA sequences expressing desired gene products, such as PhnO proteins or other similar acyltransferases, so that the acyltransferase protein is produced within the chloroplast, obviating the requirement for nuclear gene regulation, capping, splicing, or polyadenylation of nuclear regulated genes, or chloroplast or plastid targeting sequences. An expression cassette comprising a phnO or similar acyltransferase gene, which is either synthetically constructed or a native gene derived directly from an *E. coli* genome, would be inserted into a restriction site in a vector constructed for the purpose of chloroplast or plastid transformation. The cassette would be flanked upstream by a chloroplast or plastid functional promoter and downstream by a chloroplast or plastid functional transcription and translation termination sequence. The resulting cassette could be incorporated into the chloroplast or plastid genome using well known homologous recombination methods. Alternatively, chloroplast or plastid transformation could be obtained by using an autonomously replicating plasmid or other vector capable of propagation within the chloroplast or plastid. One means of effectuating this method would be to utilize a portion of the chloroplast or plastid genome required for chloroplast or plastid replication initiation as a means for maintaining the plasmid or vector in the transformed chloroplast or plastid. A sequence enabling stable replication of a chloroplast or plastid epigenetic element could easily be identified from random cloning of a chloroplast or plastid genome into a standard bacterial vector which also contains a chloroplast or plastid selectable marker gene, followed by transformation of chloroplasts or plastids and selection for transformed cells on an appropriate selection medium. Introduction of an expression cassette as described herein into a chloroplast or plastid replicable epigenetic element would provide an effective means for localizing an acyltransferase gene and protein to the chloroplast or plastid.

In view of the above, it will be seen that the several advantages of the invention are achieved and other advantageous results attained. As various changes could be made in the above methods and compositions without departing from the spirit and scope of the invention, it is intended that all matter contained in the above description, and shown in the accompanying drawings and sequences, shall be interpreted as illustrative and not in a limiting sense.

REFERENCE LITERATURE

Avila et al., J. Am. Chem. Soc. 109:6758–6764, 1987.
Berlyn, Microbiol. Molec. Biol. Rev. 62:814–984, 1998.
Chen et al., J. Biol. Chem. 265:4461–4471, 1990.
Dumora et al., Biochim. Biophys. Acta 997:193–198, 1989.
Franz, Discovery, development and chemistry of glyphosate, in The Herbicide Glyphosate. Eds. E. Grossbard and D. Atkinson. Butterworths. pp. 3–17, 1985.
Hanley-Bowden et al., Trends in Biochemical Sciences 12:67–70, 1987.
Hilderbrand et al., The role of phosphonates in living systems; Hilderbrand, R. L., Ed, pp. 5–29, CRC Press, Inc., Boca Raton, Fla., 1983.
Jacob et al., Appl. Environ. Microbiol. 54:2953–2958, 1988
Jiang et al., J. Bacteriol. 177:6411–6421, 1995.
Kishore et al., J. Biol. Chem. 262:12, 164–12, 168, 1987.
Lacoste et al., J. Gen. Microbiol. 138:1283–1287, 1992.
Lee et al., J. Bacteriol. 174:2501–2510, 1992.
Maier, Phosphorous Sulfur 14:295,1983.
Makino et al., J. Bacteriol. 173:2665–2672, 1991.
McGrath et al., Eur. J. Biochem. 234:225–230, 1995.
Metcalf et al., J. Bacteriol. 173:587–600, 1991.
Metcalf et al., Gene 129:27–32, 1993.
Ohtaki et al., Actinomyceteol. 8:66–68, 1994.
Pipke et al., Appl. Environ. Microbiol. 54:1293–1296, 1987.
Shinabarger et al., J. Bacteriol. 168:702–707, 1986.
Tanaka et al., J. Fac. Agr. Kyushu Univ. 30:209–223, 1986.
Wackett et al., J. Bacteriol. 169:710–717, 1987a
Wackett et al., J. Bacteriol. 169:1753–1756, 1987b.
Wanner et al., FEMS Microbiol. Lett. 100:133–140, 1992.
Wanner, Biodegradation 5:175–184, 1994.
Wohlleben et al., Mol. Gen. Genet. 217:202–208, 1989.

REFERENCED PATENT DOCUMENTS

Barry et al., U.S. Pat. No. 5,463,175, 1995.
Barry et al., U.S. Pat. No. 5,633,435, 1997
Comai, U.S. Pat. No. 4,535,060, 1985.
Daniell et al., U.S. Pat. No. 5,693,507; 1997.
Maliga et al., U.S. Pat. No. 5,451,513; 1995.
McBride et al., WO 95/24492.

What is claimed is:

1. A recombinant plant comprising a polynucleotide sequence encoding an AMPA-N-acetyltransferase enzyme selected from the group consisting of SEQ ID NO:4, SEQ ID NO:8, and SEQ ID NO:20 comprising:

a) a plant functional promoter sequence operably linked to;

b) a structural DNA sequence encoding said AMPA-N-acetyltransferase, operably linked to;

c) a 3' sequence which functions in said plant to cause transcription termination;

wherein expression of said AMPA-N-acetyltransferase in said plant confers upon said plant the ability to enzymatically modify AMPA to N-acetyl-AMPA.

2. A method for producing a genetically transformed AMPA herbicide tolerant plant comprising the steps of:

a) inserting into the genome of a plant cell a polynucleotide sequence comprising;

i) a promoter sequence which functions in plant cells, operably linked to;

ii) a structural DNA sequence encoding an RNA sequence which encodes an AMPA-N-acetyltransferase enzyme selected from the group consisting of SEQ ID NO:4, SEQ ID NO:8, SEQ ID NO:12, and SEQ ID NO:20 which transfers an acetyl group from an acetylated donor to the terminal amine of AMPA, operably linked to;

iii) a 3' non-translated sequence which functions in plant cells to cause the addition of a polyadenylated nucleotide sequence to the 3' end of said RNA sequence;

wherein expression of said DNA sequence in said plant cell confers AMPA herbicide tolerance to said plant cell;

b) selecting a transformed plant cell in the presence of an amount of AMPA which inhibits the growth of a plant cell lacking said polynucleotide sequence; and c) regenerating a genetically transformed plant from the transformed plant cell.

3. A method for selecting one or more cells transformed with a vector comprising a gene, which encodes an AMPA-N-acetyltransferase enzyme, selected from the group consisting of SEQ ID NO:4, SEQ ID NO:8, SEQ ID NO:12, and SEQ ID NO:20, wherein said enzyme functions to N-acetylate an AMPA herbicide compound, comprising the steps of:

a) transforming a population of cells with said vector comprising said AMPA-N-acetyltransferase-encoding gene;

b) incubating said transformed population in the presence of an amount of said AMPA herbicide compound which inhibits the growth of a cell lacking said gene;

c) identifying one or more cells that grow in the presence of said inhibitory amount of said AMPA herbicide compound; and d) isolating said one or more cells that grow in the presence of said inhibitory amount of said AMPA herbicide compound;

wherein said one or more cells transformed with said vector are isolated cells selected from the group consisting of bacterial cells and plant cells.

4. The plant of claim 1 wherein said structural DNA sequence further comprises a 5' end sequence encoding an amino-terminal chloroplast transit peptide operably linked to said structural DNA sequence, wherein said expression of said DNA sequence yields a fusion peptide which causes said AMPA-N-acetyltransferase to be localized to chloroplasts or plastids in said recombinant plant.

5. The plant of claim 4 in which the 5' end sequence encoding the amino-terminal chloroplast transit peptide is selected from the group consisting of SEQ ID NO:9, SEQ ID NO:11, SEQ ID NO:13, and SEQ ID NO:14.

6. A seed produced from the plant of claim 1, wherein said seed comprises said polynucleotide sequence.

7. A plant or progeny thereof grown from the seed of claim 6, wherein said plant or progeny thereof comprises said polynucleotide sequence.

8. A seed produced from the plant of claim 5, wherein said seed comprises said polynucleotide sequence.

9. A plant or progeny thereof grown from the seed of claim 8, wherein said plant or progeny thereof comprises said polynucleotide sequence.

10. The method of claim 2 wherein said structural DNA sequence which encodes an AMPA-N-acetyltransferase enzyme is the E. coli phnO gene sequence as set forth in SEQ ID NO:3.

11. The method of claim 2 wherein said acetylated donor is selected from the group consisting of acetyl-CoA, malonyl-CoA, propionyl-CoA, succinyl-CoA, and methyl-malonyl-CoA.

12. A plant produced by the method according to claim 2, wherein said structural DNA sequence further comprises a 5' end sequence encoding an amino-terminal chloroplast transit peptide operably linked to said structural DNA sequence, wherein said expression of said DNA sequence yields a fusion peptide which causes said AMPA-N-acetyltransferase to be localized to chloroplasts or plastids in said transformed plant.

13. The plant of claim 12 wherein said 5' end sequence encoding the amino-terminal chloroplast transit peptide is selected from the group consisting of SEQ ID NO:9, SEQ ID NO:11, SEQ ID NO:13, and SEQ ID NO:14.

14. A seed produced from the plant of claim 12, wherein said seed comprises said structural DNA sequence.

15. A plant or progeny thereof produced from the seed of claim 14, wherein said plant or progeny thereof comprises said structural DNA sequence.

16. A seed produced from the plant of claim 13, wherein said seed comprises said structural DNA sequence.

17. A plant or progeny thereof produced from the seed of claim 16, wherein said plant or progeny thereof comprises said structural DNA sequence.

18. A plant produced from the method of claim 2, wherein said plant comprises said polynucleotide sequence.

19. A seed produced from the plant of claim 18, wherein said seed comprises said polynucleotide sequence.

20. A plant or progeny thereof grown from the seed of claim 19, wherein said plant or progeny thereof comprises said polynucleotide sequence.

21. The method of claim 3, wherein said one or more cells transformed with said vector are plant cells selected from the group of monocotyledonous and dicotyledonous plant cells.

22. The method of claim 21, wherein said monocotyledonous plant cells are selected from the group of cells consisting of an asparagus plant cell, a barley plant cell, a maize plant cell, an oat plant cell, an orchardgrass plant cell, a rye plant cell, a rice plant cell, a sugarcane plant cell, a tall fescue plant cell, a wheat plant cell, a flax plant cell, a pine plant cell, a radiata pine plant cell, a loblolly pine plant cell, a spruce plant cell, a turf grass plant cell, an oilpalm plant cell, a banana plant cell, a sorghum plant cell, and a millet plant cell.

23. The method of claim 22 wherein said monocotyledonous plant cell is a maize or a rice plant cell.

24. The method of claim 21 wherein said dicotyledonous plant cells are selected from the group of cells consisting of a cotton plant cell, a soybean plant cell, a sugarbeet plant cell, a canola plant cell, an oilseed rape plant cell, a sunflower plant cell, a potato plant cell, a tobacco plant cell, a tomato plant cell, an alfalfa plant cell, a lettuce plant cell, an apple plant cell, a eucalyptus plant cell, an acacia plant cell, a poplar plant cell, a sweetgum plant cell, a teak plant cell, an clover plant cell, a coffee plant cell, a cacao plant cell, a walnut plant cell, an almond plant cell, an grape plant cell, a peanut plant cell, a petunia plant cell, a marigold plant cell, a begonia plant cell, a geranium plant cell, a pansy plant cell, and an impatiens plant cell.

25. The method of claim 24 wherein said dicotyledonous plant cells are selected from the group consisting of a cotton plant cell, a soybean plant cell, and a canola plant cell.

26. The method of claim 3 wherein said gene comprises the *E. coli* phnO gene sequence as set forth in SEQ ID NO:3.

27. The method of claim 3 wherein said gene, which encodes an AMPA-N-acetyltransferase enzyme, hybridizes under stringent hybridization conditions to the *E. coli* phnO gene sequence as set forth in SEQ ID NO:3.

28. The method of claim 3 wherein said AMPA herbicide compound is N-acetylated with an acetylated donor selected from the group consisting of acetyl-CoA, malonyl-CoA, propionyl-CoA, succinyl-CoA, and methyl-malonyl-CoA.

29. A plant produced from a transformed plant cell produced according to the method of claim 3, wherein said plant comprises said gene.

30. The plant according to claim 29, wherein said gene which encodes an AMPA-N-acetyltransferase enzyme comprises a 5' end sequence encoding an amino-terminal chloroplast transit peptide operably linked to said gene, wherein said expression of said gene yields a fusion peptide which causes said enzyme to be localized to chloroplasts or plastids in said plant.

31. The plant of claim 30 wherein said 5' end sequence encoding an amino-terminal chloroplast transit peptide is selected from the group consisting of SEQ ID NO:9, SEQ ID NO:1, SEQ ID NO:13, and SEQ ID NO:14.

32. A seed produced from the plant of claim 29, wherein said seed comprises said gene.

33. A plant or progeny thereof produced from the seed of claim 32, wherein said plant or progeny thereof comprises said gene.

34. A seed produced from the plant of claim 31, wherein said seed comprises said gene.

35. A plant or progeny thereof produced from the seed of claim 34, wherein said plant or progeny thereof comprises said gene.

\* \* \* \* \*

UNITED STATES PATENT AND TRADEMARK OFFICE
CERTIFICATE OF CORRECTION

PATENT NO. : 6,448,476 B1
DATED : September 10, 2002
INVENTOR(S) : Barry et al.

It is certified that error appears in the above-identified patent and that said Letters Patent is hereby corrected as shown below:

Title page,
Item [54], Title, the term "TRANSFORMATION" should read
-- TRANSFORMED --.

Column 148,
Line 25, "No:1" should read -- No:11 --.

Signed and Sealed this

Thirteenth Day of December, 2005

JON W. DUDAS
*Director of the United States Patent and Trademark Office*